United States Patent
Seto et al.

(10) Patent No.: US 8,226,734 B2
(45) Date of Patent: Jul. 24, 2012

(54) AZO COMPOUND, AZO PIGMENT, PIGMENT DISPERSION, COLORING COMPOSITION, INK FOR INKJET RECORDING, COLORING COMPOSITION FOR COLOR FILTER, COLOR FILTER, AND PROCESS FOR PREPARING A COLORING COMPOSITION FOR COLOR FILTER

(75) Inventors: Nobuo Seto, Shizuoka (JP); Masahiro Higashi, Shizuoka (JP); Keiichi Tateishi, Shizuoka (JP); Hideki Takakuwa, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/054,215

(22) PCT Filed: Jul. 17, 2009

(86) PCT No.: PCT/JP2009/063005
§ 371 (c)(1),
(2), (4) Date: Feb. 24, 2011

(87) PCT Pub. No.: WO2010/008081
PCT Pub. Date: Jan. 21, 2010

(65) Prior Publication Data
US 2011/0143270 A1  Jun. 16, 2011

(30) Foreign Application Priority Data

Jul. 17, 2008 (JP) ............................... P2008-186507
Sep. 2, 2008 (JP) ............................... P2008-225036

(51) Int. Cl.
*C09B 67/00* (2006.01)
(52) U.S. Cl. ............ 8/637.1; 8/639; 8/688; 8/690; 8/691
(58) Field of Classification Search .................. 8/637.1, 8/639, 688, 690, 691
See application file for complete search history.

(56) References Cited

FOREIGN PATENT DOCUMENTS
GB 1336898 11/1973
(Continued)

OTHER PUBLICATIONS

STIC Search Report dated Jun. 1, 2011.*
(Continued)

*Primary Examiner* — Eisa Elhilo
(74) *Attorney, Agent, or Firm* — Sughrue Mion, PLLC

(57) ABSTRACT

An azo pigment and pigment dispersion show excellent coloring characteristics and light fastness. The azo pigment is represented by general formula (1), its tautomer, a salt or hydrate thereof:

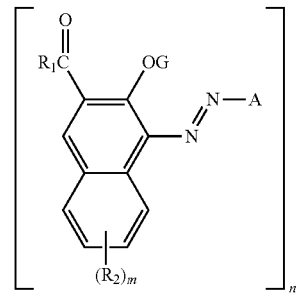

wherein G is hydrogen or an aliphatic, aryl, heterocyclic, acyl, aliphatic oxycarbonyl, carbamoyl, or sulfonyl group, $R_1$ is an amino, aliphatic oxy, aliphatic, aryl, or heterocyclic group, $R_2$ is a substituent, A is an aromatic 5- or 6-membered heterocyclic group, m is an integer of 0 to 5, n is an integer of 1 to 4 and, when n=2, 3 or 4, the formula represents a dimer, trimer, or tetramer, respectively, formed through $R_1$, $R_2$, A, or G.

22 Claims, 21 Drawing Sheets

FOREIGN PATENT DOCUMENTS

| | | | |
|---|---|---|---|
| JP | 63-148267 A | 6/1988 |
| JP | 63-158561 A | 7/1988 |
| JP | 1-152449 A | 6/1989 |
| JP | 4-27959 A | 1/1992 |
| JP | 4-88349 A | 3/1992 |
| JP | 5-005067 A | 1/1993 |
| JP | 6-075375 A | 3/1994 |
| JP | 2592271 B2 | 12/1996 |
| JP | 9-511278 A | 11/1997 |
| JP | 2003-237240 A | 8/2003 |
| JP | 2003-246148 A | 9/2003 |
| JP | 2004-123866 A | 4/2004 |
| JP | 3894726 B2 | 12/2006 |
| JP | 2008-007732 A | 1/2008 |
| JP | 2008-013472 A | 1/2008 |
| WO | 96/12768 A1 | 5/1996 |
| WO | 00/23525 A1 | 4/2000 |
| WO | 2005/052074 A1 | 6/2005 |

OTHER PUBLICATIONS

International Search Report (PCT/ISA/210) issued Oct. 6, 2009, for PCT/JP2009/063005.

Written Opinion (PCT/ISA/237) issued Oct. 6, 2009, for PCT/JP2009/063005.

Poskocil, J. et al., "Some new triazole dyes", Chemicky Prumysl, 1982, vol. 32, No. 6, p. 300-307.

Sebe, Ion et al., "Triazo hetrocyclic disperse dyes", Revue Roumaine de Chimie, 1996, vol. 41, No. 11-12, p. 971-977.

Wrubel, J. et al., "Synthesis of 4-arylazoisoxazolium salts", Journal fuer Praktische Chemie(Leipzig), 1976, vol. 318, No. 3, p. 359-368.

Andreeva, M.A. et al., "Synthesis based on dimethylpyrazoles. I. Synthesis of nitro- and amino-substituted 1,3- and 1,5-dimethylpyrazoles", Zhurnal Obshchei Khimii, 1980, vol. 50, No. 9, p. 2106-2109.

Komatsu, K. et al., "Aminoimidazole kara no Azo Senryo", The Journal of Chemical Industry, 1970, vol. 73, No. 7, p. 1694-1697.

Extended European Search Report dated May 7, 2012 in European Application No. 09798005.6.

Shah, K. H. et al., "Synthesis and dyeing performance of monoazo disperse dyes derived from 3-amino-5-nitro-2, 1-benzisothiazole," Indian Journal of Fibre & Textile Research, vol. 23, Sep. 1998, pp. 189-193.

Shah, K. H. et al., "Studies on Synthesis of Some Disazo Condensation Pigments and Their Application on Polyester, Nylon and Cellulose Triacetate," Oriental Journal of Chemistry, vol. 13(3), Sep. 1997, pp. 301-304.

\* cited by examiner

AZO COMPOUND, AZO PIGMENT, PIGMENT DISPERSION, COLORING COMPOSITION, INK FOR INKJET RECORDING, COLORING COMPOSITION FOR COLOR FILTER, COLOR FILTER, AND PROCESS FOR PREPARING A COLORING COMPOSITION FOR COLOR FILTER

TECHNICAL FIELD

The present invention relates to a novel nitrogen-containing heterocyclic azo compound, azo pigment, a pigment dispersion containing the azo pigment, a coloring composition and an ink for inkjet recording, a coloring composition for a color filter, a color filter, and a process for preparing a coloring composition for a color filter.

BACKGROUND ART

In recent years, as image-recording materials, materials for forming color images have been predominant and specifically, recording materials for an ink jet system, recording materials for a thermal transfer system, recording materials for an electro-photographic system, transfer type silver halide light-sensitive materials, printing inks, and recording pens have found widespread use. Also, in photographing devices such as CCDs for photographing equipment, and in LCDs and PDPs for display, color filters are used for recording or reproducing a color image. In these color image recording materials and color filters, colorants (dyes or pigments) of three primary colors of a so-called additive color mixing process or subtractive color mixing process have been used in order to display or record full-color images. In actuality, however, there is no fast colorant having the absorption characteristics capable of realizing a preferred color reproduction region and resisting various use conditions and environmental conditions. Thus, the improvement thereof has strongly been desired.

Dyes or pigments to be used for the above-mentioned uses are required to have in common the following properties. That is, they are required to have absorption characteristics favorable in view of color reproduction and have good fastness under the conditions of the environment wherein they are used, for example, fastness against light, heat, and an oxidative gas such as ozone. In addition, in the case where the colorant is a pigment, the pigment is further required to be substantially insoluble in water or in an organic solvent, to have a good fastness to chemicals, and not to lose the preferred absorption characteristics it shows in a molecularly dispersed state even when used as particles. Although the required properties described above can be controlled by adjusting the intensity of intermolecular mutual action, both of them are in a trade-off relation with each other, thus being difficult to allow them to be compatible with each other. Besides, in the case of using a pigment as the colorant, the pigment is additionally required to have a particle size and a particle shape necessary for realizing desired transparency, to have good fastness under the conditions of the environment wherein they are used, for example, fastness against light, heat, and an oxidative gas such as ozone, to have good fastness to an organic solvent and chemicals such as a sulfurous acid gas, and to be capable of being dispersed in a used medium to a level of fine particles, with the dispersed state being stable. In particular, there is a strong demand for a pigment which has a good hue and is fast to light, moist heat, and active gases in the environment, particularly for a pigment having high tinctorial strength and is fast against light.

That is, in comparison with a dye which is required to have properties as colorant molecules, the pigment is required to have more properties, i.e., it is required to satisfy all of the above-mentioned requirements as a solid of an aggregate of a colorant (dispersion of fine particles) as well as the properties as molecules of a colorant molecule. As a result, a group of compounds which can be used as pigments are extremely limited in comparison with dyes. Even when high-performance dyes are converted to pigments, few of them can satisfy requirement for the properties as a dispersion of fine particles. Thus, such pigments are difficult to develop. This can be confirmed from the fact that the number of pigments registered in Color Index is no more than $1/10$ of the number of dyes.

Azo pigments are excellent in hue and tinctorial strength which are characteristics of coloring, and hence they have widely been used in printing inks, ink for an inkjet system, and electro-photographic materials. Of the pigments, yellow diarylide pigments and red naphthol azo pigments are the most typically used azo pigments. Examples of such diarylide pigments include C.I. pigment yellow 12, C.I. pigment yellow 13, and C.I. pigment yellow 17. Examples of such naphthol azo pigments include C.I. pigment red 208 and C.I. pigment red 242. However, these pigments are inferior in fastness, particularly light fastness, and hence they are decomposed when prints printed by them are exposed to light, thus being inappropriate for prints which are to be stored for a long time.

In order to remove such defects, there have been disclosed azo pigments having a fastness improved by increasing molecular weight or by introducing a group having a strong intermolecular mutual action (see, for example, patent documents 1 to 3). However, with even the improved pigments, pigments described in, for example, patent document 1 have still insufficient light fastness though improved to some extent, and pigments described in, for example, patent documents 2 and 3 have the defect that their hue is greenish and shows reduced tinctorial strength, thus being inferior in coloring characteristics.

Also, patent documents 4 to 7 disclose colorants which have absorption characteristics excellent in color reproducibility and have sufficient fastness. However, all of the specific compounds described in the patent documents have the defect that fastness is insufficient though hue is good, that hue is bad though fastness is good, or that solubility in an organic solvent or water is large, thus showing insufficient chemical fastness.

In the case of expressing a full-color image based on the subtractive color mixing process using three colors of yellow, magenta, and cyan or using four colors further including black, use of a pigment having an inferior fastness as one of the pigments would change gray balance of the prints with the lapse of time, and use of a pigment having inferior coloring characteristics would reduce color reproducibility upon printing. Thus, in order to obtain prints which can maintain high color reproducibility for a long time, there have been desired a pigment and a pigment dispersion which have both good coloring characteristics and good fastness.

Azo colorants have conventionally been utilized in various fields since they absorb various visible lights. For example, they have come into use in such various fields as coloring of synthetic resins, printing inks, colorants for sublimation type thermal transfer materials, inks for inkjet recording, and colorants for color filters. Important performance required for azo colorants as colorants includes absorption spectrum. Hue of a colorant exerts a great influence on color tone and feeling of a body colored with the colorant, giving a large effect on visual sensation. Therefore, there have long been made studies on absorption spectrum of a colorant.

Conventionally known azo dyes containing a nitrogen-containing ring as an azo component are also disclosed in patent document 5. Also, in patent documents 6 to 8, naphthol series azo pigments and colorants are disclosed wherein a benzene ring and a naphthalene ring are connected to each other through an azo group.

Further, in recent years, image display devices have been required to have a reduced size, a small thickness, a light weight, a large size, a high definition, and the like. Application thereof is widened to displays for personal computers, TV sets, gaming machines, etc., and demand for color liquid crystal displays is sharply increasing.

With such background, high color purity has become required for color filters for use in liquid crystal display elements.

As a color filter to be formed on a device for realizing a color structure in a solid-state imaging device or a liquid crystal display element, there is known a color filter comprising a yellow filter layer, a magenta filter layer, and a cyan filter layer, or a color filter comprising a red filter layer, a green filter layer, and a blue filter layer, in which such filter layers are formed in an adjacent manner in the same plane on a substrate.

In recent years, color filters have been required to have a higher definition. However, resolution has not been improved with conventional pigment dispersion systems and, since such systems have the problem that there results uneven color due to coarse particles of pigments, they have not been suited for the application which requires a fine pattern as is required in a solid-state imaging device. In order to solve this problem, there have conventionally been proposed use of dyes (see, for example, patent document 9).

It is known to use a red dye for a red filter array of a red color filter (see, for example, patent document 10).

However, a colored pattern obtained by dyes has insufficient heat resistance and insufficient light fastness, and hence there has been examined a color filter using an organic pigment having excellent heat resistance and excellent light fastness.

As a manufacturing method of a color filter using an organic pigment, there are illustrated a photolithography method in which a patterning step of exposing and developing a composition containing an organic pigment dispersed in a photo-sensitive resin, and this patterning step is repeated necessary times (see, for example, patent document 11), and a printing method such as an offset printing method using an ink containing an organic pigment and an inkjet printing method.

As organic pigments for color filters, use of organic pigments having excellent heat resistance and excellent light fastness, such as anthraquinone series, diketopyrrolopyrrole series, quinacridone series, isoindoline series, perinone series, perylene series, and condensed azo series organic pigments has been examined. These pigments, however, have the problem that they are generally difficult to disperse in a color filter and therefore difficult to provide a color filter having a high transparency.

Similarly, with a color filter comprising a yellow filter layer, a magenta filter layer, and a cyan filter layer, too, it has been desired to more improve fastness of yellow colorants for use in the yellow filter.

A proposal on a red ink composition for use in a color filter containing a monoazo compound having a naphthalene ring is made in patent document 1. However, a color filter using the compound described in patent document 1 is insufficient with respect to contrast, and it has been desired to obtain enhanced contrast.

PRECEDING TECHNICAL DOCUMENTS

Patent Documents
Patent document 1: WO05/52074
Patent document 2: WO00/023525
Patent document 3: JP-A-2008-13472
Patent document 4: JP-T-9-511278 (the term "JP-T" as used herein means a published Japanese translation of a PCT patent application)
Patent document 5: JP-A-2008-7732
Patent document 6: JP-A-2004-123866
Patent document 7: Japanese patent No. 3894726
Patent document 8: Japanese patent No. 2592271
Patent document 9: JP-A-6-75375
Patent document 10: JP-A-5-5067
Patent document 11: JP-A-1-152449

SUMMARY OF THE INVENTION

Problems that the Invention is to Solve

An object of the present invention is to provide an azo compound having excellent coloring characteristics such as tinctorial strength and hue and excellent fastness such as light fastness and ozone fastness, azo pigments, an azo pigment dispersion, a coloring composition, and an ink for inkjet recording.

Another object of the invention is to provide a coloring composition for a color filter, which has good hue, exhibits good light fastness, heat fastness, and ozone fastness, shows good dispersibility, and can provide a color filter having high transparency, excellent spectral properties, excellent contrast, and excellent dispersion stability with time; and a process for preparing the coloring composition for a color filter.

A further object of the invention is to provide a color filter having high transparency, excellent spectral properties, excellent contrast, and excellent dispersion stability with time, which is obtained by using the above-described coloring composition for a color filter.

Means for Solving the Problem

As a result of intensive investigations, the inventors have found that particular nitrogen-containing, heterocyclic azo pigments show a good hue and exhibits good light fastness, heat fastness, and ozone fastness. Specific means for solving the above-described problem will be described below.

[1] An azo pigment represented by the general formula (1), its tautomer, a salt or hydrate thereof:

[Chem.1]

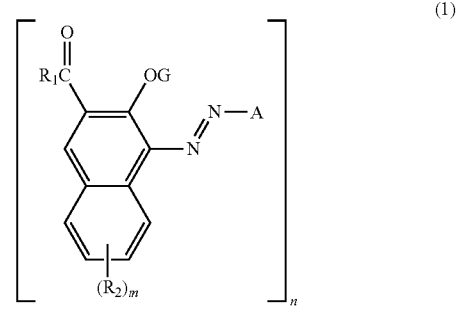

(wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A represents an aromatic 5- or 6-membered heterocyclic group, m represents an integer of from 0 to 5, n represents an integer of from 1 to 4 and, when n=2, the formula represents a dimer formed through $R_1$, $R_2$, A, or G and, when n=3, the formula represents a trimer formed through $R_1$, $R_2$, A, or G and, when n=4, the formula represents a tetramer formed through $R_1$, $R_2$, A, or G, and the general formula (1) does not contain an ionic hydrophilic group.)

[2] The azo pigment, its tautomer, a salt or hydrate thereof according to [1], wherein the azo pigment represented by the general formula (1) is represented by the following general formula (2-1):

[Chem. 2]

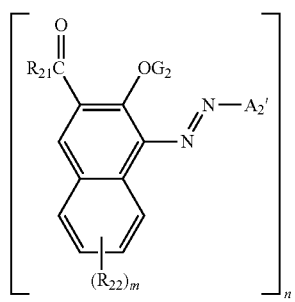

(2-1)

(wherein $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, $R_{22}$ represents a substituent, $A_2'$ represents the following general formulae (A-1) to (A-18), (A-20) to (A-28), and (A-30) to (A-32), m and n are the same as are defined with respect to the general formula (1) and, when n=2, the formula represents a dimer formed through $R_{21}$, $R_{22}$, $G_2$, or $A_2'$ and, when n=3, the formula represents a trimer formed through $R_{21}$, $R_{22}$, $G_2$, or $A_2'$ and, when n=4, the formula represents a tetramer formed through $R_{21}$, $R_{22}$, $G_2$, or $A_2'$, and the general formula (2-1) does not contain an ionic hydrophilic group:)

[Chem. 3]

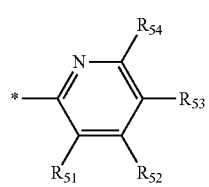
(A-1)

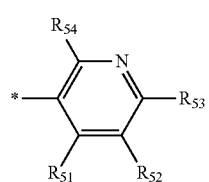
(A-2)

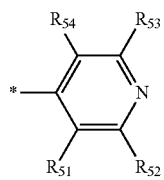
(A-3)

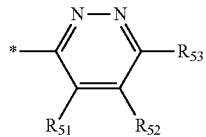
(A-4)

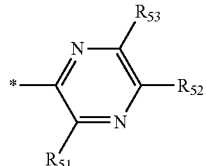
(A-5)

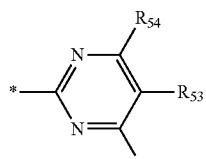
(A-6)

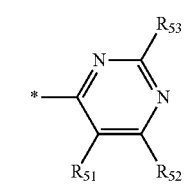
(A-7)

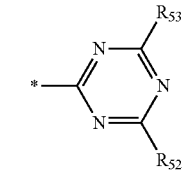
(A-8)

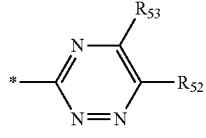
(A-9)

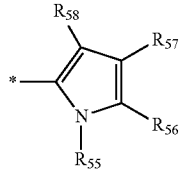
(A-10)

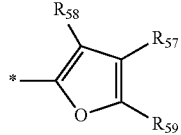
(A-11)

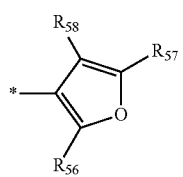 (A-12)

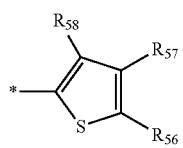 (A-13)

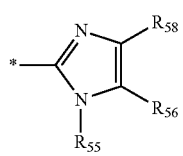 (A-14)

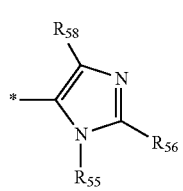 (A-15)

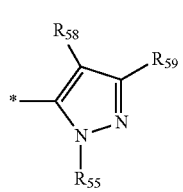 (A-16)

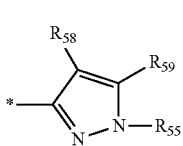 (A-17)

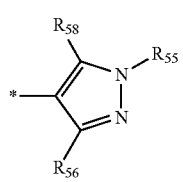 (A-18)

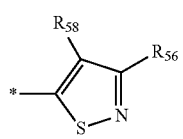 (A-20)

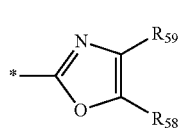 (A-21)

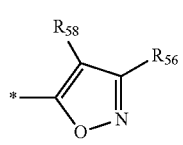 (A-22)

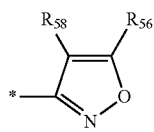 (A-23)

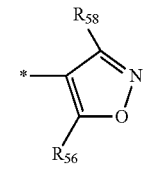 (A-24)

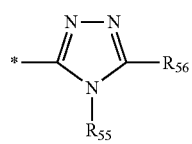 (A-25)

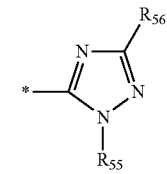 (A-26)

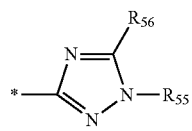 (A-27)

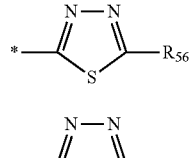 (A-28)

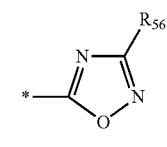 (A-30)

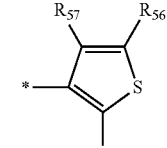 (A-31)

(A-32)

(in the general formulae (A-1) to (A-18), (A-20) to (A-28), and (A-30) to (A-32), $R_{51}$ to $R_{59}$ represent a hydrogen atom or a substituent, and adjacent substituents may be connected to each other to form a 5- or 6-membered ring, and * shows the point of attachment to the azo group in the general formula (2-1)).

[3] The azo pigment, its tautomer, a salt or hydrate thereof according to [2], wherein the azo pigment represented by the general formula (2-1) is represented by the following general formula (2'):

[Chem. 4]

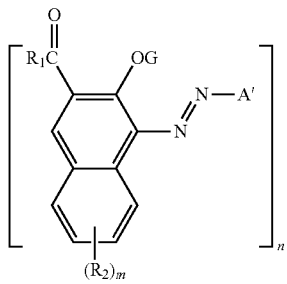

(2')

wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A' represents any of the following general formulae (A-10), (A-14) to (A-16), (A-25), and (A-26), m represents an integer of from 0 to 5, n represents an integer of from 1 to 4 and, when n=2, the formula represents a dimer formed through $R_1$, $R_2$, A', or G and, when n=3, the formula represents a trimer formed through $R_1$, $R_2$, A', or G and, when n=4, the formula represents a tetramer formed through $R_1$, $R_2$, A', or G, and the general formula (2') does not contain an ionic hydrophilic group:

[Chem. 5]

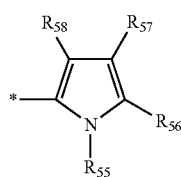 (A-10)

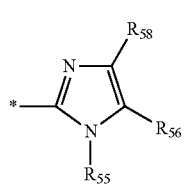 (A-14)

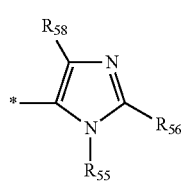 (A-15)

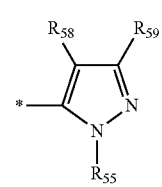 (A-16)

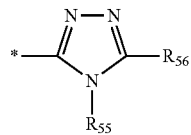 (A-25)

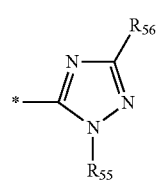 (A-26)

(in the general formulae (A-10), (A-14) to (A-16), (A-25), and (A-26), $R_{55}$ represents a substituent, $R_{56}$ to $R_{59}$ each independently represents a hydrogen atom or a substituent, and adjacent $R_{55}$ and $R_{56}$, $R_{57}$ and $R_{58}$, and $R_{56}$ and $R_{58}$ may be connected to each other to form a 5- or 6-membered ring, and * shows the point of attachment to the azo group in the general formula (2')).

[4] The azo pigment, its tautomer, a salt or hydrate thereof according to [3], wherein the azo pigment represented by the general formula (2') is represented by the following general formula (3):

[Chem. 6]

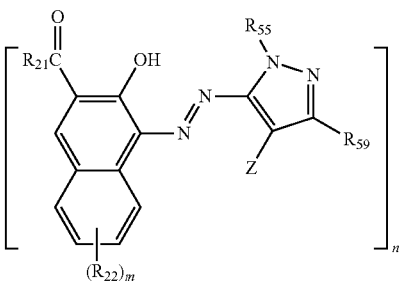 (3)

(wherein $R_{21}$, $R_{22}$, $R_{55}$, $R_{59}$, m, and n are the same as $R_1$, $R_2$, $R_{55}$, $R_{59}$, m, and n defined with respect to the general formula (2'), Z represents an electron-withdrawing group having a Hammett σp value of 0.2 or more and, when n=2, the formula represents a dimer formed through $R_{21}$, $R_{22}$, $R_{55}$, $R_{59}$, or Z and, when n=3, the formula represents a trimer formed through $R_{21}$, $R_{22}$, $R_{55}$, $R_{59}$, or Z and, when n=4, the formula represents a tetramer formed through $R_{21}$, $R_{22}$, $R_{55}$, $R_{59}$, or Z, and the general formula (3) does not contain an ionic hydrophilic group.)

[5] The azo pigment, its tautomer, a salt or hydrate thereof according to [2], wherein the azo pigment represented by the general formula (2-1) is represented by the following general formula (2-2):

[Chem. 7]

General formula (2-2)

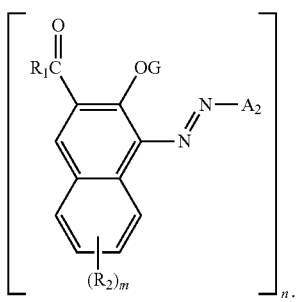

(wherein G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, $A_2$ represents any of the following formulae (A-17), (A-18), (A-20), (A-22) to (A-24), (A-27), (A-28), (A-31), and (A-32), m represents an integer of from 0 to 5, n represents an integer of from 1 to 4 and, when n=2, the formula represents a dimer formed through $R_1$, $R_2$, or $A_2$ and, when n=3, the formula represents a trimer formed through $R_1$, $R_2$, or $A_2$ and, when n=4, the formula represents a tetramer formed through $R_1$, $R_2$, or $A_2$, and the general formula (2-2) does not contain an ionic hydrophilic group:)

[Chem. 8]

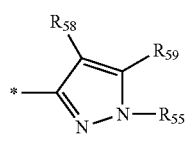 (A-17)

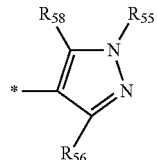 (A-18)

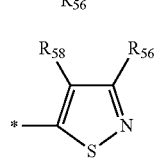 (A-20)

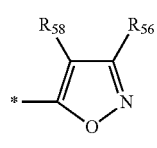 (A-22)

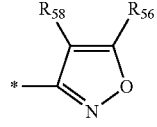 (A-23)

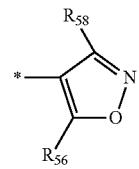 (A-24)

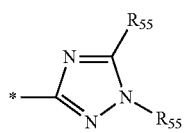 (A-27)

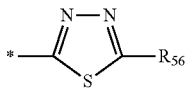 (A-28)

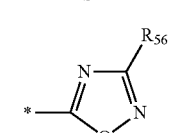 (A-31)

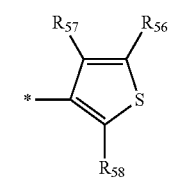 (A-32)

(in the general formulae (A-17), (A-18), (A-20), (A-22) to (A-24), (A-27), (A-28), (A-31), and (A-32), $R_{55}$ to $R_{59}$ represent a hydrogen atom or a substituent, adjacent $R_{55}$ and $R_{56}$, $R_{56}$ and $R_{57}$, $R_{55}$ and $R_{58}$, $R_{56}$ and $R_{58}$, and $R_{55}$ and $R_{59}$ may be connected to each other to form a 5- or 6-membered ring, and * shows the point of attachment to the azo group in the general formula (2-2).)

[6] The azo pigment, its tautomer, a salt or hydrate thereof according to [5], wherein the azo pigment represented by the general formula (2-2) is represented by the following general formula (2-3):

[Chem. 9]

General Formula (2-3)

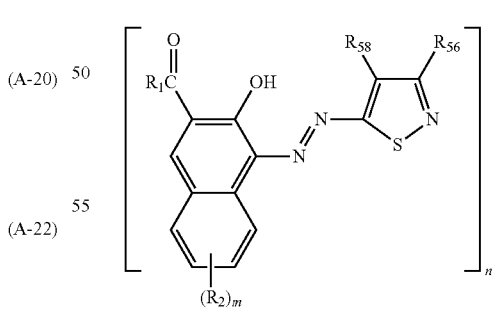

(wherein $R_1$ represents an amino group, an aliphatic oxy group, an aliphatic group, an aryl group, or a heterocyclic group, $R_2$ represents a substituent, $R_{56}$ and $R_{58}$ represent a hydrogen atom or a substituent, m represents an integer of from 0 to 5, n represents an integer of from 1 to 4, $R_{56}$ and $R_{58}$ may be connected to each other to form a 5- or 6-membered ring and, when n=2, the formula represents a dimer formed through $R_1$, $R_2$, $R_{56}$, or $R_{58}$ and, when n=3, the formula represents a trimer formed through $R_1$, $R_2$, $R_{56}$, or $R_{58}$ and, when n=4, the formula represents a tetramer formed through $R_1$, $R_2$, $R_{56}$, or $R_{58}$, and the general formula (2-3) does not contain an ionic hydrophilic group.

[7] A pigment dispersion containing at least one member of the azo pigment, its tautomer, a salt or hydrate thereof according to any one of [1] to [6].

[8] A coloring composition containing at least one member of the azo pigment, its tautomer, a salt or hydrate thereof according to any one of [1] to [6].

[9] An ink for inkjet recording, which uses the pigment dispersion according to [7].

[10] A coloring composition for color filter, which contains an azo pigment represented by the following general formula (1):

[Chem. 10]

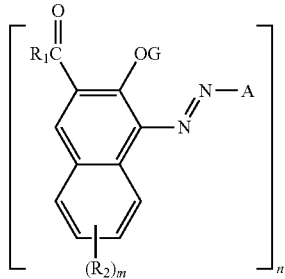

(1)

(wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A represents an aromatic 5- or 6-membered heterocyclic group, m represents an integer of from 0 to 5, n represents an integer of from 1 to 4 and, when n=2, the formula represents a dimer formed through $R_1$, $R_2$, A, or G and, when n=3, the formula represents a trimer formed through $R_1$, $R_2$, A, or G and, when n=4, the formula represents a tetramer formed through $R_1$, $R_2$, A, or G, and the general formula (1) does not contain an ionic hydrophilic group.)

[11] The coloring composition for the color filter according to [10], wherein the azo compound represented by the general formula (1) is represented by the following general formula (2):

[Chem. 11]

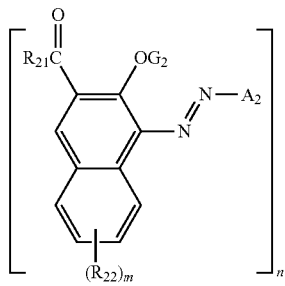

(2)

(wherein $G_2$ represents a hydrogen atom, an aliphatic group, an aryl group, or a heterocyclic group; $R_{21}$ represents an amino group, an aliphatic oxy group, an aliphatic group, an aryl group, or a heterocyclic group, $R_{22}$ represents a substituent, $A_2$ represents the following general formulae (A-1) to (A-32), m and n are the same as are defined with respect to the general formula (1) and, when n=2, the formula represents a dimer formed through $R_{21}$, $R_{22}$, $G_2$, or $A_2$ and, when n=3, the formula represents a trimer formed through $R_{21}$, $R_{22}$, $G_2$, or $A_2$ and, when n=4, the formula represents a tetramer formed through $R_{21}$, $R_{22}$, $G_2$, or $A_2$, and the general formula (2) does not contain an ionic hydrophilic group:)

[Chem. 12]

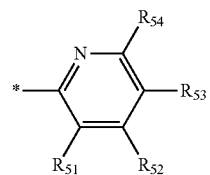

(A-1)

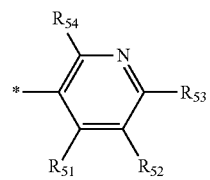

(A-2)

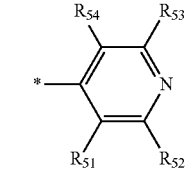

(A-3)

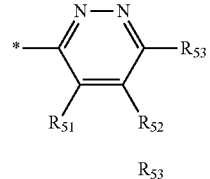

(A-4)

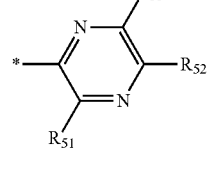

(A-5)

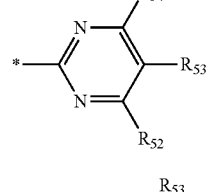

(A-6)

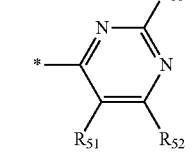

(A-7)

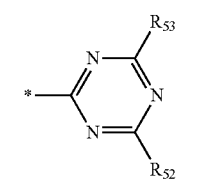 (A-8)
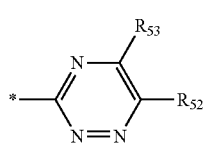 (A-9)
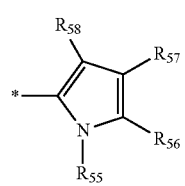 (A-10)
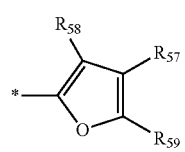 (A-11)
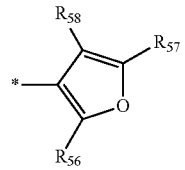 (A-12)
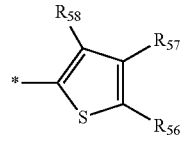 (A-13)
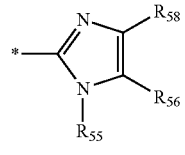 (A-14)
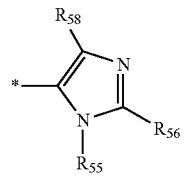 (A-15)
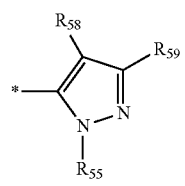 (A-16)
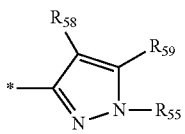 (A-17)
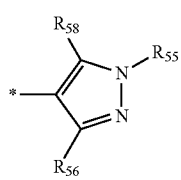 (A-18)
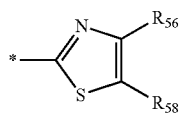 (A-19)
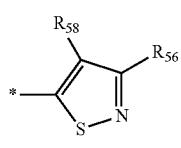 (A-20)
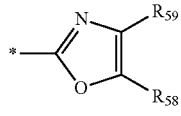 (A-21)
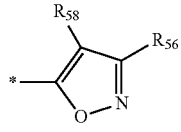 (A-22)
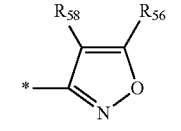 (A-23)
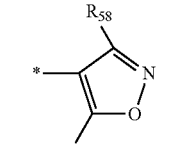 (A-24)
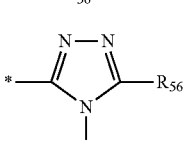 (A-25)
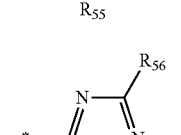 (A-26)
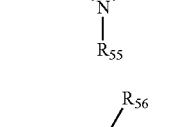 (A-27)
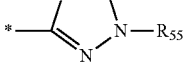

-continued

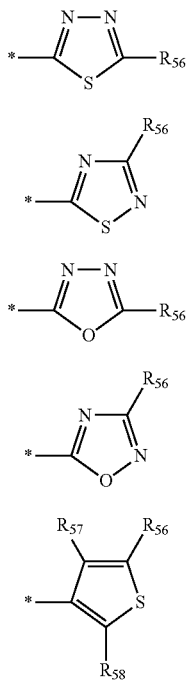

(A-28)

(A-29)

(A-30)

(A-31)

(A-32)

(in the general formulae (A-1) to (A-32), $R_{51}$ to $R_{59}$ represent a hydrogen atom or a substituent, adjacent substituents may be connected to each other to form a 5- or 6-membered ring, and * shows the point of attachment to the azo group in the general formula (2)).

[12] The coloring composition for color filter according to [10] or [11], which further contains a polymerizable compound and a solvent.

[13] The coloring composition for color filter according to [12], which contains the azo pigment represented by the general formula (1) in a content of from 0.01 to 2 parts by mass per 1 part by mass of the polymerizable compound.

[14] The coloring composition for color filter according to [12] or [13], wherein the polymerizable compound is a photo-sensitive compound.

[15] The coloring composition for color filter according to any one of [10] to [14], which further contains one or more members selected from among a surfactant, a silicone series additive, a pigment series additive, a silane series coupling agent, and a titanium series coupling agent.

[16] A color filter formed by using the coloring composition for color filter according to any one of [10] to [15].

[17] The color filter according to [16], which is formed according to photolithography method or inkjet method.

[18] A process for preparing the coloring composition for color filter according to [15], which includes a step of includes a step of obtaining a pigment dispersion by dispersing one or more dispersants selected from among a surfactant, a silicone series additive, a pigment series additive, a silane series coupling agent, and a titanium series coupling agent, and an azo compound represented by the general formula (1) in part of a solvent, and a step of mixing the pigment dispersion with a polymerizable compound and the rest of the solvent.

[19] An azo compound represented by the general formula (2-1), its tautomer, a salt or hydrate thereof:

[Chem. 13]

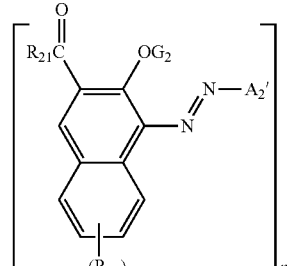

(2-1)

(wherein $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, $R_{22}$ represents a substituent, $A_2'$ represents the following general formulae (A-1) to (A-18), (A-20) to (A-28), and (A-30) to (A-32), m represents an integer of from 0 to 5, n represents an integer of from 1 to 4 and, when n=2, the formula represents a dimer formed through $R_{21}$, $R_{22}$, $G_2$, or $A_2'$ and, when n=3, the formula represents a trimer formed through $R_{21}$, $R_{22}$, $G_2$, or $A_2'$ and, when n=4, the formula represents a tetramer formed through $R_{21}$, $R_{22}$, $G_2$, or $A_2'$, and the general formula (2-1) does not contain an ionic hydrophilic group:

[Chem. 14]

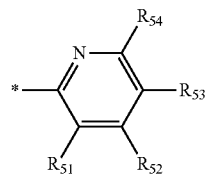

(A-1)

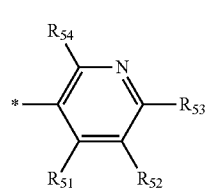

(A-2)

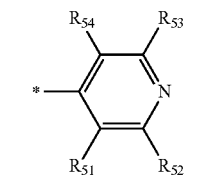

(A-3)

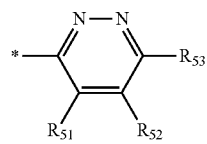

(A-4)

-continued
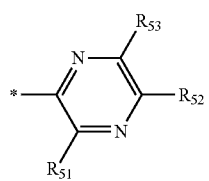 (A-5)
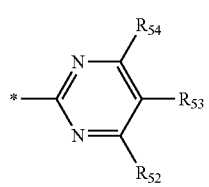 (A-6)
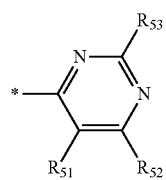 (A-7)
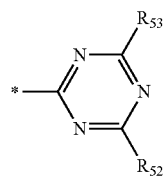 (A-8)
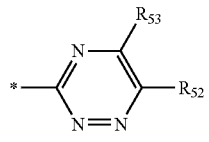 (A-9)
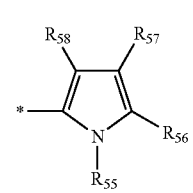 (A-10)
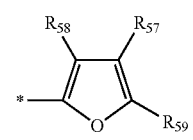 (A-11)
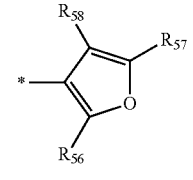 (A-12)
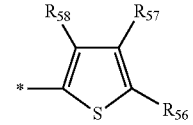 (A-13)
-continued
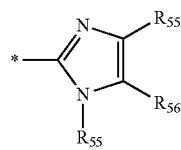 (A-14)
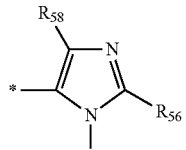 (A-15)
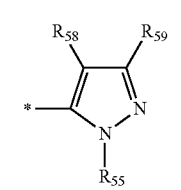 (A-16)
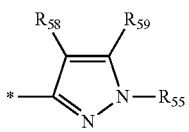 (A-17)
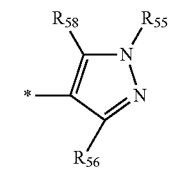 (A-18)
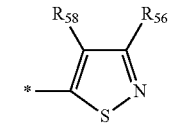 (A-20)
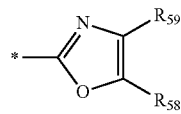 (A-21)
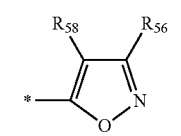 (A-22)
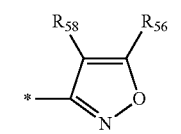 (A-23)
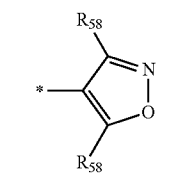 (A-24)

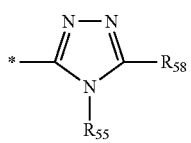
(A-25)

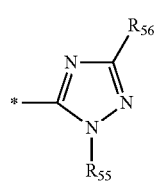
(A-26)

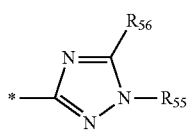
(A-27)

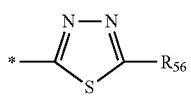
(A-28)

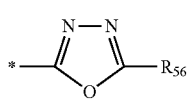
(A-30)

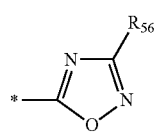
(A-31)

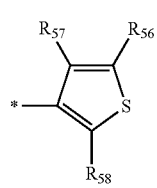
(A-32)

(in the general formulae (A-1) to (A-18), (A-20) to (A-28), and (A-30) to (A-32), $R_{51}$ to $R_{59}$ represent a hydrogen atom or a substituent, and adjacent substituents may be connected to each other to form a 5- or 6-membered ring, and * shows the point of attachment to the azo group in the general formula (2-1)).

[20] The azo compound, its tautomer, a salt or hydrate thereof according to [19], wherein the azo compound represented by the general formula (2-1) is represented by the following general formula (2'):

[Chem. 15]

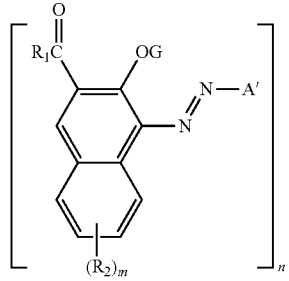
(2')

(wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A' represents any of the following general formulae (A-10), (A-14) to (A-16), (A-25), and (A-26), m represents an integer of from 0 to 5, n represents an integer of from 1 to 4 and, when n=2, the formula represents a dimer formed through $R_1$, $R_2$, A', or G and, when n=3, the formula represents a trimer formed through $R_1$, $R_2$, A', or G and, when n=4, the formula represents a tetramer formed through $R_1$, $R_2$, $A_2'$, or G, and the general formula (2') does not contain an ionic hydrophilic group:)

[Chem. 16]

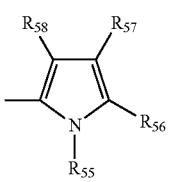
(A-10)

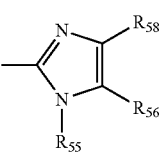
(A-14)

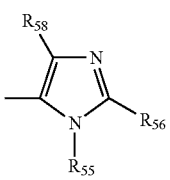
(A-15)

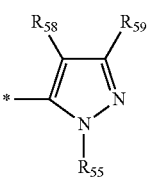
(A-16)

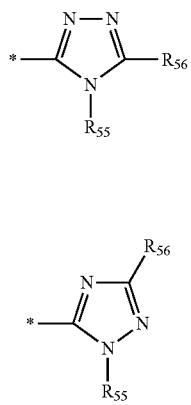

(in the general formulae (A-10), (A-14) to (A-16), (A-25), and (A-26), $R_{55}$ represents a substituent, $R_{56}$ to $R_{59}$ each independently represents a hydrogen atom or a substituent, and adjacent $R_{55}$ and $R_{56}$, $R_{57}$ and $R_{58}$, and $R_{56}$ and $R_{58}$ may be connected to each other to form a 5- or 6-membered ring, and * shows the point of attachment to the azo group in the general formula (2')).

[21] The azo compound, its tautomer, a salt or hydrate thereof according to [20], wherein the azo compound represented by the general formula (2-1) is represented by the following general formula (3):

[Chem. 17]

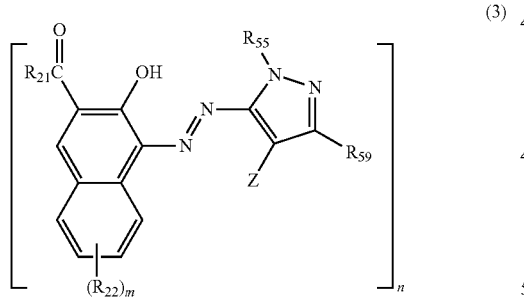

(wherein $R_{21}$, $R_{22}$, $R_{55}$, $R_{59}$, m, and n are the same as those defined with respect to the general formula (2-1), Z represents an electron-withdrawing group having a Hammett σp value of 0.2 or more and, when n=2, the formula represents a dimer formed through $R_{21}$, $R_{22}$, $R_{55}$, $R_{59}$, or Z and, when n=3, the formula represents a trimer formed through $R_{21}$, $R_{22}$, $R_{55}$, $R_{59}$, or Z and, when n=4, the formula represents a tetramer formed through $R_{21}$, $R_{22}$, $R_{55}$, $R_{59}$, or Z, and the general formula (3) does not contain an ionic hydrophilic group.)

[22] The azo compound, its tautomer, a salt or hydrate thereof according to [19], wherein the azo compound represented by the general formula (2-1) is represented by the following general formula (2-2):

[Chem. 18]

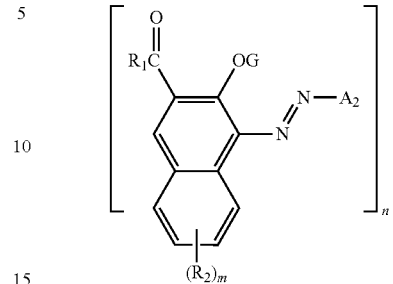

(wherein G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, $A_2$ represents any of the following formulae (A-17), (A-18), (A-20), (A-22) to (A-24), (A-27), (A-28), (A-31), and (A-32), m represents an integer of from 0 to 5, n represents an integer of from 1 to 4 and, when n=2, the formula represents a dimer formed through $R_1$, $R_2$, or $A_2$ and, when n=3, the formula represents a trimer formed through $R_1$, $R_2$, or $A_2$ and, when n=4, the formula represents a tetramer formed through $R_1$, $R_2$, or $A_2$, and the general formula (2-2) does not contain an ionic hydrophilic group:)

[Chem. 19]

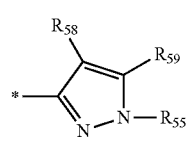

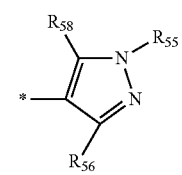

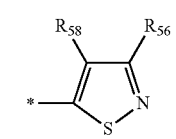

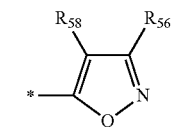

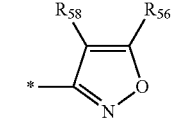

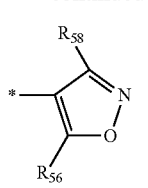
(A-24)

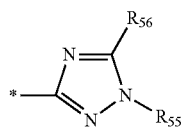
(A-27)

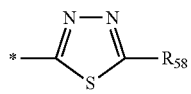
(A-28)

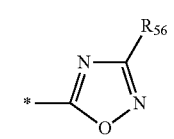
(A-31)

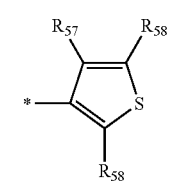
(A-32)

(in the general formulae (A-17), (A-18), (A-20), (A-22) to (A-24), (A-27), (A-28), (A-31), and (A-32), $R_{55}$ to $R_{59}$ represent a hydrogen atom or a substituent, adjacent $R_{55}$ and $R_{56}$, $R_{56}$ and $R_{57}$, $R_{55}$ and $R_{58}$, $R_{56}$ and $R_{58}$, and $R_{55}$ and $R_{59}$ may be connected to each other to form a 5- or 6-membered ring, and * shows the point of attachment to the azo group in the general formula (2-2).)

[23] The azo compound, its tautomer, a salt or hydrate thereof according to [22], wherein the azo compound represented by the general formula (2-2) is represented by the following general formula (2-3):

[Chem. 20]

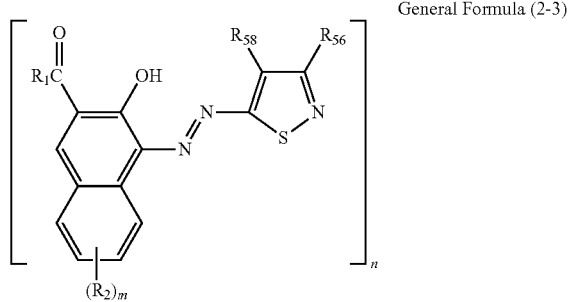

General Formula (2-3)

(wherein $R_1$ represents an amino group, an aliphatic oxy group, an aliphatic group, an aryl group, or a heterocyclic group, $R_2$ represents a substituent, $R_{56}$ and $R_{58}$ represents a hydrogen atom or a substituent, m represents an integer of from 0 to 5, n represents an integer of from 1 to 4, $R_{56}$ and $R_{58}$ may be connected to each other to form a 5- or 6-membered ring and, when n=2, the formula represents a dimer formed through $R_1$, $R_2$, $R_{56}$, or $R_{58}$ and, when n=3, the formula represents a trimer formed through $R_1$, $R_2$, $R_{56}$, or $R_{58}$ and, when n=4, the formula represents a tetramer formed through $R_1$, $R_2$, $R_{56}$, or $R_{58}$, and the general formula (2-3) does not contain an ionic hydrophilic group.)

ADVANTAGES OF THE INVENTION

The azo pigment of the present invention has excellent coloring characteristics such as high tinctorial strength and hue, and have excellent fastness, such as light fastness, ozone fastness, and heat fastness.

Further, the pigment dispersion of the invention comprises the azo pigment of the invention dispersed in various media, and show excellent coloring characteristics, excellent fastness, excellent ink liquid stability, and excellent dispersion stability.

Also, according to the invention, there can be provided a coloring composition for use in a color filter capable of providing high contrast and excellent transparency required for color liquid crystal displays in various applications and for camera modules, which composition has good dispersibility, good dispersion stability with time, excellent heat fastness, and excellent light fastness; a color filter; and a process for its preparation.

BEST MODE FOR CARRYING OUT THE INVENTION

Figure 1:
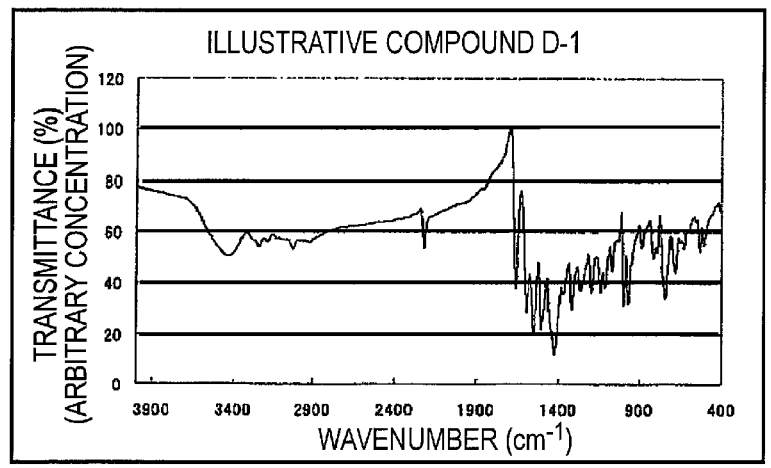
[FIG. 1] Figure of an infrared absorption spectrum of a specific illustrative compound D-1 synthesized according to Synthesis Example 1.

First, the terms "aliphatic group", "aryl group", "acyl group", "heterocyclic group", and "substituent" as used in the present invention will be described below.

In the aliphatic group in the invention, the aliphatic moiety thereof may be straight, branched, or cyclic, and may be saturated or unsaturated. Specifically, there can be illustrated an alkyl group, an alkenyl group, a cycloalkyl group, and a cycloalkenyl group. Further, the aliphatic group may be unsubstituted or may have a substituent.

Also, the aryl group may be a monocyclic group or a condensed ring group, and may be unsubstituted or may have a substituent. Also, with the heterocyclic group, the heterocyclic moiety may be any ring that contains a hetero atom (e.g., a nitrogen atom, a sulfur atom, or an oxygen atom) in the ring, and may be a saturated ring or an unsaturated ring. Also, the ring may be a monocyclic ring or a condensed ring, and may be unsubstituted or may have a substituent.

Also, the acyl group may be an aliphatic carbonyl group, an arylcarbonyl group, or a heterocyclic carbonyl group, and may have a substituent. As the substituent which the acyl group may have, any substitutable group that will be described in the following paragraph on substituents may be employed. For example, there are illustrated acetyl, propanoyl, benzoyl, and 3-pyridinecarbonyl.

Also, the substituent in the invention means any substitutable group, and examples thereof include an aliphatic group, an aryl group, a heterocyclic group, an acyl group, an acyloxy group, an acylamino group, an aliphatic oxy group, an aryloxy group, a heterocyclic oxy group, an aliphatic oxycarbonyl group, an aryloxycarbonyl group, a heterocyclic oxycarbonyl group, a carbamoyl group, an aliphatic sulfonyl group, an arylsulfonyl group, a heterocyclic sulfonyl group, an aliphatic sulfonyloxy group, an arylsulfonyloxy group, a heterocyclic sulfonyloxy group, a sulfamoyl group, an aliphatic sulfonamido group, an arylsulfonamido group, a heterocyclic sulfonamido group, an amino group, an aliphatic amino group, an arylamino group, a heterocyclic amino group, an aliphatic oxycarbonylamino group, an aryloxycarbonylamino group, a heterocyclic oxycarbonylamino group, an aliphatic sulfinyl group, an arylsulfinyl group, an aliphatic thio group, an arylthio group, a hydroxy group, a cyano group, a sulfo group, a carboxy group, an aliphatic oxyamino group, an aryloxyamino group, a carbamoylamino group, a sulfamoylamino group, a halogen atom, a sulfamoylcarbamoyl group, a carbamoylsulfamoyl group, a dialiphatic oxyphosphinyl group, and a diaryloxyphosphinyl group.

In view of solubility, the azo pigment of the invention does not contain an ionic hydrophilic group (e.g., a carboxyl group, a sulfo group, a phosphono group, or a quaternary ammonium group) as a substituent. In the case where it contains an ionic hydrophilic group, it is preferably a salt with a multi-valent metal cation (for example, magnesium ion, calcium ion, or barium ion), and is particularly preferably a lake pigment.

A Hammett substituent constant σp to be used in this specification is briefly explained below.

The Hammett's rule is an empirical rule advocated by L. P. Hammett in 1935 in an attempt to quantitatively discuss the influences of a substituent of a benzene derivative on the reaction or equilibrium, the validity of which has been widely accepted nowadays. Substituent constants obtained by the Hammett's rule include σp and σm values. These values are found in a number of general books. The details are given in, for example, J. A. Dean (ed.), *Lange's Handbook of Chemistry*, the 12th Ed., MacGraw-Hill, 1979 and *Kagakuno Ryoiki*, Extra No. 122, Nankodo, 1979, 96-103. While substituents are described in the invention by reference to their Hammett substituent constants σp, it is needless to say that such description applies to not only the substituents whose Hammett substituent constants σp are known from the literature but those whose Hammett substituent constants σp are unknown from the literature but are to fall within a range in question when determined in accordance with the Hammett's rule. Although compounds of the invention represented by the general formula (1) or (2) are not benzene derivatives, σp values are referred to as a measure of the electron effect of their substituents irrespective of the position of substitution. In the invention, the σp value will be used in this sence.

<Azo Pigments>

Pigments are in a state wherein molecules constituting them are strongly connected to each other through aggregation energy produced by strong mutual action between pigment molecules. In order to realize this state, van der Waals force and intermolecular hydrogen bond are necessary as described in, for example, *The Imaging Society of Japan*, vol. 43, p. 10 (2004).

In order to increase the intermolecular van der Waals force, introduction of an aromatic group, a polar group and/or a hetero atom to a molecule may be considered. Also, in order to form intermolecular hydrogen bond, introduction of a substituent which contains a hydrogen atom connected to a hetero atom and/or introduction of an electron donative substituent into the molecule may be considered. Further, polarity of the entire molecule may preferably be considered to be higher. For these purposes, with a chain group such as an alkyl group, a shorter group may be considered to be preferred and, with respect to the value of molecular weight/azo group, a smaller value may be considered to be preferred.

From these standpoints, pigment particles preferably contain an amido bond, a sulfonamido bond, an ether bond, a sulfon group, an oxycarbonyl group, an imido group, a carbamoylamino group, a heterocyclic ring, a benzene ring, or the like.

The azo pigments of the invention are characterized by being represented by the following general formula (1).

The compounds represented by the general formula (1) are liable to produce intermolecular mutual action between colorant molecules due to the unique structure thereof, show a low stability for water or for an organic solvent, thus being usable as azo pigments.

As is different from dyes which are used by dissolving in water or in an organic solvent in a molecular dispersion state, pigments are used by finely dispersing in a solvent as solid particles such as molecular aggregates.

Also, the pigments can show excellent coloring characteristics such as tinctorial strength and hue and excellent fastness such as light fastness and ozone fastness based on the particular structure represented by the following general formula (1).

Next, pigments represented by the general formula (1) will be described below.

[Chem. 21]

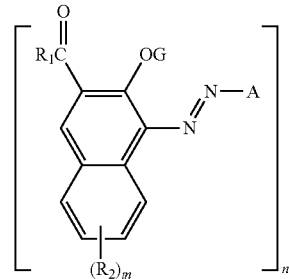

(1)

(In the general formula (1), G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, and A represents an aromatic 5- or 6-membered heterocyclic group. m represents an integer of from 0 to 5, and n represents an integer of from 1 to 4. When n=2, the formula represents a dimer formed through $R_1$, $R_2$, A, or G. When n=3, the formula represents a trimer formed through $R_1$, $R_2$, A, or G. When n=4, the formula represents a tetramer formed through $R_1$, $R_2$, A, or G. The general formula (1) does not contain an ionic hydrophilic group.)

The aliphatic group represented by G may have a substituent, and may be saturated or unsaturated. As a group which may be the substituent, any group that has been described hereinbefore in the aforesaid paragraph on substituents and that is substitutable may be employed, and preferred substituents are a hydroxy group, an aliphatic oxy group, a carbamoyl group, an aliphatic oxycarbonyl group, an aliphatic thio group, an amino group, analiphatic amino group, an acylamino group, and a carbamoylamino group. As the aliphatic group represented by G, an aliphatic group containing a total of from 1 to 8 carbon atoms is preferred, and an alkyl group containing a total of from 1 to 4 carbon atoms is more preferred. Examples thereof include methyl, ethyl, vinyl, cyclohexyl, and carbamoylmethyl.

The aryl group represented by G may be a condensed ring, and may have a substituent. As a group which may be the substituent, any group that has been described hereinbefore in the aforesaid paragraph on substituents and that is substitutable may be employed, and preferred substituents are a nitro group, a halogen atom, an aliphatic oxy group, a carbamoyl group, an aliphatic oxycarbonyl group, an aliphatic thio group, an amino group, aliphatic amino group, acylamino group, and a carbamoylamino group. As the aryl group represented by G, an aryl group containing a total of from 6 to 12 carbon atoms is preferred, and an aryl group containing a total of from 6 to 10 carbon atoms is more preferred. Examples thereof include phenyl, 4-nitrophenyl, 4-acetylaminophenylo, and 4-methanesulfonylphenyl.

The heterocyclic group represented by G may have a substituent, may be saturated or unsaturated, and may be a condensed ring. As a group which may be the substituent, any group that has been described hereinbefore in the aforesaid paragraph on substituents and that is substitutable may be employed, and preferred substituents are a halogen atom, a hydroxy group, an aliphatic oxy group, a carbamoyl group, an aliphatic oxycarbonyl group, an aliphatic thio group, an amino group, an aliphatic amino group, an acylamino group, and a carbamoylamino group. The heterocyclic group represented by G is preferably a heterocyclic group containing a total of from 2 to 12 carbon atoms and being connected at a carbon atom, more preferably a 5- or 6-membered heterocyclic group containing a total of from 2 to 10 carbon atoms and being connected at a carbon atom. Examples thereof include 2-tetrahydrofuryl and 2-pyrimidyl.

The acyl group represented by G may be an aliphatic carbonyl group, an aryl carbonyl group, or heterocyclic carbonyl group, and may have a substituent. As a group which may be the substituent, any group that has been described hereinbefore in the aforesaid paragraph on substituents and that is substitutable may be employed, and preferred substituents are a hydroxy group, a halogen atom, an aryl group, an aliphatic oxy group, a carbamoyl group, an aliphatic oxycarbonyl group, an aliphatic thio group, an amino group, an aliphatic amino group, an acylamino group, and a carbamoylamino group. The acyl group represented by G is preferably an acyl group containing a total of from 2 to 8 carbon atoms, more preferably an acyl group containing a total of from 2 to 4 carbon atoms. Examples thereof include acetyl, propanoyl, benzoyl, and 3-pyridinecarbonyl.

The aliphatic oxycarbonyl group represented by G may be saturated or unsaturated, and may have a substituent. As a group which may be the substituent, any group that has been described hereinbefore in the aforesaid paragraph on substituents and that is substitutable may be employed, and preferred substituents are a hydroxy group, an aliphatic oxy group, a carbamoyl group, an aliphatic oxycarbonyl group, an aliphatic thio group, an amino group, an aliphatic amino group, an acylamino group, and a carbamoylamino group. The aliphatic oxycarbonyl group represented by G is preferably an alkoxycarbonyl group containing a total of from 2 to 8 carbon atoms, more preferably an alkoxycarbonyl group containing a total of from 2 to 4 carbon atoms. Examples thereof include methoxycarbonyl, ethoxycarbonyl, and (t)-butoxycarbonyl.

The carbamoyl group represented by G may have a substituent. As a group which may be the substituent, any group that has been described hereinbefore in the aforesaid paragraph on substituents and that is substitutable may be employed, and preferred substituents are an aliphatic group, an aryl group, and a heterocyclic group. As the carbamoyl group which is represented by G and which may have a substituent, an unsubstituted carbamoyl group, an alkylcarbamoyl group containing a total of from 2 to 9 carbon atoms, and a carbamoyl group containing a total of from 7 to 11 carbon atoms are preferred, and an unsubstituted carbamoyl group and an alkylcarbamoyl group containing a total of from 2 to 5 carbon atoms are more preferred. Examples thereof include N-methylcarbamoyl, N,N-dimethylcarbamoyl, and N-phenylcarbamoyl.

The aliphatic sulfonyl group represented by G may be saturated or unsaturated, and may have a substituent. As a group which may be the substituent, any group that has been described hereinbefore in the aforesaid paragraph on substituents and that is substitutable may be employed, and preferred substituents are a hydroxy group, an aryl group, an aliphatic oxy group, a carbamoyl group, an aliphatic oxycarbonyl group, an aliphatic thio group, an amino group, an aliphatic amino group, an acylamino group, and a carbamoylamino group. The aliphatic sulfonyl group represented by G is preferably an alkylsulfonyl group containing a total of from 1 to 6 carbon atoms, more preferably an alkylsulfonyl group containing a total of from 1 to 4, carbon atoms, and is exemplified by methanesulfonyl.

The arylsulfonyl group represented by G may have a substituent. As a group which may be the substituent, any group that has been described hereinbefore in the aforesaid paragraph on substituents and that is substitutable may be employed, and preferred substituents are a hydroxy group, an aliphatic group, an aliphatic oxy group, a carbamoyl group, an aliphatic oxycarbonyl group, an aliphatic thio group, an amino group, an aliphatic amino group, an acylamino group, and a carbamoylamino group. The arylsulfonyl group represented by G is preferably an arylsulfonyl group containing a total of from 6 to 10 carbon atoms, and is exemplified by benzenesulfonyl.

G is preferably a hydrogen atom, an aliphatic group, an aryl group, or a heterocyclic group, more preferably a hydrogen atom. Because, an intramolecular hydrogen bond or an intramolecular cross hydrogen bond is easily formed.

The amino group represented by $R_1$ may have a substituent. As a group which may be the substituent, any group that has been described hereinbefore in the aforesaid paragraph on substituents and that is substitutable may be employed, and preferred substituents are an aliphatic group, an aryl group, and a heterocyclic group.

These substituents may further have a substituent and, as such substituent, an aliphatic group, a hydroxy group, and a substituent having, for example, an amido bond, an ether bond, an oxycarbonyl bond or a thioether bond are preferred, and substituents having a bond between a hetero atom and a hydrogen atom are more preferred in the point that they facilitate intramolecular mutual action such as intramolecular hydrogen bonding.

The amino group which is represented by $R_1$ and which may have a substituent is preferably an unsubstituted amino group, an alkylamino group containing a total of from 1 to 10 carbon atoms, a dialkylamino group containing a total of from 2 to 10 carbon atoms, an arylamino group containing a total of from 6 to 13 carbon atoms, or a saturated or unsaturated heterocyclic amino group containing a total of from 2 to 12 carbon atoms, more preferably an unsubstituted amino group, an alkylamino group containing a total of from 1 to 8 carbon atoms, an arylamino group containing a total of from 6 to 13 carbon atoms, or a saturated or unsaturated heterocyclic amino group containing a total of from 2 to 12 carbon atoms. Examples thereof include methylamino, N,N-dimethylamino, N-phenylamino, and N-(2-pyrimidyl)amino.

More preferred are an arylamino group optionally having a substituent and containing a total of from 6 to 13 carbon atoms and a saturated or unsaturated heterocyclic amino group optionally having a substituent and containing a total of from 2 to 12 carbon atoms.

In the case where $R_1$ is an arylamino group, the substituent on the aryl group is preferably at a p-position with respect to the amino group-bonding position and, the case that the substituent is only at the p-position is most preferable. As the substituent, any group that has been described hereinbefore in the aforesaid paragraph on substituents and that is substitutable may be employed, and preferred substituents are an aliphatic group optionally having a substituent and containing a total of from 1 to 7 carbon atoms, more preferably from 1 to 4 carbon atoms (e.g., methyl, ethyl, allyl, (i)-propyl, or (t)-butyl), an aliphatic oxy group optionally having a substituent and containing a total of from 1 to 7 carbon atoms, more preferably from 1 to 4 carbon atoms (e.g., methoxy, ethoxy, (i)-propyloxy, or allyloxy), a halogen atom (e.g., fluorine, chlorine, or bromine), a carbamoyl group optionally having a substituent and containing a total of from 1 to 7 carbon atoms, more preferably from 1 to 4 carbon atoms (e.g., carbamoyl, N-phenylcarbamoyl, or N-methylcarbamoyl), a ureido group optionally having a substituent and containing a total of from 1 to 7 carbon atoms, more preferably from 1 to 4 carbon atoms (e.g., ureido, N-methylureido, N,N-dimethylureido, N-4-pyridylureido, or N-phenylureido), a nitro group, a heterocyclic group condensed with an aryl group and containing a total of from 1 to 7 aryl group (e.g., imidazolone), a hydroxy group, an aliphatic thio group optionally having a substituent and containing a total of from 1 to 7 carbon atoms, more preferably from 1 to 4 carbon atoms (e.g., methylthio, ethylthio, (i)-propylthio, allylthio, or (t)-butylthio), an acylamino group optionally having a substituent and containing a total of from 2 to 7 carbon atoms, more preferably from 2 to 4 carbon atoms (e.g., acetamino, propionylamino, pivaloylamino, or benzoylamino), an aliphatic oxycarbonylamino group optionally having a substituent and containing a total of from 1 to 7 carbon atoms, more preferably from 1 to 4 carbon atoms (e.g., methoxycarbonylamino or propyloxycarbonylamino), an aliphatic oxycarbonyl group optionally having a substituent and containing a total of from 2 to 7 carbon atoms, more preferably from 2 to 4 carbon atoms (e.g., methoxycarbonyl or ethoxycarbonyl), and an acyl group optionally having a substituent and containing a total of from 2 to 7 carbon atoms, more preferably from 2 to 4 carbon atoms (which may be an aliphatic carbonyl group, an aryl carbonyl group, or a heterocyclic carbonyl group, and may have a substituent; as the group which may be the substituent, any group that has been described hereinbefore in the aforesaid paragraph on substituents and that is substitutable may be employed; preferred stituents are acyl groups containing a total of from 2 to 7 carbon atoms, more preferably an acyl group containing a total of from 2 to 4 carbon atoms, and are exemplified by acetyl, propanoyl, benzoyl, and 3-pyridinecarbonyl).

In the case where the substituent on the aryl group is positioned at a p-position with respect to the amino group-binding position, the substituent exists at the end of the molecule, which serves to facilitate intramolecular mutual action such as intramolecular hydrogen bonding. Thus, there results a sharp hue. In the case where the substituent on the aryl group further has a substituent, the substituent is preferably an aliphatic group, a hydroxyl group, and a substituent having, for example, an amido bond, an ether bond, an oxycarbonyl bond or a thioether bond are preferred, and substituents having a bond between a hetero atom and a hydrogen atom are more preferred in the point that they facilitate intramolecular mutual action such as intramolecular hydrogen bonding.

In the case where $R_1$ is a heterocyclic amino group, any group that has been described hereinbefore in the aforesaid paragraph on substituents and that is substitutable may be employed as the substituent, and preferred substituents are those substituents which are the same as with the aforesaid arylamino group. In the case where the substituent on the heterocyclic group further has a substituent, the substituent is preferably an aliphatic group, a hydroxy group, and a substituent having, for example, an amido bond, an ether bond, an oxycarbonyl bond or a thioether bond are preferred, with substituents having a bond between a hetero atom and a hydrogen atom being more preferred in the point that they facilitate intramolecular mutual action such as intramolecular hydrogen bonding.

Preferred substituents in the case where $R_1$ is an arylamino group or a heterocyclic amino group are an aliphatic group, an aliphatic oxy group, a halogen atom, a carbamoyl group, a heterocyclic group condensed with the aryl group, and an aliphatic oxycarbonyl group. More preferred substituents are an aliphatic group containing a total of from 1 to 4 carbon atoms, an aliphatic oxy group containing a total of from 1 to 4 carbon atoms, a halogen atom, a carbamoyl group containing a total of from 1 to 4 carbon atoms, a nitro group, and an aliphatic oxycarbonyl group containing a total of from 2 to 4 carbon atoms.

The aliphatic oxy group represented by $R_1$ may have a substituent and may be saturated or unsaturated. As the substituent, any group that has been described hereinbefore in the aforesaid paragraph on substituents and that is substitutable may be employed, and preferred substituents are a hydroxy group, an aliphatic oxy group, a carbamoyl group, an aliphatic oxycarbonyl group, an aliphatic thio group, an amino group, an aliphatic amino group, an acylamino group, and a carbamoylamino group. As the aliphatic oxy group of $R_1$, an alkoxy group containing a total of from 1 to 8 carbon atoms is preferred, an alkoxy group containing a total of from 1 to 4 carbon atoms is more preferred, and an alkoxy group containing a total of 1 or 2 is still more preferred. Examples thereof include methoxy, ethoxy, (t)-butoxy, methoxyethoxy, and carbamoylmethoxy.

The aliphatic group represented by $R_1$ may have a substituent and may be saturated or unsaturated. As the substituent, any group that has been described hereinbefore in the aforesaid paragraph on substituents and that is substitutable may be employed, and preferred substituents are a hydroxy group, an aliphatic oxy group, a carbamoyl group, an aliphatic oxycarbonyl group, an aliphatic thio group, an amino group, an aliphatic amino group, an acylamino group, and a carbamoylamino group. As the aliphatic group of $R_1$, an alkyl group containing a total of from 1 to 8 carbon atoms is preferred, and an alkyl group containing a total of from 1 to 4 carbon atoms is more preferred. Examples thereof include methyl, ethyl, (s)-butyl, methoxyethyl, and carbamoylmethyl.

The aryl group represented by $R_1$ may have a substituent. As the substituent, any group that has been described hereinbefore in the aforesaid paragraph on substituents and that is substitutable may be employed, and preferred substituents are an aliphatic group, an aliphatic oxy group, a halogen atom, a carbamoyl group, a heterocyclic group condensed with the aryl group, and an aliphatic oxycarbonyl group. The aryl group of $R_1$ is preferably an aryl group containing a total of from 6 to 12 carbon atoms, more preferably an aryl group containing a total of from 6 to 10 carbon atoms. Examples thereof include phenyl, 4-methylphenyl, and 3-chlorophenyl.

The heterocyclic group represented by $R_1$ may be a saturated heterocyclic group or an unsaturated heterocyclic group, may have a substituent, and may be a condensed ring. As the substituent, any group that has been described hereinbefore in the aforesaid paragraph on substituents and that is substitutable may be employed, and preferred substituents are an aliphatic group, an aliphatic oxy group, a carbamoyl group, a heterocyclic group condensed with the heterocyclic group, and an aliphatic oxycarbonyl group. The heterocyclic group represented by $R_1$ is preferably a heterocyclic group containing a total of from 2 to 10 carbon atoms, more preferably a saturated heterocyclic group containing a total of from 2 to 8 carbon atoms and being connected through a nitrogen atom. Examples thereof include 1-piperidyl, 4-morpholinyl, 2-pyrimidyl, and 4-pyridyl.

$R_1$ is preferably an amino group which may have a substituent, an aliphatic oxy group, or a saturated heterocyclic group connected through a nitrogen atom, more preferably an amino group which may have a substituent or an aliphatic oxy group, still more preferably an amino group which may have a substituent.

The substituent represented by $R_2$ may be any group that has been described hereinbefore in the aforesaid paragraph on substituents and that is substitutable may be employed, and preferred substituents are an aliphatic group, an aryl group, a heterocyclic group, an aliphatic oxycarbonyl group, a carboxyl group, a carbamoyl group which may have a substituent, an acylamino group, a sulfonamido group, a carbamoylamino group which may have a substituent, a sulfamoyl group which may have a substituent, an aliphatic oxy group, an aliphatic thio group, a cyano group, a halogen atom, and a hydroxy group, more preferred substituents are an aliphatic oxycarbonyl group, a carbamoyl group which may have a substituent, an acylamino group, a carbamoyl amino group which may have a substituent, an aliphatic oxy group, and a halogen atom, and an aliphatic oxy group is most preferred.

In the case where these substituents further have a substituent, an aliphatic group, a hydroxy group, and a substituent having, for example, an amido bond, an ether bond, an oxycarbonyl bond or a thioether bond are preferred, and substituents having a bond between a hetero atom and a hydrogen atom are more preferred in the point that they facilitate intramolecular mutual action such as intramolecular hydrogen bonding.

The aliphatic group represented by $R_2$ may have a substituent, and may be saturated or unsaturated and, as a group which may be substituted, any group that has been described hereinbefore as a substituent and that is substitutable may be employed. The aliphatic group of $R_2$ is preferably an alkyl group containing a total of from 1 to 8 carbon atoms, more preferably an alkyl group containing a total of from 1 to 6 carbon atoms, and examples thereof include methyl, ethyl, i-propyl, cyclohexyl, and t-butyl.

The aryl group represented by $R_2$ may have a substituent and, as a group which may be substituted, any group that has been described hereinbefore as a substituent and that is substitutable may be employed. The aryl group of $R_2$ is preferably an aryl group containing a total of from 6 to 12 carbon atoms, more preferably an aryl group containing a total of from 6 to 10 carbon atoms, and examples thereof include phenyl, 3-methoxyphenyl, and 4-carbamoylphenyl.

The heterocyclic group represented by $R_2$ may have a substituent and may be saturated or unsaturated or a condensed ring. As a group which may be substituted, any group that has been described hereinbefore as a substituent and that is substitutable may be employed. The heterocyclic group of $R_2$ is preferably a heterocyclic group containing a total of from 2 to 16 carbon atoms, more preferably a 5- or 6-membered heterocyclic ring containing a total of from 2 to 12 carbon atoms. Examples thereof include 1-pyrrolidinyl, 4-morpholinyl, 2-pyridyl, 1-pyrrolyl, 1-imidazolyl, and 1-benzimidazolyl.

The aliphatic oxycarbonyl group represented by $R_2$ may have a substituent and may be saturated or unsaturated. As a group which may substituted, any group that has been described hereinbefore as a substituent and that is substitutable may be employed. The aliphatic oxycarbonyl group of $R_2$ is preferably an alkoxycarbonyl group containing a total of from 1 to 8 carbon atoms, more preferably an alkoxycarbonyl group containing a total of from 1 to 6 carbon atoms. Examples thereof include methoxycarbonyl, i-propyloxycarbonyl, and carbamoylmethoxycarbonyl.

The carbamoyl group represented by $R_2$ may have a substituent and, as a group which may be substituted, any group that has been described hereinbefore as a substituent and that is substitutable may be employed. The substituent is preferably an aliphatic group, an aryl group, or a heterocyclic group. The carbamoyl group of $R_2$ which may have a substituent is preferably a carbamoyl group, an alkylcarbamoyl group containing a total of from 2 to 9 carbon atoms, a dialkylcarbamoyl group containing a total of from 3 to 10 carbon atoms, an arylcarbamoyl group containing a total of from 7 to 13 carbon atoms, or a heterocyclic carbamoyl group containing a total of from 3 to 12 carbon atoms, more preferably a carbamoyl group, an alkylcarbamoyl group containing a total of from 2 to 7 carbon atoms, a dialkylcarbamoyl group containing a total of from 3 to 6 carbon atoms, an arylcarbamoyl group containing a total of from 7 to 11 carbon atoms, or a heterocyclic carbamoyl group containing a total of from 3 to 10 carbon atoms. Examples thereof include carbamoyl, methylcarbamoyl, dimethylcarbamoyl, phenylcarbamoyl, and 4-pyridinecarbamoyl.

The acylamino group represented by $R_2$ may have a substituent and may be aliphatic, aromatic, or heterocyclic and, as a group which may be substituted, any group that has been described hereinbefore as a substituent and that is substitutable may be employed. The acylamino group of $R_2$ is preferably an acylamino group containing a total of from 2 to 12 carbon atoms, more preferably an acylamino group containing a total of from 2 to 8 carbon atoms, still more preferably an alkylcarbonylamino group containing a total of from 2 to 8 carbon atoms. Examples thereof include acetylamino, benzoylamino, 2-pyridinecarbonylamino, and propanoylamino.

The sulfonamido group represented by $R_2$ may have a substituent and may be aliphatic, aromatic, or heterocyclic and, as a group which may be substituted, any group that has been described hereinbefore as a substituent and that is substitutable may be employed. The sulfonamido group of $R_2$ is preferably a sulfonamido group containing a total of from 1 to 12 carbon atoms, more preferably a sulfonamido group containing a total of from 1 to 8 carbon atoms, still more preferably an alkyl sulfonamido group containing a total of from 1 to 8 carbon atoms. Examples thereof include methanesulfonamido, benzenesulfonamido, and 2-pyridinesulfonamido.

The carbamoylamino group represented by $R_2$ may have a substituent and, as a group which may be substituted, any group that has been described hereinbefore as a substituent and that is substitutable may be employed. The substituent is preferably an aliphatic group, an aryl group, or a heterocyclic group. The carbamoylamino group of $R_2$ which may have a substituent is preferably a carbamoylamino group, an alkylcarbamoylamino group containing a total of from 2 to 9 carbon atoms, a dialkylcarbamoylamino group containing a total of from 3 to 10 carbon atoms, an arylcarbamoylamino group containing a total of from 7 to 13 carbon atoms, or a heterocyclic carbamoylamino group containing a total of from 3 to 12 carbon atoms, more preferably a carbamoylamino group, an alkylcarbamoylamino group containing a total of from 2 to 7 carbon atoms, a dialkylcarbamoylamino group containing a total of from 3 to 6 carbon atoms, an arylcarbamoylamino group containing a total of from 7 to 11 carbon atoms, or a heterocyclic carbamoylamino group containing a total of from 3 to 10 carbon atoms. Examples thereof include carbamoylamino, methylcarbamoylamino, N,N-dimethylcarbamoylamino, and phenylcarbamoylamino, 4-pyridinecarbamoylamino.

With the sulfamoyl group which is represented by $R_2$ and which may have a substituent, and, as a group which may be substituted, any group that has been described hereinbefore as a substituent and that is substitutable may be employed. The substituent is preferably an aliphatic group, an aryl group, or a heterocyclic group. The sulfamoyl group of $R_2$ which may have a substituent is preferably a sulfamoyl group, an alkylsulfamoyl group containing a total of from 1 to 9 carbon atoms, a dialkylsulfamoyl group containing a total of from 2 to 10 carbon atoms, an arylsulfamoyl group containing a total of from 7 to 13 carbon atoms, or a heterocyclic sulfamoyl group containing a total of from 2 to 12 carbon atoms, more preferably a sulfamoyl group, an alkylsulfamoyl group containing a total of from 1 to 7 carbon atoms, a dialkylsulfamoyl group containing a total of from 3 to 6 carbon atoms, an arylsulfamoyl group containing a total of from 6 to 11 carbon atoms, or a heterocyclic sulfamoyl group containing a total of from 2 to 10 carbon atoms. Examples thereof include sulfamoyl, methylsulfamoyl, N,N-dimethylsulfamoyl, phenylsulfamoyl, and 4-pyridinesulfamoyl.

The aliphatic oxy group represented by $R_2$ may have a substituent and may be saturated or unsaturated and, as a group which may be substituted, any group that has been described hereinbefore as a substituent and that is substitutable may be employed. The aliphatic oxy group of $R_2$ is preferably an alkoxy group containing a total of from 1 to 8 carbon atoms, more preferably an alkoxy group containing a total of from 1 to 6 carbon atoms, and examples thereof include methoxy, ethoxy, i-propyloxy, cyclohexyloxy, and methoxyethoxy.

The aliphatic thio group represented by $R_2$ may have a substituent and may be saturated or unsaturated and, as a group which may be substituted, any group that has been described hereinbefore as a substituent and that is substitutable may be employed. The aliphatic thio group of $R_2$ is preferably an alkyl thio group containing a total of from 1 to 8 carbon atoms, more preferably an alkyl thio group containing a total of from 1 to 6 carbon atoms, and examples thereof include methylthio, ethylthio, carbamoylmethylthio, and t-butylthio.

The halogen atom represented by $R_2$ is preferably a fluorine atom, a chlorine atom, or a bromine atom, more preferably a chlorine atom.

In view of the effect of the invention, $R_2$ is preferably an aliphatic oxy group, an aliphatic oxycarbonyl group, or a carbamoyl group which may have a substituent, more preferably an aliphatic oxy group.

The aromatic 5- or 6-membered heterocyclic group represented by A may be a condensed ring or may be monocyclic, and the condensed ring may be carbocyclic, and the condensed ring may be carbocyclic, heterocyclic, aromatic, or non-aromatic. The heterocyclic group is preferably an aromatic 5- or 6-membered ring containing from 1 to 3 hetero atoms. The aromatic 5- or 6-membered heterocyclic group which is represented by A and which may be a condensed ring preferably contains a total of from 2 to 15 carbon atoms, more preferably from 2 to 10 carbon atoms. Examples thereof include a pyridine ring, a pyrazine ring, a pyrimidine ring, a pyridazine ring, a triazine ring, a pyrrole ring, a furan ring, a thiophene ring, an imidazole ring, a pyrazole ring, an oxazole ring, a thiazole ring, an isoxazole ring, an isothiazole ring, a triazole ring, a thiadiazole ring, an oxadiazole ring, and a condensed heterocyclic group wherein one of these groups is condensed with a benzene ring derivative or a heterocyclic derivative.

m is preferably from 0 to 3, more preferably from 0 to 1, still more preferably 0. n is preferably 1 or 2.

The pigment represented by the general formula (1) is preferably an azo pigment represented by the following general formula (2-1).

[Chem. 22]

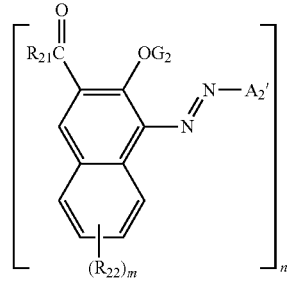

(2-1)

(In the general formula (2-1), $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, and $R_{22}$ represents a substituent. $A_2'$ represents the following general formulae (A-1) to (A-18), (A-20) to (A-28), and (A-30) to (A-32). m and n are the same as are defined with respect to the general formula (1). When n=2, the formula represents a dimer formed through $R_{21}$, $R_{22}$, $G_2$, or $A_2'$. When n=3, the formula represents a trimer formed through $R_{21}$, $R_{22}$, $G_2$, or $A_2'$. When n=4, the formula represents a tetramer formed through $R_{21}$, $R_{22}$, $G_2$, or $A_2'$. The general formula (2-1) does not contain an ionic hydrophilic group.)

[Chem. 23]

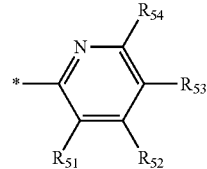

(A-1)

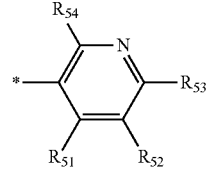

(A-2)

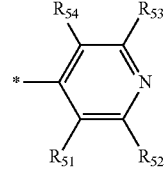

(A-3)

-continued
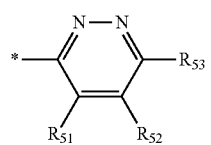 (A-4)
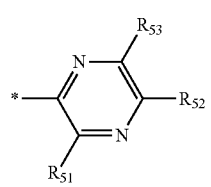 (A-5)
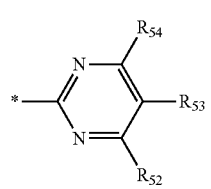 (A-6)
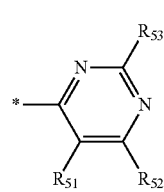 (A-7)
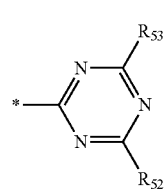 (A-8)
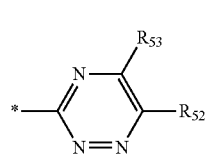 (A-9)
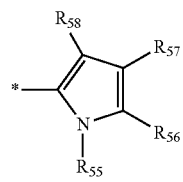 (A-10)
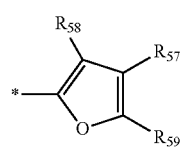 (A-11)
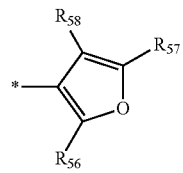 (A-12)
-continued
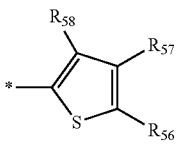 (A-13)
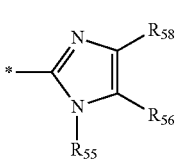 (A-14)
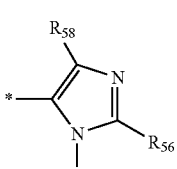 (A-15)
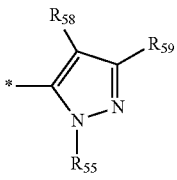 (A-16)
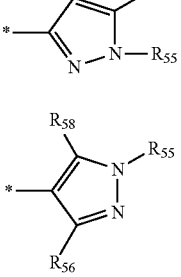 (A-17)
(A-18)
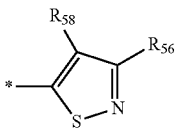 (A-20)
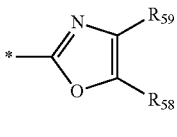 (A-21)
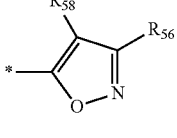 (A-22)
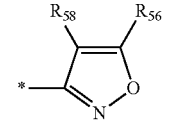 (A-23)

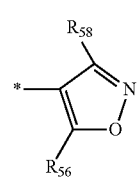 (A-24)

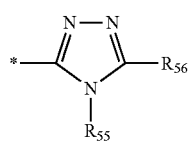 (A-25)

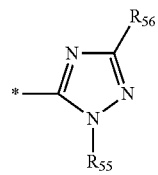 (A-26)

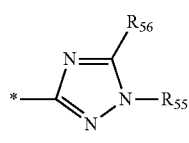 (A-27)

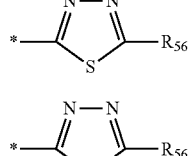 (A-28)

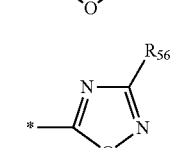 (A-30)

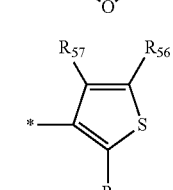 (A-31)

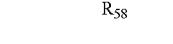

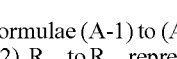

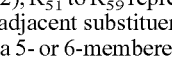

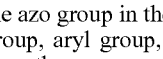 (A-32)

(In the general formulae (A-1) to (A-18), (A-20) to (A-28), and (A-30) to (A-32), $R_{51}$ to $R_{59}$ represent a hydrogen atom or a substituent, and adjacent substituents may be connected to each other to form a 5- or 6-membered ring. * shows the point of attachment to the azo group in the general formula (2-1).

The aliphatic group, aryl group, and heterocyclic group represented by $G_2$ are the same as are described for G in the general formula (1). In view of the effects of the invention, $G_2$ is preferably a hydrogen atom.

The amino group, aliphatic oxy group, and saturated heterocyclic group connected through the nitrogen atom, which are represented by $R_{21}$, are the same as are described for $R_1$ with respect to the general formula (1). In view of the effects of the invention, $R_{21}$ is preferably an amino group which may have a substituent or a saturated heterocyclic group connected through the nitrogen atom, more preferably an amino group which may have a substituent.

The substituent represented by $R_{22}$ is the same as is described for $R_2$ in the general formula (1).

The general formulae (A-1) to (A-32) represented by $A_2'$ will be described.

As the substituent represented by $R_{51}$ to $R_{54}$, any group that has been described hereinbefore as a substituent and that is substitutable may be employed. The substituent of $R_{51}$ to $R_{54}$ is preferably an aliphatic group, an aryl group, a heterocyclic group, an aliphatic oxycarbonyl group, a carbamoyl group which may have a substituent, an acylamino group, a sulfonamido group, an aliphatic oxy group, an aliphatic thio group, a cyano group, or the like, more preferably an aliphatic group, an aliphatic oxycarbonyl group, a carbamoyl group which may have a substituent, an aliphatic oxy group, a cyano group, or the like.

In view of the effects of the invention, $R_{51}$ to $R_{54}$ are preferably a hydrogen atom, an aliphatic group, an aryl group, a heterocyclic group, an aliphatic oxycarbonyl group, a carbamoyl group which may have a substituent, an acylamino group, a sulfonamido group, an aliphatic oxy group, an aliphatic thio group, a cyano group, or the like, more preferably a hydrogen atom, an aliphatic group, an aliphatic oxycarbonyl group, a carbamoyl group which may have a substituent, an aliphatic oxy group, or a cyano group.

As the substituent represented by $R_{55}$, any group that has been described hereinbefore as a substituent and that is substitutable may be employed. The substituent of $R_{55}$ is preferably an aliphatic group, an aryl group, a heterocyclic group, or the like, more preferably an aliphatic group, an aryl group, or an aromatic 5- or 6-membered heterocyclic group containing a nitrogen atom at a position adjacent to the position connected to the nitrogen atom.

In view of the effects of the invention, $R_{55}$ is preferably an aliphatic group, an aryl group, or a heterocyclic group, more preferably an aliphatic group, an aryl group, or an aromatic 5- or 6-membered heterocyclic group containing a nitrogen atom at a position adjacent to the position connected to the nitrogen atom, still more preferably an aromatic 5- or 6-membered heterocyclic group containing a nitrogen atom at a position adjacent to the position connected to the nitrogen atom. When $R_{55}$ is an aromatic 5- or 6-membered heterocyclic group containing a nitrogen atom at a position adjacent to the position connected to the nitrogen atom, not only the intermolecular mutual action of the colorant molecules but the intramolecular mutual action is easily strengthened. This is favorable in the point that it facilitates formation of a pigment having a stable molecular arrangement, which serves to show good hue and high fastness (light fastness, gas fastness, heat fastness, water fastness, etc.).

The aromatic 5- or 6-membered heterocyclic group containing a nitrogen atom at a position adjacent to the position connected to the nitrogen atom, which is preferred as $R_{55}$ in view of the effects of the invention, may have a substituent and, as a group which may be substituted, any group that has been described hereinbefore as a substituent and that is substitutable may be employed. Preferred substituents are a hydroxy group, an aliphatic oxy group, a carbamoyl group, an aliphatic oxycarbonyl group, an aliphatic thio group, an amino group, an aliphatic amino group, an acylamino group, and a carbamoylamino group. The heterocyclic group may be a saturated heterocyclic group or an unsaturated heterocyclic group, or may be a condensed heterocyclic group, and is preferably an aromatic 5- or 6-membered heterocyclic group containing a nitrogen atom at a position adjacent to the position connected to the nitrogen atom and containing a total of from 2 to 12 carbon atoms, more preferably an aromatic 5- or 6-membered heterocyclic group containing a nitrogen atom at a position adjacent to the position connected to the nitrogen atom and containing a total of from 2 to 10 carbon atoms.

Examples thereof include 2-thiazolyl, 2-benzothiazolyl, 2-oxazolyl, 2-benzoxazolyl, 2-pyridyl, 2-pyrazinyl, 3-pyridazinyl, 2-pyrimidinyl, 4-pyrimidinyl, 2-imidazolyl, 2-benzimidazolyl, and 2-triazinyl. These heterocyclic groups may be a tautomer structure together with the substituent.

The aryl group preferred as $R_{55}$ in view of the effects of the invention may have a substituent and, as a group which may be substituted, any group that has been described hereinbefore as a substituent and that is substitutable may be employed. Preferred substituents are a hydroxy group, a nitro group, an aliphatic oxy group, a carbamoyl group, an aliphatic oxycarbonyl group, an aliphatic thio group, an amino group, an aliphatic amino group, an acylamino group, and a carbamoylamino group. The aryl group of $R_{55}$ is preferably an aryl group containing a total of from 6 to 12 carbon atoms, more preferably an aryl group containing a total of from 6 to 10 carbon atoms. Examples thereof include phenyl, 3-methoxyphenyl, 4-carbamoylphenyl, etc., and a phenyl group is preferred.

In the general formula (2-1), $R_{55}$ is preferably any one of the following (Y-1) to (Y-13) and, in order to form a structure which easily forms an intramolecular hydrogen bond structure, any one of the 6-membered following (Y-1) to (Y-6) are more preferred, any one of the following (Y-1), (Y-3), (Y-4), and (Y-6) is still more preferred, and the following (Y-1) or (Y-4) is particularly preferred. * in the general formulae (Y-1) to (Y-13) shows the point of attachment to the N atom of the pyrazole ring. $Y_1$ to $Y_{11}$ represent a hydrogen atom or a substituent. $G_{11}$ in (Y-13) represents non-metallic atoms capable of forming a 5- or 6-membered heterocyclic ring. The heterocyclic ring represented by $G_{11}$ may be unsubstituted or may have a substituent, and may be a monocyclic ring or a condensed ring. Formulae (Y-1) to (Y-13) may be a tautomer structure together with the substituent.

[Chem. 24]

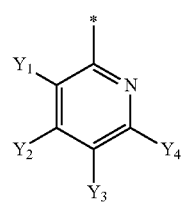
(Y-1)

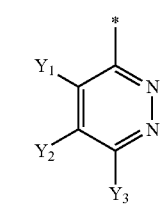
(Y-2)

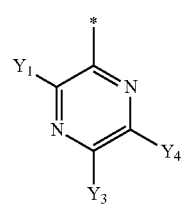
(Y-3)

-continued

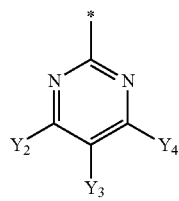
(Y-4)

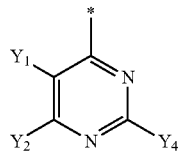
(Y-5)

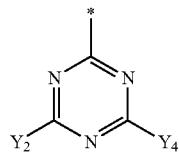
(Y-6)

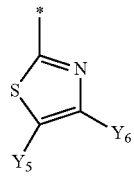
(Y-7)

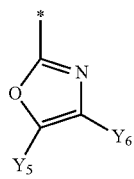
(Y-8)

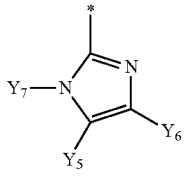
(Y-9)

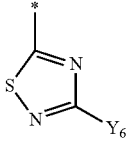
(Y-10)

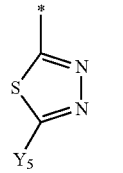
(Y-11)

(Y-12)

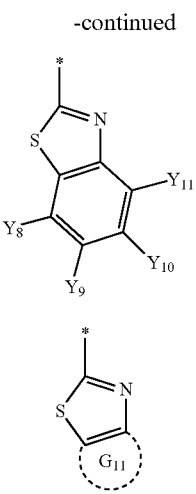

(Y-13)

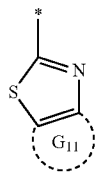

In view of the effects of the invention, $Y_1$ to $Y_{11}$ are preferably a hydrogen atom, an aliphatic group, an aryl group, a heterocyclic group, an aliphatic oxycarbonyl group, a carbamoyl group which may have a substituent, an acylamino group, a sulfonamido group, an aliphatic oxy group, an aliphatic thio group, a cyano group, or the like, more preferably a hydrogen atom, an aliphatic group, an aliphatic oxycarbonyl group, a carbamoyl group which may have a substituent, an aliphatic oxy group, or a cyano group.

As the substituent represented by $R_{56}$, $R_{57}$, or $R_{59}$, any group that has been described hereinbefore as a substituent and that is substitutable may be employed. The substituent of $R_{56}$, $R_{57}$, or $R_{59}$ is preferably an aliphatic group, an aryl group, a heterocyclic group, an aliphatic oxycarbonyl group, a carbamoyl group which may have a substituent, an acylamino group, a sulfonamido group, an aliphatic oxy group, an aliphatic thio group, a cyano group, etc., more preferably an aliphatic group, an aliphatic oxy group, an aliphatic thio group, a cyano group, etc.

In view of the effects of the invention, $R_{56}$, $R_{57}$, and $R_{59}$ is preferably a hydrogen atom, an aliphatic group, an aryl group, a heterocyclic group, an aliphatic oxycarbonyl group, a carbamoyl group which may have a substituent, an acylamino group, a sulfonamido group, an aliphatic oxy group, an aliphatic thio group, a cyano group, etc., more preferably a hydrogen atom, an aliphatic group, an aliphatic oxy group, an aliphatic thio group, or a cyano group.

As the substituent represented by $R_{58}$, any group that has been described hereinbefore as a substituent and that is substitutable may be employed. In view of the effects of the invention, $R_{58}$ is preferably a heterocyclic group or an electron-withdrawing group having a Hammett substituent σp value of 0.2 or more, more preferably an electron-withdrawing group having a Hammett substituent σp value of 0.3 or more. With the electron-withdrawing group, the upper limit of the Hammett substituent σp value is 1.0 or less. As long as $R_{58}$ has a σp value within this range, the pigment can be synthesized in the similar manner, and there can be obtained similar effects with respect to hue wavelength shift toward longer wavelength side.

Specific examples of $R_{58}$ having a σp value of 0.2 or more include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanato group, a thiocarbonyl group, a halogenated alkyl group, a halogenated alkoxy group, a halogenated aryloxy group, a halogenated alkylamino group, a halogenated alkylthio group, an aryl group substituted with other electron-withdrawing group having a σp value of 0.2 or more, a heterocyclic group, a halogen atom, an azo group, and a selenocyanato group.

In view of the effects of the invention, the pigment represented by the general formula (2-1) is preferably a pigment wherein $G_2$ represents a hydrogen atom, $R_{21}$ represents an amino group which may have a substituent or a saturated heterocyclic group connected at the nitrogen atom, m is 0 or 1 and, when m is 1, $R_{22}$ represents an aliphatic oxycarbonyl group or a carbamoyl group which may have a substituent, $A_2'$ represents any one of (A-1), (A-10) to (A-17), (A-20) to (A-23), (A-27), (A-28), and (A-30) to (A-32), and n is 1 or 2, more preferably a pigment wherein $G_2$ represents a hydrogen atom, $R_{21}$ represents an amino group which may have a substituent or a saturated heterocyclic group connected at the nitrogen atom, m is 0 or 1 and, when m is 1, $R_{22}$ represents an aliphatic oxycarbonyl group or a carbamoyl group which may have a substituent, $A_2'$ represents any one of (A-10), (A-11), (A-13) to (A-17), (A-20), (A-22) to (A-23), (A-27), (A-28), and (A-30) to (A-32), and n is 1 or 2, still more preferably a pigment wherein $G_2$ represents a hydrogen atom, $R_{21}$ represents an amino group which may have a substituent or a saturated heterocyclic group connected at the nitrogen atom, in is 0, $A_2'$ represents any one of (A-10), (A-11), (A-13) to (A-17), (A-20), (A-22) to (A-23), (A-27), (A-28), and (A-30) to (A-32), and n is 1 or 2, particularly preferably a pigment wherein $G_2$ represents a hydrogen atom, $R_{21}$ represents an amino group which may have a substituent, m is 0, $A_2'$ represents any one of (A-16) to (A-17), (A-20), (A-28), and (A-32), and n is 1 or 2, most preferably a pigment wherein $G_2$ represents a hydrogen atom, $R_{21}$ represents an amino group which may have a substituent, m is 0, $A_2'$ represents (A-16), and n is 1 or 2.

In one embodiment, the azo pigment represented by the foregoing general formula (2-1) is preferably a pigment wherein $A_2'$ is (A-10), (A-14) to (A-16), (A-25) or (A-26), more preferably a pigment wherein $A_2'$ is (A-10), (A-14) to (A-16), or (A-26), still more preferably a pigment wherein $A_2'$ is (A-16).

In view of the effects of the invention, the azo pigments represented by the general formulae (1) and (2-1) are preferably an azo pigment represented by the following general formula (3).

The azo pigment represented by the general formula (3), and its tautomer, a salt or hydrate thereof will be described in detail below.

[Chem. 25]

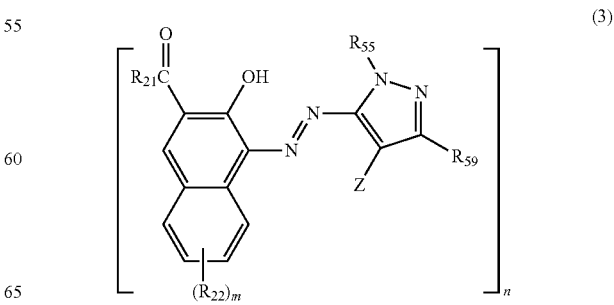

(3)

(In the general formula (3), $R_{21}$, $R_{22}$, $R_{55}$, $R_{59}$, m, and n are the same as those defined with respect to the general formula (2-1). Z represents an electron-withdrawing group having a Hammett σp value of 0.2 or more. When n=2, the formula represents a dimer formed through $R_{21}$, $R_{22}$, $R_{55}$, $R_{59}$, or Z. When n=3, the formula represents a trimer formed through $R_{21}$, $R_{22}$, $R_{55}$, $R_{59}$, or Z. When n=4, the formula represents a tetramer formed through $R_{21}$, $R_{22}$, $R_{55}$, $R_{59}$, or Z. The general formula (3) does not have an ionic hydrophilic group.)

As the substituent represented by Z and having a Hammett σp value of 0.2 or more, there are illustrated those groups which have been mentioned in the description on $R_{58}$ in the general formula (2-1).

Preferred substituents or scopes of $R_{21}$, $R_{22}$, $R_{55}$, $R_{59}$, m, and n in the pigment represented by the general formula (3) are the same as those in the general formula (2-1).

In view of the effects of the invention, Z is preferably an acyl group, a carbamoyl group, an alkyloxycarbonyl group, a cyano group, an alkylsulfonyl group, or a sulfamoyl group, more preferably a carbamoyl group, an alkyloxycarbonyl group, or a cyano group, most preferably a cyano group.

In view of the effects of the invention, the pigment represented by the general formula (3) is a pigment wherein $R_{21}$ represents an amino group which may have a substituent or a saturated heterocyclic group connected at the nitrogen atom, m is 0 or 1 and, when m is 1, $R_{22}$ represents an aliphatic oxycarbonyl group or a carbamoyl group which may have a substituent, $R_{55}$ represents an aromatic 5- or 6-membered heterocyclic group containing a nitrogen atom at a position adjacent to the position connected to the nitrogen atom, $R_{59}$ represents a hydrogen atom or an aliphatic group, Z represents an acyl group, a carbamoyl group, an alkyloxycarbonyl group, a cyano group, an alkylsulfonyl group, or a sulfamoyl group, and n represents 1 or 2, more preferably a pigment wherein $R_{21}$ represents an amino group which may have a substituent or a saturated heterocyclic group connected at the nitrogen atom, m is 0, $R_{55}$ is any of (Y-1) to (Y-13), $R_{59}$ represents a hydrogen atom or an aliphatic group, Z represents a carbamoyl group, an alkyloxycarbonyl group, or a cyano group, and n represents 1 or 2, still more preferably a pigment wherein $R_{21}$ represents an amino group which may have a substituent, m is 0, $R_{55}$ is any of (Y-1) to (Y-6), $R_{59}$ represents a hydrogen atom or an aliphatic group, Z represents a carbamoyl group, an alkyloxycarbonyl group, or a cyano group, and n represents 1 or 2, yet more preferably a pigment wherein $R_{21}$ represents an amino group which may have a substituent, m is 0, $R_{55}$ is any of (Y-1), (Y-4), and (Y-6), $R_{59}$ represents a hydrogen atom, Z represents a cyano group, and n represents 1 or 2.

In view of the effects of the invention, the pigment represented by the general formula (1) is preferably a pigment which has a "total carbon number/azo group number" ratio of 40 or less, more preferably 30 or less. In view of the effects of the invention, the pigment represented by the general formula (1) is preferably a pigment which has a "molecular weight/azo group number" ratio of 700 or less. In view of the effects of the invention, the pigment represented by the general formula (1) is preferably a pigment which does not have an ionic substituent such as a sulfo group or a carboxyl group.

In another embodiment, the azo pigment represented by the foregoing general formula (2-1) is preferably a pigment wherein $A_2'$ is (A-1) to (A-9) (A-11) to (A-13), (A-17), (A-20) to (A-23), (A-27), (A-28), or (A-30) to (A-32), more preferably a pigment wherein $A_2'$ is (A-11) to (A-13), (A-17), (A-20) to (A-23), (A-27), (A-28), or (A-30) to (A-32), still more preferably a pigment wherein $A_2'$ is (A-17), (A-20), (A-22) to (A-23), (A-27), (A-28), (A-31), or (A-32), still more preferably a pigment wherein $A_2'$ is (A-20), (A-28), or (A-32), particularly preferably a pigment wherein $A_2'$ is (A-20). Also, $R_{56}$ in (A-20) is particularly preferably $R_{59}$.

Of these, the azo pigment represented by the general formula (2-1) is preferably an azo pigment represented by the following general formula (2-2), and its tautomer, a salt or hydrate thereof.

[Chem. 26]

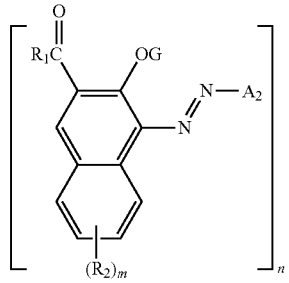

General formula (2-2)

(In the general formula (2-2), G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, and $A_2$ represents any of the following formulae (A-17), (A-18), (A-20), (A-22) to (A-24), (A-27), (A-28), (A-31), and (A-32). m represents an integer of from 0 to 5, and n represents an integer of from 1 to 4. When n=2, the formula represents a dimer formed through $R_1$, $R_2$, or $A_2$. When n=3, the formula represents a trimer formed through $R_1$, $R_2$, or $A_2$. When n=4, the formula represents a tetramer formed through $R_1$, $R_2$, or $A_2$. The general formula (2-2) does not have an ionic hydrophilic group.)

[Chem. 27]

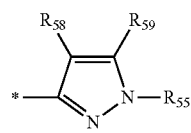

(A-17)

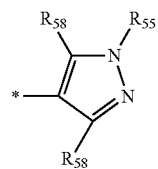

(A-18)

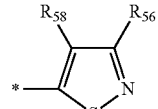

(A-20)

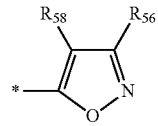

(A-22)

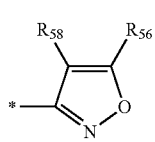
(A-23)

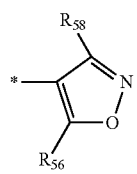
(A-24)

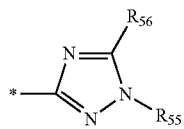
(A-27)

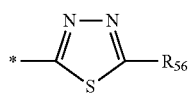
(A-28)

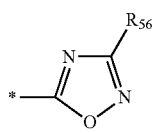
(A-31)

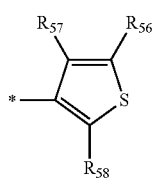
(A-32)

(In the general formulae (A-17), (A-18), (A-20), (A-22) to (A-24), (A-27), (A-28), (A-31), and (A-32), $R_{55}$ to $R_{59}$ represents a hydrogen atom or a substituent. Adjacent $R_{51}$ and $R_{52}$, $R_{52}$ and $R_{53}$, $R_{53}$ and $R_{54}$, $R_{55}$ and $R_{56}$, $R_{56}$ and $R_{57}$, $R_{55}$ and $R_{58}$, $R_{56}$ and $R_{58}$, $R_{57}$ and $R_{58}$, and $R_{55}$ and $R_{59}$ may be connected to each other to form a 5- or 6-membered ring. * shows the point of attachment to the azo group in the general formula (2-2).)

Preferred substituents and preferred scopes of $R_1$, $R_2$, $A_2$, $R_{55}$ to $R_{59}$, m, and n of the pigment represented by the general formula (2-2) are the same as $R_{21}$, $R_{22}$, $A_2'$, $R_{55}$ to $R_{59}$, m, and n in the general formula (2-1).

The azo pigment represented by the general formula (2-2) is preferably represented by the following general formula (2-3).

[Chem. 28]

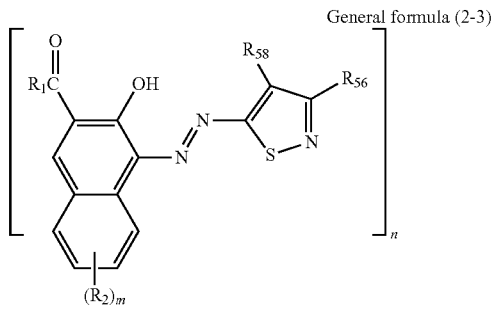
General formula (2-3)

(In the general formula (2-3), $R_1$ represents an amino group, an aliphatic oxy group, an aliphatic group, an aryl group, or a heterocyclic group, $R_2$ represents a substituent, $R_{56}$ and $R_{58}$ represent a hydrogen atom or a substituent, m represents an integer of from 0 to 5, and n represents an integer of from 1 to 4. $R_{56}$ and $R_{58}$ may be connected to each other to form a 5- or 6-membered ring. When n=2, the formula represents a dimer formed through. $R_1$, $R_2$, $R_{56}$, or $R_{58}$. When n=3, the formula represents a trimer formed through $R_1$, $R_2$, $R_{56}$, or $R_{58}$. When n=4, the formula represents a tetramer formed through $R_1$, $R_2$, $R_{56}$, or $R_{58}$. The general formula (2-3) does not contain an ionic hydrophilic group.)

Preferred substituents and preferred scopes of $R_1$, $R_2$, $A_2$, $R_{56}$, $R_{58}$, m, and n of the pigment represented by the general formula (2-2) are the same as $R_{21}$, $R_{22}$, $A_2'$, $R_{56}$, $R_{58}$, m, and n in the general formula (2-1).

The invention includes in its scope tautomers of the azo pigment represented by the general formula (1), general formula (2-1), and general formula (3). Although the general formula (1), general formula (2-1), and general formula (3) are shown in the form of limiting structure among several tautomer forms which are possible in view of chemical structure, the azo pigments may be tautomers of other structure than the shown ones, and may be used as a mixture containing plural tautomers.

For example, as for the pigment represented by the general formula (1), an azo-hydrazone tautomer represented by the following general formula (1') can be considered.

The invention also includes in its scope a tautomer of the azo pigment represented by the following general formula (1') which is a tautomer of the azo pigment represented by the general formula (1).

[Chem. 29]

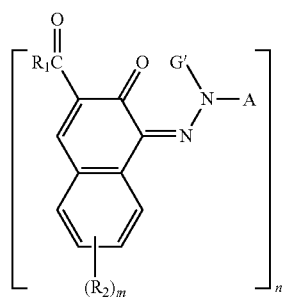
(1')

In the general formula (1'), $R_1$, $R_2$, A, m, and n are the same as those defined with respect to the general formula (1). In the general formula (1'), G' is a group corresponding to G defined with respect to the general formula (1). The general formula (1') does not have an ionic hydrophilic group.

Of the azo pigments represented by the general formula (1) and general formula (2-1), there can be illustrated, as has been described hereinbefore, azo pigments represented by the following general formula (3-1) to the general formula (3-4) as examples of particularly preferred pigments. The pigment represented by the above general formula (1) is preferably an azo pigment represented by the following general formula (3-1) to the general formula (3-4).

The azo pigment represented by the following general formula (3-1) to (3-4), and its tautomer, a salt or hydrate thereof will be described in detail below.

[Chem. 30]

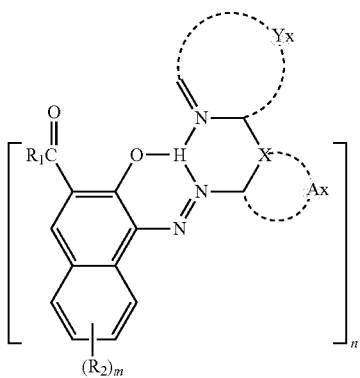
(3-1)

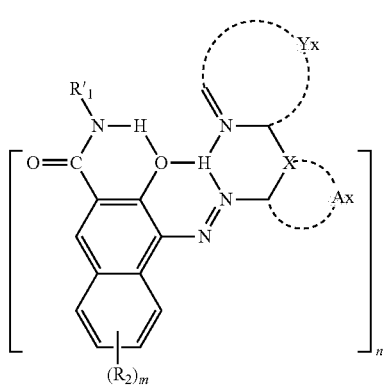
(3-2)

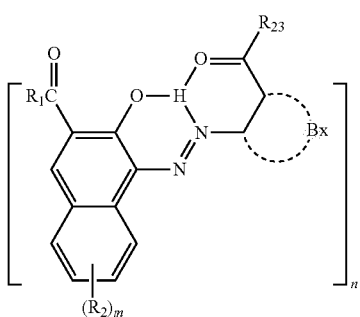
(3-3)

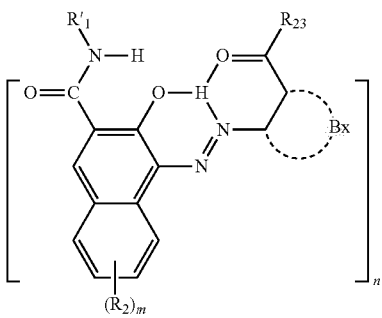
(3-4)

(In the general formula (3-1) to the general formula (3-4), $R_1$, $R_2$, m, and n are the same as those defined with respect to the general formula (1) and the general formula (2-1). X represents a carbon atom or a nitrogen atom, $A_x$ and $B_x$ represent those which correspond to (A-1) to (A-18), (A-20) to (A-28), and (A-30) to (A-32) defined for $A_2'$ in the general formula (2-1). $R_{23}$ represents a substituent formed by removing carbonyl from a corresponding substituent among the substituents of $R_{51}$, $R_{54}$, $R_{57}$, $R_{58}$, etc. specified with respect to the general formula (2-1). Each of the formed heterocyclic groups represents a group corresponding to the group defined with respect to $A_2'$ in the general formula (2-1). $Y_x$ represents a corresponding heterocyclic group defined for $R_{55}$ in the general formula (2-1) together with the nitrogen atom and carbon atoms. $R_{23}$ represents a substituent formed by removing carbonyl from a corresponding substituent among the substituents of $R_{51}$, $R_{54}$, $R_{58}$, etc. specified with respect to the general formula (2-1). $R'_1$ represents a substituent formed by removing —NH— from the amino group of $R_1$ defined with respect to the general formula (1). The general formula (3-1) to the general formula (3-4) do not have an ionic hydrophilic group.)

With the azo pigments represented by the above-described general formulae (1), (2-1), (3), and (3-1) to (3-4), many tautomers may be considered.

Also, in the invention, the azo pigment represented by the general formula (1) preferably has a substituent capable of forming an intramolecular hydrogen bond or intramolecular crosslinking hydrogen bond. It is more preferred for the azo pigment to have a substituent capable of forming at least one or more intramolecular hydrogen bonds, particularly a substituent capable of forming at least one or more intramolecular crosslinking hydrogen bonds.

The reason why this structure is preferred is that, as is shown by the general formulae (3-1) to (3-4), nitrogen atom constituting the heterocyclic group contained in the azo pigment structure, hydrogen atom and oxygen atom of the hydroxy group of the naphthalene substituent, nitrogen atom of the azo group or of its tautomer of the hydrazone group, a carbonyl group which is substituted with the azo component contained in the azo pigment structure, hydrogen atom and oxygen atom of the hydroxyl group of the naphthalene substituent, and nitrogen atom of the azo group or of its tautomer of the hydrazone group are liable to form intramolecular crosslinking hydrogen bonds.

As a result, flatness of the molecule is enhanced, the intramolecular and intermolecular mutual action is improved, crystallinity of the azo pigment represented by the general formulae (3-1) to the general formulae (3-4) is enhanced (higher structure of the pigment becoming liable to be formed), and hence performances required as pigments, i.e., light fastness, heat stability, moist heat stability, water resistance, gas resistance, and/or solvent resistance, can markedly be improved, thus such pigments being more preferred.

In view of this point, too, the pigment represented by the general formulae (1) and (2-1) are preferably a pigment represented by the general formulae (3) and (3-1) to (3-4), more preferably a pigment represented by the general formulae (3), (3-2), and (3-4), particularly preferably a pigment represented by the general formula (3).

<Azo Compounds>

The invention also relates to an azo compound represented by the general formula (2-1), and its tautomer, a salt or hydrate thereof.

[Chem. 31]

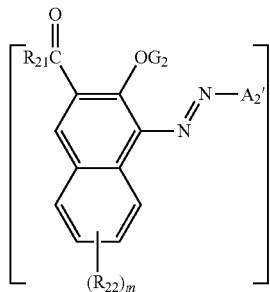

(2-1)

(In the general formula (2-1), $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, and $R_{22}$ represents a substituent. $A_2'$ represents the following general formulae (A-1) to (A-18), (A-20) to (A-28), and (A-30) to (A-32). m and n are the same as are defined with respect to the general formula (1). When n=2, the formula represents a dimer formed through $R_{21}$, $R_{22}$, $G_2$, or $A_2'$. When n=3, the formula represents a trimer formed through $R_{21}$, $R_{22}$, $G_2$, or $A_2'$. When n=4, the formula represents a tetramer formed through $R_{21}$, $R_{22}$, $G_2$, or $A_2'$. The general formula (2-1) does not have an ionic hydrophilic group.)

[Chem. 32]

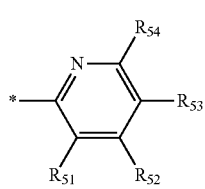

(A-1)

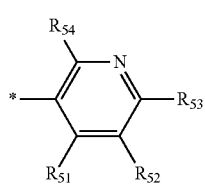

(A-2)

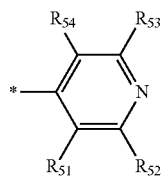

(A-3)

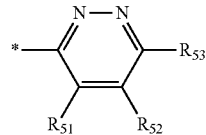

(A-4)

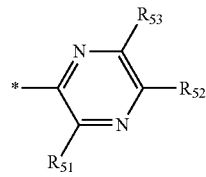

(A-5)

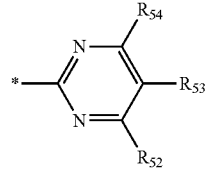

(A-6)

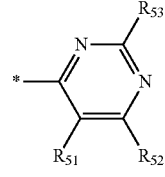

(A-7)

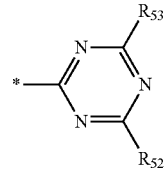

(A-8)

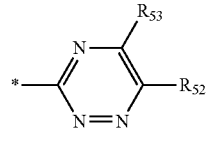

(A-9)

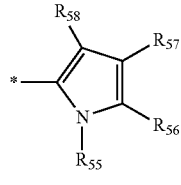

(A-10)

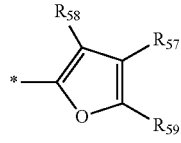

(A-11)

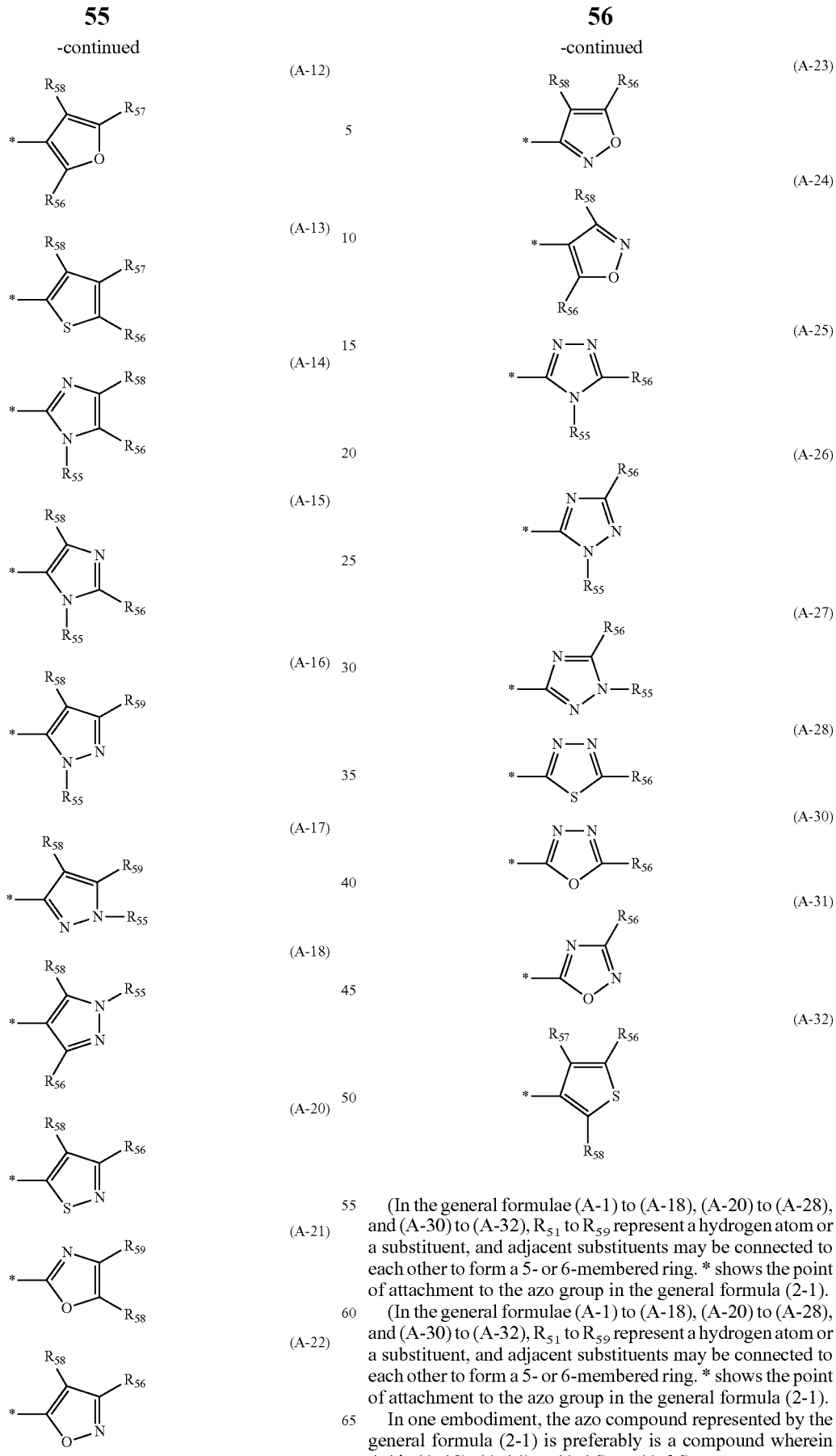

(In the general formulae (A-1) to (A-18), (A-20) to (A-28), and (A-30) to (A-32), $R_{51}$ to $R_{59}$ represent a hydrogen atom or a substituent, and adjacent substituents may be connected to each other to form a 5- or 6-membered ring. * shows the point of attachment to the azo group in the general formula (2-1).

(In the general formulae (A-1) to (A-18), (A-20) to (A-28), and (A-30) to (A-32), $R_{51}$ to $R_{59}$ represent a hydrogen atom or a substituent, and adjacent substituents may be connected to each other to form a 5- or 6-membered ring. * shows the point of attachment to the azo group in the general formula (2-1).

In one embodiment, the azo compound represented by the general formula (2-1) is preferably is a compound wherein $A_2'$ is (A-10), (A-14) to (A-16), or (A-26).

The azo compound represented by the general formula (2-1) is preferably am azo compound represented by the following general formula (3), its tautomer, a salt or hydrate thereof.

[Chem. 33]

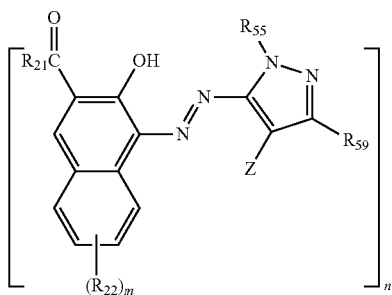

(3)

(In the general formula (3), $R_{21}$, $R_{22}$, $R_{55}$, $R_{59}$, m, and n are the same as those defined with respect to the general formula (2-1). Z represents an electron-withdrawing group having a Hammett σp value of 0.2 or more. When n=2, the formula represents a dimer formed through $R_{21}$, $R_{22}$, $R_{55}$, $R_{59}$, or Z. When n=3, the formula represents a trimer formed through $R_{21}$, $R_{22}$, $R_{55}$, $R_{59}$, or Z. When n=4, the formula represents a tetramer formed through $R_{21}$, $R_{22}$, $R_{55}$, $R_{59}$, or Z. The general formula (3) does not contain an ionic hydrophilic group.)

In another embodiment, the azo compound represented by the foregoing general formula (2-1) is preferably a compound wherein $A_2'$ is (A-1) to (A-9) (A-11) to (A-13), (A-17), (A-20) to (A-23), (A-27), (A-28), or (A-30) to (A-32), more preferably a compound wherein $A_2'$ is (A-11) to (A-13), (A-17), (A-20) to (A-23), (A-27), (A-28), or (A-30) to (A-32), still more preferably a compound wherein $A_2'$ is (A-17), (A-20), (A-22) to (A-23), (A-27), (A-28), (A-31), or (A-32), still more preferably a compound wherein $A_2'$ is (A-20), (A-28), or (A-32), particularly preferably a compound wherein $A_2'$ is (A-20). Also, $R_{56}$ in (A-20) is particularly preferably $R_{59}$.

Of these, the azo compound represented by the general formula (2-1) is preferably an azo compound represented by the following general formula (2-2), its tautomer, a salt or hydrate thereof.

[Chem. 34]

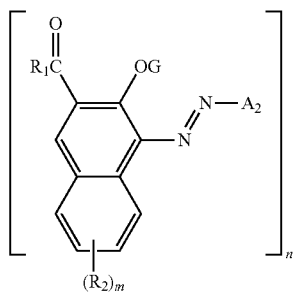

General formula (2-2)

(In the general formula (2-2), G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, and $A_2$ represents any of the following formulae (A-17), (A-18), (A-20), (A-22) to (A-24), (A-27), (A-28), (A-31), and (A-32). m represents an integer of from 0 to 5, and n represents an integer of from 1 to 4. When n=2, the formula represents a dimer formed through $R_1$, $R_2$, or $A_2$. When n=3, the formula represents a trimer formed through $R_1$, $R_2$, or $A_2$. When n=4, the formula represents a tetramer formed through $R_1$, $R_2$, or $A_2$. The general formula (2-2) does not have an ionic hydrophilic group.)

[Chem. 35]

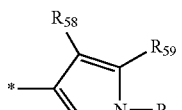

(A-17)

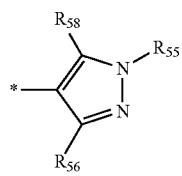

(A-18)

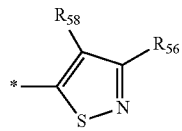

(A-20)

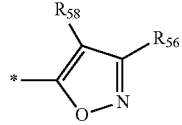

(A-22)

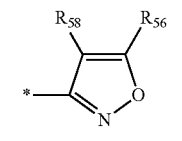

(A-23)

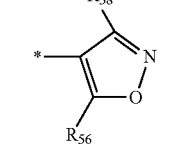

(A-24)

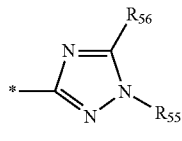

(A-27)

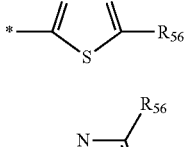

(A-28)

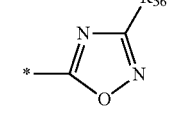

(A-31)

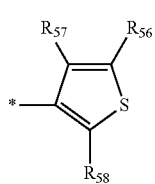

(A-32)

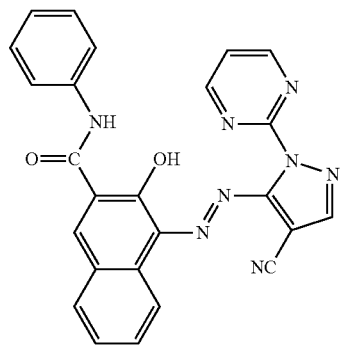

D-1

(In the general formulae (A-17), (A-18), (A-20), (A-22) to (A-24), (A-27), (A-28), (A-31), and (A-32), $R_{55}$ to $R_{59}$ represent a hydrogen atom or a substituent. Adjacent $R_{55}$ and $R_{56}$, $R_{56}$ and $R_{57}$, $R_{55}$ and $R_{58}$, $R_{56}$ and $R_{58}$, and $R_{55}$ and $R_{59}$ may be connected to each other to form a 5- or 6-membered ring. * shows the point of attachment to the azo group in the general formula (2-2).)

The azo compound represented by the general formula (2-2) is preferably represented by the following general formula (2-3).

[Chem. 36]

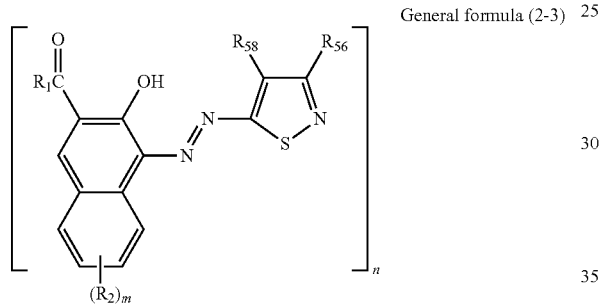

General formula (2-3)

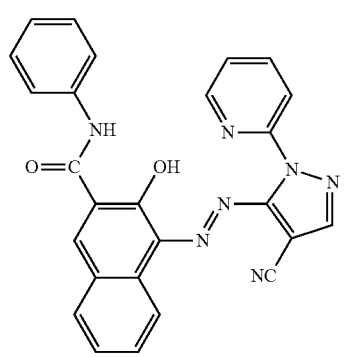

D-2

(In the general formula (2-3), $R_1$ represents an amino group, an aliphatic oxy group, an aliphatic group, an aryl group, or a heterocyclic group, $R_2$ represents a substituent, $R_{56}$ and $R_{58}$ represent a hydrogen atom or a substituent, m represents an integer of from 0 to 5, and n represents an integer of from 1 to 4. $R_{56}$ and $R_{58}$ may be connected to each other to form a 5- or 6-membered ring. When n=2, the formula represents a dimer formed through $R_1$, $R_2$, $R_{56}$, or $R_{58}$. When n=3, the formula represents a trimer formed through $R_1$, $R_2$, $R_{56}$, or $R_{58}$. When n=4, the formula represents a tetramer formed through $R_1$, $R_2$, $R_{56}$, or $R_{58}$. The general formula (2-3) does not contain an ionic hydrophilic group.)

As the salts, hydrates, and tautomers of the compounds of the invention represented by the general formulae (2-1), (2-2), (2-3), (2), and the general formula (3), there can be illustrated those which are similar to the azo pigments, hydrates, and tautomers of the invention.

The novel azo compounds of the invention are useful as azo pigments.

Specific examples of the azo pigment and the azo compound represented by the general formula (1) will be shown below. However, the azo pigment and the azo compound to be used in the invention are not limited only to the following examples. Also, although the structures of the following specific examples are shown in the form of limiting structure among several tautomer forms which are possible in view of chemical structure, the azo pigment and the azo compound may be a tautomer of other structure than the shown ones.

[Chem. 37]

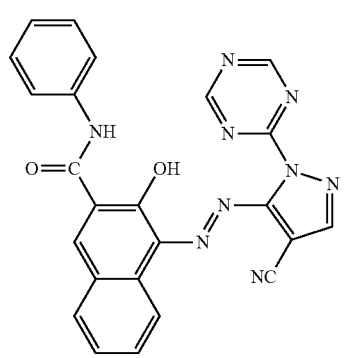

D-3

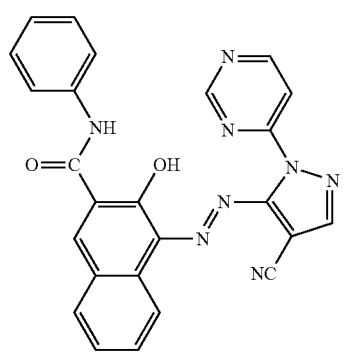

D-4

-continued
D-5
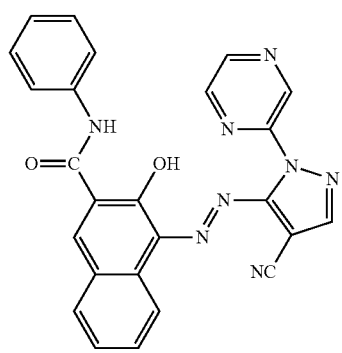
D-6
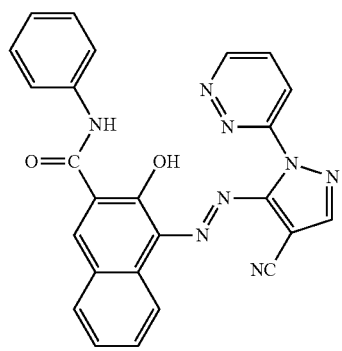
D-7
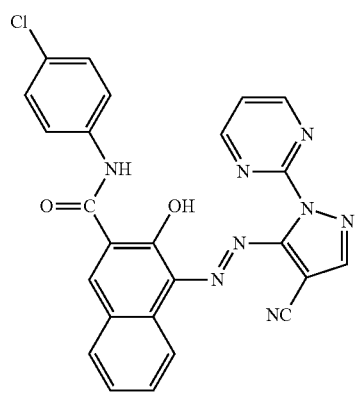
D-8
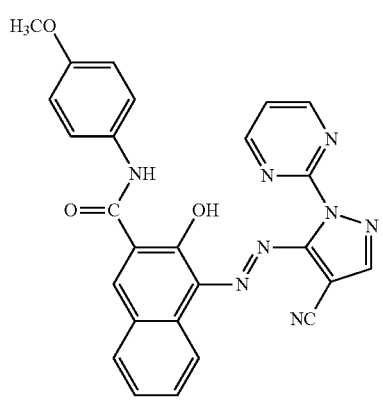
-continued
D-9
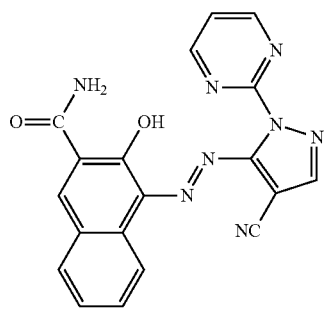
D-10
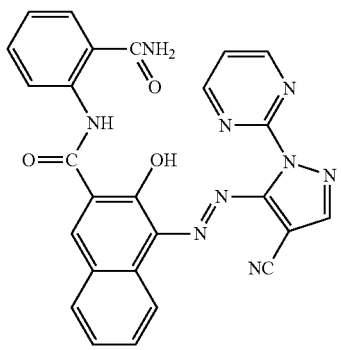
[Chem. 38]
D-11
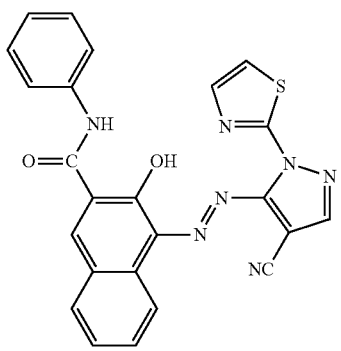
D-12
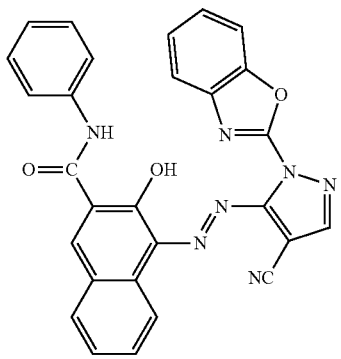

D-13
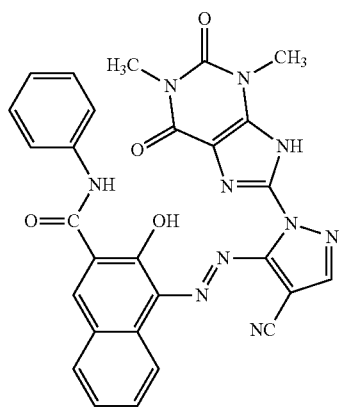
D-14
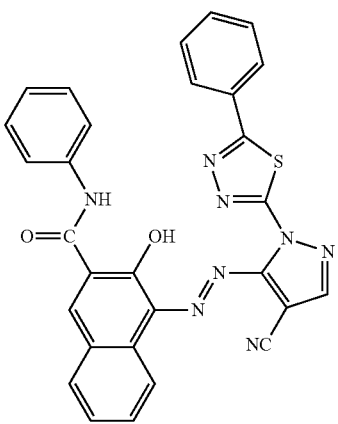
D-15
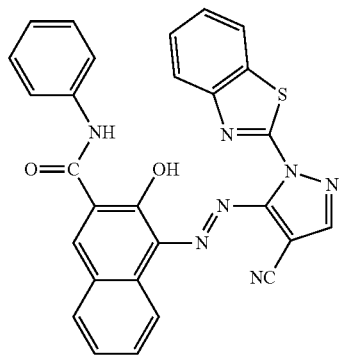
D-16
D-17
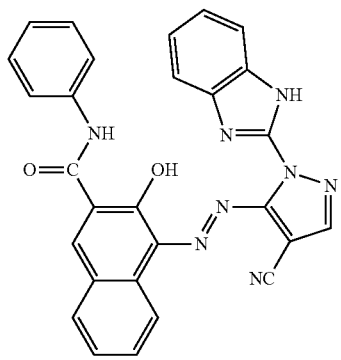
D-18
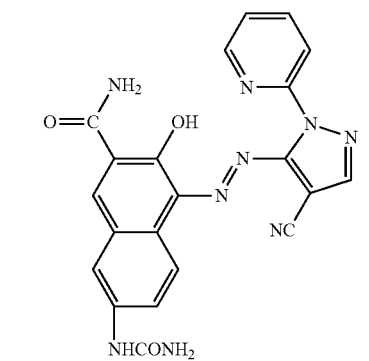
D-19
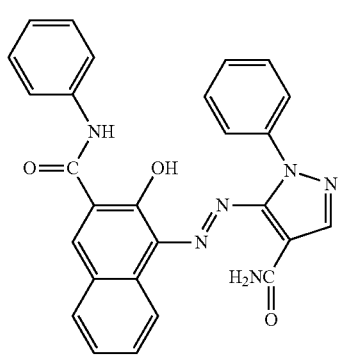
D-20

[Chem. 39]
D-21
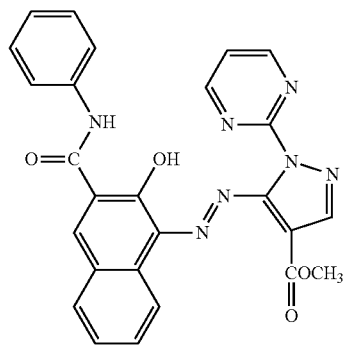
D-22
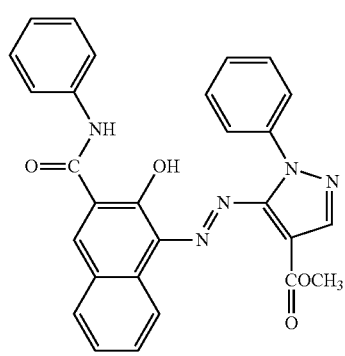
D-23
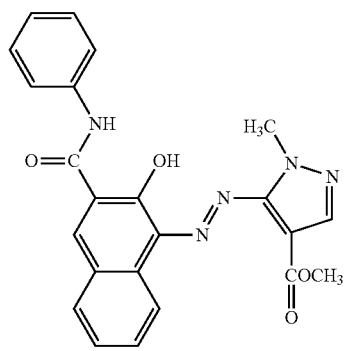
D-24
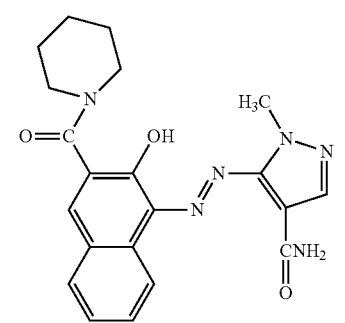
D-25
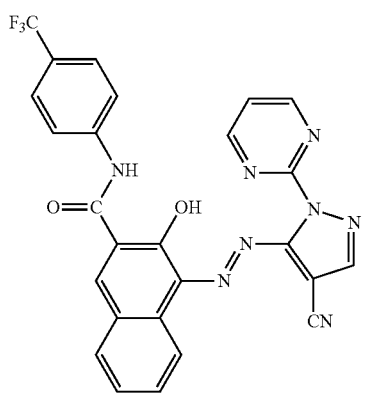
D-26
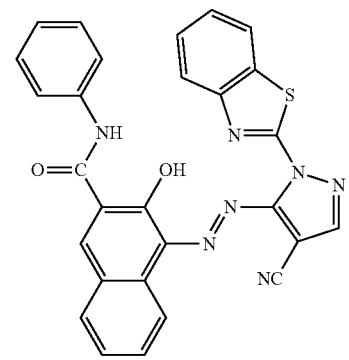
D-27
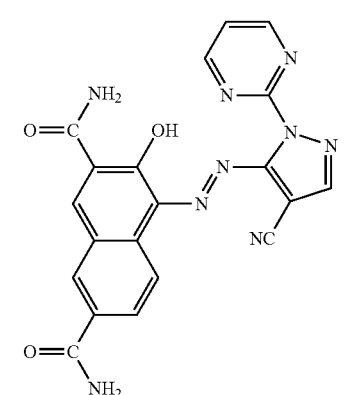
D-28
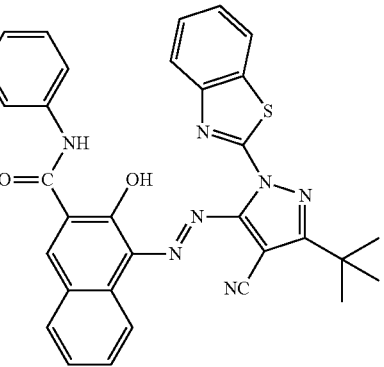

-continued

D-29

D-30

[Chem. 40]

D-31

D-32

-continued

D-33

D-34

D-35

D-36

-continued
D-37
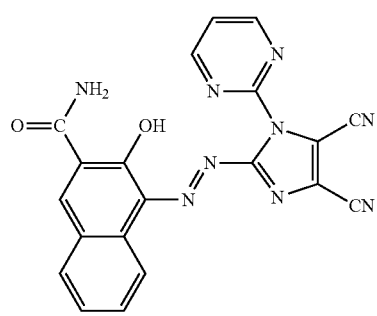
D-38
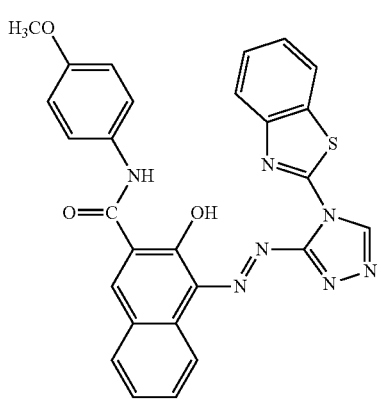
D-39
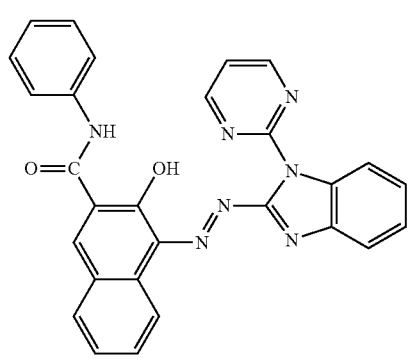
D-40
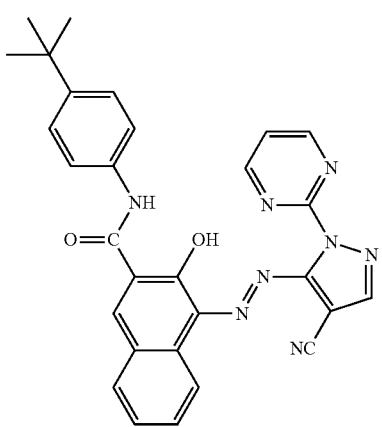
[Chem. 41]
-continued
D-41
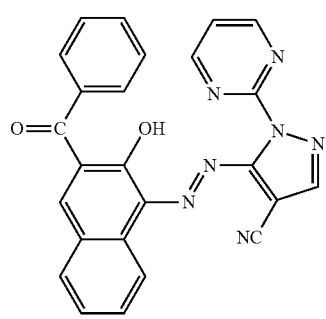
D-42
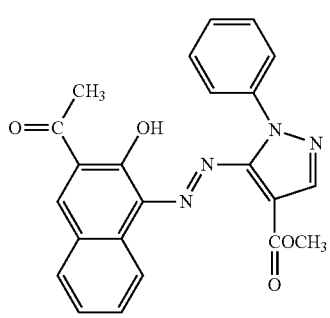
D-43
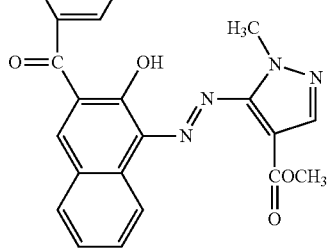
D-44
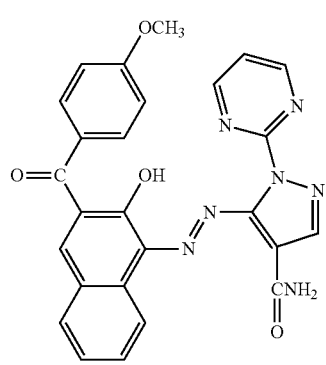
D-45
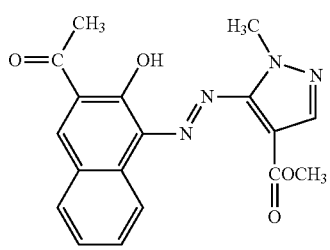

-continued
[Chem. 42]
D-71
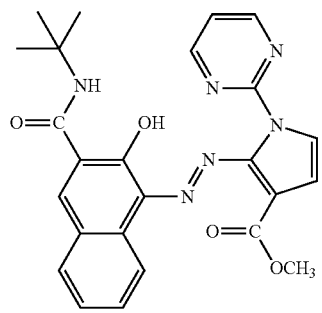
D-72
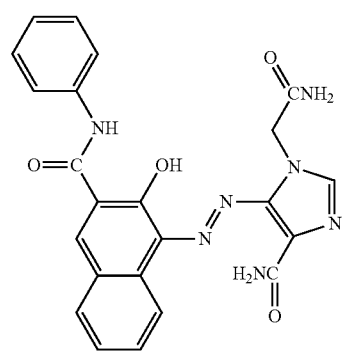
D-73
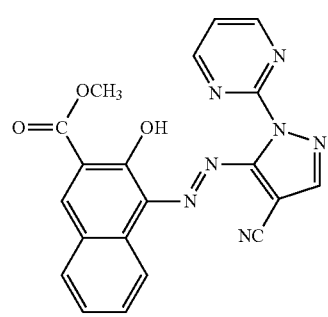
D-74
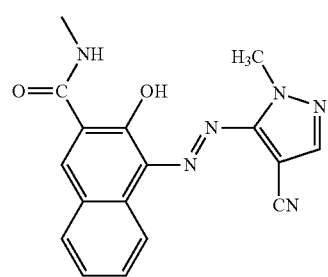
-continued
D-75
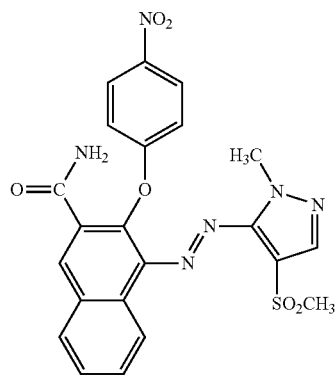
D-76
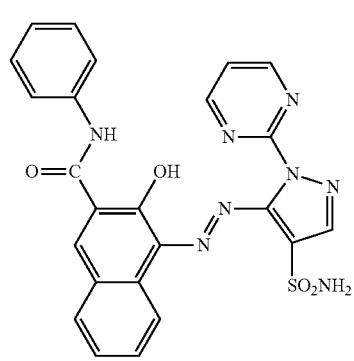
D-77
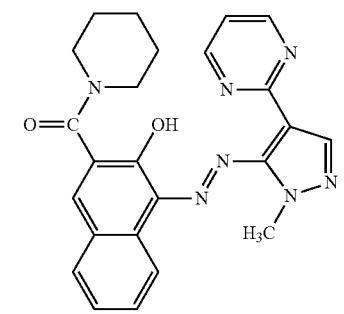
D-78
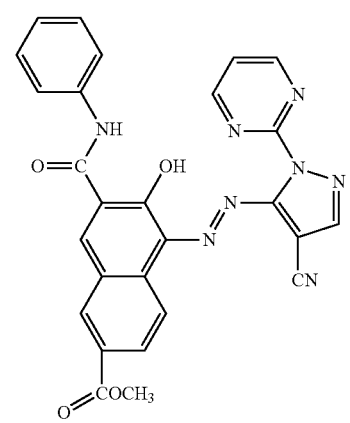

-continued
D-79
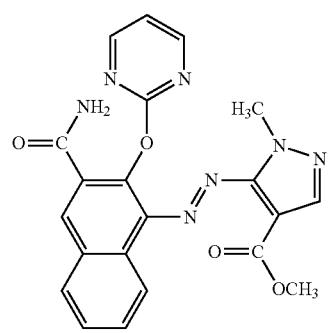
D-80
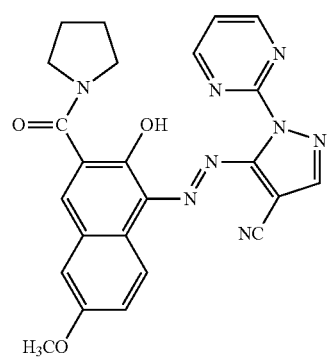
[Chem. 43]
D-81
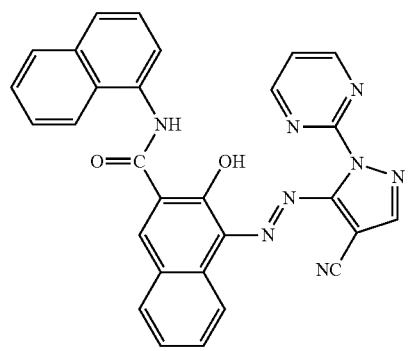
D-82
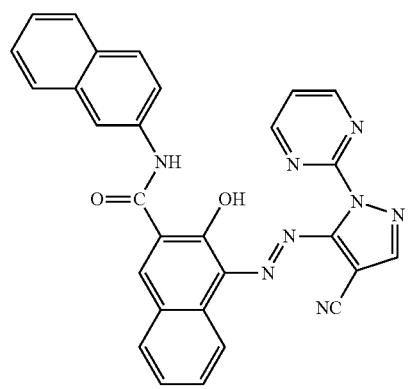
-continued
D-83
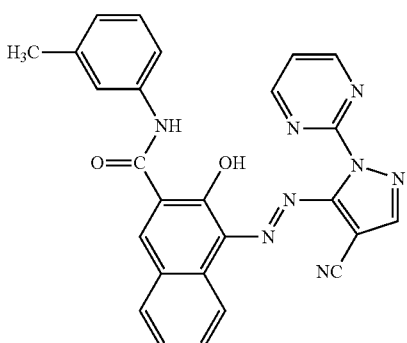
D-84
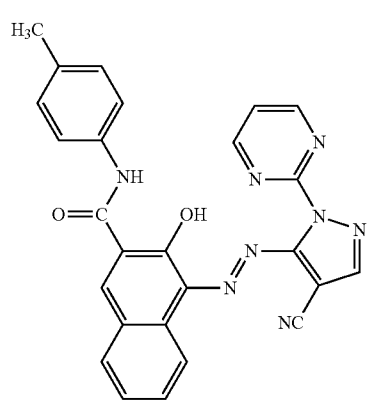
D-85
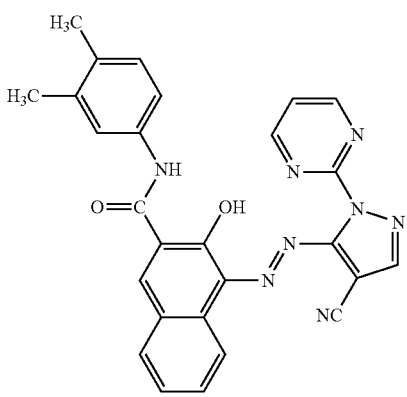
D-86
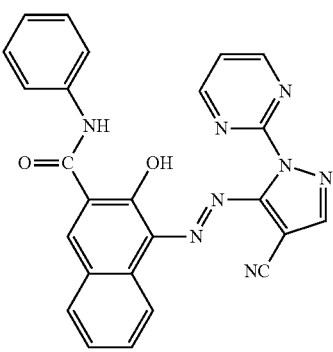

-continued
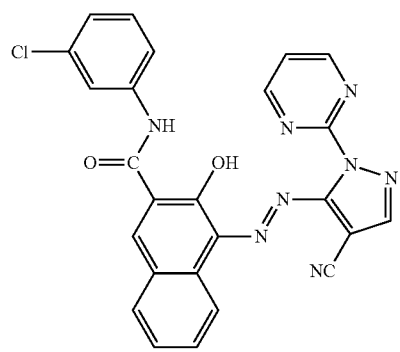
D-87
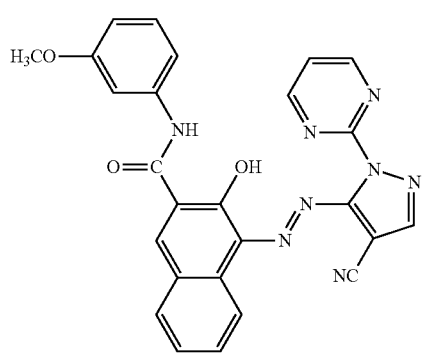
D-88
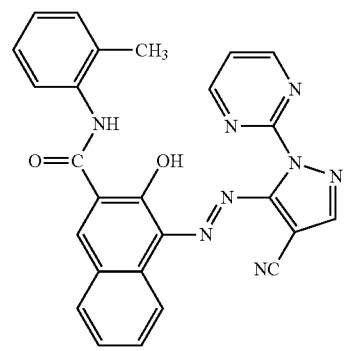
D-89
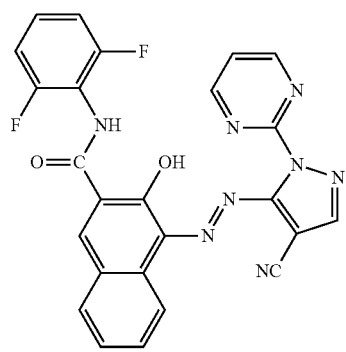
D-90
[Chem. 44]
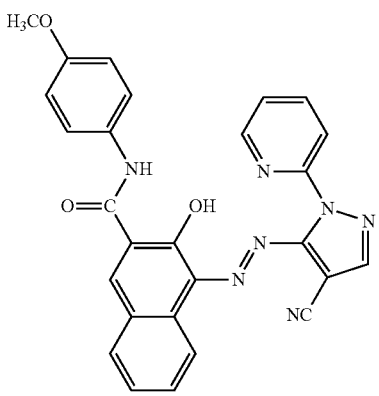
D-91
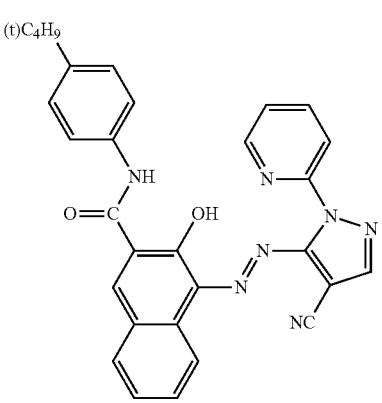
D-92
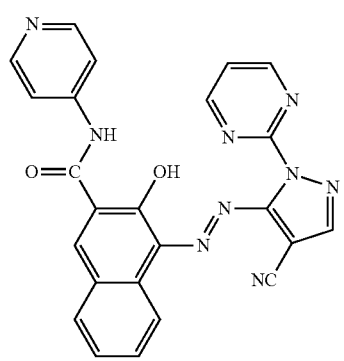
D-93
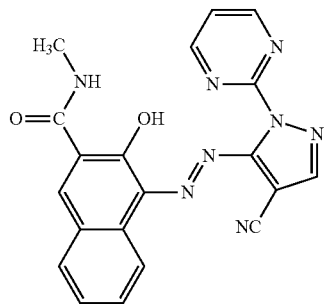
D-94

-continued

D-95

D-96

D-97

D-98

-continued

D-99

D-100

[Chem. 45]

D-151

D-152

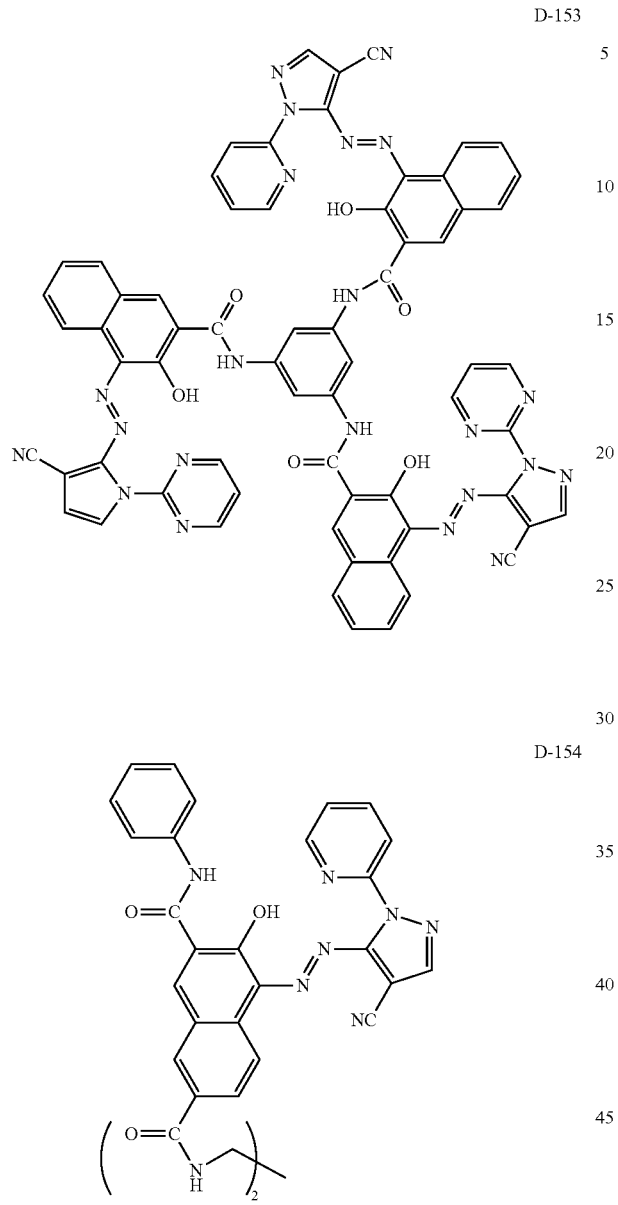
D-153
D-154
D-155
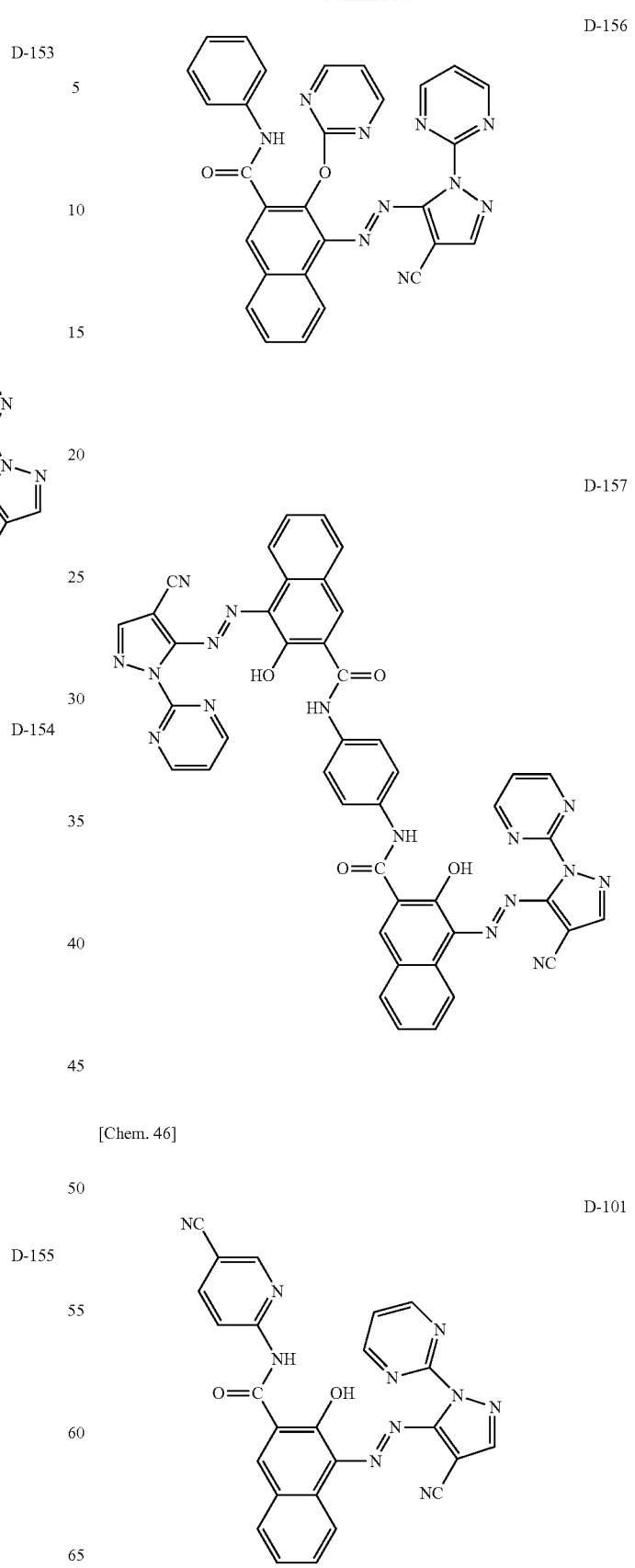
D-156
D-157
[Chem. 46]
D-101

D-102
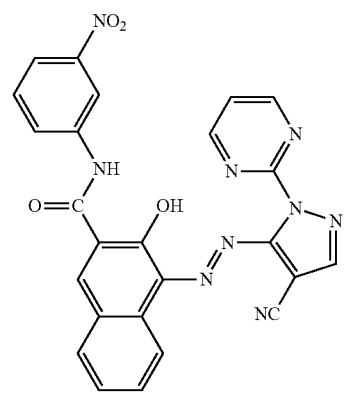
D-103
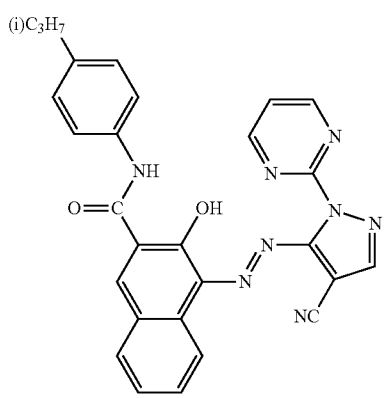
D-104
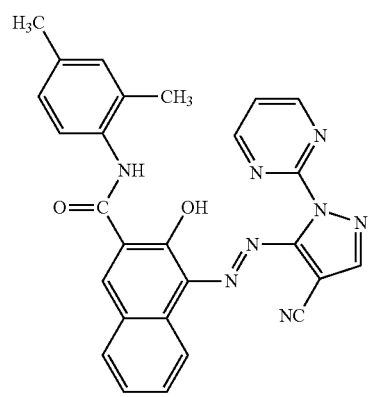
D-105
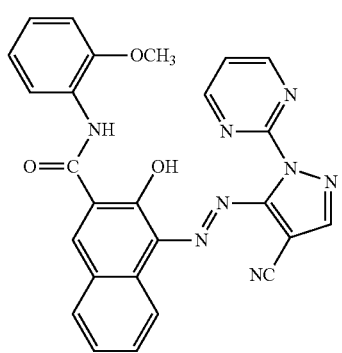
D-106
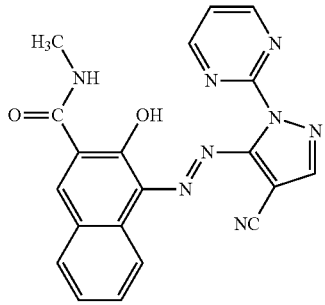
D-107
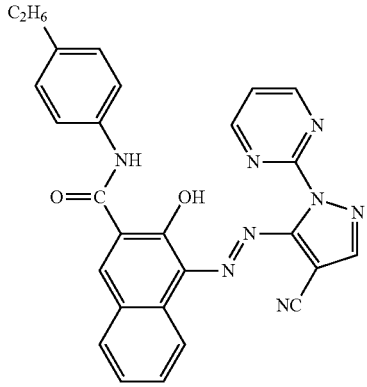
D-108
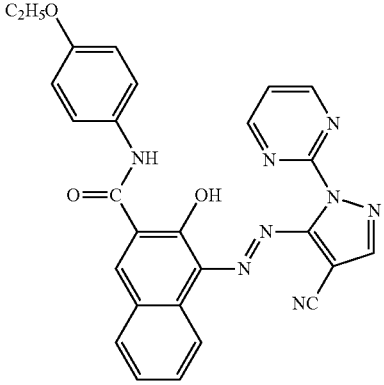
D-109
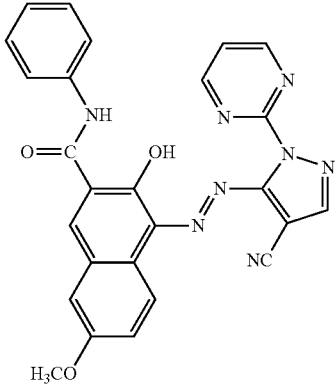

D-110
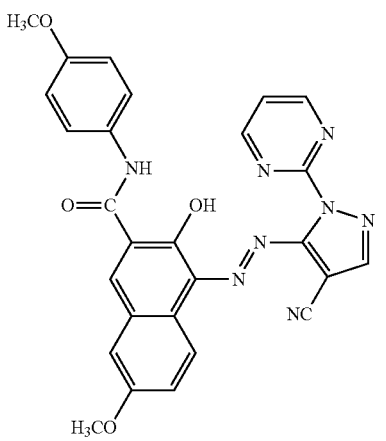
[Chem. 47]
D-111
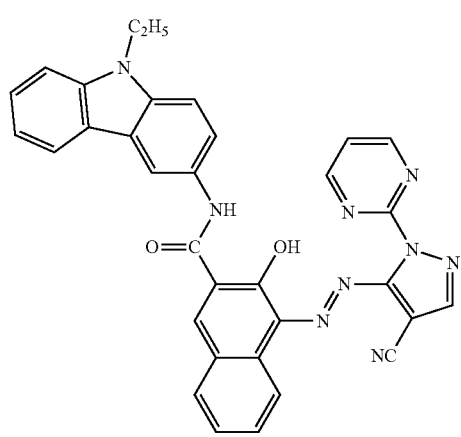
D-112
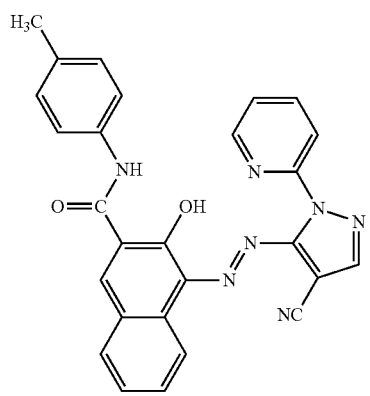
D-113
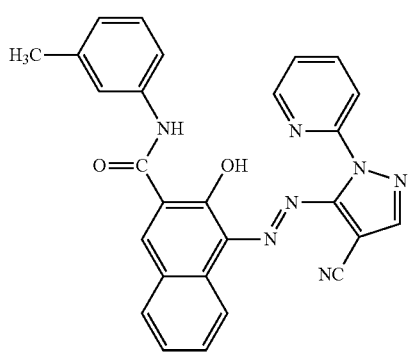
D-114
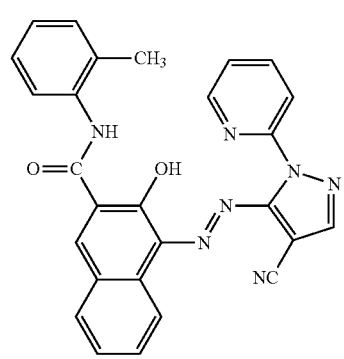
D-115
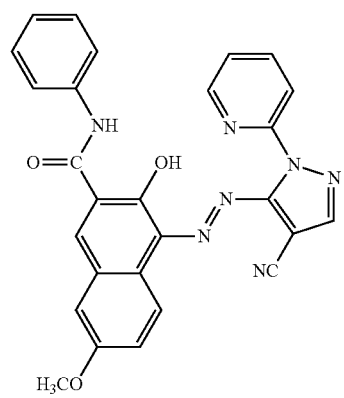
D-116
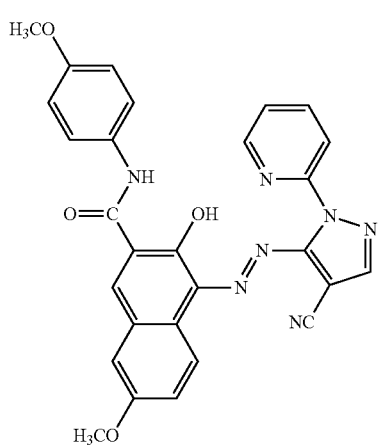
D-117
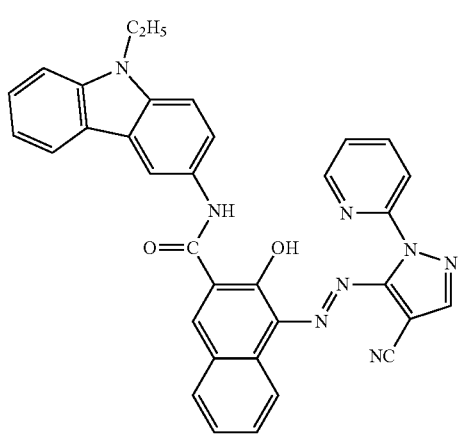

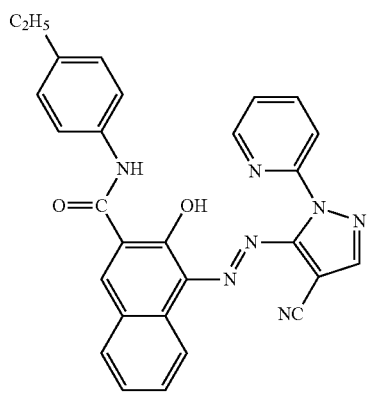
D-118
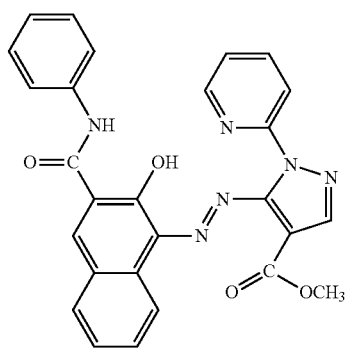
D-119
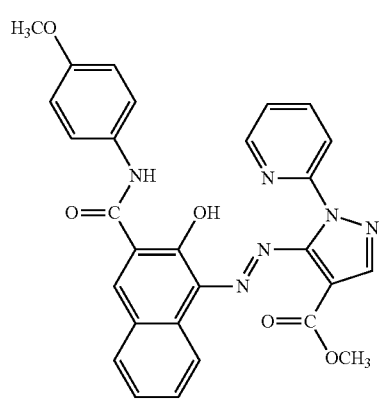
D-120
[Chem. 48]
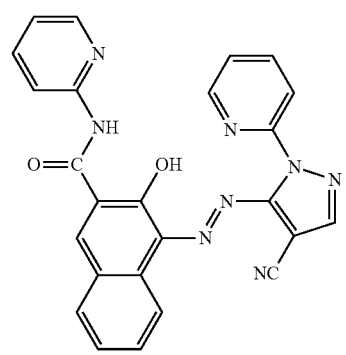
D-121
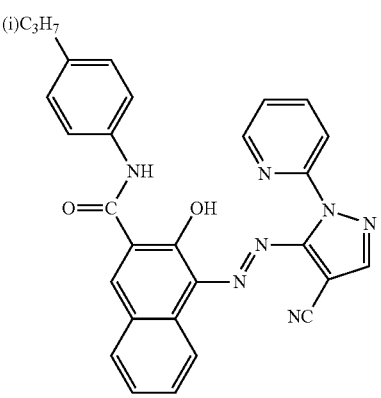
D-122
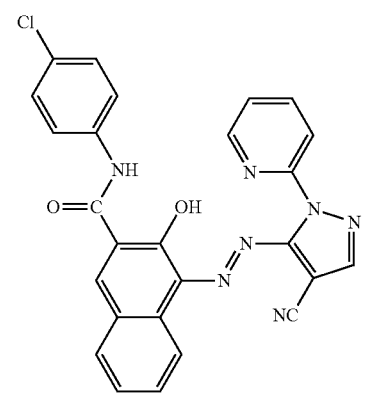
D-123
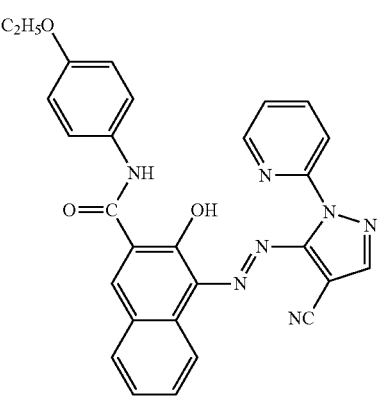
D-124
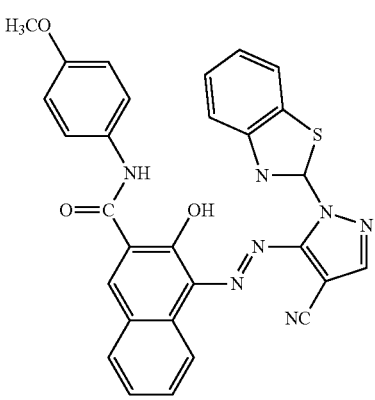
D-125

D-126
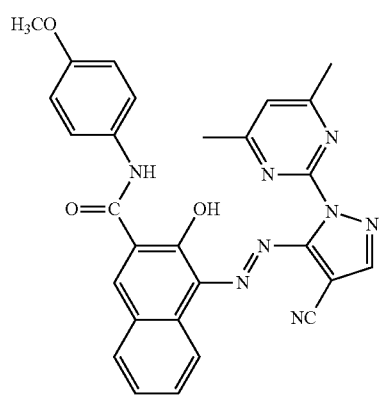
D-127
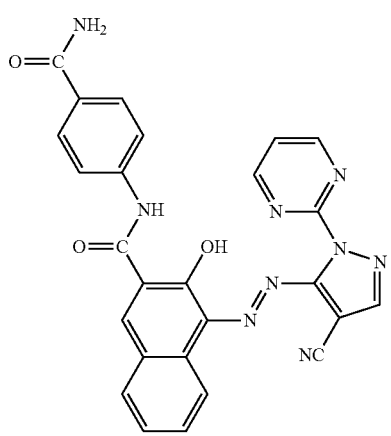
D-128
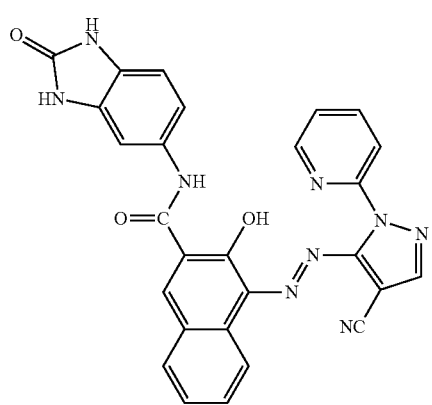
D-129
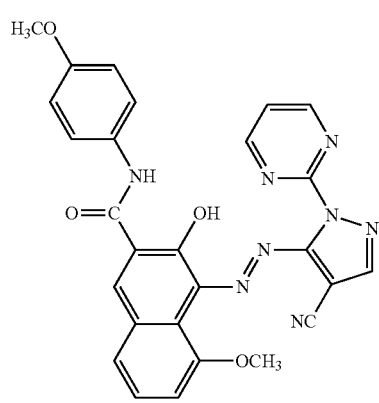
[Chem. 49]
D-130
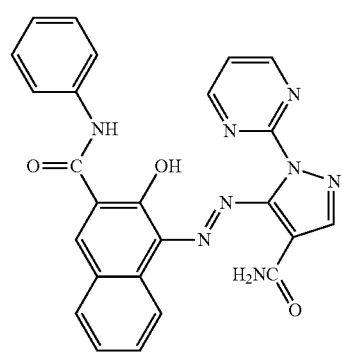
D-131
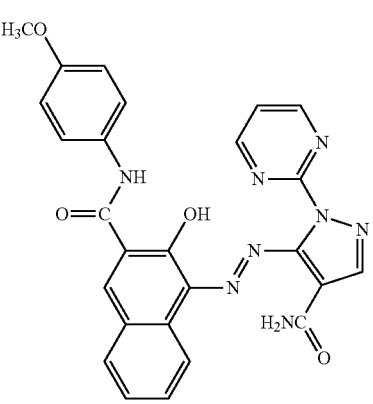
D-132
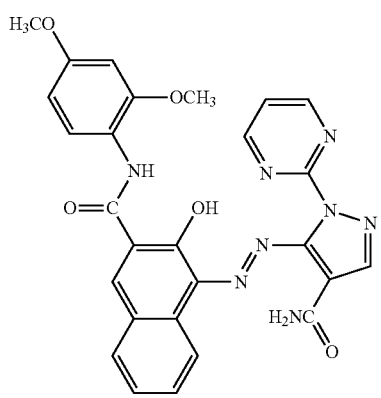
D-133
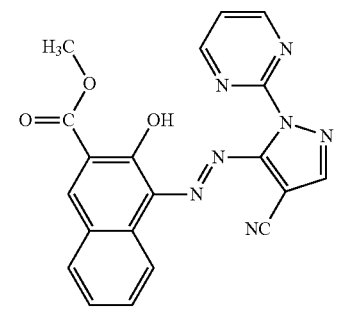

D-134
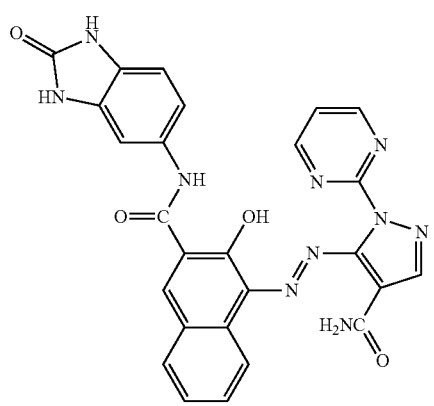
D-135
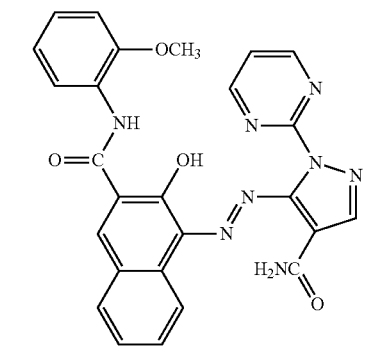
D-136
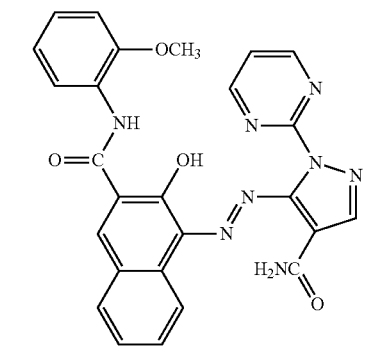
D-137
D-138
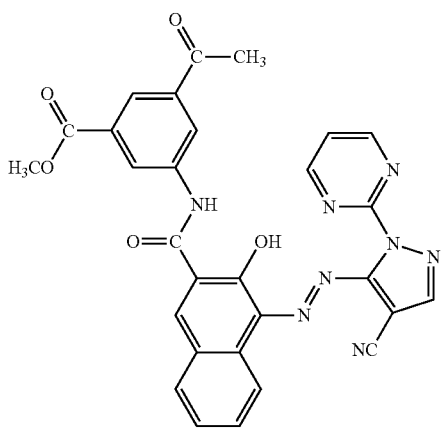
D-139
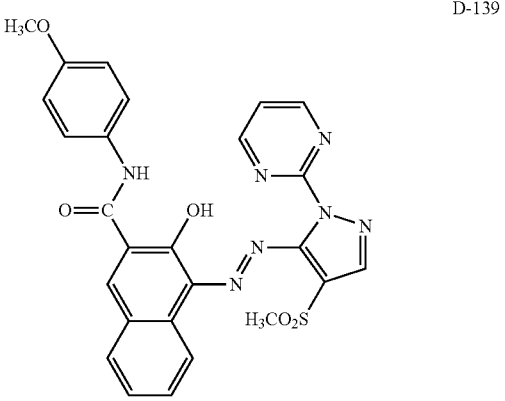
D-140
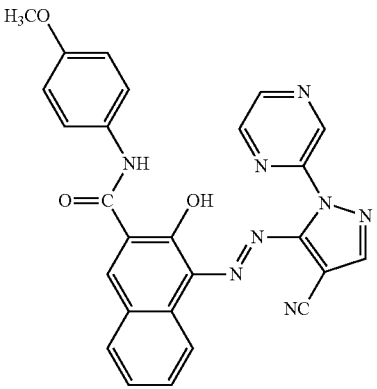
[Chem. 50]
D-141
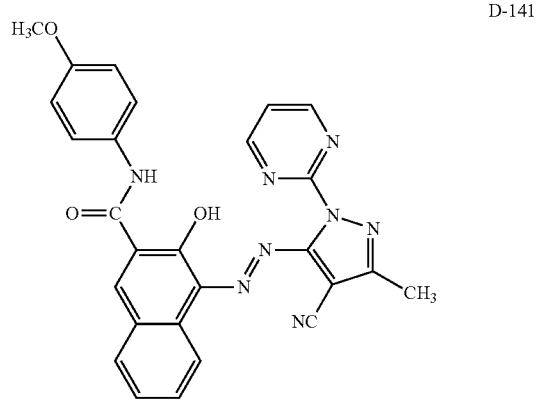

-continued
D-142
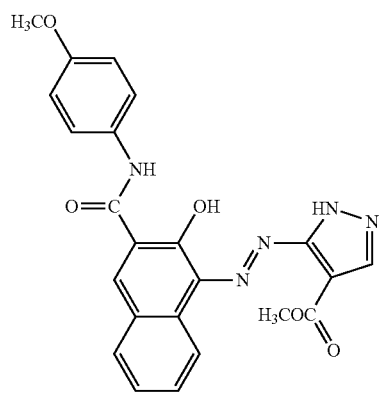
D-143
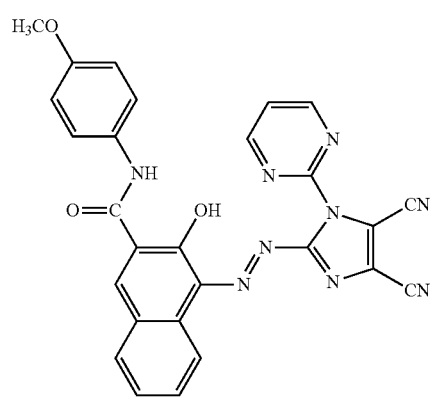
D-144
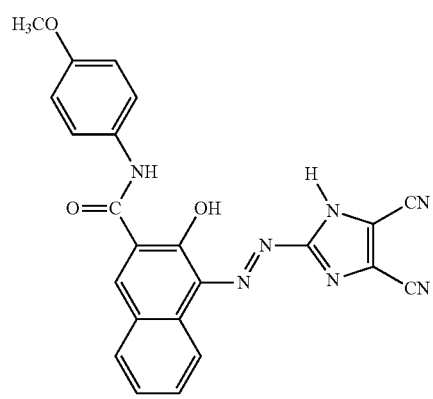
D-145
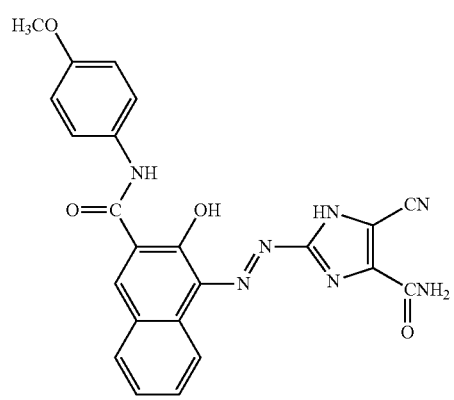
-continued
D-146
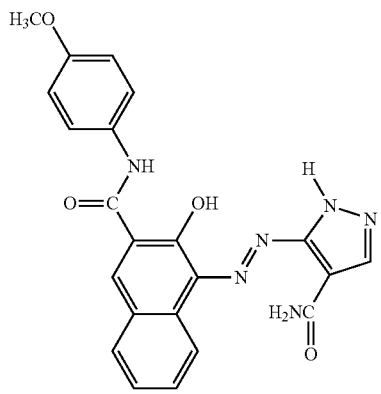
D-147
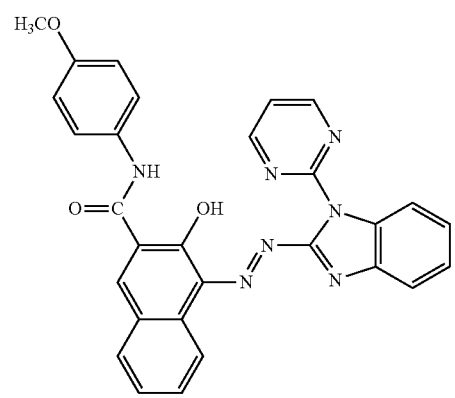
D-148
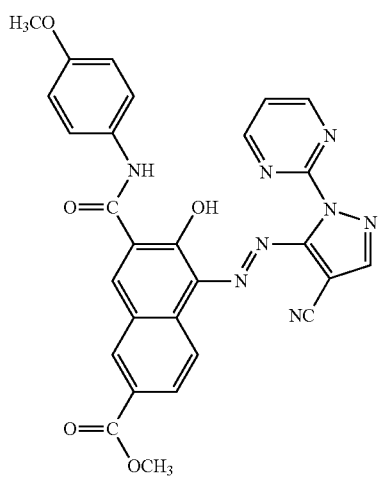
D-149
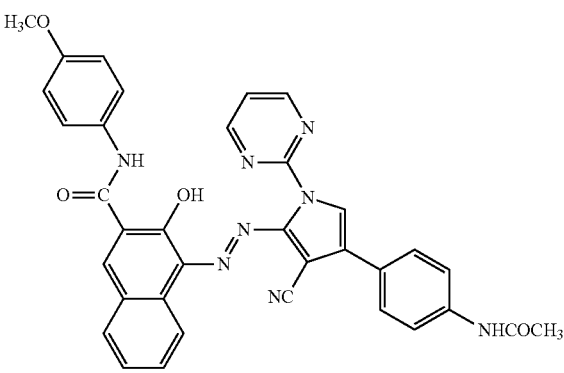

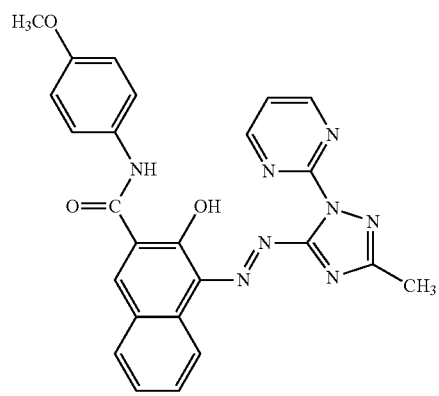
D-150
[Chem. 51]
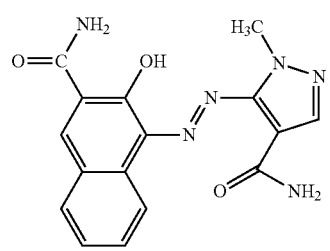
D-171
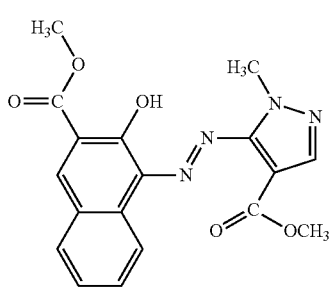
D-172
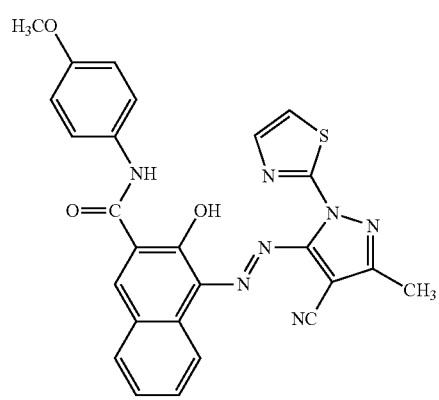
D-173
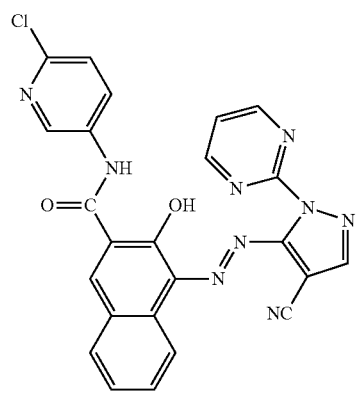
D-174
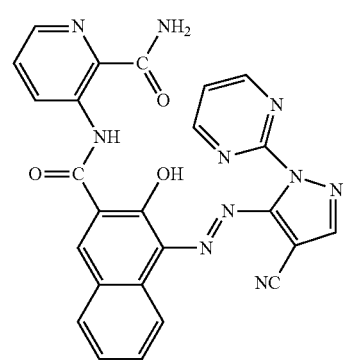
D-175
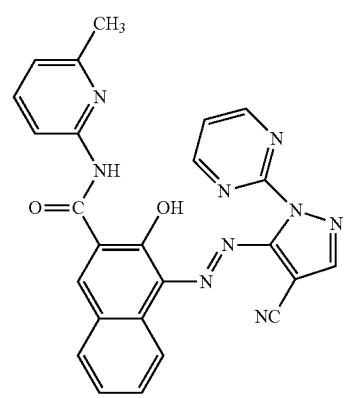
D-176
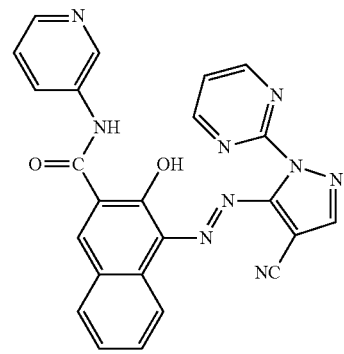
D-177

[Chem. 52]
D-201
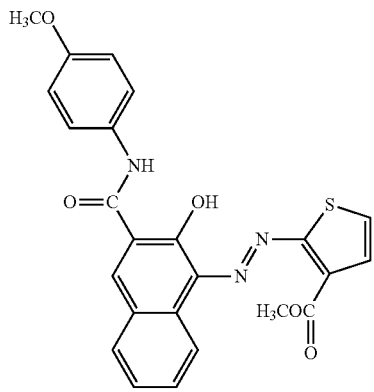
D-202
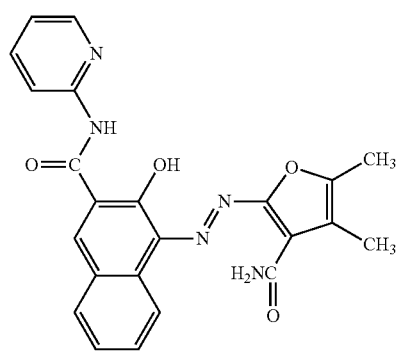
D-203
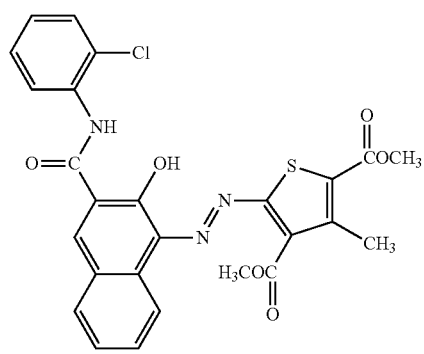
D-204
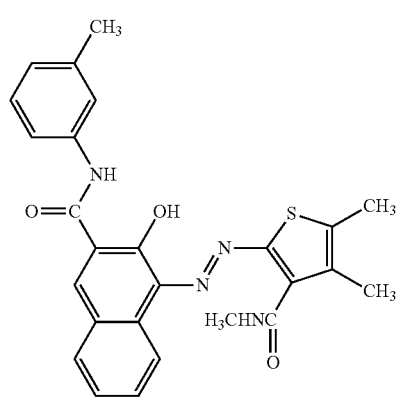
D-205
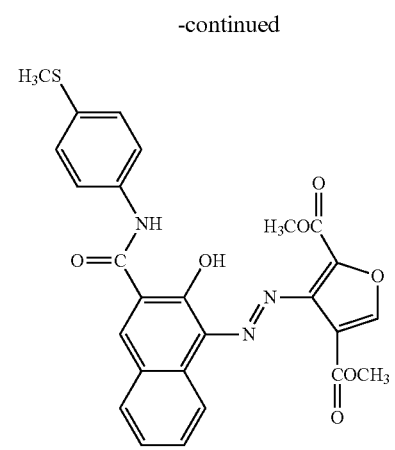
D-206
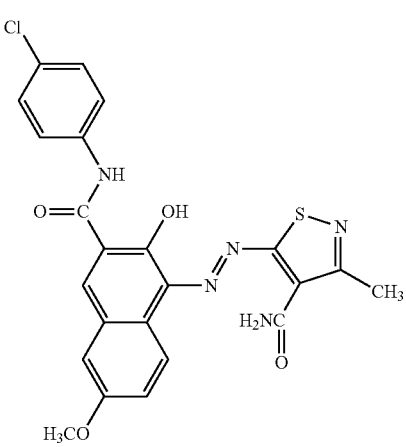
D-207
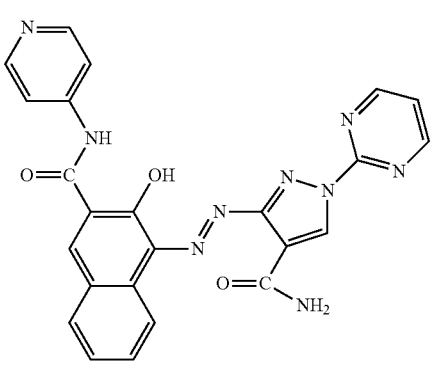
D-208
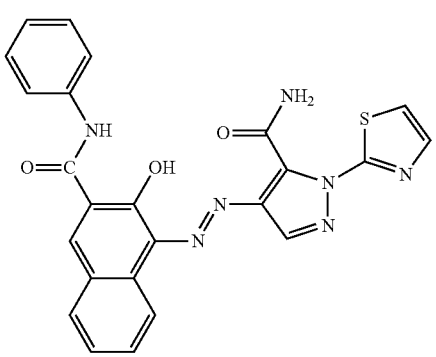

-continued
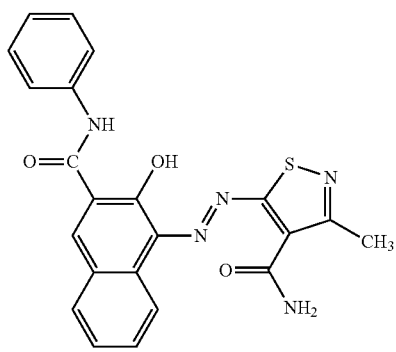
D-209
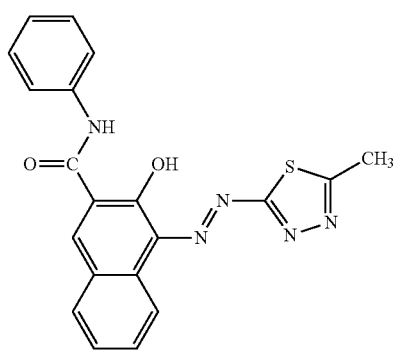
D-213
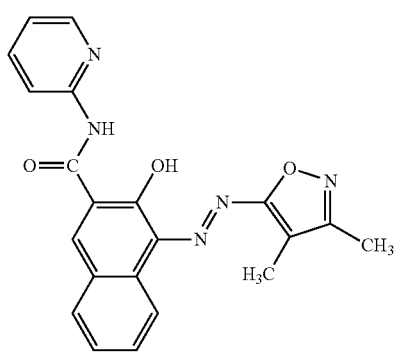
D-210
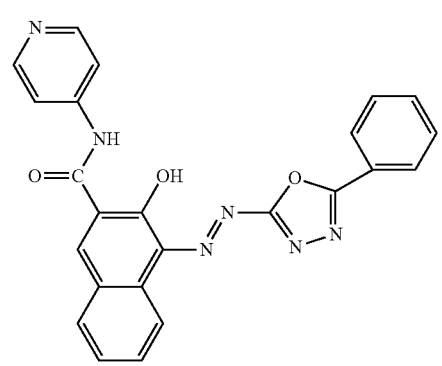
D-214
[Chem. 53]
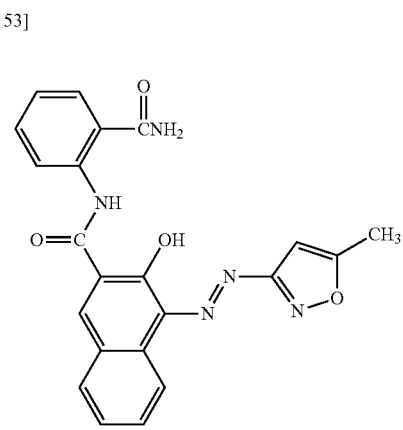
D-211
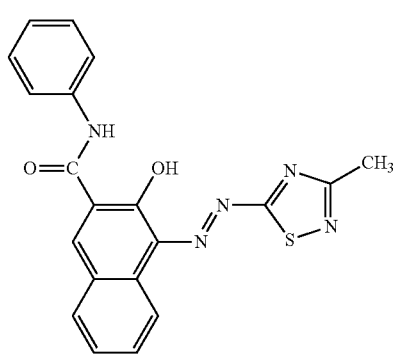
D-215
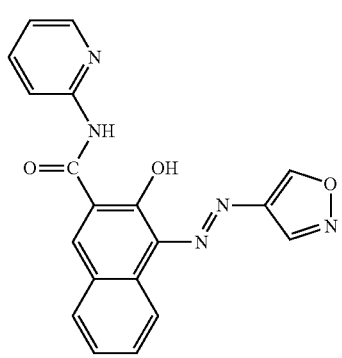
D-212
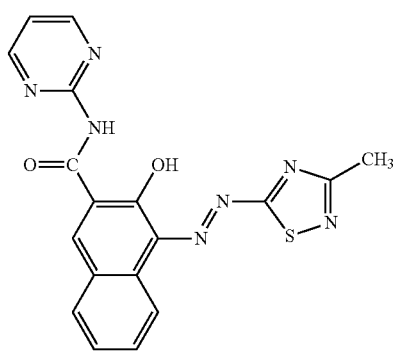
D-216

D-217
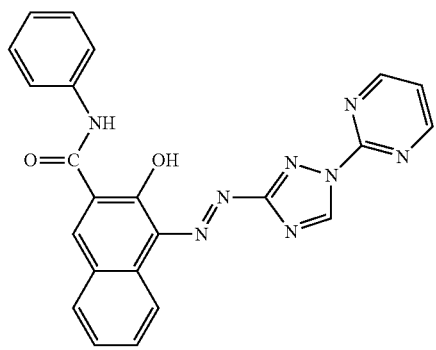
D-218
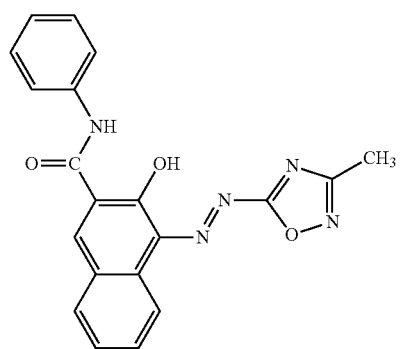
D-219
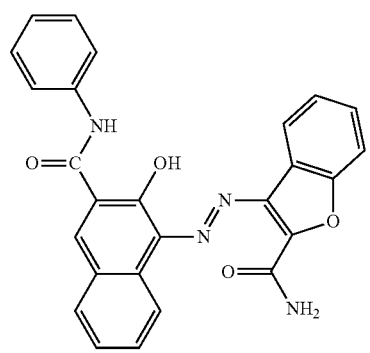
D-220
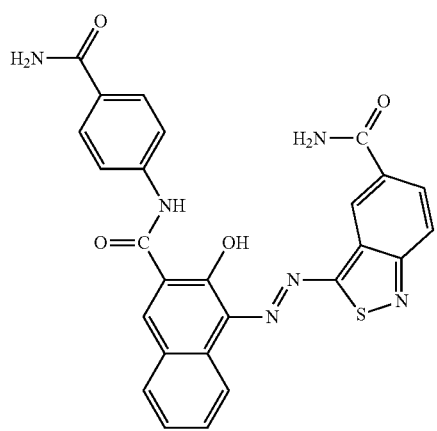
[Chem. 54]
D-221
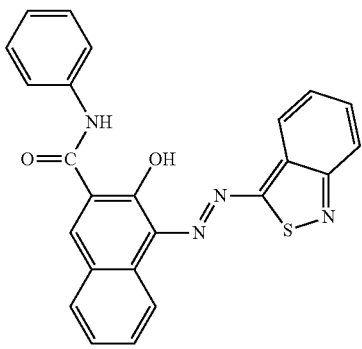
D-222
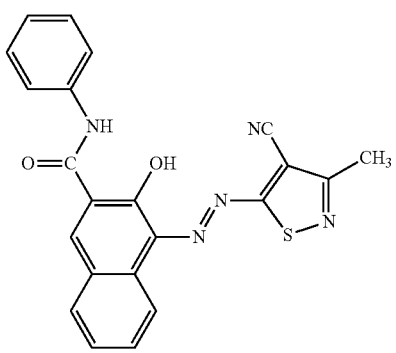
D-223
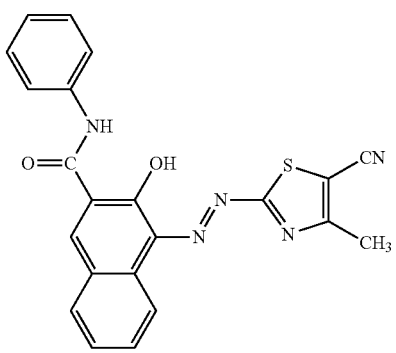
D-224
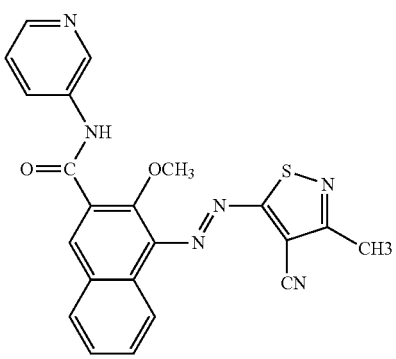

-continued
D-225
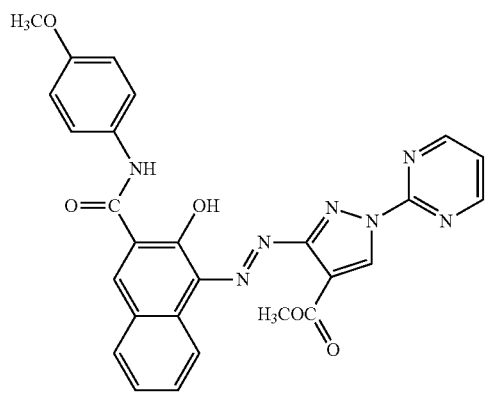
D-226
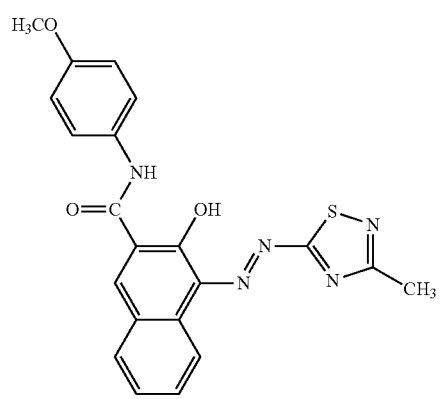
D-227
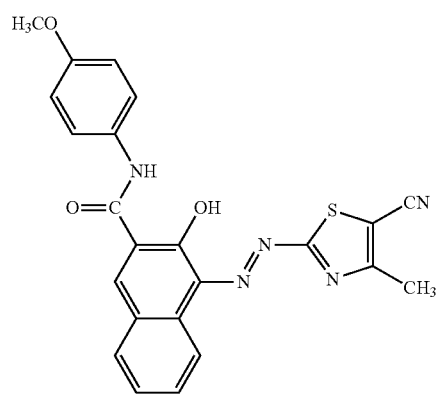
D-228
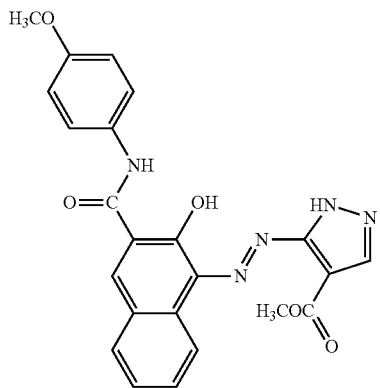
-continued
D-229
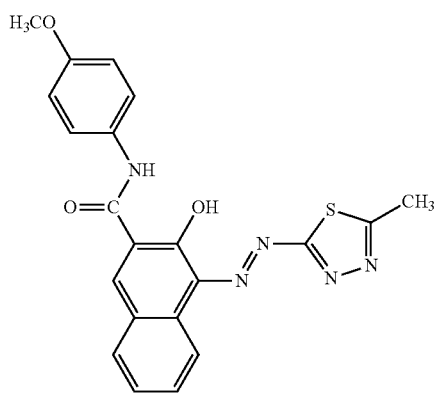
D-230
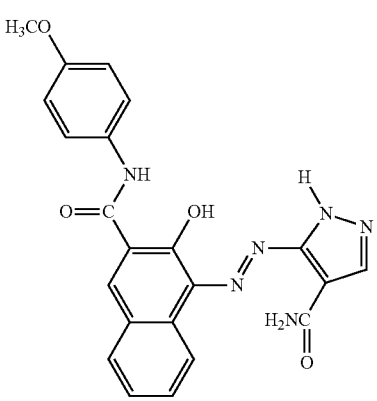
[Chem. 55]
D-231
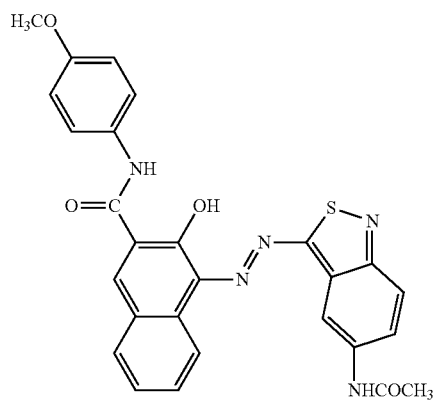
D-232
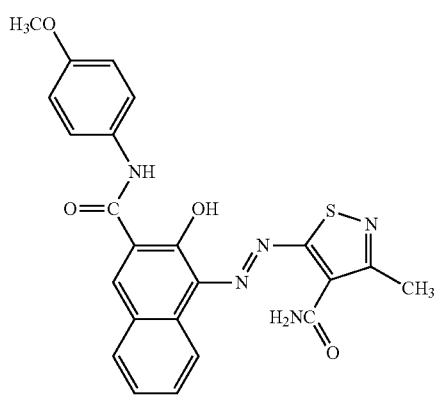

D-233
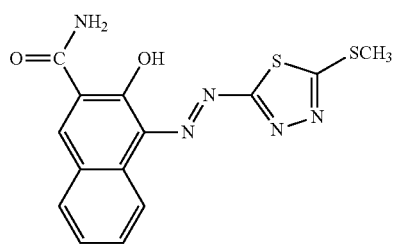
D-234
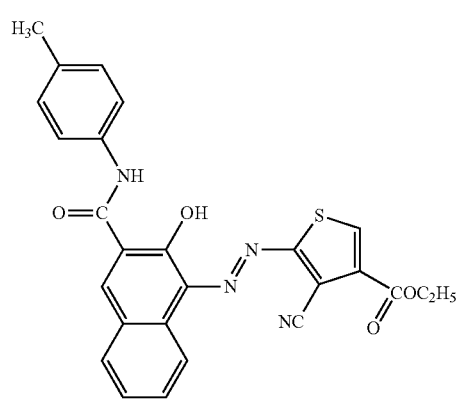
D-235
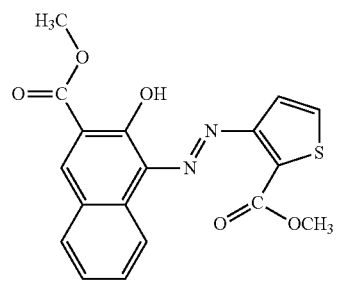
D-236
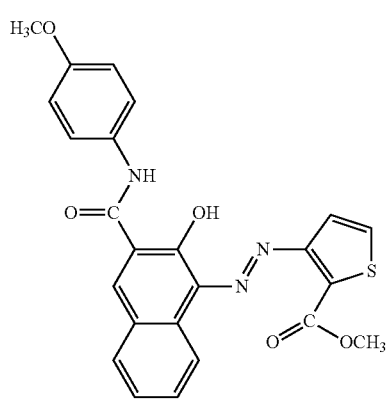
D-237
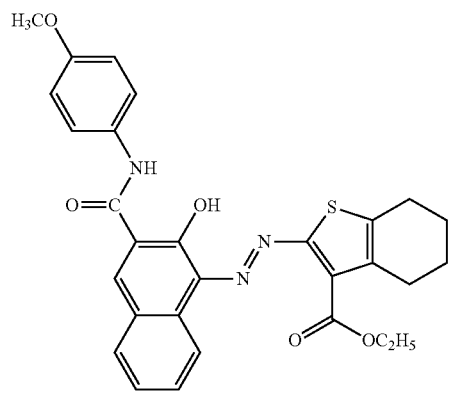
D-238
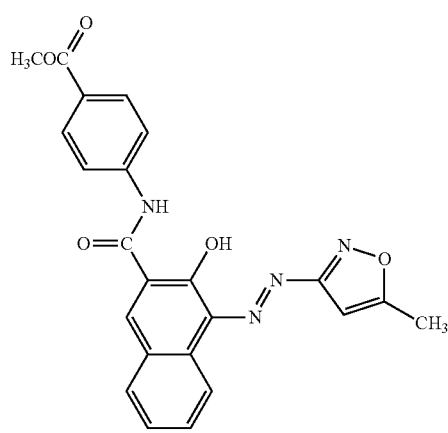
D-239
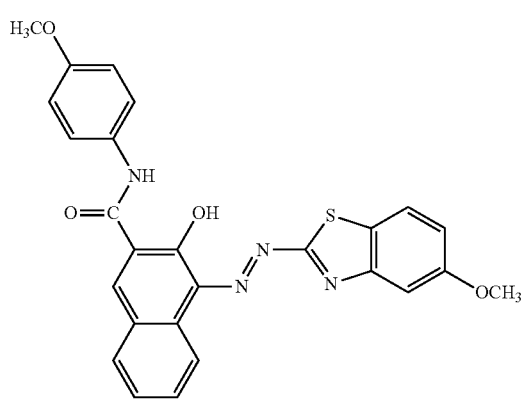
D-240
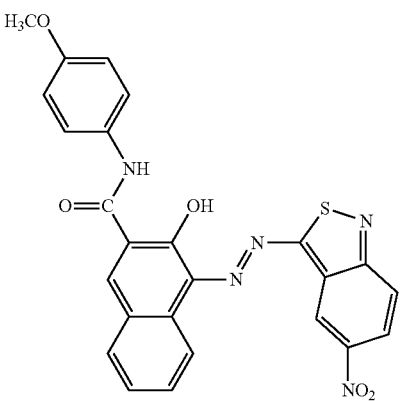

[Chem. 56]
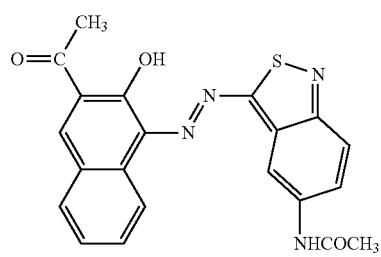
D-241
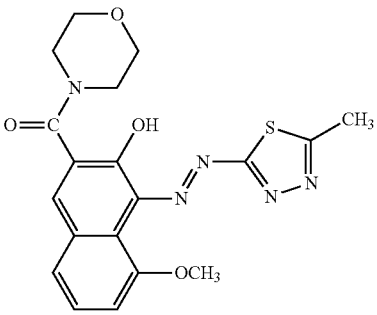
D-245
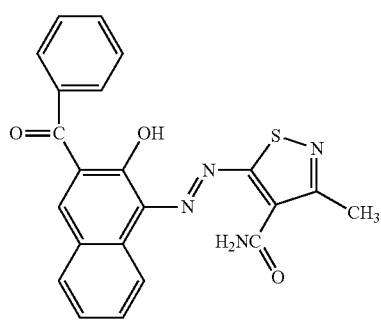
D-242
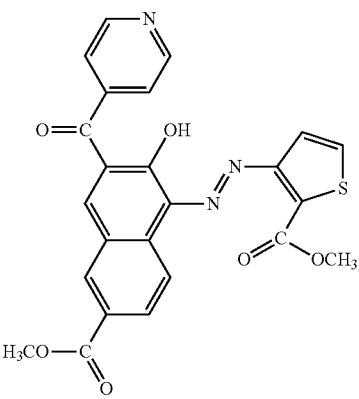
D-246
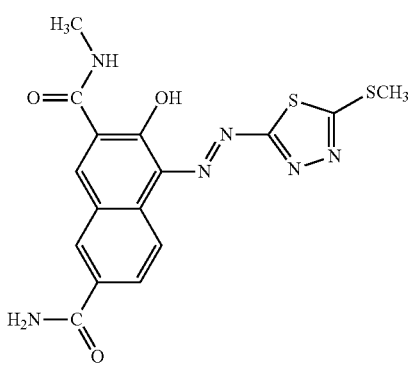
D-243
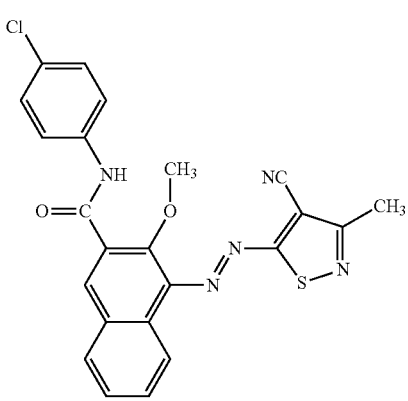
D-247
[Chem. 57]
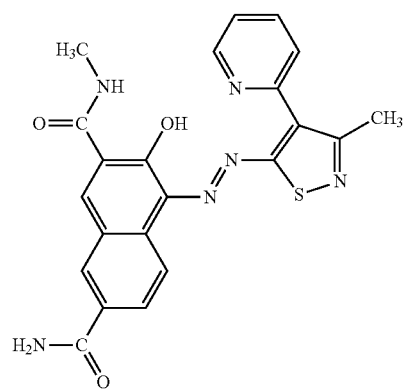
D-244
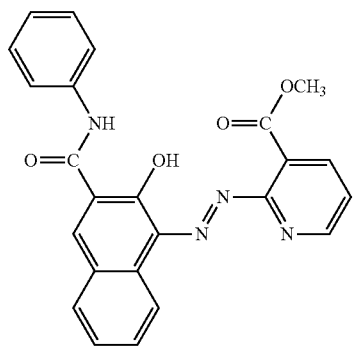
D-251

D-252
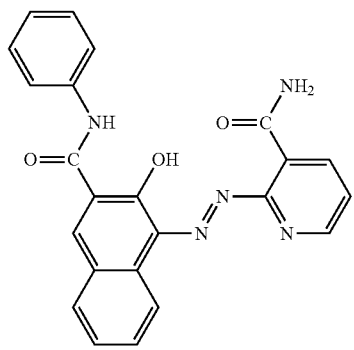
D-253
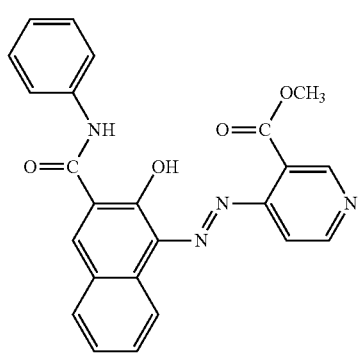
D-254
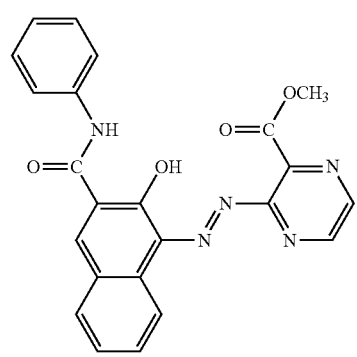
D-255
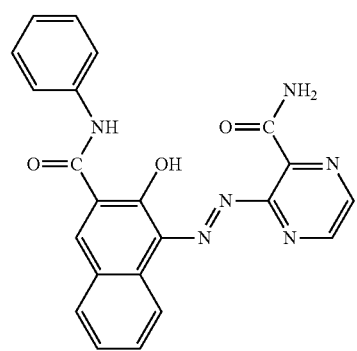
D-256
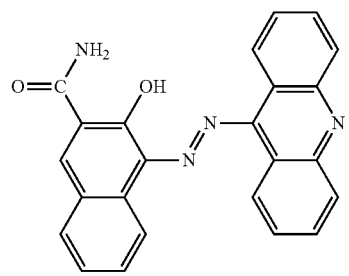
D-257
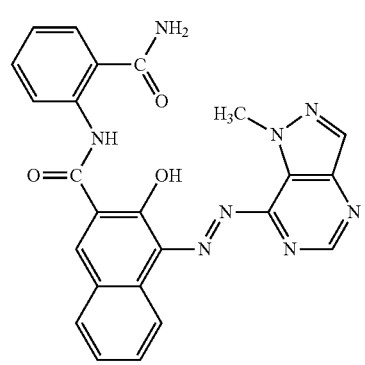
D-258
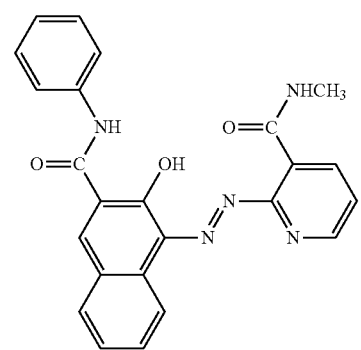
D-259
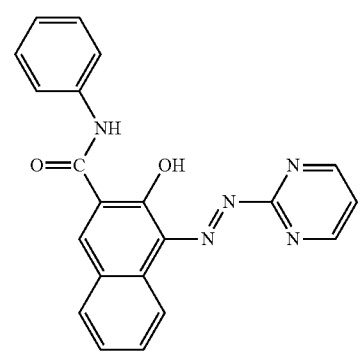

D-260
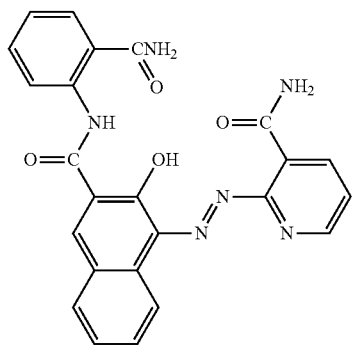
[Chem. 58]
D-261
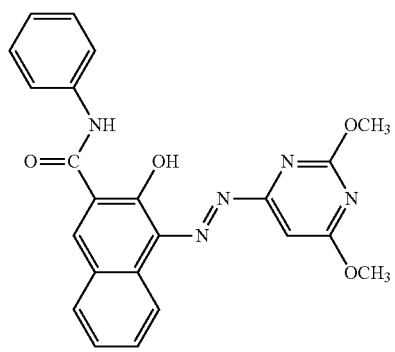
D-262
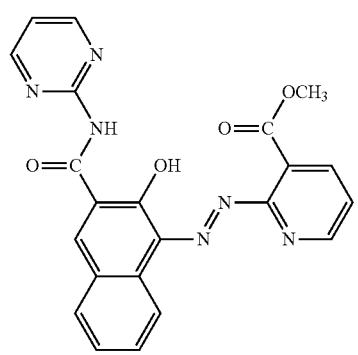
D-263
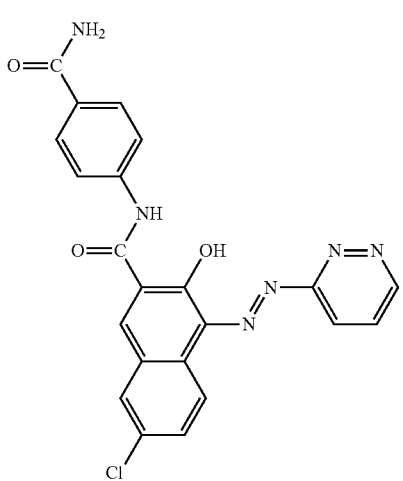
D-264
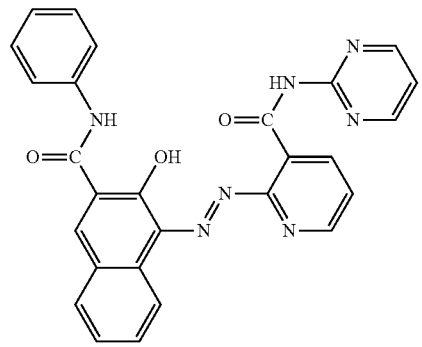
D-265
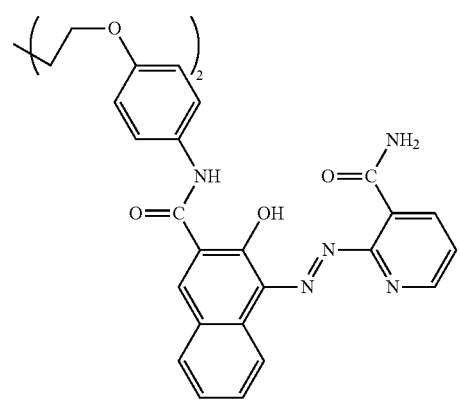
D-266
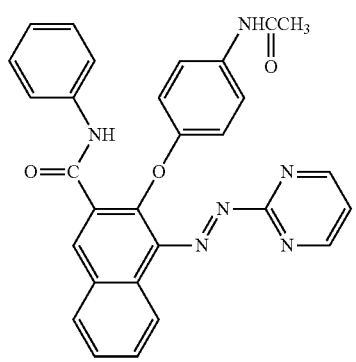

D-267

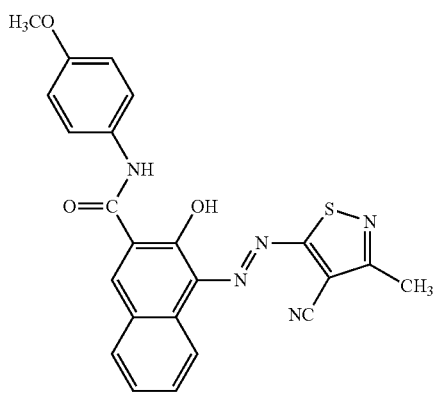

The pigments of the invention represented by the general formula (1) may have a chemical structure represented by the general formula (1) or may be the tautomers thereof, and may be of any crystal form called polymorphic form.

Polymorphism means that crystals having the same chemical composition can be different from each other in the conformation of building block (molecules or ions) in the crystal. Chemical and physical properties of the pigments are decided by the crystal structure, and polymorphic forms of the same pigment can be discriminated from each other by rheology, color, and other color characteristics. Also, different polymorphic forms can be confirmed by X-Ray Diffraction (results of powder X-ray diffractiometry) or by X-Ray Analysis (results of X-ray analysis of crystal structure).

In the case where the pigments of the invention represented by the general formulae (1) and (2) exhibit polymorphism, they may be in any polymorphic forms and may be a mixture of two or more polymorphic forms. However, pigments wherein a single crystal form is predominant are preferred. That, is, pigments not contaminated with polymorphic form crystals are preferred. The content of the azo pigment having a single crystal form is from 70% to 100%, preferably from 80% to 100%, more preferably from 90% to 100%, still more preferably from 95% to 100, particularly preferably 100%, based on the entire azo pigment. When the azo pigment contains a single crystal form azo pigment as a major component, regularity of alignment of the pigment molecules is improved, and the intramolecular and intermolecular mutual action is enhanced, thus a high-level three-dimensional network being easily formed. As a result, performances required for pigments, such as hue, light fastness, heat fastness, humidity fastness, fastness to an oxidative gas, and solvent resistance, are improved, thus the above-described content being preferred.

The mixing ratio of polymorphic forms in the azo pigment can be confirmed from values obtained by physicochemical measurement of solid such as X-ray crystal structure analysis of single crystal, powder X-ray diffractiometry (XRD), microscopic photography of the crystals (TEM), or IR (KBr method).

Control of the above-described tautomerism and/or polymorphism may be achieved by controlling production conditions upon coupling reaction.

Also, with those which have acid groups among the azo pigments of the invention represented by the general formula (1), part or all of the acid groups may be in a salt form, and the pigment may be a mixture of a salt type pigment and a free acid type pigment. Examples of the salt type include salts of an alkali metal such as Na, Li, or K, salts of ammonium optionally substituted by an alkyl group or by a hydroxyalkyl group, and salts of an organic amine. Examples of the organic amine include a lower alkyl amine, a hydroxyl-substituted lower alkyl amine, a carboxy-substituted lower alkyl amine, and a polyamine having from 2 to 10 alkyleneimine units containing from 2 to 4 carbon atoms. With these salt type pigments, they are not necessarily limited to one as to kind, but may be in a mixture of two or more thereof.

Further, as to the structure of the pigment to be used in the invention, in the case where plural acid groups exist in one molecule, the plural acid groups may be of a salt type or an acid type, and may be different from each other.

In the invention, the azo pigment represented by the general formula (1) may be a hydrate which contains a water molecule within the crystal.

Next, an example of processes for producing the azo pigment represented by the above general formula (1) will be described hereinafter. For example, the azo pigment of the invention represented by the general formula (6) can be produced by diazotizing a heterocyclic amine represented by the following general formula (4) under a non-aqueous, acidic condition, conducting a coupling reaction with a compound represented by the following general formula (5) in an acidic state, and conducting conventional after-treatment. An azo pigment represented by the general formula (1) can be produced by conducting the similar procedures using a heterocyclic amine corresponding to A in the general formula (1) in place of the compound of the general formula (4).

[Chem. 59]

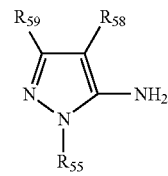

(4)

(In the above formula, $R_{55}$, $R_{58}$, and $R_{59}$ are the same as those defined with respect to the foregoing general formula (2-1).)

[Chem. 60]

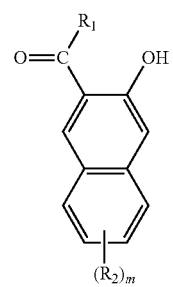

(5)

(In the above formula, $R_1$, $R_2$, and m are the same as those defined with respect to the foregoing general formula (1).)

The reaction scheme is shown below.

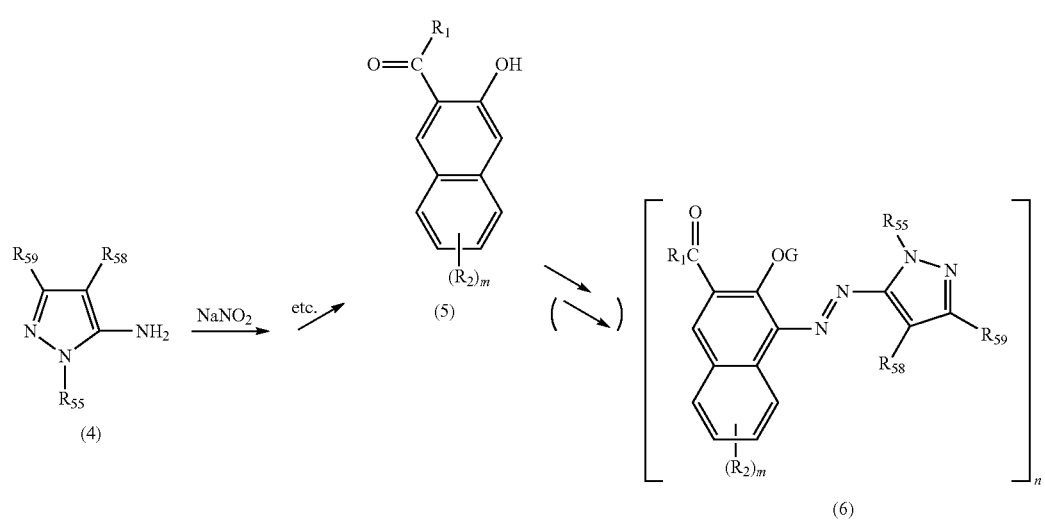

(In the above formulae, G, $R_1$ to $R_2$, $R_{55}$, $R_{58}$, $R_{59}$ n, and m are the same as those defined with respect to the foregoing general formula (1), the general formula (2-1), and the general formula (3).)

Some of the heterocyclic amine corresponding to the amino compound of the above general formula (4), and (A-1) to (A-32) may be commercially available but, generally, the heterocyclic amines may be produced in a conventionally known manner by, for example, the process described in Japanese Patent No. 4,022,271. The heterocyclic coupler represented by the above general formula (5) is commercially available, or can be produced by, or according to, the processes described in JP-A-2008-13472. The diazotization reaction of the heterocyclic amine shown by the above-described reaction scheme can be conducted, for example, by reacting it with a reagent such as sodium nitrite, nitrosylsulfuric acid, or isoamyl nitrite in an acidic solvent such as sulfuric acid, phosphoric acid, or acetic acid at a temperature of 15° C. or less for about 10 minutes to about 6 hours. The coupling reaction is preferably conducted by reacting the diazonium salt obtained by the above-mentioned process with the compound represented by the above general formula (5) at 40° C. or less, preferably 25° C. or less, for about 10 minutes to about 12 hours.

Regarding synthesis of the azo pigment of the general formula (1) wherein n is 2 or more, they can be synthesized in the same manner as in the aforesaid scheme by synthesizing a starting material wherein a substitutable divalent, trivalent, or tetravalent substituent is introduced into $R_1$ to $R_2$, $R_{55}$, $R_{59}$, Z, and the like in the general formula (4) or (5).

The thus-obtained reaction product may form precipitated crystals but, in general, water or an alcoholic solvent is added to the reaction solution to thereby precipitate crystals, and the precipitated crystals can be collected by filtration. Also, an alcoholic solvent, water, or the like may be added to the reaction solution to thereby precipitate crystals, and the precipitated crystals can be collected by filtration. The crystals thus collected by filtration are washed and dried, as needed, to obtain the azo pigment represented by the general formula (1).

The pigments represented by the above-described general formula (1) are obtained as a crude azo pigment (crude) by the above-described production process. In the case of using them as the pigments of the invention, they are preferably subjected to after-treatment. As methods of the after-treatment, there are illustrated, for example, a pigment particle-controlling step such as milling treatment (e.g., solvent-salt milling, salt milling, dry milling, solvent milling, or acid pasting) or solvent heating treatment; and a surface-treating step using, for example, a resin, a surfactant, or a dispersant.

The pigment of the invention represented by the general formula (1) are preferably subjected to the solvent heating treatment and/or the solvent-salt milling as the after-treatment.

As a solvent to be used in the solvent heating treatment, there are illustrated, for example, water; aromatic hydrocarbon series solvents such as toluene and xylene; halogenated hydrocarbon series solvents such as chlorobenzene and o-dichlorobenzene; alcoholic solvents such as isopropanol and isobutanol; polar aprotic organic solvents such as N,N-dimethylformamide, N,N-dimethylacetamide, and N-methyl-2-pyrrolidone; glacial acetic acid; pyridine; and a mixture thereof. An inorganic or organic acid or base may further be added to the above-described solvents. The temperature of the solvent heating treatment varies depending upon the desired primary particle size of the pigment, but is preferably from 40 to 150° C., more preferably from 60 to 100° C. Also, the treating time is preferably from 30 minutes to 24 hours.

As the solvent-salt milling, there is illustrated, for example, the procedure wherein a crude azo pigment, an inorganic salt, and an organic solvent which does not dissolve them are placed in a kneader, and knead-milling of the mixture is conducted therein. As the above-described inorganic salt, water-soluble inorganic salts can preferably be used. For example, inorganic salts such as sodium chloride, potassium chloride, and sodium sulfate are preferably used. Also, it is more preferred to use inorganic salts having an average particle size of from 0.5 to 50 μm. The amount of the inorganic salt to be used is preferably a 3- to 20-fold amount by mass, more preferably a 5- to 15-fold amount by mass, based on the crude azo pigment. As the organic solvent, water-soluble organic solvents can preferably be used and, since the solvent becomes easily vaporizable due to an increase in temperature upon kneading, high-boiling solvents are preferred in view of safety. Examples of such organic solvents include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy) ethanol, 2-(hexyloxy)ethanol, diethylene glycol monomethyl ether, diethylene glycol monoethyl ether, diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and a mixture thereof. The amount of the water-soluble organic solvent to be used is preferably a 0.1- to 5-fold amount by mass based on the crude azo pigment. The kneading temperature is preferably from 20 to 130° C., particularly preferably from 40 to 110° C. As a kneader, there can be used, for example, a kneader and a mix muller.

[Pigment Dispersion (1)]

The pigment dispersion of the invention is characterized in that it contains at least one of the azo pigments represented by the general formula (1), the tautomers of the azo pigments, and the salts or hydrates thereof. Thus, there can be obtained a pigment dispersion having excellent coloring characteristics, fastness, and dispersion stability.

The pigment dispersion of the invention may be aqueous or non-aqueous, but is preferably an aqueous pigment dispersion. As the aqueous liquid for dispersing the pigment in the aqueous pigment dispersion of the invention, a mixture containing water as a major component and, as needed, a hydrophilic organic solvent can be used as an aqueous liquid in which the pigment is to be diepsersed.

Examples of the aforesaid hydrophilic organic solvent include alcohols such as methanol, ethanol, propanol, isopropanol, butanol, isobutanol, sec-butanol, t-butanol, pentanol, hexanol, cyclohexanol, and benzyl alcohol; polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol; glycol derivatives such as ethylene glycol monomethyl ether, ethylene glycol monoehyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, and ethylene glycol monophenyl ether; amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine; formamide; N,N-dimethylformamide; N,N-dimethylacetamide; dimethylsulfoxide; sulfolane; 2-pyrrolidone; N-methyl-2-pyrrolidone; N-vinyl-2-pyrolidone; 2-oxazolidone; 1,3-dimethyl-2-imidazolidinone; acetonitrile; and acetone.

Further, the aqueous pigment dispersion of the invention may contain an aqueous resin. As the aqueous resin, there are illustrated water-soluble resins which dissolve in water, there are illustrated water-dispersible resins which can be dispersed in water, colloidal dispersion resins, and a mixture thereof. Specific examples of the aqueous resins include acryl series resins, styrene-acryl series resins, polyester resins, polyamide resins, polyurethane resins, and fluorine-containing resins.

In the case where the aqueous pigment dispersion in the invention contains the aqueous resin, the content is not particularly limited. For example, the content may be from 0 to 100% by mass based on the pigment.

Further, in order to improve dispersibility of the pigment and quality of image, a surfactant and a dispersant may be used. As the surfactant, there are illustrated anionic, nonionic, cationic, and amphoteric surfactants, and any of them may be used. However, anionic or nonionic surfactants are preferred to use.

In the case where the aqueous pigment dispersion in the invention contains the surfactant, the content is not particularly limited. For example, the content may be from 0 to 100% by mass based on the pigment.

Examples of the anionic surfactants include aliphatic acid salts, alkyl sulfate salts, alkylbenzene sulfonate salts, alkylnaphthalene sulfonate salts, dialkyl sulfosuccinate salts, alkyldiaryl ether disulfonate salts, alkyl phosphate salts, polyoxyethylene alkyl ether sulfate salts, polyoxyethylene alkylaryl ether sulfate salts, naphthalenesulfonic acid-formalin condensates, polyoxyethylene alkyl phosphate salts, glycerol borate fatty acid esters, and polyoxyethylene glycerol fatty acid esters.

Examples of the nonionic surfactants include polyoxyethylene alkyl ethers, polyoxyethylene alkylaryl ethers, polyoxyethylene-oxypropylene block copolymers, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkylamines, fluorine-containing surfactants, and silicon-containing surfactants.

The non-aqueous pigment dispersion of the invention comprises the pigment represented by the foregoing general formula (1) dispersed in a non-aqueous vehicle. Examples of resin to be used as the non-aqueous vehicle include petroleum resin, casein, shellac, rosin-modified maleic acid resin, rosin-modified phenol resin, nitrocellulose, cellulose acetate butyrate, cyclized rubber, chlorinated rubber, oxidized rubber, rubber hydrochloride, phenol resin, alkyd resin, polyester resin, unsaturated polyester resin, amino resin, epoxy resin, vinyl resin, vinyl chloride, vinyl chloride-vinyl acetate copolymer, acryl resin, methacryl resin, polyurethane resin, silicone resin, fluorine-containing resin, drying oil, synthetic drying oil, styrene/maleic acid resin, styrene/acryl resin, polyamide resin, polyimide resin, benzoguanamine resin, melamine resin, urea resin, chlorinated polypropylene, butyral resin, and vinylidene chloride resin. It is also possible to use a photo-curable resin as the non-aqueous vehicle.

Examples of the solvents to be used in the non-aqueous vehicles include aromatic solvents such as toluene, xylene, and methoxybenzene; acetate series solvents such as ethyl acetate, butyl acetate, propylene glycol monomethyl ether acetate, and propylene glycol monoethyl ether acetate; propionate series solvents such as ethoxyethyl propionate; alcoholic solvents such as methanol and ethanol; ether series solvents such as butyl cellosolve, propylene glycol monomethyl ether, diethylene glycol ethyl ether, and diethylene glycol dimethyl ether; ketone series solvents such as methyl ethyl ketone, methyl isobutyl ketone, and cyclohexanone; aliphatic hydrocarbon series solvents such as hexane; nitrogen-containing compound series solvents such as N,N-dimethylformamide, γ-butyrolactam, N-methyl-2-pyrrolidone, aniline, and pyridine; lactone series solvents such as γ-butyrolactone; and carbamic acid esters such as a 48:52 mixture of methyl carbamate and ethyl carbamate.

[Coloring Composition]

The coloring composition of the invention means a coloring composition containing at least one kind of the azo pigments of the invention. The coloring composition of the invention can contain a medium and, in the case where a solvent is used as the medium, the composition is particularly appropriate as an ink for inkjet recording. The coloring composition of the invention can be prepared by using an oleophilic medium or an aqueous medium as the medium and dispersing the azo pigment of the invention in the medium. Preferably, the aqueous medium is used as the medium. The coloring composition of the invention includes an ink composition excluding the medium. The coloring composition of the invention may contain, as needed, other additives within the range of not spoiling the advantages of the invention. Examples of the other additives include known additives (described in JP-A-2003-306623) such as a drying-preventing agent (a wetting agent), an antifading agent, an emulsion stabilizer, a penetration accelerator, an ultraviolet ray absorbent, an antiseptic, an antifungal agent, a pH-adjusting agent, a surface tension-adjusting agent, an anti-foaming agent, a viscosity-adjusting agent, a dispersant, a dispersion stabilizer, a rust inhibitor, and a chelating agent. In the case of water-soluble ink compositions, these various additives are added directly to the ink solution. In the case of oil-soluble ink compositions, it is general to add to a dispersion after preparing the azo pigment dispersion, but they may be added to an oil phase or an aqueous phase upon preparation.

[Ink for Inkjet Recording]

Next, the ink of the invention for inkjet recording will be described below.

The ink of the invention for inkjet recording (hereinafter also referred to as "ink") contains the pigment dispersion described above, and is preferably prepared by mixing with a water-soluble solvent, water, or the like. However, in the case where no particular problems are involved, the pigment dispersion of the invention described above may be used as such.

In view of hue, color density, saturation, and transparency of an image formed on a recording medium, the content of the pigment dispersion in the ink of the invention is in the range of preferably from 1 to 100% by mass, particularly preferably from 3 to 20% by mass, most preferably from 3 to 10% by mass.

The azo pigment or azo compound of the invention is contained in an amount of preferably from 0.1 part by mass to 20 parts by mass, more preferably from 0.2 part by mass to 10 parts by mass, still more preferably from 1 to 10 parts by mass, in 100 parts by mass of the ink of the invention. Also, the ink of the invention may further contain other pigment in combination with the pigment of the invention. In the case of using two or more kinds of pigments in combination, the total amount of the pigments is preferably within the above-described range.

The ink of the invention can be used for forming a full-color image as well as a mono-color image. In order to form the full-color image, a magenta tone ink, a cyan tone ink, and a yellow tone ink can be used and, further, a black tone ink can be used for adjusting tone.

Further, in the ink of the invention may be used other pigments in addition to the azo pigment of the invention. As yellow pigments to be applied, there are illustrated, for example, C.I.P.Y.74, C.I.P.Y.128, C.I.P.Y.155, and C.I.P.Y.213. As magenta pigments to be applied, there are illustrated C.I.P.V.19 and C.I.P.R.122. As cyan pigments to be applied, there are illustrated C.I. P.B.15:3 and C.I.P.B.15:4. Apart from these pigments, any pigment may be used as each color pigment. As a black color material, there can be illustrated a dispersion of carbon black as well as disazo, trisazo, and tetrazo pigments.

As the water-soluble solvents to be used in the ink of the invention for inkjet recording, polyhydric alcohols, polyhydric alcohol derivatives, nitrogen-containing solvents, alcohols, and sulfur-containing solvents are used.

Specific examples of the polyhydric alcohols include ethylene glycol, diethylene glycol, propylene glycol, butylenes glycol, triethylene glycol, 1,5-pentanediol, 1,2,6-hexanetriol, and glycerin.

Examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and an ethylene oxide adduct of diglycerin.

Also, examples of the nitrogen-containing solvents include pyrrolidone, N-methyl-2-pyrrolidone, cyclohexylpyrrolidone, and triethanolamine, examples of the alcohols include ethanol, isopropyl alcohol, butyl alcohol, and benzyl alcohol, and examples of the sulfur-containing solvents include thiodiethanol, thiodiglycerol, sulfolane, and dimethylsulfoxide. Besides, propylene carbonate and ethylene carbonate may also be used.

The water-soluble solvents to be used in the invention may be used alone or as a mixture of two or more thereof. As to the content of the water-soluble solvent, the solvent is used in an amount of from 1% by mass to 60% by mass, preferably from 5% by mass to 40% by mass, based on the total weight of the ink. In case when the content of the water-soluble solvent in the entire ink is less than 1% by mass, there might result an insufficient optical density in some cases whereas, in case when the content exceeds 60% by mass, there might result unstable jet properties of the ink liquid in some cases due to the large viscosity of the liquid.

The preferred physical properties of the ink of the invention are as follows. The surface tension of the ink is preferably from 20 mN/m to 60 mN/m, more preferably from 20 mN/m to 45 mN/m, still more preferably from 25 mN/m to 35 mN/m. In case when the surface tension is less than 20 mN/m, the liquid might, in some cases, overflow onto the nozzle surface of the recording head, thus normal printing not being performed. On the other hand, in case when the surface tension exceeds 60 mN/m, the ink might, in some cases, slowly penetrate into the recording medium, thus the drying time becoming longer.

Additionally, the above-described surface tension is measured under the environment of 23° C. and 55% RH by using a Wilhelmy surface tension balance as is the same described hereinbefore.

The viscosity of the ink is preferably from 1.2 mPa·s to 8.0 mPa·s, more preferably from 1.5 mPa·s to 6.0 mPa·s, still more preferably from 1.8 mPa·s to 4.5 mPa·s. In case when the viscosity is more than 8.0 mPa·s, ink ejection properties might, in some cases, be deteriorated. On the other hand, in case when the viscosity is less than 1.2 mPa·s, the long-term ejection properties might be deteriorated in some cases.

Additionally, the viscosity (including that to be described hereinafter) is measured by using a rotational viscometer Rheomat 115 (manufactured by Contraves Co.) at 23° C. and a shear rate of $1,400$ $s^{-1}$.

In addition to the above-mentioned individual components, water is added to the ink within an amount of providing the preferred surface tension and viscosity described above. The addition amount of water is not particularly limited, but is in the range of preferably from 10% by mass to 99% by mass, more preferably from 30% by mass to 80% by mass, based on the total weight of the entire ink.

Further, for the purpose of controlling characteristic properties such as improvement of ejection properties, there can be used, as needed, polyethyleneimine, polyamines, polyvinylpyrolidone, polyethylene glycol, cellulose derivatives such as ethyl cellulose and carboxymethyl cellulose, polysaccharides and derivatives thereof, water-soluble polymers, polymer emulsions such as an acrylic polymer emulsion, a polyurethane series emulsion, and a hydrophilic latex, hydrophilic polymer gels, cyclodextrin, macrocyclic amines, dendrimers, crown ethers, urea and derivatives thereof, acetamide, silicone surfactants, and fluorine-containing surfactants.

Also, in order to adjust electrical conductivity and pH, there can be used compounds of alkali metals such as potassium hydroxide, sodium hydroxide, and lithium hydroxide; nitrogen-containing compounds such as ammonium hydroxide, triethanolamine, diethanolamine, ethanolamine, and 2-amino-2-methyl-1-propanol; compounds of alkaline earth metals such as calcium hydroxide; acids such as sulfuric acid, hydrochloric acid, and nitric acid; and salts between a strong acid and a weak alkali, such as ammonium sulfate.

Besides, pH buffers, antioxidants, antifungal agents, viscosity-adjusting agents, electrically conductive agents, ultraviolet ray absorbents, and the like may also be added as needed.

[Coloring Composition for Color Filter]

The coloring composition of the invention for color filter contains an azo pigment represented by the foregoing general formula (1). The coloring composition of the invention for color filter (hereinafter also referred to merely as "coloring composition") means a coloring composition containing at least one azo pigment represented by the general formula (1).

The coloring composition of the invention preferably further contains a polymerizable compound and a solvent.

Also, in producing the coloring composition of the invention, the azo pigment obtained in the above-described manner may be blended as such or may be blended as a pigment dispersion wherein the pigment is dispersed in a solvent. The azo pigment exhibits excellent coloring characteristics, durability, dispersion stability, light fastness, and weatherability in the form of a pigment dispersion, thus such pigment dispersion being preferred.

The amount of the azo pigment represented by the general formula (1) (in the case where other pigments are used in combination, the total amount of the pigments used) in the coloring composition of the invention is preferably from 0.01 to 2 parts by mass, particularly preferably from 0.1 to 1 part by mass, per 1 part by mass of a polymerizable compound.

[Polymerizable Compounds]

The polymerizable compound may properly be selected in consideration of the production process of a color filter and as the polymerizable compound, there are illustrated photo-sensitive compounds and/or thermosetting compounds, with photo-sensitive compounds being particularly preferred.

The photo-sensitive compound is selected from at least one of photo-polymerizable resins, photo-polymerizable monomers, and photo-polymerizable oligomers, with those which have an ethylenically unsaturated bond being preferred. It suffices for the coloring composition for color filter to contain a material which becomes a resin in a cured state, and a composition containing only components which are not resinous in an uncured state is included.

As the photo-polymerizable compounds, photo-polymerizable monomers, and photo-polymerizable oligomers, there are illustrated, for example, (meth)acrylates such as 2-hydroxyethyl (meth)acrylate, 2-hydroxypropyl (meth)acrylate, 2-ethylhexyl (meth)acrylate, ethylene glycol di(meth)acrylate, diethylene glycol di(meth)acrylate, triethylene glycol di(meth)acrylate, polyethylene glycol di(meth)acrylate, pentaerythritol di(meth)acrylate, dipentaerythritol tetra(meth)acrylate, dipentaerythritol hexa(meth)acrylate, bisphenol A type epoxy di(meth)acrylate, bisphenol F type epoxy di(meth)acrylate, and bisphenol fluorene type epoxy di(meth)acrylate. Also, there are illustrated vinyl resins such as acrylic acid (co)polymers, (meth)acrylic acid (co)polymers, maleic acid (co)polymers, and resins having an ethylenic double bond in its side chain such as polyethylene oxide, polyvinylpyrrolidone, polyamide, polyurethane, polyether, polyester, etc. These may be used alone or in combination of two or more thereof. The content of the polymerizable compound is from 20 to 90% by mass, preferably from 40 to 80% by mass.

The blending ratio of the polymerizable compound is preferably from 40 to 95% by mass, more preferably from 50 to 90% by mass, based on all the solid components in the composition for color filter. The composition may contain, as needed, other resins or the like. In such cases, the sum amount of the polymerizable and the other resins is preferably within the above-described range. Additionally, all solid components means those components which remain as solid components after drying and curing, with no solvents being contained and monomers being contained.

[Photo-polymerization Initiators]

In the case of using a photo-sensitive compound as the photo-polymerizable compound, a photo-polymerization initiator is used together with a monomer and/or an oligomer of the light-sensitive compound. As the photo-polymerization initiator, there are illustrated one or more members selected from among benzophenone derivatives, acetophenone derivatives, benzoin derivatives, benzoin ether derivatives, thioxanthone derivatives, anthraquinone derivatives, naphthoquinone derivatives, and triazine derivatives. Known photo-sensitizers may further be used together with these photo-polymerization initiators.

As the thermosetting resins, there are illustrated, for example, melamine resin, urea resin, alkyd resin, epoxy resin, phenol resin, cyclopentadione resin, etc.

Additionally, in this specification and claims, the terms "photo-sensitive resins" and "thermosetting resins" mean not only cured resins but polymerizable monomers or oligomers as well.

Together with the above-described photo-sensitive resins and/or thermosetting resins, those other resins which are generally used in an ink, such as binder resins having an acid group, and acryl resins and urethane resins may be used.

[Solvent]

The pigment dispersion may be an aqueous system or a non-aqueous system, which depends on the production process of the color filter. For example, in a photo lithography process, a non-aqueous system is preferred and, in an inkjet process, either system may be employed.

As a solvent for the coloring composition of the invention, there are illustrated fatty acid esters such as ethyl acetate, butyl acetate, ethylene glycol monomethyl ether acetate, and propylene glycol monomethyl ether acetate; ketones such as acetone, methyl ethyl ketone, methyl isobutyl ketone, cyclohexanone, and diacetone alcohol; aromatic compounds such as benzene, toluene, and xylene; alcohols such as methanol, ethanol, n-propanol, isopropanol, and n-butanol; glycols such as ethylene glycol, diethylene glycol; triethylene glycol, tetraethylene glycol, polyethylene glycol, propylene glycol, dipropylene glycol, tripropylene glycol, polypropylene glycol, trimethylene glycol, and hexanetriol; glycerin; alkylene glycol monoalkyl ethers such as ethylene glycol monomethyl ether, ethylene glycol monoethyl ether, diethylene glycol monomethyl ether, diethylene glycol monoethyl ether, propylene glycol monomethyl ether, and propylene glycol monoethyl ether; alkylene glycol dialkyl ethers such as triethylene glycol dimethyl ether, triethylene glycol diethyl ether, tetraethylene glycol dimethyl ether, and tetraethylene glycol diethyl ether; ethers such as tetrahydrofuran, dioxane, and diethylene glycol diethyl ether; alkanolamines such as monoethanolamine, diethanolamine, and triethanolamine; nitrogen-containing polar organic solvents such as N,N-dimethylformamide, N,N-dimethylacetamide, N-methyl-2-pyrrolidone, 2-pyrrolidone, and 1,3-dimethyl-2-imidazolidinone; water; and the like.

Of these solvents, water-soluble solvents may be mixed with water to use as an aqueous medium. Also, two or more solvents selected from the above-described solvents excluding water may be mixed to use as an oily medium.

An azo pigment in the form of a pigment dispersion has better light fastness and weatherability in comparison with an azo pigment not in the form of a pigment dispersion.

The coloring composition of the invention may be a composition containing two or more of the azo pigments represented by the general formula (1). The coloring composition of the invention for color filter preferably contains an azo pigment represented by the following general formula (2).

[Chem. 62]

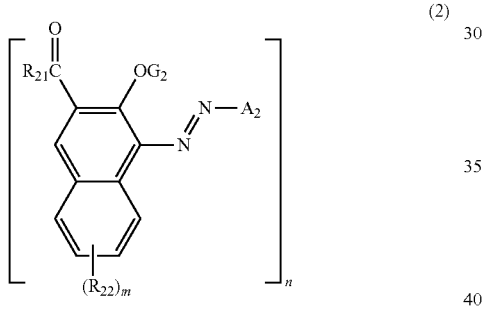

(2)

(In the general formula (2), $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, and $R_{22}$ represents a substituent. $A_2$ represents the following general formulae (A-1) to (A-32). m and n are the same as those defined with respect to the general formula (1). When n=2, the formula represents a dimer formed through $R_{21}$, $R_{22}$, $G_2$, or $A_2$. When n=3, the formula represents a trimer formed through $R_{21}$, $R_{22}$, $G_2$, or $A_2$. When n=4, the formula represents a tetramer formed through $R_{21}$, $R_{22}$, $G_2$, or $A_2$. The general formula (2) does not contain an ionic hydrophilic group.)

[Chem. 63]

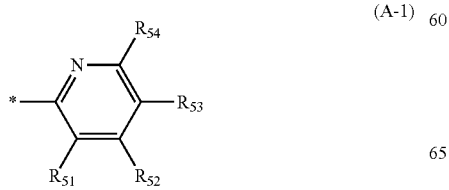 (A-1)

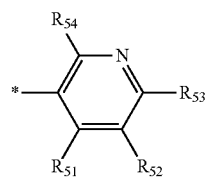 (A-2)

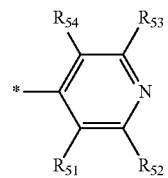 (A-3)

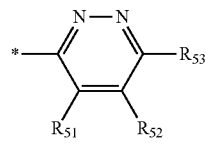 (A-4)

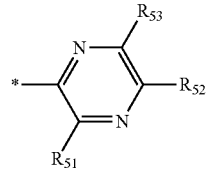 (A-5)

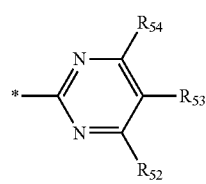 (A-6)

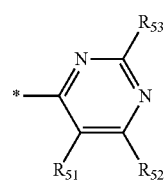 (A-7)

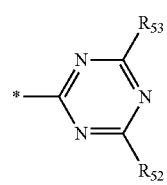 (A-8)

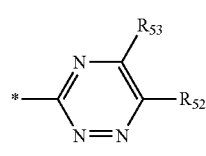 (A-9)

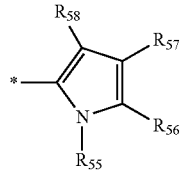 (A-10)

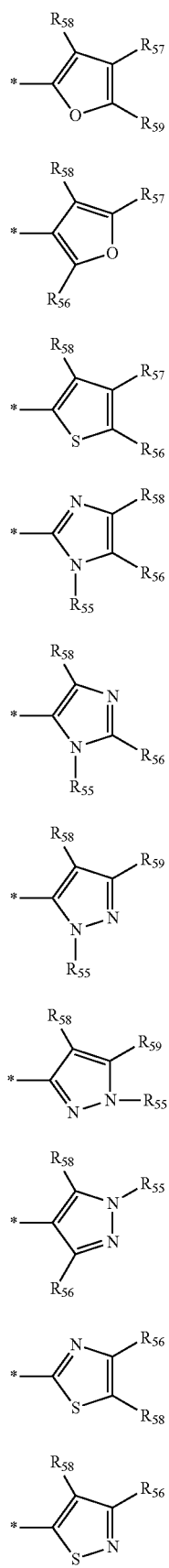
(A-11)
(A-12)
(A-13)
(A-14)
(A-15)
(A-16)
(A-17)
(A-18)
(A-19)
(A-20)
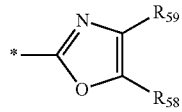 (A-21)
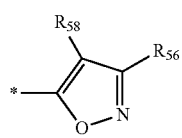 (A-22)
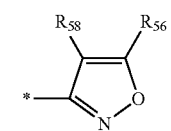 (A-23)
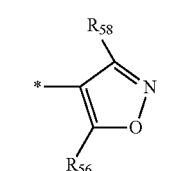 (A-24)
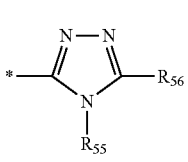 (A-25)
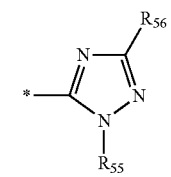 (A-26)
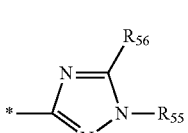 (A-27)
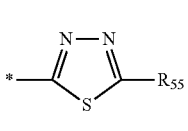 (A-28)
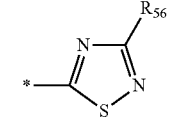 (A-29)
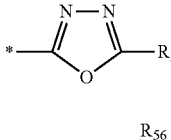 (A-30)
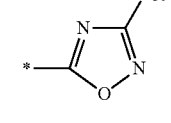 (A-31)

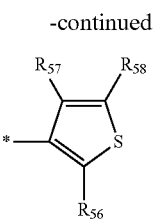
(A-32)

(In the general formulae (A-1) to (A-32), $R_{51}$ to $R_{59}$ represents a hydrogen atom or a substituent, and adjacent substituents may be connected to each other to form a 5- or 6-membered ring. * shows the point of attachment to the azo group in the general formula (2).

In the general formula (2), $A_2$ is preferably any of (A-1), (A-4) to (A-11), (A-13) to (A-17), (A-19) to (A-23), and (A-25) to (A-32).

Also, the pigment represented by the general formula (2) which is used in the coloring composition of the invention for color filter is preferably a pigment represented by the foregoing general formula (3).

Also, one or more of pigments selected from other pigments such as azo series pigments, disazo series pigments, benzimidazolone series pigments, condensed azo series pigments, azo lake series pigments, anthraquinone series pigments, diketopyrrolopyrrole series pigments, quinacridone series pigments, isoindoline series pigments, isoindolinone series pigments, perinone series pigments, and perylene series pigments, or derivatives thereof may be used together with the azo pigments represented by the general formula (1) within the range of not inhibiting the objects of the invention.

Pigments which may be used together in the invention are not particularly limited. Specifically, there are illustrated compounds whose classification in Color index (C.I.; published by The Society of Dyers and Colourists) are pigments, that is, those which have the following color index (C.I.) number: yellow pigments such as C.I. pigment yellow 1, C.I. pigment yellow 3, C.I. pigment yellow 12, C.I. pigment yellow 13, C.I. pigment yellow 83, C.I. pigment yellow 138, C.I. pigment yellow 139, C.I. pigment yellow 150, C.I. pigment yellow 180, and C.I. pigment yellow 185; red pigments such as C.I. pigment red 1, C.I. pigment red 2, C.I. pigment red 3, C.I. pigment red 177, and C.I. pigment red 254; blue pigments such as C.I. pigment blue 15, C.I. pigment blue 15:3, C.I. pigment blue 15:4, and C.I. pigment blue 15:6; green pigments such as C.I. pigment green 7 and C.I. pigment green 36; and C.I. pigment violet 23 and C.I. pigment violet 23:19.

Also, as specific examples of the aforesaid inorganic pigment, there are illustrated titanium oxide, barium sulfate, calcium carbonate, zinc white, lead sulfate, yellow lead, zinc yellow, iron oxide red (red iron oxide (III)), cadmium red, ultramarine, deep blue, chromium oxide green, cobalt green, amber, titanium black, synthetic iron black, carbon black, etc. In the invention, these pigments may be used alone or as a mixture of two or more kinds thereof.

In the case of using other pigments than the azo pigments represented by the general formula (1) together therewith, the content thereof is preferably 50% by mass or less, particularly preferably 20% by mass or less, based on the mass of the total pigments in the coloring composition.

Additionally, in this specification, the term "azo pigment represented by the general formula (1)" is used to mean not only one kind of azo pigment represented by the general formula (1) but also a combination of two or more of azo pigments represented by the general formula (1) and a combination of an azo pigment represented by the general formula (1) and other pigment.

[Pigment Dispersion (2)]

The pigment dispersion is preferably obtained by dispersing the azo pigment and the aqueous or non-aqueous medium using a dispersing apparatus. As the dispersing apparatus, there can be used a simple stirrer, an impeller-stirring system, an in-line stirring system, a mill system (for example, colloid mill, ball mill, sand mill, beads mill, attritor, roll mill, jet mill, paint shaker, or agitator mill), an ultrasonic wave system, a high-pressure emulsion dispersion system (high-pressure homogenizer; specific commercially available apparatuses being Gaulin homogenizer, a microfluidizer, and DeBEE2000).

In the invention, the volume-average particle diameter of the pigment is preferably from 10 nm to 250 nm. Additionally, the term "volume-average particle diameter of the pigment" means the particle diameter of the pigment itself or, in the case where an additive such as a dispersant is adhered to the pigment particles, means the diameter of the particle with the additive being adhered thereto. In the invention, as an apparatus for measuring the volume-average particle diameter of the pigment, a particle size analyzer of Nanotrac UPA (UPA-EX150; manufactured by Nikkiso Co., Ltd.) is used. The measurement is conducted according to a predetermined measuring method placing 3 ml of a pigment dispersion in a measuring cell. Additionally, with respect to parameters to be inputted upon measurement, an ink viscosity is used as a viscosity, and a pigment density is used as a density of the pigment.

The volume-average particle diameter of the pigment is more preferably from 20 nm to 250 nm, still more preferably from 30 nm to 230 nm. In case when the volume-average particle diameter of the particles in the pigment dispersion is less than 20 nm, storage stability might not be ensured in some cases whereas, in case when the volume-average particle diameter of the particles in the pigment dispersion exceeds 250 nm, the optical density might be reduced in some cases.

The content of the pigment contained in the pigment dispersion of the invention is preferably in the range of from 1 to 35% by mass, more preferably in the range of from 2 to 25% by mass. When the content is within the above-described range, physical properties of the dispersion such as surface tension and viscosity can be adjusted with ease, thus such content being preferred.

With the azo pigments of the invention, physical properties such as solvent resistance, dispersibility, and thermal mobility are adjusted so as to be adequate for their use through substituents. Also, the azo pigments of the invention can be used in an emulsion dispersion state or, further, in a solid dispersion state depending upon the system wherein they are used.

Also, in order to well disperse the components in a short time, a dispersant may be contained in the composition.

The coloring composition in the invention for color filter preferably further contains one or more dispersants selected from among surfactants, silicone series additives, pigment series additives, silane series coupling agents, and titanium series coupling agents. These dispersants may be used in combination of two or more thereof.

The aforesaid dispersants will be described below.

The surfactants are not particularly limited as long as they have surface-active action, and there can be illustrated cationic, anionic, nonionic, and amphoteric surfactants, etc. Specific examples include anionic surfactants such as alkane sulfonate salts, straight chain alkylbenzenesulfonate salts, branched alkylbenzenesulfonate salts, alkylnaphthalenesulfonate salts, naphthalenesulfonic acid-formalin condensates, alkylsulfate salts, polyoxyethylene alkyl ether sulfate salts, alkyl phosphate salts, polyoxyethylene alkyl ether phosphate salts, and aliphatic monocarbooxylic acid salts; cationic surfactants such as alkylamine salts and quaternary amine salts; nonionic surfactants such as glycerin fatty acid esters, sorbitan fatty acid esters, polyoxyethylene alkyl ethers, polyoxyethylene alkylphenyl ethers, polyethylene glycol fatty acid esters, and polyoxyethylene sorbitan fatty acid esters; amphoteric surfactants such as alkylbetaines; and cationic, anionic, nonionic, and amphoteric high-molecular surfactants.

Specific examples of the silicone series additives include polyalkylsiloxanes, polyalkylphenylsiloxanes, polyorganosiloxanes, polydimethylsiloxane, polyorganosiloxane polyether copolymers, polyfluorosiloxanes, and organosiloxanes. These silicone series additives may be used in combination of two or more thereof.

The pigment series additives are pigment derivatives wherein a substituent such as a basic group, an acidic group, a straight chain alkyl group, a branched alkyl group, or a polyoxyethylene group is introduced to the pigment structure. As preferred pigment structures, there are illustrated monoazo series pigments, disazo series pigments, benzimidazolone series pigments, condensed azo series pigments, azo lake series pigments, anthraquinone series pigments, diketopyrrolopyrrole series pigments, quinacridone series pigments, isoindoline series pigments, isoindolinone series pigments, perinone series pigments, and perylene series pigments.

Of these pigment series additives, those wherein the above-described substituent is introduced to the azo series pigment structure have good affinity for the azo compounds represented by the general formula (1), thus being preferred.

As specific examples of the silane coupling agents, there are illustrated vinyltrimethoxysilane, vinyltriethoxysilane, lane, vinyltris(β-methoxyethoxy)silane, β-(3,4-epoxycyclohexyl)ethyltrimethoxysilane, γ-glycidoxypropyltrimethoxysilane, γ-glycidoxypropylmethyldiethoxysilane, γ-aminopropyltriethoxysilane, N-phenyl-γ-aminopropyl trimethoxysilane, γ-methacryloxypropyltrimethoxysilane, vinyltriacetoxysilane, methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, n-butyltrimethoxysilane, isobutyltrimethoxysilane, trimethylmethoxysilane, hydroxypropyltrimethoxysilane, n-hexadecyltrimethoxysilane, and n-octadecyltrimethoxysilane.

As specific examples of the titanium series coupling agents, there are illustrated isopropyltri(N-aminoethylaminoethyl) titanate and dibutoxybistriethanolamine titanate.

The amount of the above-described dispersant to be used is preferably from 0.1 to 100 parts by mass, particularly preferably from 0.5 to 80 parts by mass, per 100 parts by mass of the azo compound represented by the general formula (1), though depending upon kind of the dispersant to be used.

Methods of using the dispersant are not particularly limited, and may be conducted according to the known photolithography process of preparing a coloring composition.

The invention relates to a process of preparing a coloring composition for color filter as well. The process of preparing a coloring composition for color filter includes a step of obtaining a pigment dispersion by dispersing one or more dispersants selected from among the surfactants, silicone series additives, pigment series additives, silane series coupling agents, and titanium series coupling agents, and an azo compound represented by the general formula (1) in part of a solvent, and a step of mixing the pigment dispersion with a polymerizable compound and the rest of the solvent.

As the process of preparing a coloring composition for color filter, it is preferred to employ the process of the invention.

The invention further provides a color filter formed by using the above-described coloring composition for color filter. The color filter shows a high contrast and good light transmittance. Specifically, it shows light transmittance of preferably 85% or more, more preferably 90% or more at a wavelength of 650 nm.

For producing the color filter of the invention, any known process may be employed, and there are preferably illustrated a photolithography process and an inkjet process. The photolithography process and the inkjet process will be described in detail below.

1) Photolithography Method

In the case of forming a color filter according to photolithography method, a photo-sensitive resin is used as a polymerizable compound in the coloring composition of the invention for color filter. The photo-sensitive resin is contained in the coloring composition as a monomer and/or an oligomer together with a polymerization initiator, and is cured by irradiation with light to form a film on a transparent substrate.

As the photo-sensitive resin, a polymer or copolymer of the aforesaid polymerizable monomer having one or more ethylenic double bond within the molecule is preferably used.

As these photo-sensitive resins (polymerizable monomers), acrylates and methacrylates are particularly preferred and, specifically, there are illustrated methyl acrylate, methyl methacrylate, butyl methacrylate, butyl acrylate, pentaerythritol tetraacrylate, pentaaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, glycerol diacrylate, glycerol dimethacrylat, 1,4-butanediol diacrylate, 1,4-butanediol dimethacrylate, bisphenol A diacrylate, and bisphenol A dimethacrylate.

In the case of using the photolithography method, a binder resin having an acidic group is used in the coloring composition of the invention in addition to the aforesaid photo-sensitive resin. As the binder resin having an acidic group, there are illustrated resins having a carboxyl group, a hydroxyl group, a sulfonic acid group, or the like, with binder resins having a carboxyl group and/or a hydroxyl group being preferred.

As the above-described binder resins having an acidic group, there are preferably used copolymers between a monomer having an ethylenic double bond, such as those which are selected from acrylates, methacrylates, styrene, vinyl acetate, vinyl chloride, N-vinylpyrrolidone, and acrylamide, and a monomer having an acidic group and an ethylenic double bond, such as those which are selected from acrylic acid, methacrylic acid, p-styrenecarboxylic acid, p-styrene-sulfonic acid, p-hydroxystyrene, and maleic anhydride.

The binder resin having an acidic group is used in an amount of preferably from 0.5 to 4 parts by mass, particularly preferably from 1 to 3 parts by mass, per 1 part by mass of the photo-sensitive resin (polymerizable monomer).

As a solvent to be used in the coloring composition for the photolithography method, there are illustrated one or more oily media selected from fatty acid esters, ketones, aromatic compounds, alcohols, glycols, glycerin, alkylene glycol monoalkyl ethers, alkylene glycol dialkyl ethers, ethers, and nitrogen-containing polar organic solvents.

The amount of these solvents to be used is preferably a 3- to 30-fold amount by mass, particularly preferably a 4- to 15-fold amount by mass, based on the whole mass of components other than the solvent in the coloring composition.

Also, the coloring composition in the invention for use in the photolithography method may contain, as needed, known additives in addition to the aforesaid components, such as a wetting agent, an antifading agent, an emulsion stabilizer, an ultraviolet ray absorbent, an antiseptic, an antifungal agent, a pH-adjusting agent, a surface tension-adjusting agent, an anti-foaming agent, a viscosity-adjusting agent, a dispersion stabilizer, a rust inhibitor, and a chelating agent (described in JP-A-2003-306623). These various additives may be added to the oil phase or the aqueous phase upon preparation.

The coloring composition of the invention for color filter can be prepared by the process including a step of uniformly dispersing and dispersing the azo compound represented by the general formula (1), the polymerizable compound, a solvent, and other various additives using an apparatus such as a beads mill, a ball mill, a sand mill, a two-roll mill, a three-roll mill, a homogenizer, a kneader, or a vibration dispersing apparatus; and a step of adjusting the viscosity using the aforesaid solvent or the like.

As a method for forming a color filter on a substrate by using the coloring composition of the invention for color filter, a known photolithography method may be employed. For example, a color filter is obtained by a process including a step of uniformly coating the coloring composition of the invention on a display substrate according to a known method such as a spraying method, a bar-coating method, a roll-coating method, or a spin-coating method; a step of removing the solvent in the ink by heating; a step of exposing a color filter pattern on the display substrate using a high-pressure mercury lamp or the like; an alkali-developing step; a washing step; and a baking step.

As a developing solution for use in the process of producing a color filter of the invention, any one can be employed that dissolves the composition of the invention but does not dissolve the radiation-irradiated portion. Specifically, a combination of various organic solvents or an alkaline aqueous solution can be used.

As the organic solvent, there are illustrated those which have been described hereinbefore and are to be used upon preparation of the composition of the invention.

As the alkaline aqueous solution, there are used, for example, alkaline aqueous solutions containing dissolved therein 0.001 to 10% by mass, preferably 0.01 to 1% by mass, of an alkaline compound such as sodium hydroxide, potassium hydroxide, sodium carbonate, sodium silicate, sodium metasilicate, aqueous ammonia, ethylamine, diethylamine, dimethylethanolamine, tetramethylammonium hydroxide, tetraethylammonium hydroxide, choline, pyrrole, piperidine, or 1,8-diazobicyclo-[5.4.0]-7-undecene. Additionally, in the case of using such developing solution comprising an alkaline aqueous solution, water washing is generally conducted after development.

2) Inkjet Method

In the case of forming a color filter by employing an inkjet method, the polymerizable compound in the coloring composition of the invention for color filter is not particularly limited, and any conventionally known one which has been used in an ink for inkjet system may be used. A monomer of a photo-sensitive resin and/or a thermosetting resin is preferably used.

As these photo-sensitive resins, there are illustrated acryl resins, methacryl resins, and epoxy resins, with acryl resins and methacryl resins being preferably used. The acryl resins and the methacryl resins are preferably those which are obtained by using a combination of a photo-polymerizable monomer selected from among acrylates, methacrylates, urethane acrylate, urethane methacrylate, acrylamide, methacrylamide, alkyl acrylates, benzyl methacrylate, benzyl acrylate, aminoalkyl methacrylate, etc. and a photo-polymerization initiator selected from among benzophenone derivatives, acetophenone derivatives, benzoin derivatives, benzoin ether derivatives, thioxanthone derivatives, anthraquinone derivatives, naphthoquinone derivatives, and triazine derivatives. Also, in addition to the above-described photo-polymerizable monomers, photo-polymerizable monomers having a hydrophilic group, such as acrylic acid, methacrylic acid, maleic acid, and vinyl acetate may further be added.

As the thermosetting resins, there are illustrated, for example, melamine resin, urea resin, alkyd resin, epoxy resin, phenol resin, and cyclopentadiene resin.

In the case of employing the inkjet process, the solvent to be used in the coloring composition may be an oily medium or an aqueous medium, with an aqueous medium being more preferably used. As the aqueous medium, water or a mixed solvent of water and a water-soluble organic solvent is used, with a mixed solvent of water and a water-soluble organic solvent being preferred. Also, it is preferred to use deionized water.

The oily medium to be used in the above-described coloring composition is not particularly limited; but there can be used, for example, those which have been illustrated as solvents for the coloring composition for use in photolithography.

Solvents to be used in the aqueous medium are selected from among those alcohols, ketones, ethers, glycols, glycerin, alkylene glycol monoalkyl ethers, alkylene glycol dialkyl ethers, alkanolamines, nitrogen-containing polar organic solvents, etc. which are soluble in water. These water-soluble organic solvents may be used alone or in combination of two or more thereof.

The amount of these solvents to be used is not particularly limited, but it is preferred to properly adjust the amount so that the viscosity of the coloring composition at room temperature becomes 20 mPa·s or less, preferably 10 mPa·s or less.

The coloring composition of the invention for inkjet use can be prepared by a process including a step of dispersing and mixing components as is the same with the coloring composition for use in photolithography process. Upon dispersing, a dispersant may be contained, as needed, as is the same with the case of photolithography.

Also, the coloring composition in the invention for inkjet use may contain, as needed, known additives in addition to the aforesaid components, such as a wetting agent, an antifading agent, an emulsion stabilizer, an ultraviolet ray absorbent, an antiseptic, an antifungal agent, a pH-adjusting agent, a surface tension-adjusting agent, an anti-foaming agent, a viscosity-adjusting agent, and a dispersion stabilizer.

Methods for forming a color filter using the coloring composition obtained as described above are not particularly limited, and any known method of forming a color filter according to the inkjet system may be employed. For example, a color filter can be formed by a method including a step of forming a predetermined color filter pattern in a droplet state on a substrate, a step of drying this, and a step of heat treatment, irradiation with light, or both of them to cure the color filter pattern on the substrate, thus forming a film.

Although description has been made hereinbefore with respect to photolithography method and inkjet method, the color filter of the invention may be obtained by other method.

In the case of employing other color filter-forming methods (for example, various printing methods such as an offset printing method) than the above-described methods, coloring compositions for color filter and resulting color filters fall within the scope of the invention as long as the coloring composition contains the aforesaid polymerizable compound and the solvent and contains the azo pigment represented by the general formula (1) as a coloring material.

For example, components such as polymerizable compounds, solvents, and additives and formulation upon formation of a color filter may be selected according to conventional examples, and are not limited only to those which have been illustrated with respect to the above-described photolithography method and inkjet method.

The color filter obtained as described above forms pixels together with color filter patterns of G (green) and B (blue) according to a known method. Such filter has an extremely high transparency and excellent spectral characteristics and can provide a liquid crystal display which can display a distinct image with less polarization extinction. Also, use of a device having formed therein this color filter can provide a camera module having good spectral characteristics.

The color filter of the invention can be used in a liquid crystal display element or solid state imaging devices such as CCDs and CMOSs, and is appropriate for CCD elements or CMOS elements having high resolution exceeding 1,000,000 pixels.

EXAMPLES

The invention will be specifically described by reference to Examples, but the invention is not limited only to the Examples. Additionally, in the following Examples, "%" and "parts" mean "% by mass" and "parts by mass", respectively, unless otherwise specified.

Synthesis Example 1

Synthesis of Specific Compound D-1

Specific compound example D-1 is synthesized according to the following route.

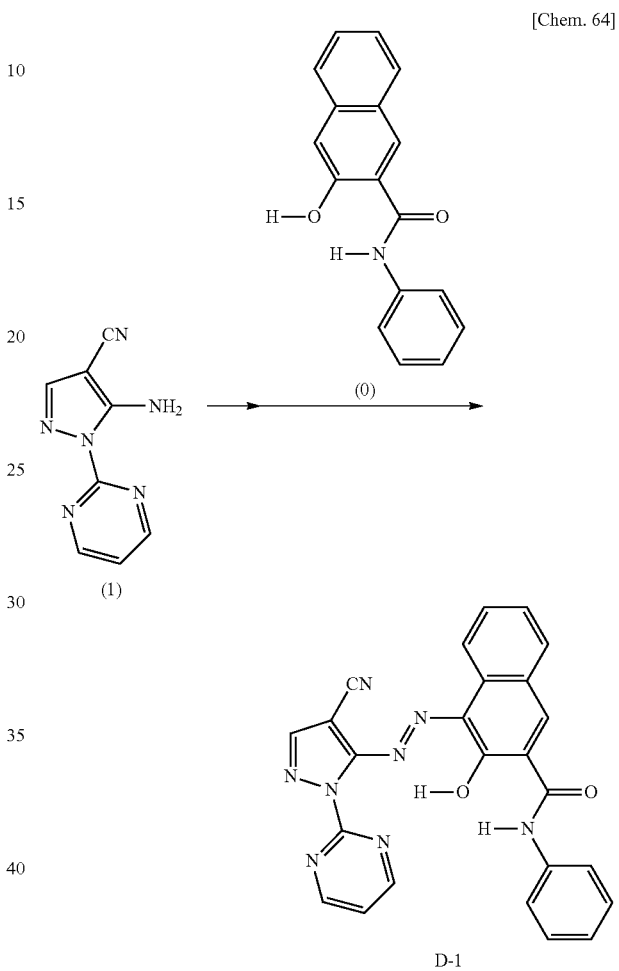

Synthesis of D-1

1.0 g of compound (1) is added to 10 ml of phosphoric acid (Wako Pure Chemical Industries, Ltd.; special grade reagent; purity: 85%; hereinafter the same) to dissolve. This solution is ice-cooled to keep the temperature to −5 to 0° C., and 0.38 g of sodium nitrite is added thereto, followed by stirring for 1 hour to obtain a diazonium salt solution. Separately, 25 ml of acetonitrile is added to 1.30 g of compound (0) and, under stirring, the aforesaid diazonium salt solution is added thereto at 8° C. or lower. Simultaneously with completion of the addition, the ice bath is removed, and stirring is continued for further 3 hours. 50 ml of acetonitrile is added to the reaction solution, and the resulting mixture is stirred for 30 minutes. Crystals precipitated are collected by filtration, and spray-washed with 30 ml of acetonitrile. The thus-obtained crystals are added, without drying, to 100 ml of water, and a solution prepared by dissolving 0.5 g of sodium hydrogencarbonate in 30 ml of water is added thereto, followed by stirring at 20 to 25° C. for 30 minutes. Crystals precipitated are collected by filtration, and sufficiently spray-washed with water. The thus-obtained crystals are added, without drying, to 50 ml of dimethylacetamide, followed by stirring for 30 minutes at 100° C.

After stirring for 30 minutes at room temperature, crystals precipitated are collected by filtration, and spray-washed with 30 ml of dimethylacetamide. The thus-obtained crystals are added, without drying, to 50 ml of dimethylacetamide, 25 ml of water is gradually dropwise added thereto, and the mixture is stirred at 80° C. for 1 hour and, further, at room temperature for 30 minutes. Crystals precipitated are collected by filtration, and spray-washed with 20 ml of dimethylacetamide/water=2/1 and 20 ml of methanol. The thus-obtained crystals are dried to obtain 1.2 g of compound D-1 of the invention. Yield: 52%.

Infrared absorption chart is shown in FIG. 1.

Synthesis Example 2

Synthesis of Specific Compound D-33

Specific compound example D-33 is synthesized according to the following route.

[Chem. 65]

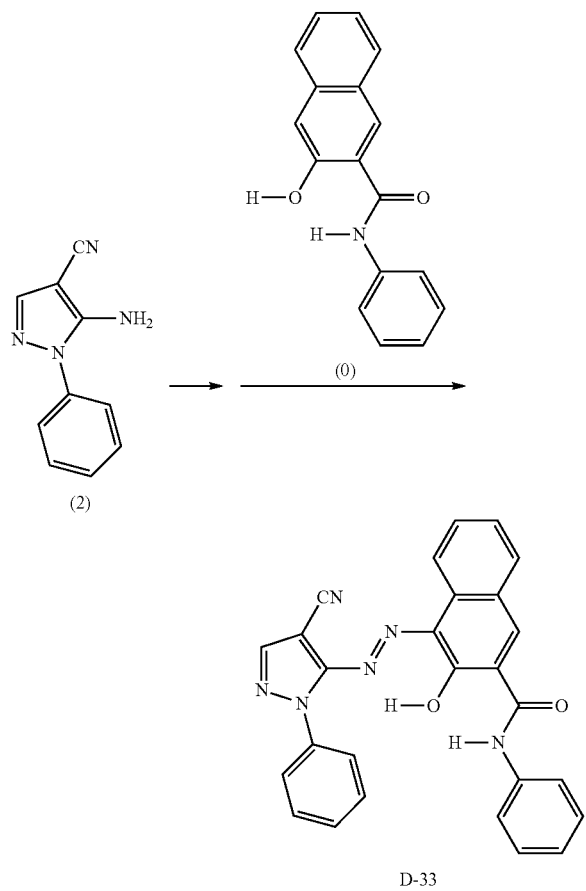

Synthesis of D-33

1.0 g of compound (2) is added to 10 ml of phosphoric acid, and is heated to 30° C. to dissolve. This solution is ice-cooled to keep the temperature to 0 to 5° C., and 0.38 g of sodium nitrite is added thereto, followed by stirring for 1.5 hours to obtain a diazonium salt solution. This diazonium salt solution is dropwise added to a solution of 1.4 g of compound (0) in 5 ml of dimethylacetamide while keeping the temperature at 5 to 10° C., followed by stirring for 1 hour while keeping the temperature at 5 to 10° C. Thereafter, the ice bath is removed, and stirring is continued for further 0.5 hour. 50 ml of ethyl acetate is added to the reaction solution, and the resulting mixture is heated at 80° C. to completely dissolve. To the reaction solution is added 50 ml of hexane, followed by stirring at 80° C. for 20 minutes, then at room temperature for 40 minutes. Crystals precipitated are collected by filtration, and spray-washed with 50 ml of hexane. To the thus-obtained crystals are added, without drying, 200 ml of water and 0.1 ml of saturated sodium hydrogencarbonate to neutralize. 100 ml of acetonitrile is added to the crystals, followed by stirring at 80° C. for 3 hours, then at room temperature for 1 hour. Crystals precipitated are collected by filtration, and spray-washed with 50 ml of acetonitrile. The thus-obtained crystals are dried to obtain 0.51 g of compound D-33 of the invention. Yield: 21%.

$\lambda_{max}$: 504 nm; $\epsilon$: 1.59×10$^4$ (CHCl$_3$)

Figure 2:
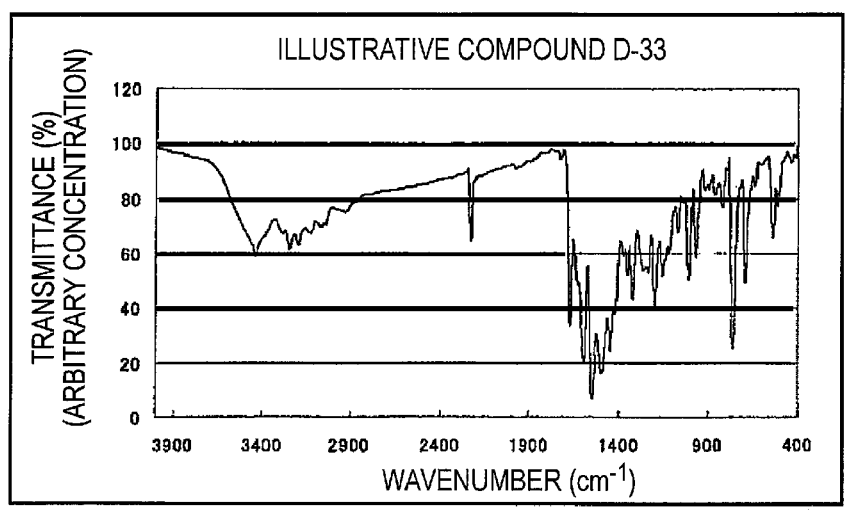
[FIG. 2] Figure of an infrared absorption spectrum of a specific illustrative compound D-33 synthesized according to Synthesis Example 2.

Infrared absorption chart is shown in FIG. 2.

Synthesis Example 3

Synthesis of Specific Compound D-20

Specific compound example D-20 is synthesized according to the following route.

[Chem. 66]

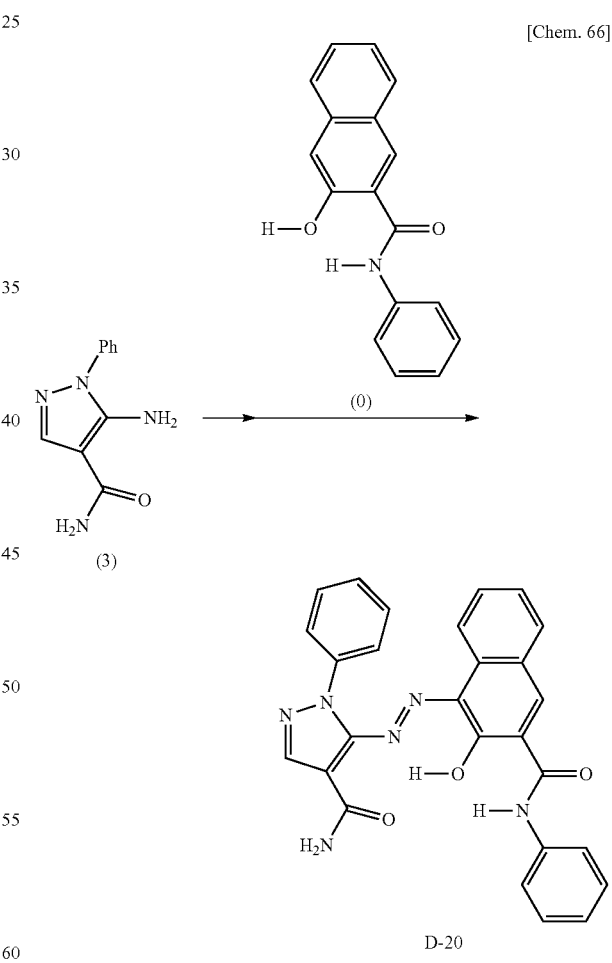

Synthesis of D-20

1.0 g of compound (3) is added to 10 ml of phosphoric acid, and is heated to 30° C. to dissolve. This solution is ice-cooled to keep the temperature to 0 to 5° C., and 0.35 g of sodium nitrite is added thereto, followed by stirring for 2 hours to obtain a diazonium salt solution. This diazonium salt solution is dropwise added to a solution of 1.3 g of compound (0) in 5 ml of dimethylacetamide while keeping the temperature at 5 to 10° C., followed by stirring for 20 minutes while keeping the temperature at 5 to 10° C., then for further 20 minutes with removing the ice bath. 100 ml of dimethylacetamide is added to the reaction solution, and the resulting mixture is stirred at 40° C. for 20 minutes. To the reaction solution is added 100 ml of acetonitrile, followed by stirring at room temperature for 10 minutes. Crystals precipitated are collected by filtration, and spray-washed with 50 ml of acetonitrile. To the thus-obtained crystals are added, without drying, 200 ml of water and 0.1 ml of saturated sodium hydrogencarbonate to neutralize, and 30 ml of dimethylacetamide/water=1/1 is added thereto, followed by stirring for 45 minutes at an internal temperature of 80° C. Then, the mixture is stirred under air-cooling, and crystals precipitated are collected by filtration, and spray-washed with 10 ml of dimethylacetamide/water=1/1, then spray-washed with 20 ml of water. The thus-obtained crystals are dried to obtain 0.49 g of compound D-20 of the invention. Yield: 21%. $\lambda_{max}$: 493 nm; $\epsilon$: 1.93×10$^4$ (CHCl$_3$)

Figure 3:
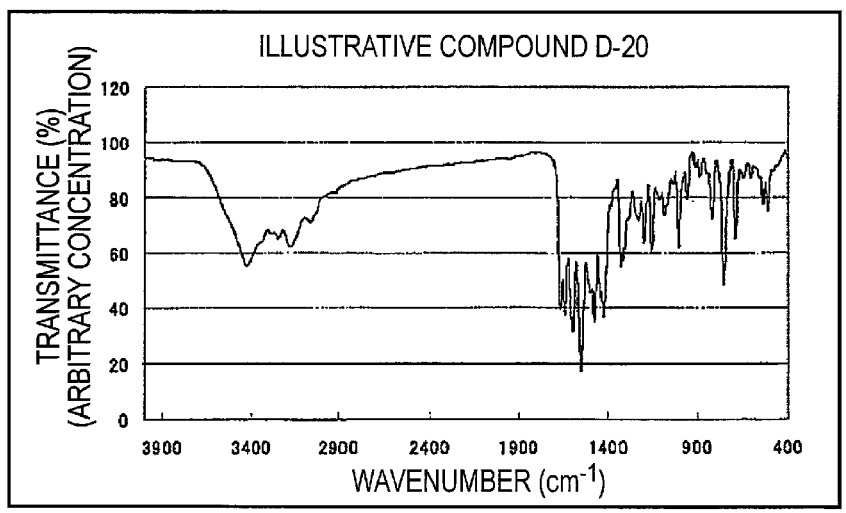
[FIG. 3] Figure of an infrared absorption spectrum of a specific illustrative compound D-20 synthesized according to Synthesis Example 3.

Infrared absorption chart is shown in FIG. 3.

Synthesis Example 4

Synthesis of Specific Compound D-22

Specific compound example D-22 is synthesized according to the following route.

[Chem. 67]

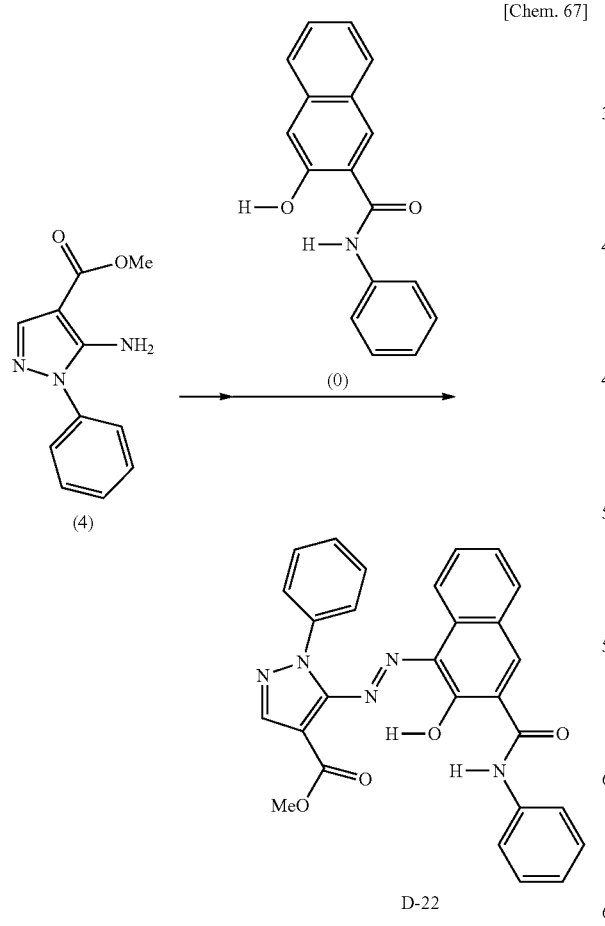

Synthesis of D-22

4.5 g of compound (4) is added to 45 ml of phosphoric acid, and is heated to 30° C. to dissolve. This solution is ice-cooled to keep the temperature to 0 to 5° C., and 1.47 g of sodium nitrite is added thereto, followed by stirring for 1 hour to obtain a diazonium salt solution. This diazonium salt solution is dropwise added to a solution of 4.5 g of compound (0) in 70 ml of dimethylacetamide while keeping the temperature at 5 to 10° C., followed by stirring for 30 minutes while keeping the temperature at 5 to 10° C., then for further 1 hour with removing the ice bath. 200 ml of water is added to the reaction solution. Crystals precipitated are collected by filtration, and spray-washed with 200 ml of water. To the thus-obtained crystals are added 200 ml of acetonitrile, followed by stirring at 80° C. for 2 hours. Thereafter, the mixture is stirred at room temperature for 2 hours, then crystals precipitated are collected by filtration. To the crystals is added 0.1 ml of saturated sodium hydrogencarbonate to neutralize, and 30 ml of dimethylacetamide/water=1/1 is added thereto, followed by stirring for 45 minutes at an internal temperature of 80° C. Then, the mixture is stirred under air-cooling for 1 hour, and crystals precipitated are collected by filtration, and spray-washed with 10 ml of dimethylacetamide/water=1/1, then spray-washed with 20 ml of water. The thus-obtained crystals are dried to obtain 6.9 g of compound D-22 of the invention. Yield: 82%.

$\lambda_{max}$: 494 nm; $\epsilon$: 1.91×10$^4$ (CHCl$_3$)

Figure 4:
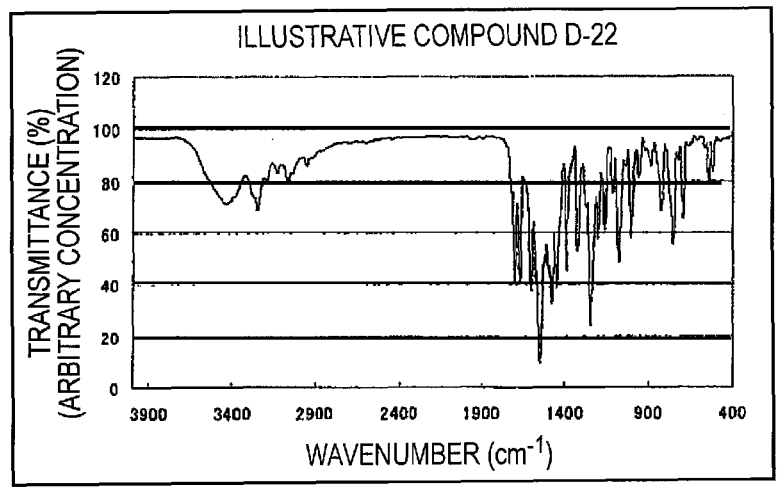
[FIG. 4] Figure of an infrared absorption spectrum of a specific illustrative compound D-22 synthesized according to Synthesis Example 4.
Figure 5:
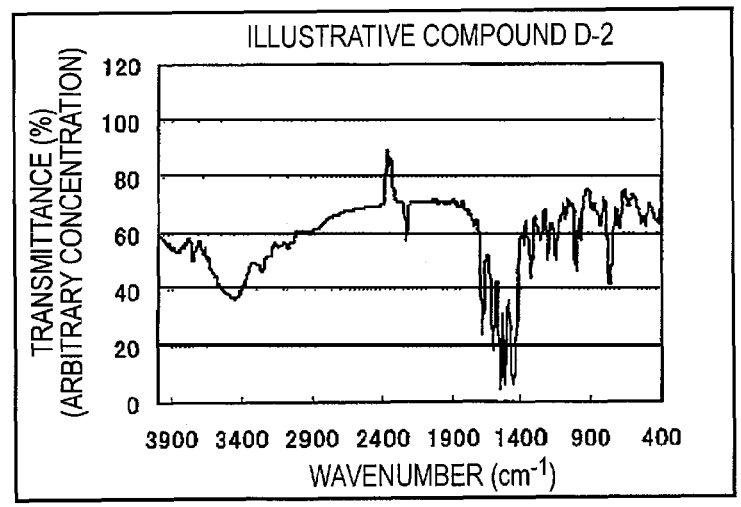
[FIG. 5] Figure of an infrared absorption spectrum of a specific illustrative compound D-2.
Figure 6:
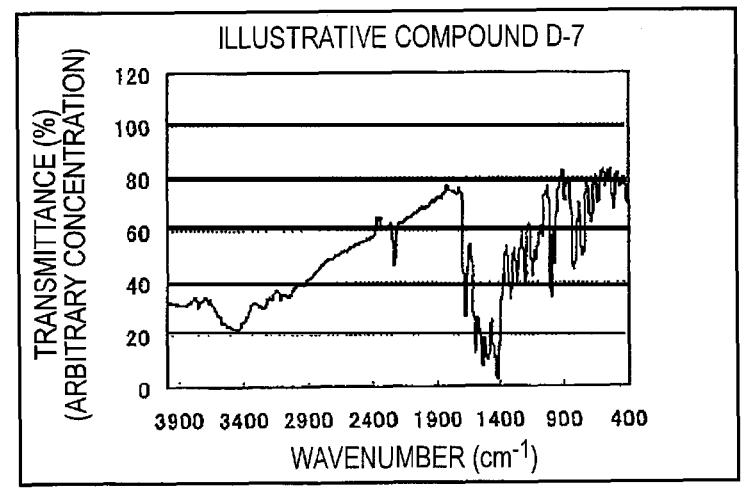
[FIG. 6] Figure of an infrared absorption spectrum of a specific illustrative compound D-7.
Figure 7:
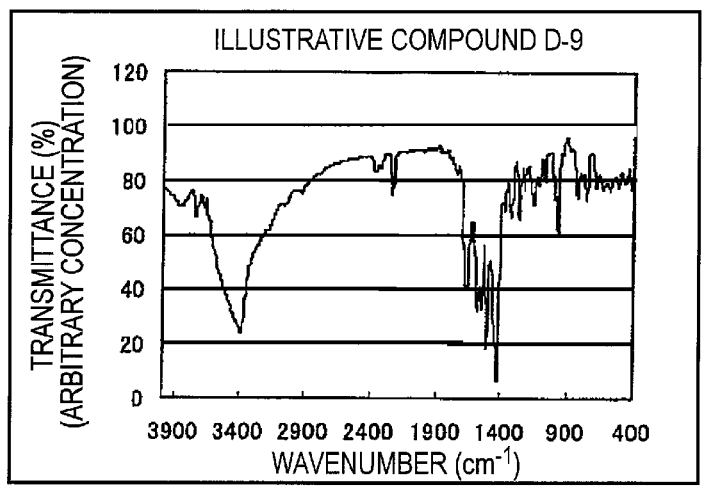
[FIG. 7] Figure of an infrared absorption spectrum of a specific illustrative compound D-9.
Figure 8:
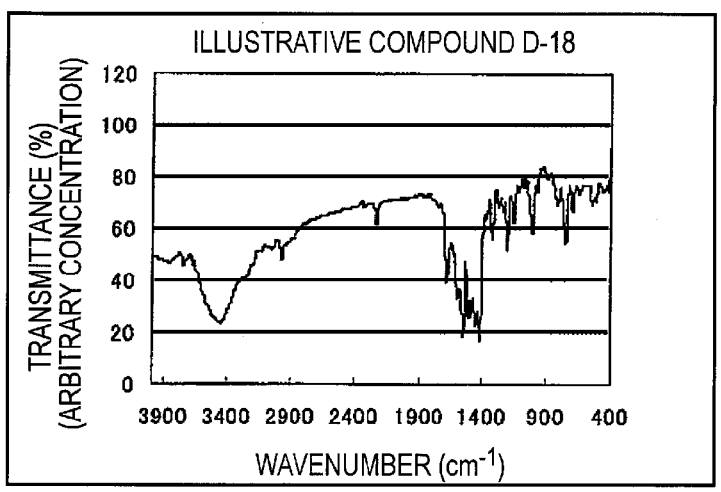
[FIG. 8] Figure of an infrared absorption spectrum of a specific illustrative compound D-18.
Figure 9:
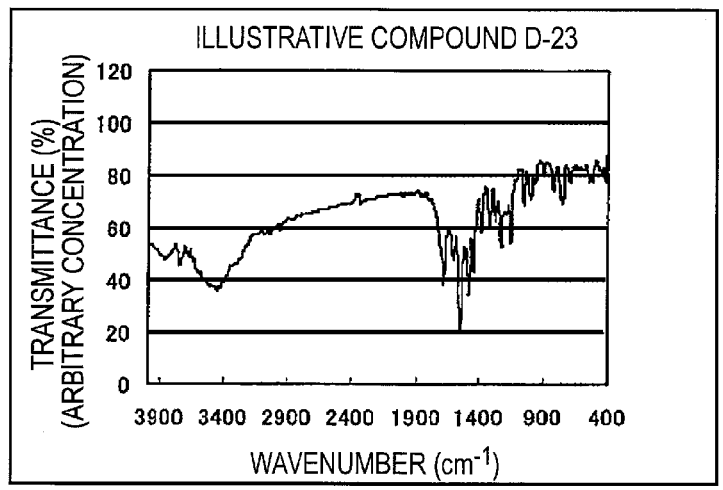
[FIG. 9] Figure of an infrared absorption spectrum of a specific illustrative compound D-23.
Figure 10:
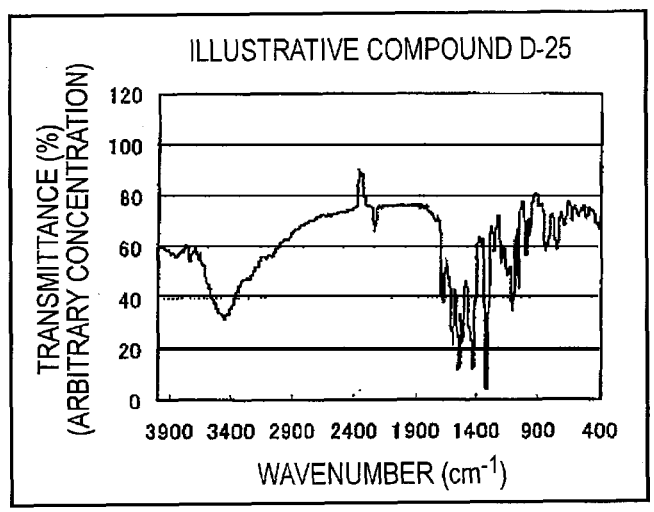
[FIG. 10] Figure of an infrared absorption spectrum of a specific illustrative compound D-25.
Figure 11:
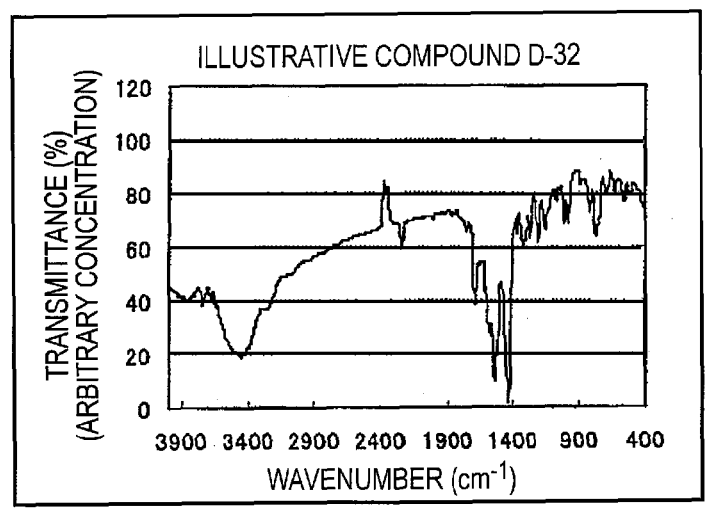
[FIG. 11] Figure of an infrared absorption spectrum of a specific illustrative compound D-32.
Figure 12:
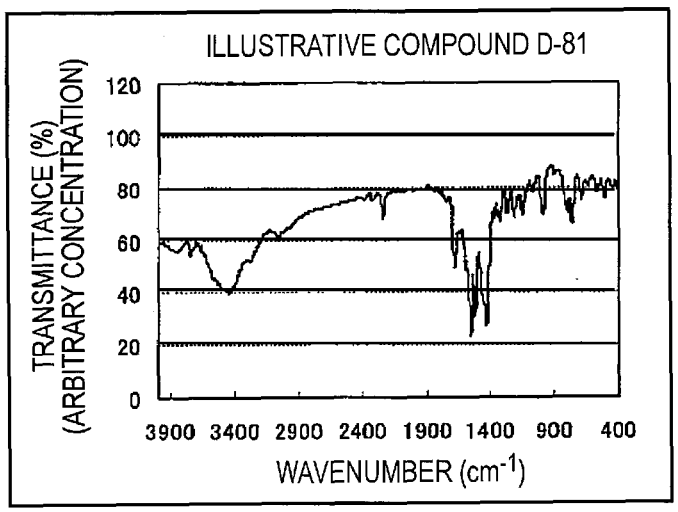
[FIG. 12] Figure of an infrared absorption spectrum of a specific illustrative compound D-81.
Figure 13:
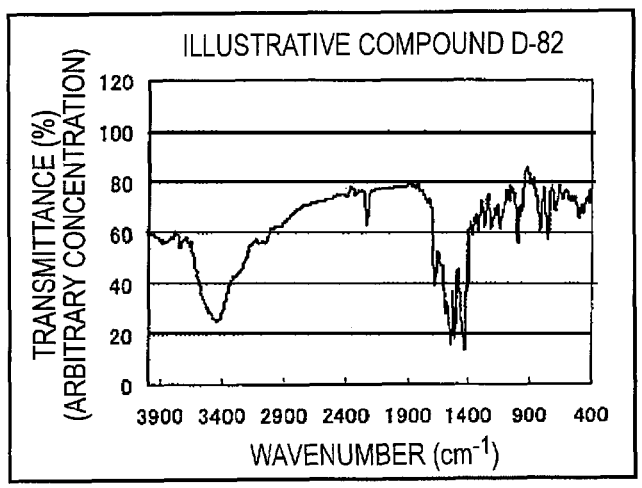
[FIG. 13] Figure of an infrared absorption spectrum of a specific illustrative compound D-82.
Figure 14:
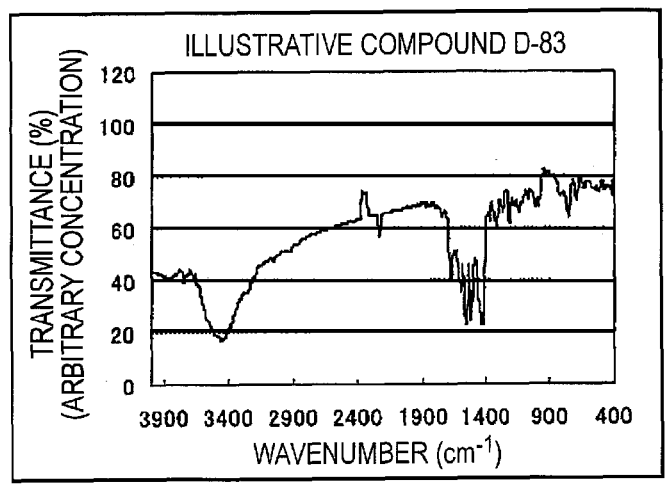
[FIG. 14] Figure of an infrared absorption spectrum of a specific illustrative compound D-83.
Figure 15:
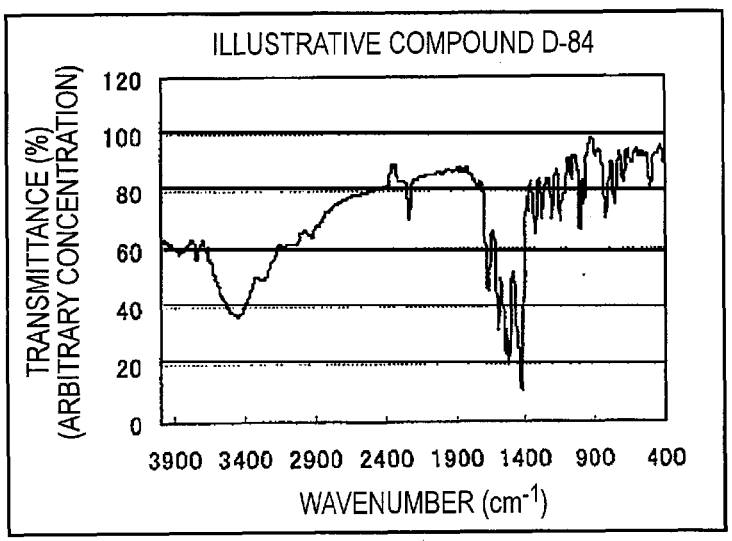
[FIG. 15] Figure of an infrared absorption spectrum of a specific illustrative compound D-84.
Figure 16:
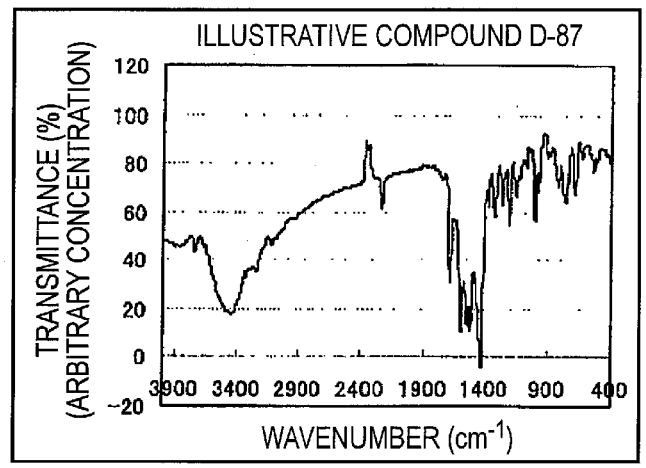
[FIG. 16] Figure of an infrared absorption spectrum of a specific illustrative compound D-87.
Figure 17:
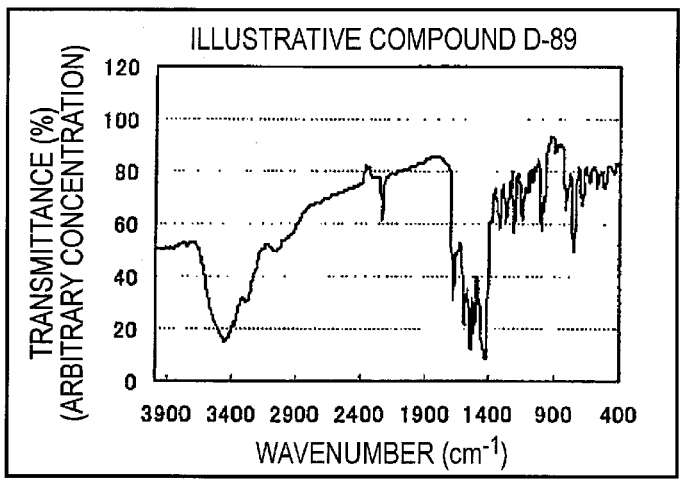
[FIG. 17] Figure of an infrared absorption spectrum of a specific illustrative compound D-89.
Figure 18:
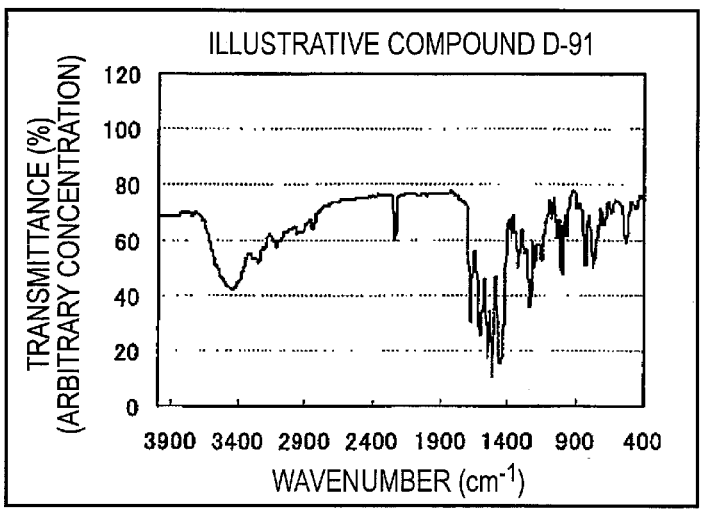
[FIG. 18] Figure of an infrared absorption spectrum of a specific illustrative compound D-91.
Figure 19:
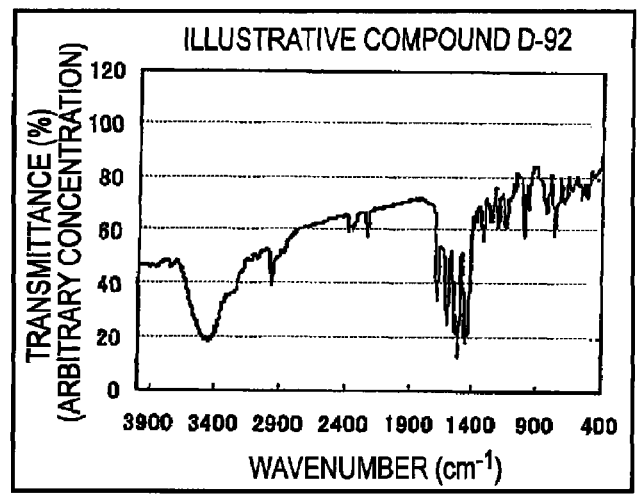
[FIG. 19] Figure of an infrared absorption spectrum of a specific illustrative compound D-92.
Figure 20:
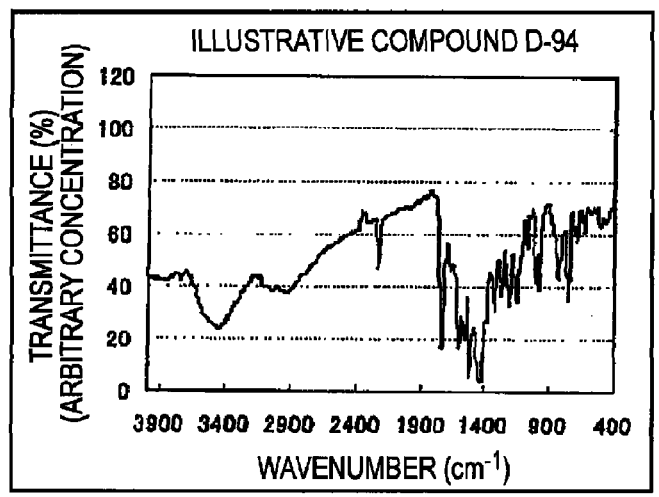
[FIG. 20] Figure of an infrared absorption spectrum of a specific illustrative compound D-94.
Figure 21:
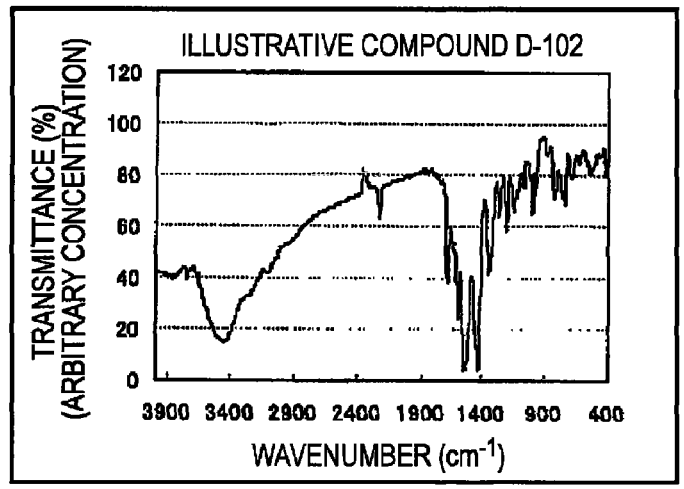
[FIG. 21] Figure of an infrared absorption spectrum of a specific illustrative compound D-102.
Figure 22:
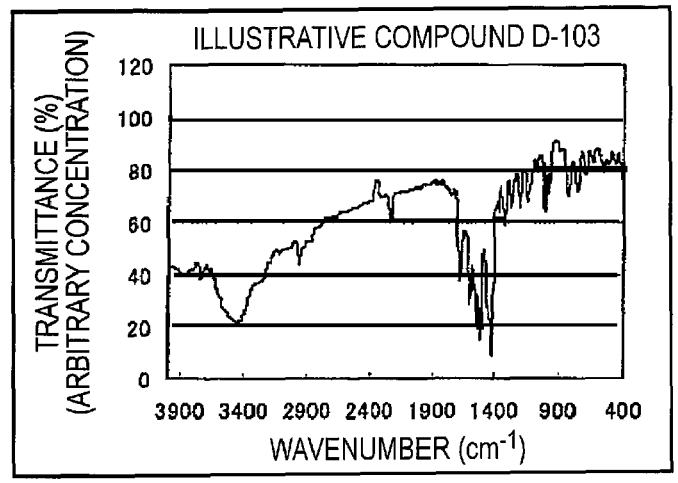
[FIG. 22] Figure of an infrared absorption spectrum of a specific illustrative compound D-103.
Figure 23:
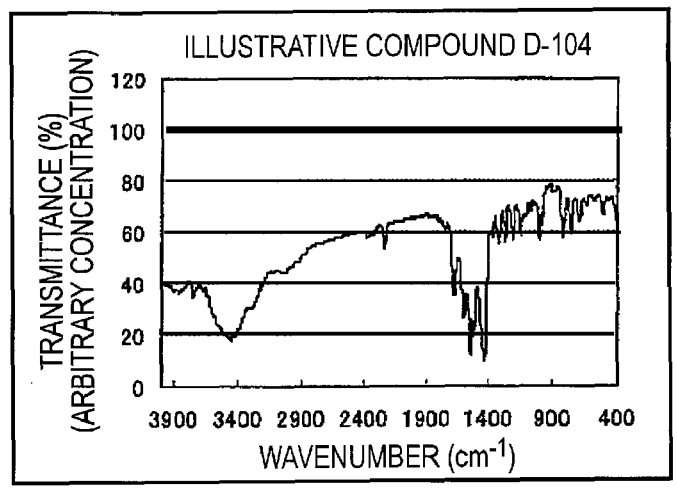
[FIG. 23] Figure of an infrared absorption spectrum of a specific illustrative compound D-104.
Figure 24:
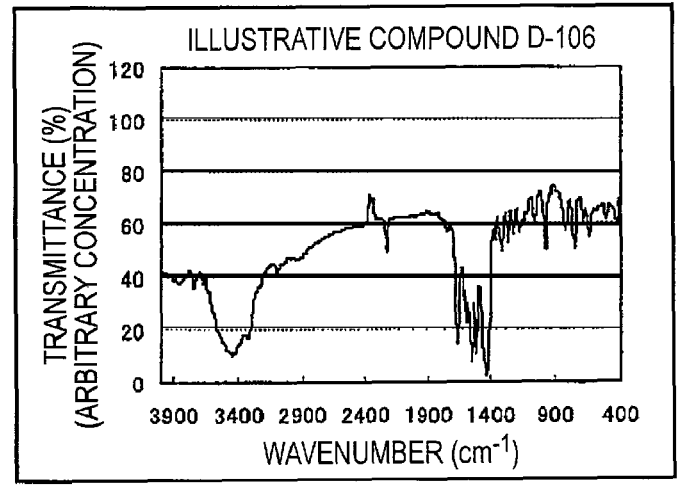
[FIG. 24] Figure of an infrared absorption spectrum of a specific illustrative compound D-106.
Figure 25:
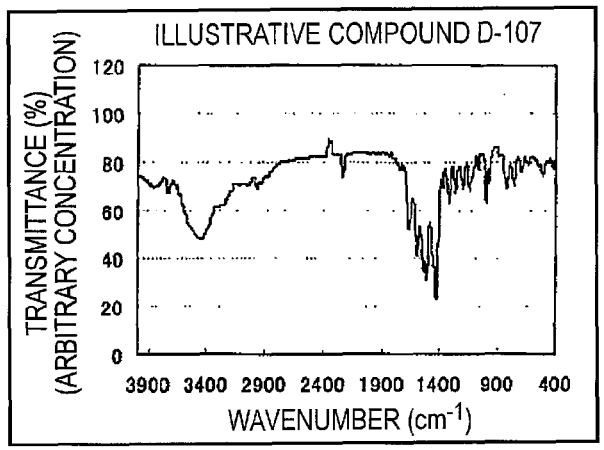
[FIG. 25] Figure of an infrared absorption spectrum of a specific illustrative compound D-107.
Figure 26:
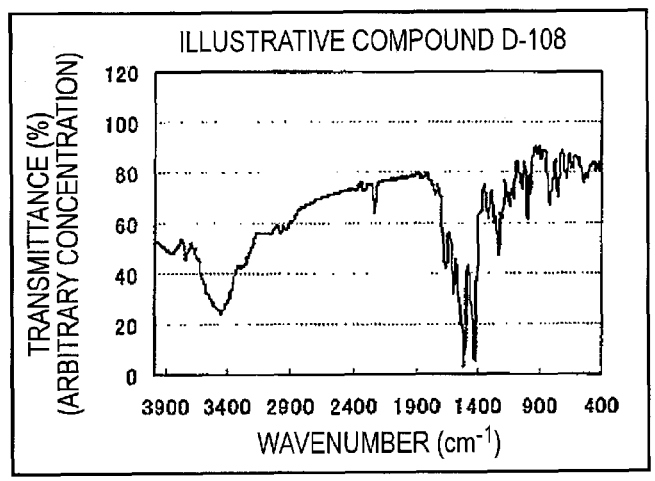
[FIG. 26] Figure of an infrared absorption spectrum of a specific illustrative compound D-108.
Figure 27:
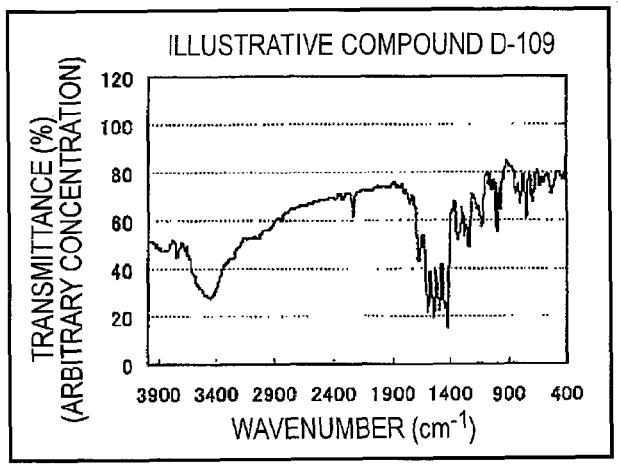
[FIG. 27] Figure of an infrared absorption spectrum of a specific illustrative compound D-109.
Figure 28:
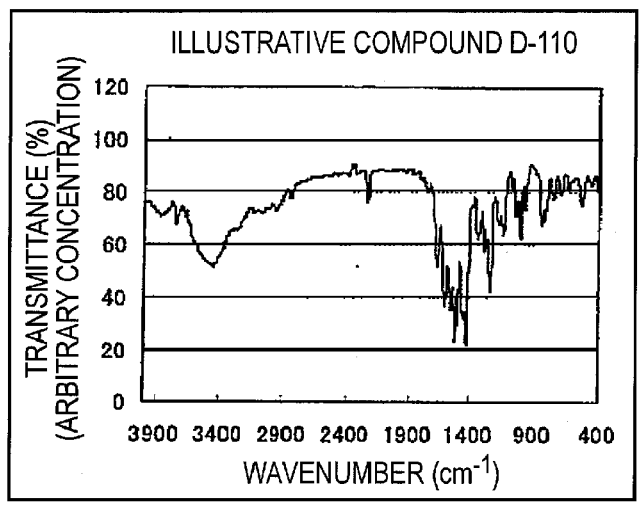
[FIG. 28] Figure of an infrared absorption spectrum of a specific illustrative compound D-110.
Figure 29:
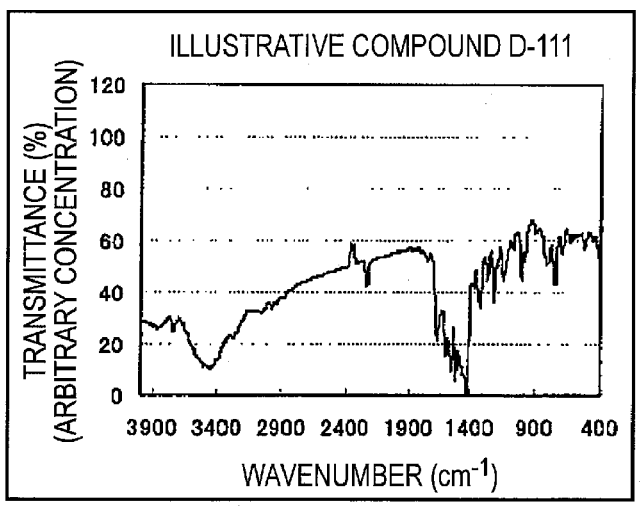
[FIG. 29] Figure of an infrared absorption spectrum of a specific illustrative compound D-111.
Figure 30:
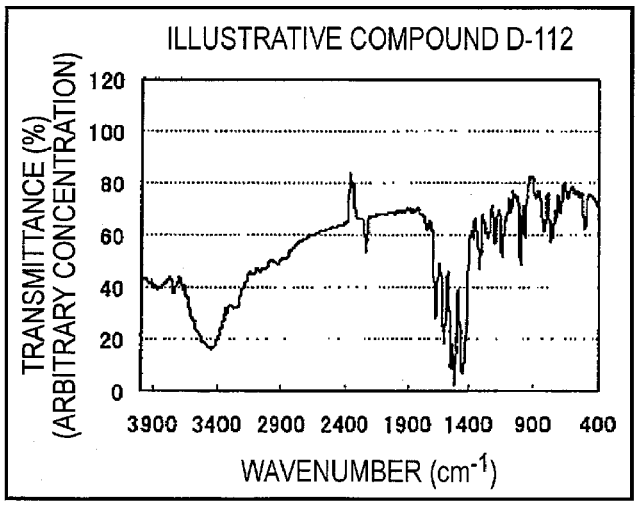
[FIG. 30] Figure of an infrared absorption spectrum of a specific illustrative compound D-112.
Figure 31:
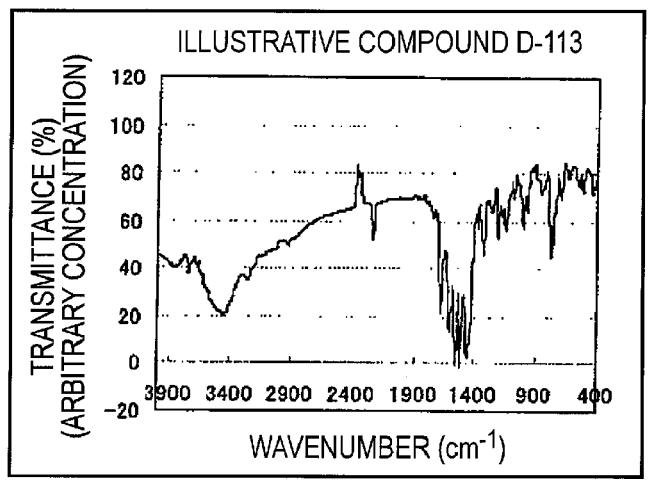
[FIG. 31] Figure of an infrared absorption spectrum of a specific illustrative compound D-113.
Figure 32:
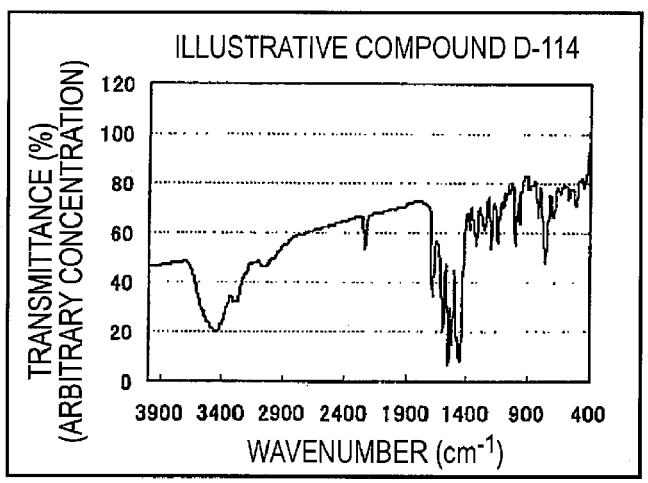
[FIG. 32] Figure of an infrared absorption spectrum of a specific illustrative compound D-114.
Figure 33:
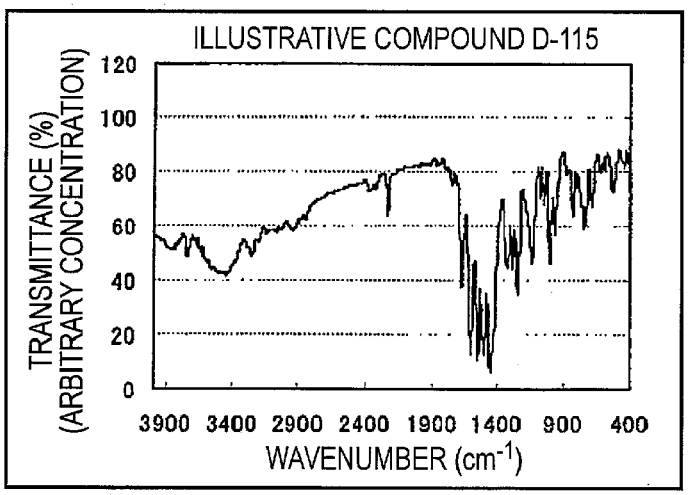
[FIG. 33] Figure of an infrared absorption spectrum of a specific illustrative compound D-115.
Figure 34:
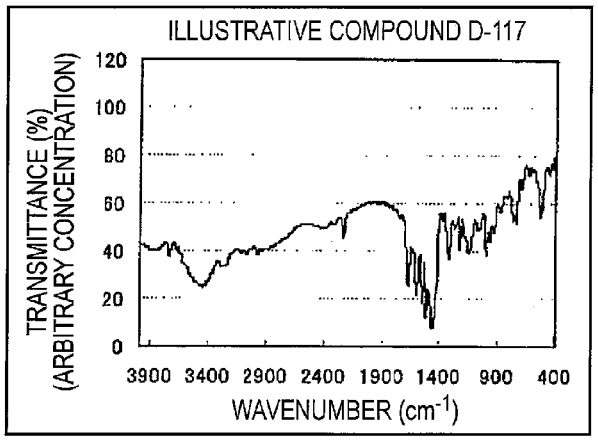
[FIG. 34] Figure of an infrared absorption spectrum of a specific illustrative compound D-117.
Figure 35:
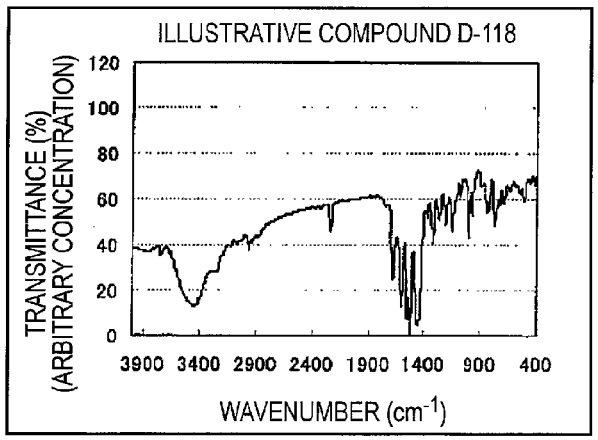
[FIG. 35] Figure of an infrared absorption spectrum of a specific illustrative compound D-118.
Figure 36:
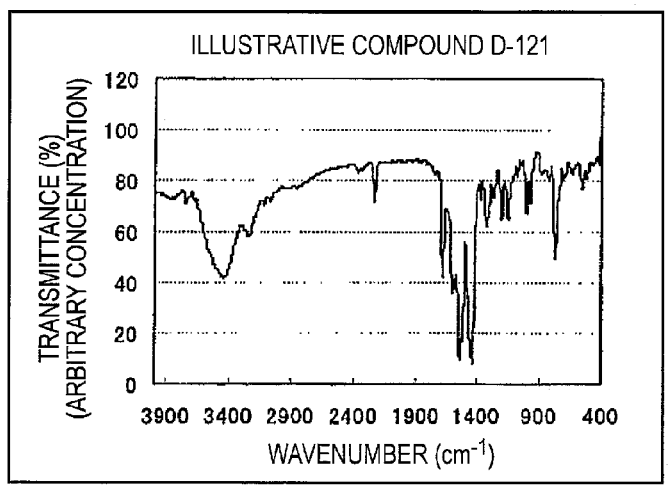
[FIG. 36] Figure of an infrared absorption spectrum of a specific illustrative compound D-121.
Figure 37:
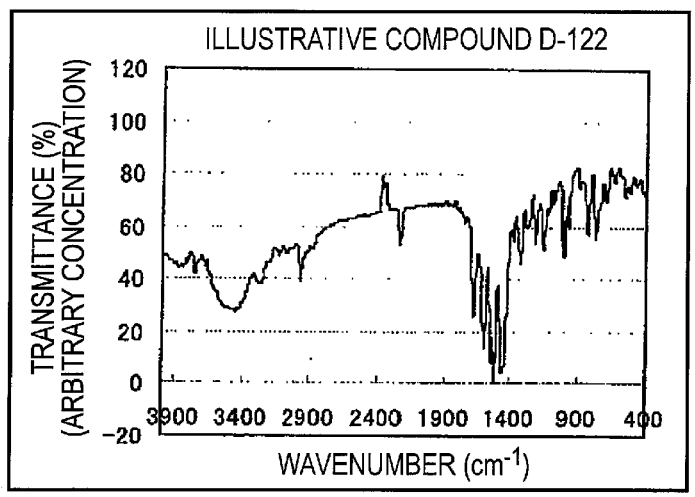
[FIG. 37] Figure of an infrared absorption spectrum of a specific illustrative compound D-122.
Figure 38:
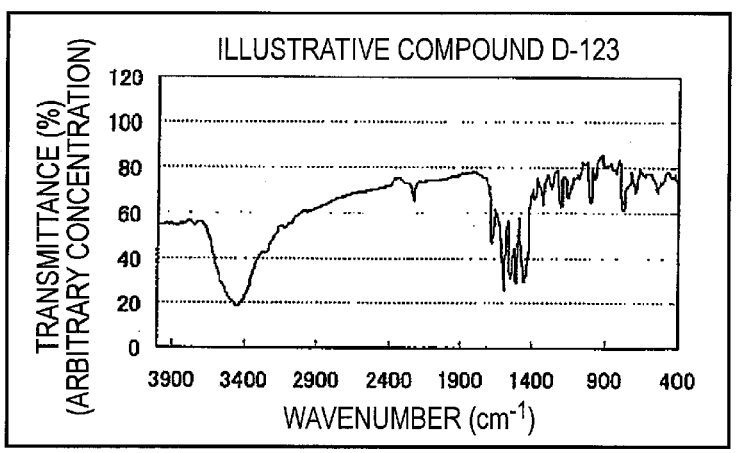
[FIG. 38] Figure of an infrared absorption spectrum of a specific illustrative compound D-123.
Figure 39:
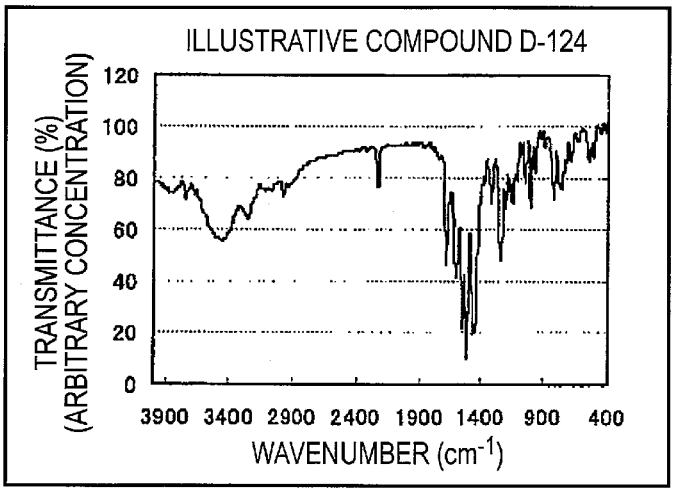
[FIG. 39] Figure of an infrared absorption spectrum of a specific illustrative compound D-124.
Figure 40:
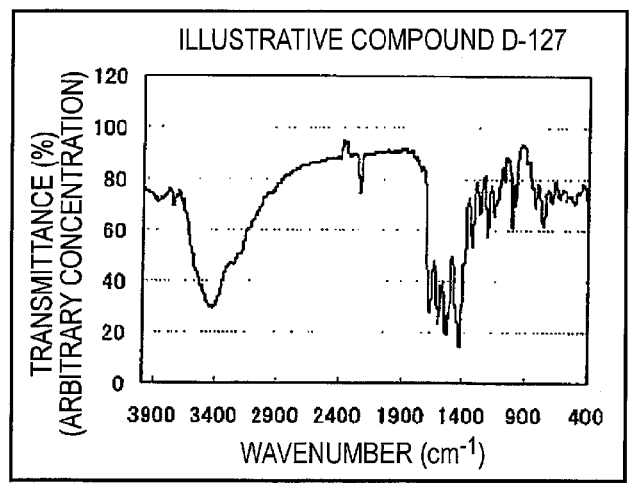
[FIG. 40] Figure of an infrared absorption spectrum of a specific illustrative compound D-127.
Figure 41:
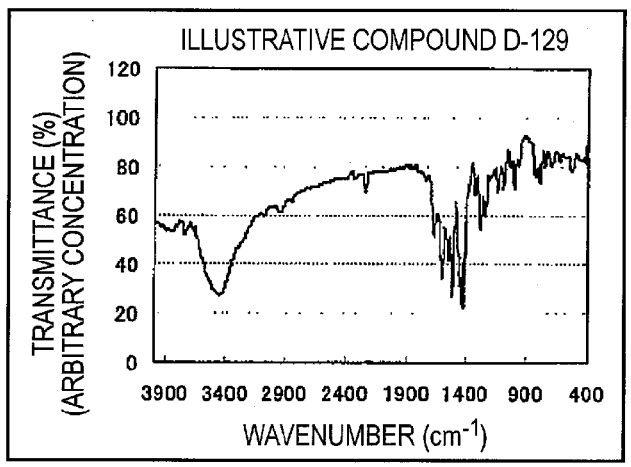
[FIG. 41] Figure of an infrared absorption spectrum of a specific illustrative compound D-129.
Figure 42:
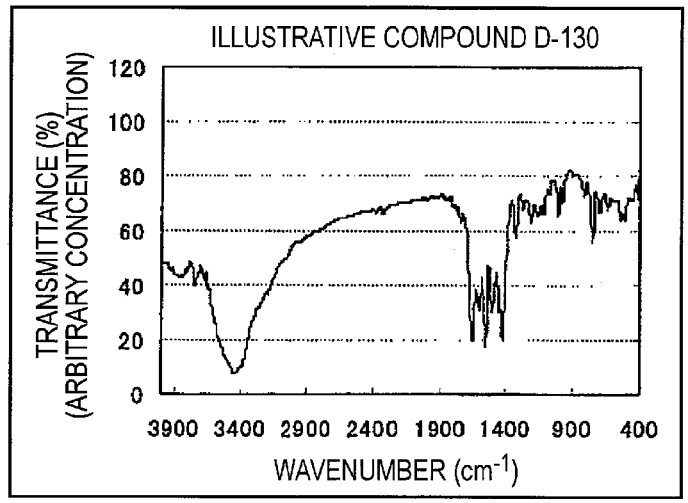
[FIG. 42] Figure of an infrared absorption spectrum of a specific illustrative compound D-130.
Figure 43:
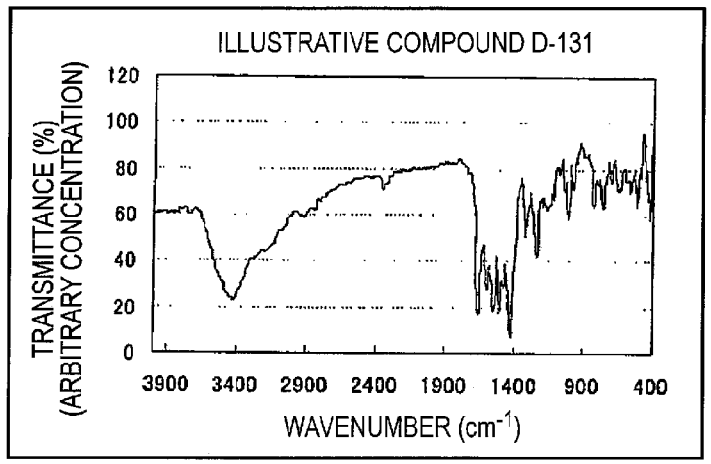
[FIG. 43] Figure of an infrared absorption spectrum of a specific illustrative compound D-131.
Figure 44:
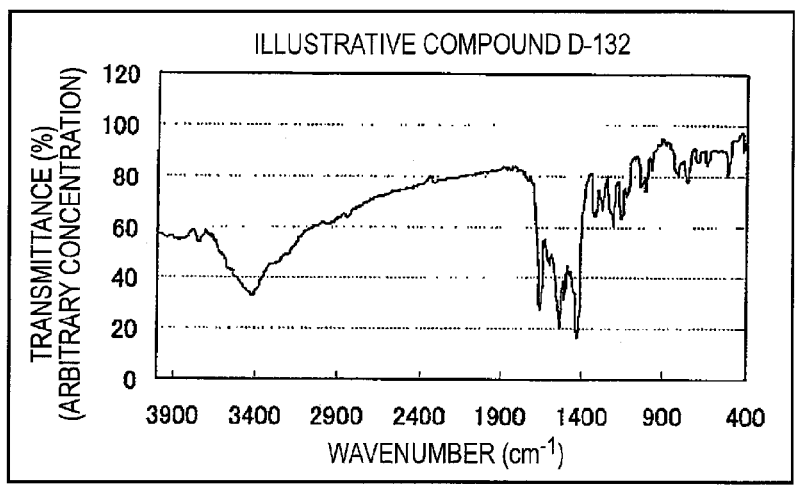
[FIG. 44] Figure of an infrared absorption spectrum of a specific illustrative compound D-132.
Figure 45:
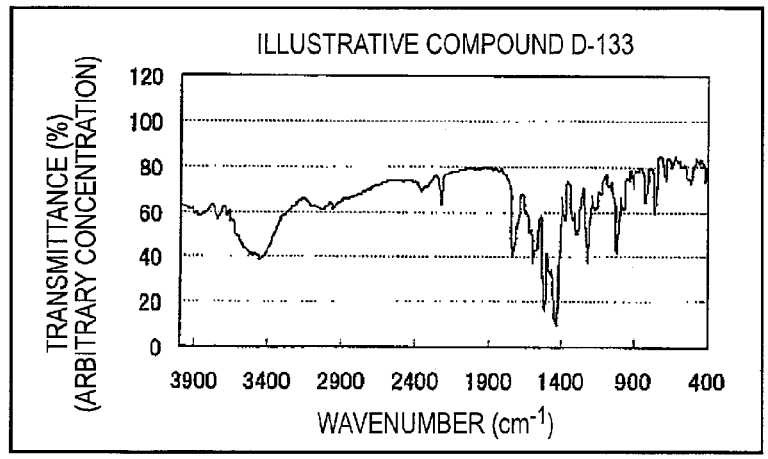
[FIG. 45] Figure of an infrared absorption spectrum of a specific illustrative compound D-133.
Figure 46:
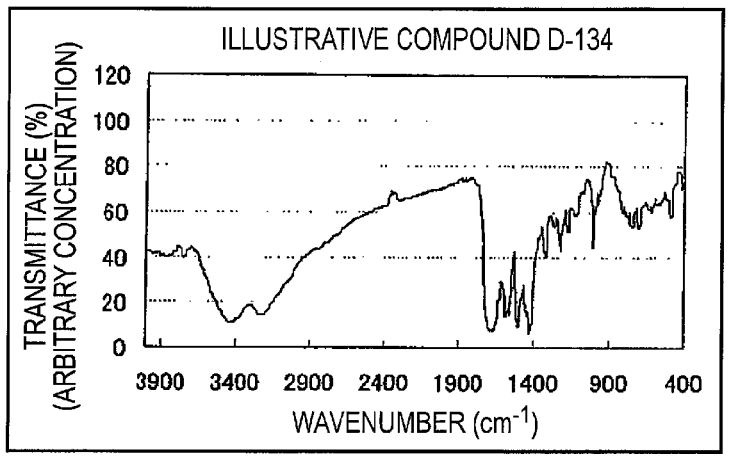
[FIG. 46] Figure of an infrared absorption spectrum of a specific illustrative compound D-134.
Figure 47:
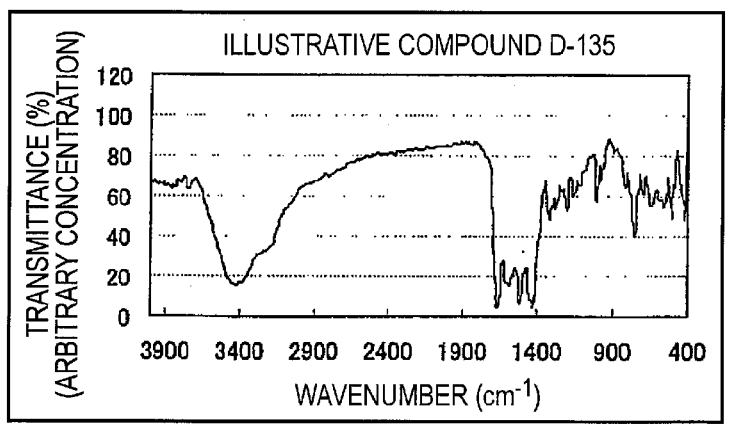
[FIG. 47] Figure of an infrared absorption spectrum of a specific illustrative compound D-135.
Figure 48:
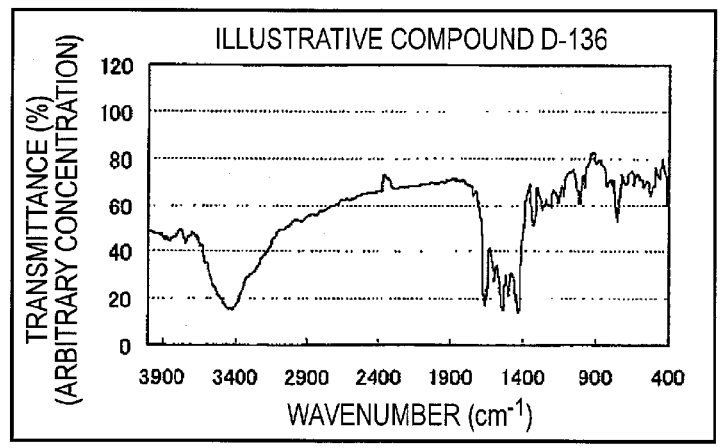
[FIG. 48] Figure of an infrared absorption spectrum of a specific illustrative compound D-136.
Figure 49:
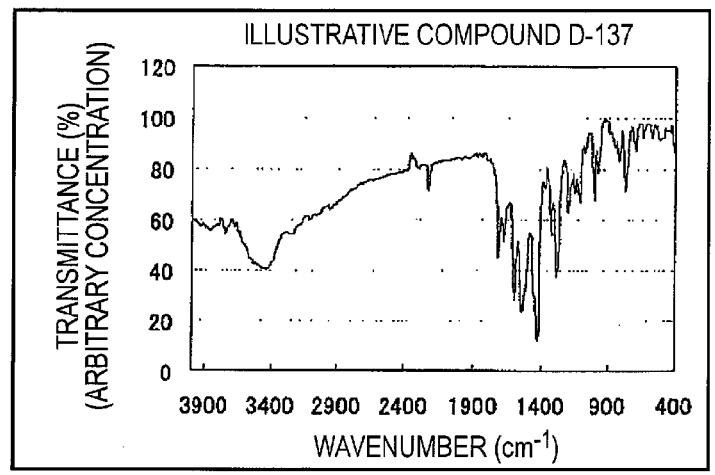
[FIG. 49] Figure of an infrared absorption spectrum of a specific illustrative compound D-137.
Figure 50:
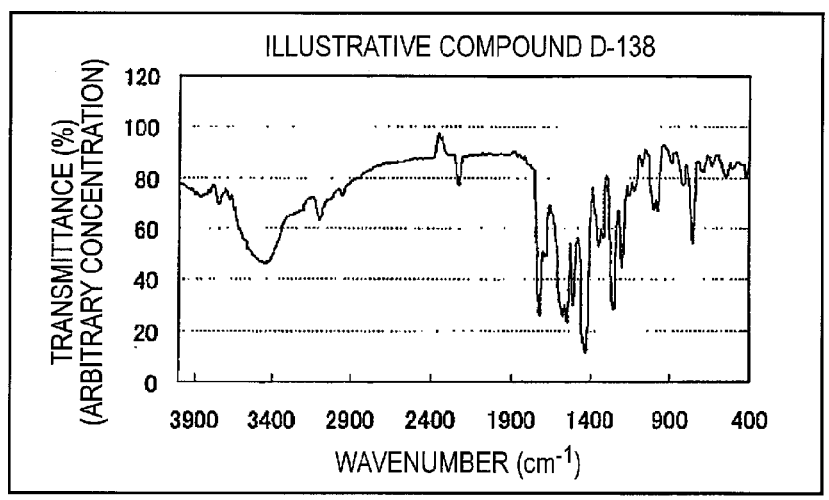
[FIG. 50] Figure of an infrared absorption spectrum of a specific illustrative compound D-138.
Figure 51:
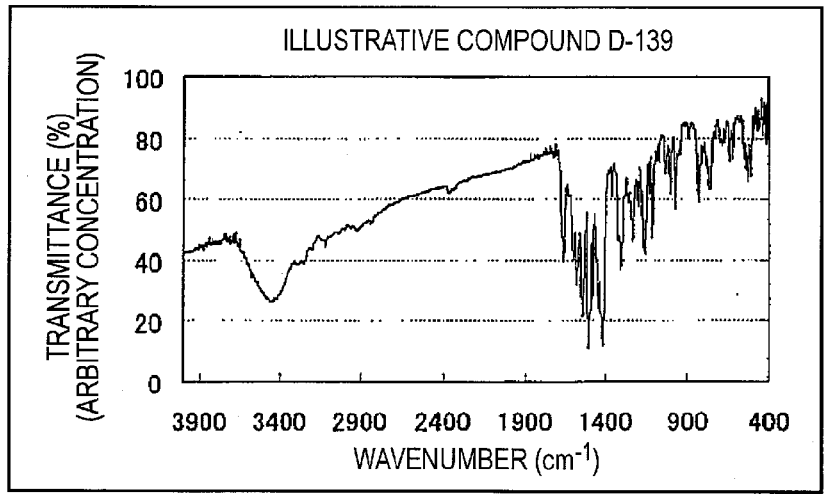
[FIG. 51] Figure of an infrared absorption spectrum of a specific illustrative compound D-139.
Figure 52:
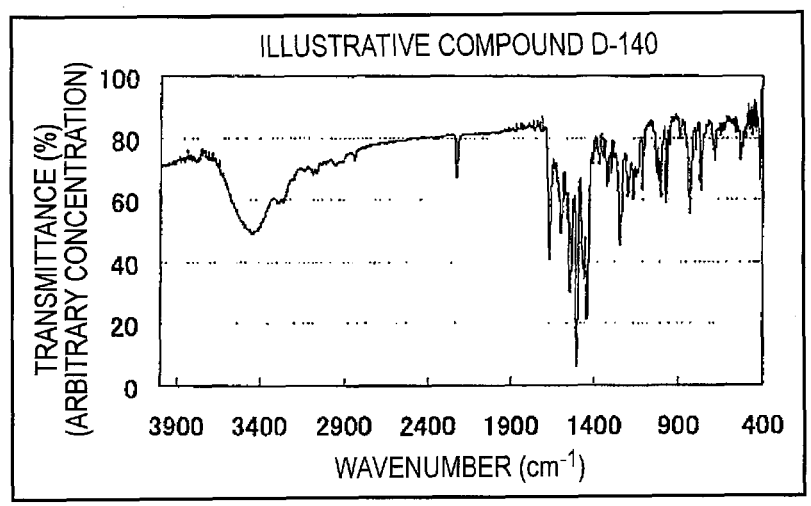
[FIG. 52] Figure of an infrared absorption spectrum of a specific illustrative compound D-140.
Figure 53:
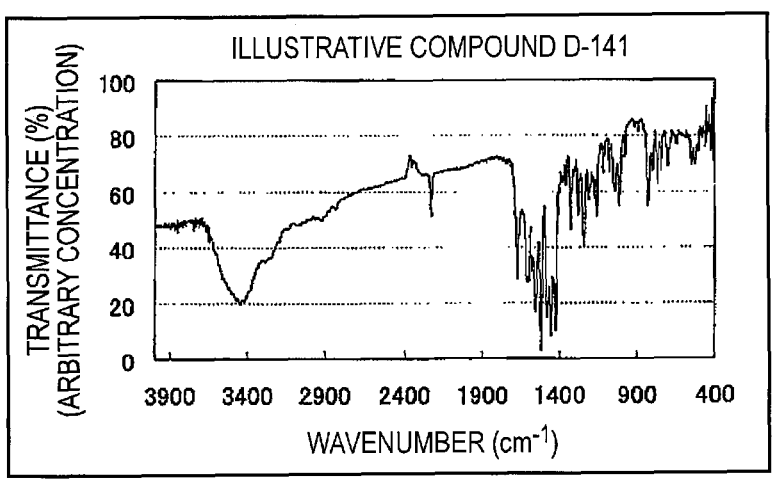
[FIG. 53] Figure of an infrared absorption spectrum of a specific illustrative compound D-141.

Infrared absorption chart is shown in FIG. 4.

Synthesis Example 5

Synthesis of Specific Compound D-222

Specific compound example D-222 is synthesized according to the following route.

[Chem. 68]

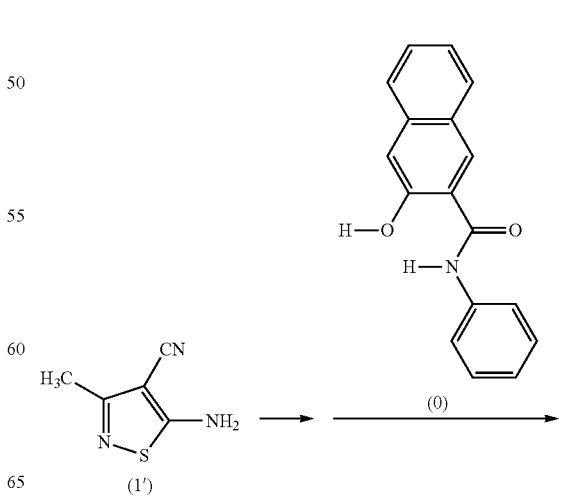

-continued

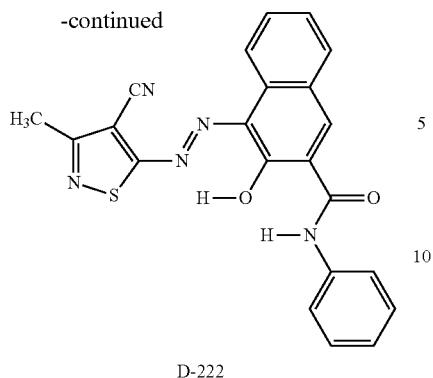

D-222

1.0 g of compound (1') is added to 10 ml of phosphoric acid (Wako Pure Chemical Industries, Ltd.; special grade reagent; purity: 85%; hereinafter the same) to dissolve. This solution is ice-cooled to keep the temperature to −5 to 0° C., and 0.55 g of sodium nitrite is added thereto, followed by stirring for 1 hour to obtain a diazonium salt solution. Separately, 20 ml of NMP (N-methylpyrrolidone) is added to 1.60 g of compound (0) and, under stirring, the aforesaid diazonium salt solution is added thereto at 8° C. or lower. Simultaneously with completion of the addition, the ice bath is removed, and stirring is continued for further 3 hours. 50 ml of methanol is added to the reaction solution, and the resulting mixture is stirred for 30 minutes. Crystals precipitated are collected by filtration, and spray-washed with 30 ml of methanol. The thus-obtained crystals are added, without drying, to 100 ml of water, and a solution prepared by dissolving 0.5 g of sodium hydrogencarbonate in 30 ml of water is added thereto, followed by stirring at 20 to 25° C. for 30 minutes. Crystals precipitated are collected by filtration, and sufficiently spray-washed with water. The thus-obtained crystals are added, without drying, to 20 ml of NMP and 10 ml of water, followed by stirring for 30 minutes under heating at 100° C. After stirring for 30 minutes at room temperature, crystals precipitated are collected by filtration, and spray-washed with 20 ml of NMP/water=2/1 and 20 ml of water. The thus-obtained crystals are dried to obtain 1.8 g of compound D-222 of the invention. Yield: 72%.

Figure 54:
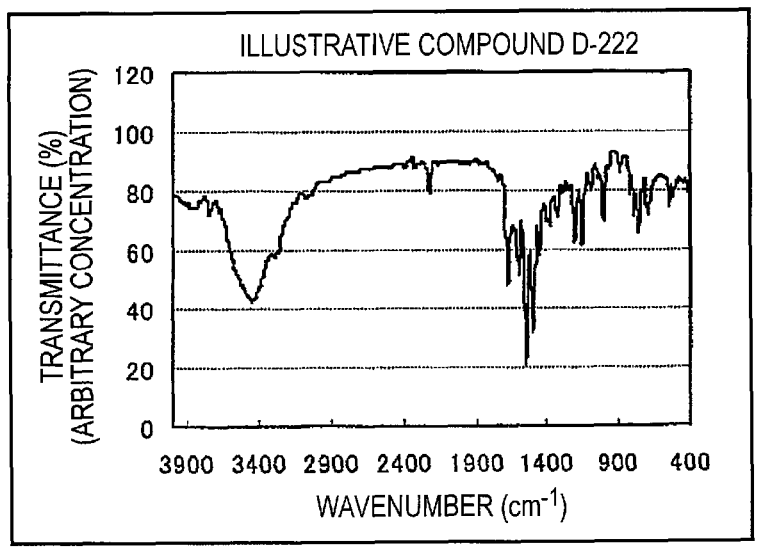
[FIG. 54] Figure of an infrared absorption spectrum of a specific illustrative compound D-222.
Figure 55:
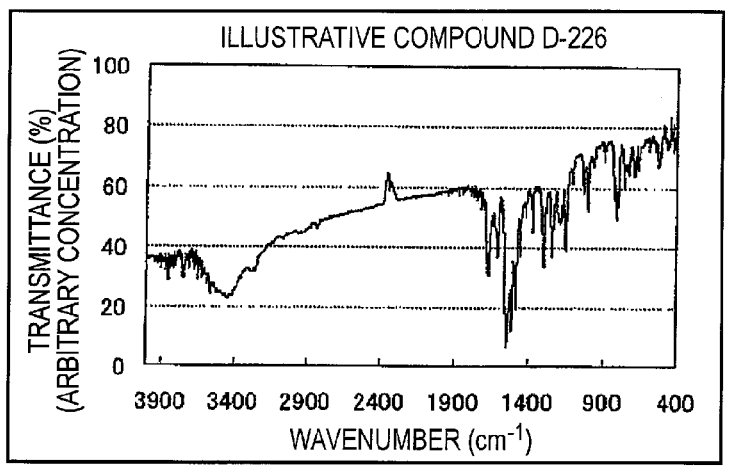
[FIG. 55] Figure of an infrared absorption spectrum of a specific illustrative compound D-226.
Figure 56:
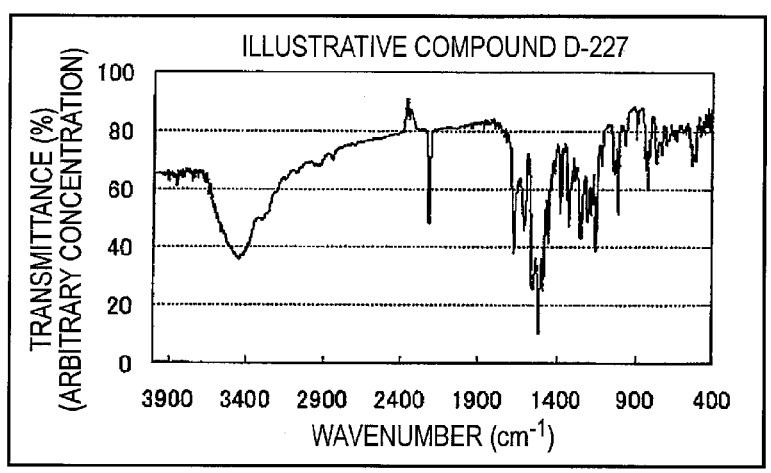
[FIG. 56] Figure of an infrared absorption spectrum of a specific illustrative compound D-227.

Infrared absorption chart is shown in FIG. 54.

Synthesis Example 6

Synthesis of Specific Compound D-228

Specific compound example D-228 is synthesized according to the following route.

[Chem. 69]

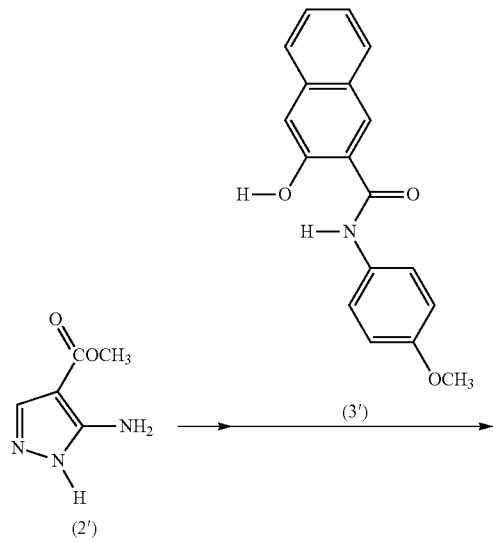

-continued

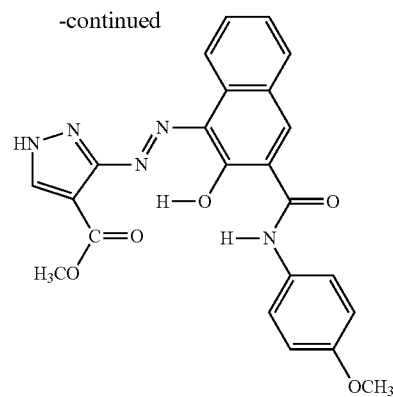

D-228

1.0 g of compound (2') is added to 10 ml of phosphoric acid to dissolve. This solution is ice-cooled to keep the temperature to −5 to 0° C., and 0.54 g of sodium nitrite is added thereto, followed by stirring for 1 hour to obtain a diazonium salt solution. Separately, 20 ml of NMP (N-methylpyrrolidone) is added to 1.60 g of compound (3') and, under stirring, the aforesaid diazonium salt solution is added thereto at 8° C. or lower. Simultaneously with completion of the addition, the ice bath is removed, and stirring is continued for further 1 hour. 40 ml of methanol is added to the reaction solution, and the resulting mixture is stirred for 30 minutes. Crystals precipitated are collected by filtration, and spray-washed with 30 ml of methanol. The thus-obtained crystals are added, without drying, to 100 ml of water, followed by stirring at 20 to 25° C. for 30 minutes. Crystals precipitated are collected by filtration, and sufficiently spray-washed with water. The thus-obtained crystals are added, without drying, to 20 ml of NMP and 10 ml of water, followed by stirring for 30 minutes under heating at 100° C. After stirring for 30 minutes at room temperature, crystals precipitated are collected by filtration, and spray-washed with 20 ml of NMP/water=2/1 and 20 ml of water. The thus-obtained crystals are dried to obtain 2.0 g of compound D-228 of the invention. Yield: 80%.

Figure 57:
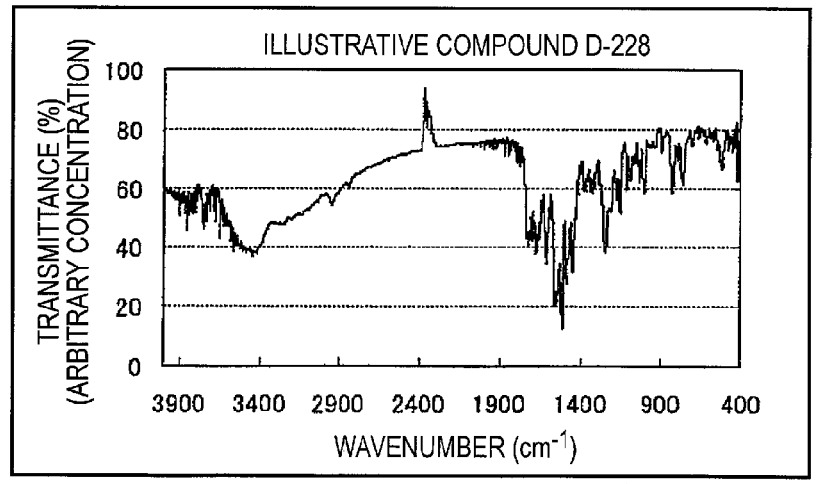
[FIG. 57] Figure of an infrared absorption spectrum of a specific illustrative compound D-228.
Figure 58:
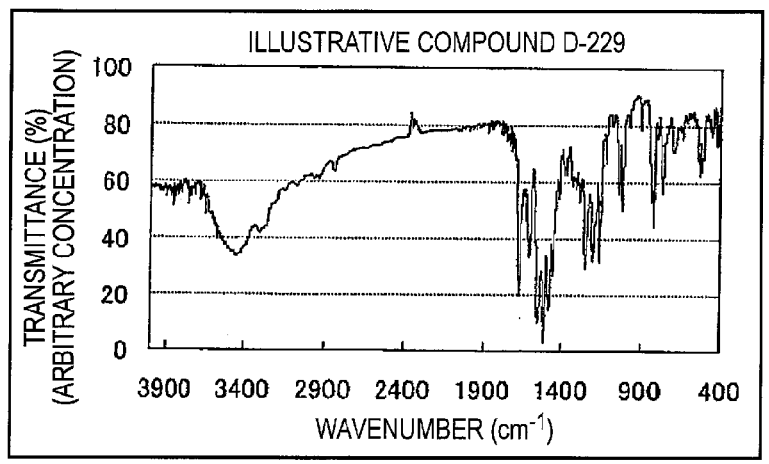
[FIG. 58] Figure of an infrared absorption spectrum of a specific illustrative compound D-229.
Figure 59:
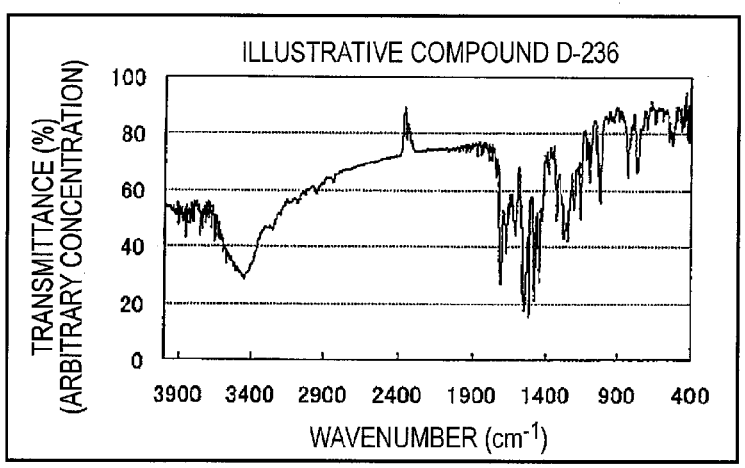
[FIG. 59] Figure of an infrared absorption spectrum of a specific illustrative compound D-236.
Figure 60:
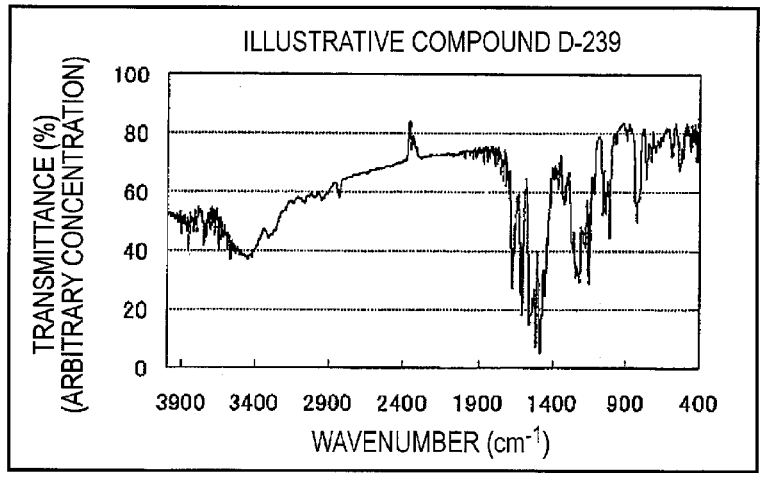
[FIG. 60] Figure of an infrared absorption spectrum of a specific illustrative compound D-239.
Figure 61:
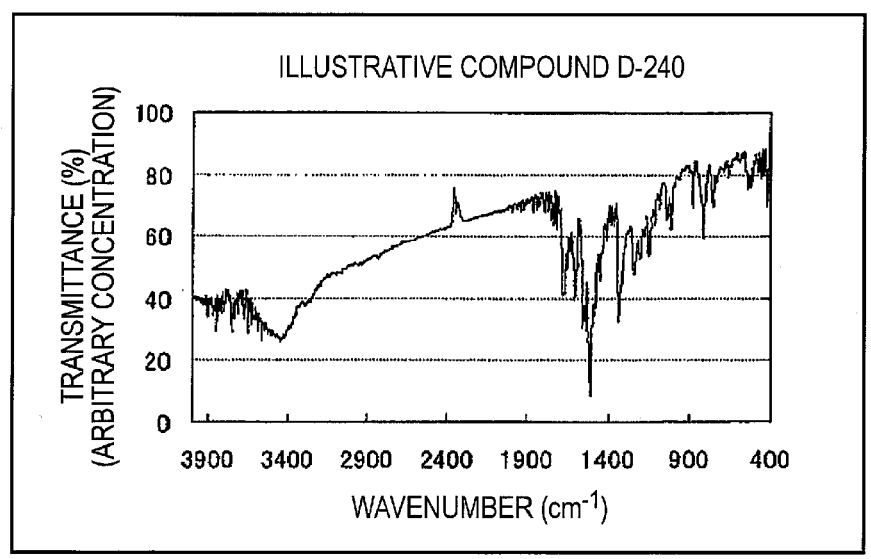
[FIG. 61] Figure of an infrared absorption spectrum of a specific illustrative compound D-240.

Infrared absorption chart is shown in FIG. 57:

Other compounds are synthesized in the same manner as with the specific compound examples. Infrared absorption charts of synthesized compounds are shown in FIGS. 5 to 53, 55, 56, and 58 to 61.

Synthesis Example 1 of Comparative Compound

Synthesis of Comparative Compound 4

Comparative compound 4 is synthesized according to the following route.

[Chem. 70]

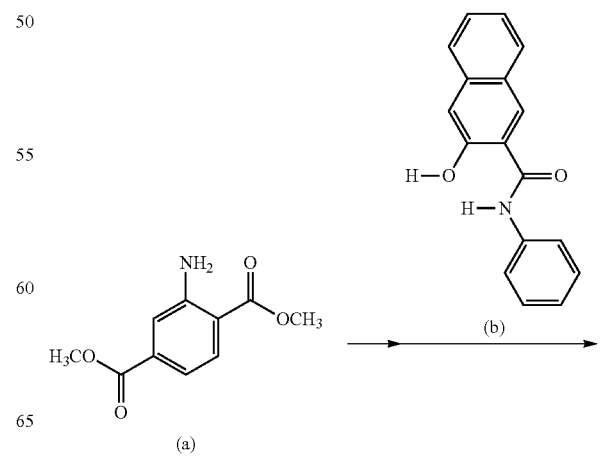

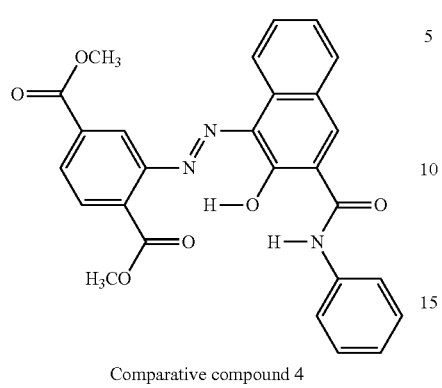

Comparative compound 4

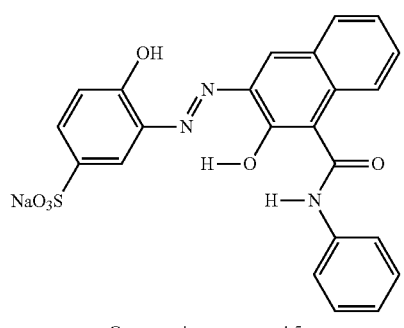

Comparative compound 5

15 ml of water and 2.2 ml of concentrated hydrochloric acid are added to 2.1 g of compound (a), followed by stirring at −2° C. to 2°. To this solution is dropwise added in 10 minutes a solution of 0.72 g of sodium nitrite dissolved in 5 ml of water to obtain a diazonium salt solution. Separately, 10 ml of DMAc is added to 2.50 g of compound (b) and, under stirring, the aforesaid diazonium salt solution is added thereto at 5° C. to 10° C. Simultaneously with completion of the addition, the ice bath is removed, and stirring is continued for further 2 hours. Crystals precipitated are collected by filtration, and spray-washed with 50 ml of water. The thus-obtained crystals are recrystallized from 50 ml of methanol, followed by cooling to 25° C. Crystals precipitated are collected by filtration. The thus-obtained crystals are dried to obtain 2.4 g of comparative compound 4. Yield: 51.8%.

[Synthesis Example 2 of Comparative Compound]

Synthesis of Comparative Compound 5

Comparative compound 5 is synthesized according to the following route.

[Chem. 71]

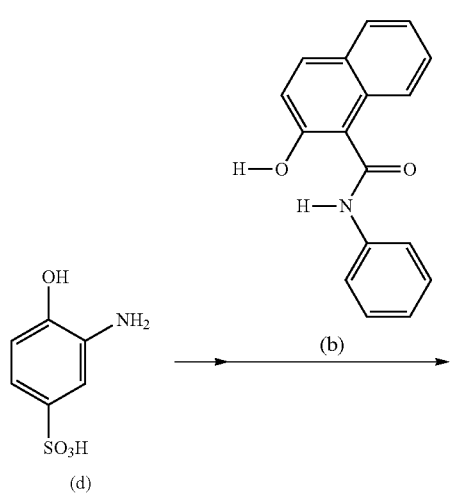

15 ml of water and 2.2 ml of concentrated hydrochloric acid are added to 1.9 g of compound (d), followed by stirring at −2° C. to 2°. To this solution is dropwise added in 10 minutes a solution of 0.72 g of sodium nitrite dissolved in 5 ml of water to obtain a diazonium salt solution. Separately, 40 ml of water and 2 g of sodium carbonate are added to 2.6 g of compound (b) and, under stirring, the aforesaid diazonium salt solution is added thereto at 5° C. to 10° C. Simultaneously with completion of the addition, the ice bath is removed, and stirring is continued for further 2 hours. 200 ml of a saturated sodium chloride aqueous solution is added to the reaction solution. Crystals precipitated are collected by filtration, and spray-washed with 30 ml of a saturated sodium chloride aqueous solution, followed by drying. The thus-obtained crystals are heated in 100 ml of methanol, and insolubles are removed by filtration. The solution is purified by Cephadex column chromatography, the water/methanol solution is concentrated, and crystals precipitated are collected by filtration, and spray-washed with methanol to obtain 1.7 g of comparative compound 5. Yield: 35.4%.

[Comparative Compound 6]

Compound Described in Japanese Patent No. 3894726

[Chem. 72]

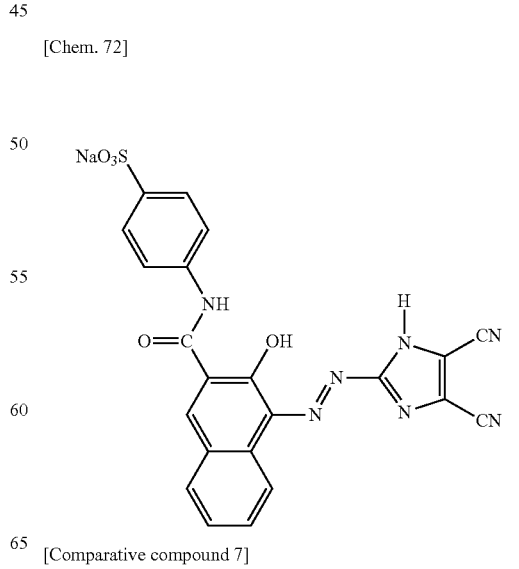

[Comparative compound 7]

-continued

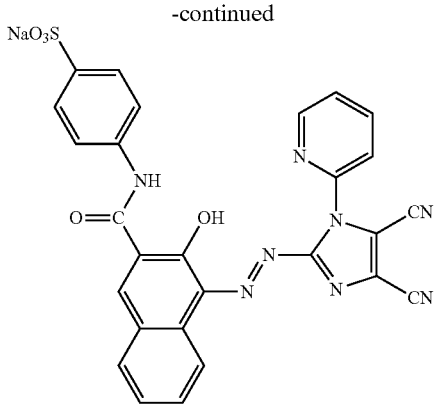

Example 1

2.5 parts of the pigment of the specific illustrative compound D-1, 0.5 part of sodium oleate, 5 parts of glycerin, and 42 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain pigment dispersion 1.

Example 2

5 parts of the pigment D-1 synthesized in Example 1, 25.5 parts of an aqueous solution of methacrylic acid-methacrylate copolymer shown as Dispersant Solution 10 described in WO 2006/064193, page22 as a high-molelcular dispersant, and 19.5 parts of water are mixed, and the resulting mixture is subjected to dispersing procedure together with 100 parts of 0.1-mm diameter zirconia beads for 6 hours at 300 rpm in a planetary ball mill. After completion of the dispersing procedure, the zirconia beads are removed to obtain pigment dispersion 2.

Comparative Example 1

The same procedures as described in Example 1 are conducted except for using C.I. Pigment Red 254 (BT-CF; manufactured by CIBA Specialty Chemicals) in place of the pigment used in Example 1 to obtain red comparative pigment dispersion 1.

Comparative Example 2

The same procedures as described in Example 1 are conducted except for using C.I. Pigment Yellow 74 (halite YELLOW GO; manufactured by CIBA Specialty Chemicals) in place of the pigment (D-1) used in Example 1 to obtain yellow comparative pigment dispersion 2.

Comparative Example 3

The same procedures as described in Example 1 are conducted except for using C.I. Pigment Yellow 155 (INKJET YELLOW 4G VP2532; manufactured by Clariant Co.) in place of the pigment (D-1) used in Example 1 to obtain yellow comparative pigment dispersion 3.

Comparative Example 4

The same procedures as described in Example 1 are conducted except for using comparative compound 4 in place of the pigment (D-1) used in Example 1 to obtain red comparative pigment dispersion 4.

Comparative Example 5

The same procedures as described in Example 1 are conducted except for using comparative compound 5 in place of the pigment (D-1) used in Example 1 to obtain red comparative pigment dispersion 5.

Comparative Example 6

The same procedures as described in Example 1 are conducted except for using comparative compound 6 in place of the pigment (D-1) used in Example 1 to obtain red comparative pigment dispersion 6.

Comparative Example 7

The same procedures as described in Example 1 are conducted except for using comparative compound 7 in place of the pigment (D-1) used in Example 1 to obtain red comparative pigment dispersion 6.

(Evaluation)
<Dispersion Stability>

Each of the pigment dispersions obtained above are subjected to measurement of volume-average particle size in a conventional manner using a dynamic light-scattering particle size-measuring apparatus (Microtrack UPA150; manufactured by Nikkiso Co., Ltd.). Dispersion stability of each of the pigment dispersions is evaluated according to the following criteria: samples with which the volume-average particle size measured 2 hours after preparation of the pigment dispersion and the volume-average particle size measured after being stored at 70° C. for 2 days are both 230 nm or less are ranked A (very good); and samples with which either of the volume-average particle sizes is 230 nm or more are ranked B (bad). The results are shown in Table 1.

<Evaluation of Tinctorial Strength>

Each of the pigment dispersions obtained is coated on a photo mat paper ("pigment only") manufactured by Seiko Epson Corporation by using a No. 3 bar coater. Image density of each of the thus-obtained coated products is measured by means of a reflection densitometer (X-Rite 938; manufactured by X-Rite Co.), and the results are shown in Table 1 as "tinctorial strength (OD: Optical Density)".

<Evaluation of Light Fastness>

Each of the coated products of 1.0 in image density used for evaluation of tinctorial strength is irradiated with xenon light (170000 lux; in the presence of a cut filter which cuts light having a wavelength of 325 nm or less) for 14 days using a fade meter. Image density before and after irradiation with xenon light is measured using the reflection densitometer, and the pigment dispersions are evaluated in terms of colorant residual ratio [(density after irradiation/density before irradiation)×100%]. The results are shown in Table 1.

Examples 3 to 31

Pigment dispersions 3 to 31 are prepared in the same manner as in Example 1 except for changing the specific illustrative compound D-1 to those shown in Table 1, and are evaluated in the same manner.

[Table 1]

TABLE 1

| | Pigment Dispersion | Pigment | Dispersion Stability | Tinctorial Strength | Light Fastness |
|---|---|---|---|---|---|
| Example 1 | Pigment dispersion 1 | D-1 | A | 1.41 | 90.0% |
| Example 2 | Pigment dispersion 2 | D-1 | A | 1.42 | 91.3% |
| Example 3 | Pigment dispersion 3 | D-10 | A | 1.39 | 90.8% |
| Example 4 | Pigment dispersion 4 | D-20 | A | 1.39 | 88.4% |
| Example 5 | Pigment dispersion 5 | D-22 | A | 1.37 | 88.0% |
| Example 6 | Pigment dispersion 6 | D-201 | A | 1.32 | 85.6% |
| Example 7 | Pigment dispersion 7 | D-7 | A | 1.40 | 91.0% |
| Example 8 | Pigment dispersion 8 | D-84 | A | 1.42 | 90.5% |
| Example 9 | Pigment dispersion 9 | D-87 | A | 1.37 | 89.9% |
| Example 10 | Pigment dispersion 10 | D-93 | A | 1.38 | 88.3% |
| Example 11 | Pigment dispersion 11 | D-114 | A | 1.37 | 92.0% |
| Example 12 | Pigment dispersion 12 | D-128 | A | 1.42 | 90.0% |
| Example 13 | Pigment dispersion 13 | D-139 | A | 1.39 | 88.6% |
| Example 14 | Pigment dispersion 14 | D-131 | A | 1.42 | 92.6% |
| Example 15 | Pigment dispersion 15 | D-125 | A | 1.39 | 87.6% |
| Example 16 | Pigment dispersion 16 | D-150 | A | 1.32 | 83.6% |
| Example 17 | Pigment dispersion 17 | D-73 | A | 1.37 | 85.6% |
| Example 18 | Pigment dispersion 18 | D-41 | A | 1.27 | 65.6% |
| Example 19 | Pigment dispersion 19 | D-44 | A | 1.24 | 70.5% |
| Example 20 | Pigment dispersion 20 | D-79 | A | 1.27 | 65.6% |
| Example 21 | Pigment dispersion 21 | D-222 | A | 1.45 | 86.5% |
| Example 22 | Pigment dispersion 22 | D-225 | A | 1.35 | 75.6% |
| Example 23 | Pigment dispersion 23 | D-214 | A | 1.32 | 71.5% |
| Example 24 | Pigment dispersion 24 | D-244 | A | 1.41 | 79.5% |
| Example 25 | Pigment dispersion 25 | D-229 | A | 1.43 | 82.2% |
| Example 26 | Pigment dispersion 26 | D-217 | A | 1.31 | 70.2% |
| Example 27 | Pigment dispersion 27 | D-228 | A | 1.30 | 72.0% |
| Example 28 | Pigment dispersion 28 | D-236 | A | 1.35 | 79.2% |
| Example 29 | Pigment dispersion 29 | D-240 | A | 1.43 | 81.0% |
| Example 30 | Pigment dispersion 30 | D-251 | A | 1.28 | 75.6% |
| Example 31 | Pigment dispersion 31 | D-247 | A | 1.26 | 71.6% |
| Comparative Example 1 | Comparative pigment dispersion 1 | P.R.254 | A | 1.26 | 62.3% |
| Comparative Example 2 | Comparative pigment dispersion 2 | P.Y.74 | A | 1.45 | 12.5% |
| Comparative Example 3 | Comparative pigment dispersion 3 | P.Y.155 | A | 1.10 | 51.9% |
| Comparative Example 4 | Comparative pigment dispersion 4 | Comparative compound 4 | A | 1.27 | 20.5% |
| Comparative Example 5 | Comparative pigment dispersion 5 | Comparative compound 5 | B | 0.80 | 6.0% |
| Comparative Example 6 | Comparative pigment dispersion 6 | Comparative compound 6 | B | 0.95 | 15.5% |
| Comparative Example 7 | Comparative pigment dispersion 7 | Comparative compound 7 | B | 1.02 | 25.6% |

Example 101

The high-molecular dispersant represented by Dispersant 10 described in WO2006/064193, page 22 is neutralized with a potassium hydroxide aqueous solution. To 75 parts by mass (concentration of solid components: 20%) of the thus-obtained dispersant aqueous solution are added 30 parts by mass of the azo pigment (D-1) synthesized hereinbefore and 95 parts by mass of deionized water, and the resulting mixture is mixed to roughly disperse by means of a disper agitating element. 600 parts by mass of zirconia beads are added to the mixed and roughly dispersed liquid and, after conducting dispersing procedure for 4 hours in a dispersing machine (sand grinder mill), the liquid is separated into beads and the dispersion. To the thus-obtained mixture is gradually added 2 parts by mass of polyethylene glycol diglycidyl ether at 25° C., and the mixture is stirred at 50° C. for 6 hours. Further, impurities are removed from the mixture by using a ultra-filtration membrane with the fractional molecular weight of 300K, followed by filtering the mixture by using a syringe of 20 ml in volume equipped with a filter having a pore size of 5 μm (acetylcellulose membrane; outer diameter: 25 mm; manufactured by FUJIFILM Corporation) to remove coarse particles. Thus, pigment dispersion 101 having a solid content of 10% (particle size: 80 nm; measured by using Nanotrac 150 (UPA-EX150) manufactured by Nikkiso Co., Ltd.) is obtained.

Comparative Example 101

Comparative pigment dispersion 101 is obtained in the same manner as in Example 101 using a red pigment (C.I. Pigment Red 254 (BT-CF; manufactured by CIBA Specialty Chemicals)) in place of the pigment used in Example 101.

Example 102

5% by mass (as a solid component) of the pigment dispersion 101 obtained in Example 101, 10% by mass of glycerin, 5% by mass of 2-pyrrolidone, 2% by mass of 1,2-hexanediol, 2% by mass of triethylene glycol monobutyl ether, 0.5% by mass of propylene glycol, and 75.5% by mass of deionized water are mixed, and the resulting mixed liquid is filtered by using a syringe of 20 ml in volume equipped with a filter having a pore size of 1 μm (acetylcellulose membrane; outer diameter: 25 mm; manufactured by FUJIFILM Corporation) to remove coarse particles. Thus, pigment ink liquid 5 shown in Table 2 is obtained.

Comparative Example 102

Comparative pigment ink liquid 5 is obtained in the same manner as in Example 102 except for using the comparative pigment dispersion 101 obtained in Comparative Example 101 in place of the pigment dispersion 101 obtained in Example 101.

Additionally, in Table 2, "ejection stability", "light fastness", "heat fastness", "ozone fastness", "metallic gloss", and "ink liquid stability" are evaluated as follows. Each ink is placed in a cartridge for a magenta ink liquid adapted for an inkjet printer PX-V630 manufactured by Seiko Epson Corporation, whereas, as other color inks, pigment ink liquids adapted for PX-630 are used, and a mono-color image pattern and green, red, and gray image patterns wherein density is stepwise changed are printed on image-receiving sheets of photographic paper <Kotaku>manufactured by Seiko Epson Corporation and photographic paper CRISPIA <Ko-kotaku>manufactured by Seiko Epson Corporation selecting recommended kirei mode to thereby evaluate image quality (metallic gloss), ejecting properties of the ink, and image fastness. Evaluations are conducted with respect to mono-color samples except for evaluation of metallic gloss.

The inkjet inks of the above-described Example 102 (pigment ink liquid 5) and of Comparative Example 102 (comparative pigment ink liquid 5) are subjected to the following evaluations. The results are shown in Table 2.

(Evaluation Experiments)
1) Regarding ejection stability, the cartridge is mounted on a printer and, after confirming ejection of the ink through all nozzles, an image is outputted on 20 sheets of A4 size paper and evaluated according to the following criteria:
  A: Printing is not disordered from the start to the end.
  B: Printing is disordered in some outputs.
  C: Printing is disordered from the start to the end.
2) Regarding image storage stability, the following evaluation is conducted using printed image samples.
[1] Light fastness is evaluated as follows. Image density Ci of the sample just after printing is measured by X-rite 310. The sample is irradiated with xenon light (100,000 lux) using a weather meter (manufactured by Atlas Co., Ltd.) for 14 days and then image density Cf of the sample is measured to determine an image remaining ratio, Cf/Ci× 100, whereby the light fastness is evaluated. The image remaining ratio is determined at 3 points having reflection density of 1, 1.5 and 2 respectively, and a case wherein the image remaining ratio is 80% or more at all three points is ranked A, a case wherein the image remaining ratio is less than 80% at two points is ranked B, and a case wherein the image remaining ratio is less than 80% at all three points is ranked C.
[2] Heat fastness is evaluated as follows. Density of the printed sample is measured by X-rite 310 before and after preservation of the sample under conditions of 80° C. and 60% RH for 7 days and an image remaining ratio is determined, whereby the heat fastness is evaluated. The image remaining ratio is determined at 3 points having reflection density of 1, 1.5 and 2 respectively, and a case wherein the image remaining ratio is 95% or more at all three points is ranked A, a case wherein the image remaining ratio is less than 95% at two points is ranked B, and a case wherein the image remaining ratio is less than 95% at all three points is ranked C.
[3] Ozone resistance (ozone fastness) is evaluated as follows. The printed sample is left for 14 days in a box wherein the ozone gas concentration is adjusted to 5 ppm (25° C., 50%), and the image density is measured before and after leaving the paper in the ozone gas atmosphere using a reflection densitometer (Photographic Densitometer 310 manufactured by X-rite) to determine the image-remaining ratio. Additionally, the reflection density is measured at three points where the densities are 1, 1.5 and 2.0, respectively. The ozone gas density within the box is monitored by means of an ozone gas monitor (model: OZG-EM-01) made by APPLICS.

The evaluation is conducted in three ranks: a case wherein the image remaining ratio is 80% or more at all three points is ranked A; a case wherein the image remaining ratio is less than 80% at two points is ranked B; and a case wherein the image remaining ratio is less than 70% at all three points is ranked C.

3) Generation of metallic gloss:
Yellow, green, and red solid printed portions of the samples are visually observed under reflected light to evaluate.

A sample with which no metallic gloss is observed is ranked A, and a sample with which metallic gloss is observed is ranked B.

4) Ink liquid stability: Each of the pigment ink liquids obtained in Examples and Comparative Examples are allowed to stand at 60° C. for 10 days, and ink liquid stability is evaluated as follows. A sample wherein particle size of the particles in the pigment ink is not changed is ranked A, and a sample wherein particle size of the particles is changed is ranked B. The results are shown in the following Table 2.

[Table 2]

TABLE 2

| Ink Liquid | Ejection Stability | Light Fastness | Heat Fastness | Ozone Fastness | Metallic Gloss | Ink Liquid Stability | Pigment |
| --- | --- | --- | --- | --- | --- | --- | --- |
| Example 102 (photogra-phic paper Kotaku) | A | A | A | A | A | A | D-1 |
| Example 102 (CRISPIA Ko-kotaku) | A | A | A | A | A | A | D-1 |
| Comparative Example 102 (photogra-phic paper Kotaku) | B | B | A | A | A | B | C.I.P.R. 254 |
| Comparative Example 102 (CRISPIA Ko-kotaku) | B | B | A | A | A | B | C.I.P.R. 254 |

It is seen from the results shown in Table 2 that the pigment ink liquid using the pigment of the invention has excellent ejection properties and excellent weatherability, can suppress generation of metallic gloss, and shows excellent pigment ink liquid stability.

As is apparent from the results shown in Table 2, it is seen that the system using the ink liquid of the invention is excellent in every performance. In particular, in comparison with the samples of Comparative Examples, the sample of the invention shows excellent light fastness and ink liquid stability.

Example 104

When an image is printed on inkjet paper of photographic glossy paper "Gasai" manufactured by Fuji Film Co., Ltd. by using the pigment ink liquid prepared in Example 102 and using PX-V 630 manufactured by Seiko Epson Corporation, and then the printed paper is subjected to the same evaluation as in Example 102 to obtain the same results.

As is apparent from the results shown in Tables 1 and 2, the pigment dispersions 1 to 31 and the pigment liquid 5 using the pigments of the invention are excellent in color tone, and show high tinctorial strength and high light fastness.

Therefore, the pigment dispersions using the pigments of the invention can favorably be used for an ink for printing such as inkjet printing.

Example 201

[Preparation of Color Filter According to Photolithography Method]

A pigment shown by compound D-1 synthesized in Synthesis Example 1 is used. The materials shown below are placed in a 70-cc mayonnaise bottle, and the bottle is shaken for 6 hours in a dispersing shaker (DAS200; manufactured by LAU Industries) to obtain a pigment dispersion 201.
[Table 3]

| (Formulation of pigment dispersion 201) | |
|---|---|
| Pigment (Compound D-1) | 0.6 g |
| 1,2-propanediol-1-monomethyl ether 2-acetate (solvent 1) (manufactured by Tokyo Chemical Industry Co., Ltd.) | 5.0 g |
| Zirconia beads (φ0.3 mm) | 10 g |

The following materials are added to the pigment dispersion 201, and the resulting mixture is further shaken for 30 minutes to prepare a coloring composition 201 for color filter for use in photolithography.
[Table 4]

| (Formulation of coloring composition 201 for color filter) | |
|---|---|
| pigment dispersion 201 | 15.6 g |
| photo-sensitive resin (manufactured by Dicel Chemical Industries, Ltd., Cyclomer P200) | 2.5 g |
| Pentaerythritol tetraacrylate (manufactured by Aldrich) | 0.2 g |
| 2-benzyl-2-dimethylamino-4'-morpholinoburitophenone (manufactured by Aldrich) | 0.05 g |
| 2,4-diethyl-9H-thioxanthen-9-one (manufactured by Tokyo Chemical Industry Co., Ltd.) | 0.05 g |

| (Formulation of coloring composition 201 for color filter) -continued | |
|---|---|
| 1,2-propanediol-1-monomethyl ether 2-acetate (manufactured by Tokyo Chemical Industry Co., Ltd.) | 0.8 g |
| Cyclohexanone (manufactured by Tokyo Chemical Industry Co., Ltd.) | 0.2 g |

The thus-obtained coloring composition 201 for color filter is applied on a slide glass with a bar-coater Rod No. 10, and the slide glass is dried for 5 minutes in an oven at 80° C. to obtain a coated film of ink.

An appropriate masking is applied on a part of the thus-obtained coated film, and the film is then exposed to a high-pressure mercury lamp with an irradiation condition of 200 ml/cm$^2$. Thereafter, the film is developed using a 0.5% sodium carbonate aqueous solution at 25° C., and dried for 20 minutes in an oven at 220° C. to obtain a color filter. The optical transmittance of the obtained film is determined with a spectrophotometer (U-3310; manufactured by Hitachi, Ltd.). Also, a wavelength at which the obtained color filter exhibits the lowest transmittance is determined within the wavelength range of 540-610 nm. Results are shown in Table 5.

Example 202

A coloring composition is prepared in the same manner as in Example 201 except for using a pigment shown by compound D-33 synthesized in Synthesis Example 2 in place of the pigment used in Example 201 and changing the amount of the solvent (1,2-propanediol 1-monomethyl ether 2-acetate) in the formulation of the pigment dispersion 201 to the amount shown in Table 3. A color filter is prepared by using the thus-obtained coloring composition, and the light transmittance thereof is measured. Also, a wavelength at which the obtained color filter exhibits the lowest transmittance is determined within the wavelength range of 540-610 nm. Results are shown in Table 5.

Examples 203 to 211

Coloring compositions are prepared in the same manner as in Example 201 except for using a pigment shown in Table 3 in place of the pigment used in Example 201 and changing the amount of the solvent 1 (1,2-propanediol 1-monomethyl ether 2-acetate) in the formulation of the pigment dispersion 201 to the amount shown in Table 3. A color filter is prepared by using the thus-obtained coloring composition. Also, a wavelength at which the obtained color filter exhibits the lowest transmittance is determined within the wavelength range of 540-610 nm. Results are shown in Table 5.
[Table 5]

TABLE 3

| | Pigment | Amount of solvent 1 used |
|---|---|---|
| Example 201 | D-1 | 5 g |
| Example 202 | D-33 | 5 g |
| Example 203 | D-20 | 6 g |
| Example 204 | D-22 | 5 g |
| Example 205 | D-213 | 5 g |
| Example 206 | D-221 | 5 g |
| Example 207 | D-222 | 5 g |
| Example-208 | D-246 | 5 g |
| Example 209 | D-35 | 5 g |
| Example 210 | D-143 | 6 g |
| Example 211 | D-207 | 5 g |

Example 212

When dispersing procedure is conducted in Example 201 by adding 0.5 g of a surfactant (pigment-wetting dispersant BYK-161; manufactured by Byk-Chemie GmbH) as a dispersant for 0.6 g of the pigment, there is obtained a color filter having the same performance as in Example 201 by dispersing for 6 hours.

Examples 213 to 218

When pigment dispersions are prepared in the same manner as in Example 201 using a dispersing shaker (DAS 200; manufactured by LAU Industries) except for using the dispersants shown in Table 4 and changing the amounts thereof used as shown in Table 4, there are respectively obtained color filters having the same performance as in Example 201 by dispersing for 6 hours.

[Table 6]

TABLE 4

| | Dispersant | Amount of dispersant used |
|---|---|---|
| Example 213 | Pigment series additive (SOLSPERSE 22000; manufactured by Zeneca) | 0.012 g |
| Example 214 | Silicone series additive (PAINTAD 32; manufactured by Dow Corning Asia) | 0.006 g |
| Example 215 | Silicone series additive (PAINTAD 57; manufactured by Dow Corning Asia) | 0.0012 g |
| Example 216 | Silicone series additive (DK Q8-8011; manufactured by Dow Corning Asia) | 0.0012 g |
| Example 217 | Surfactant (DISPARLON DA-325; manufactured by Enomoto Chemicals, Ltd.) | 0.200 g |
| Example 218 | Surfactant (DISPARLON DA-1860; manufactured by Enomoto Chemicals, Ltd.) | 0.120 g |

Comparative Examples 201 and 202

In absolutely the same manner as in Example 201 except for using C.I. Pigment Red 254 (IRGAPHORE DPP RED; manufactured by CIBA Specialty Chemicals) and a pigment shown by the following formula [I], respectively, in place of the pigment used in Example 201, there are prepared colored films. Measurement of light transmittance of the thus-obtained films is conducted to determine the wavelength at which the films show the lowest light transmittance and the light transmittance at 650 nm and at 540 nm. Results are shown in Table 5.

[Chem. 73]

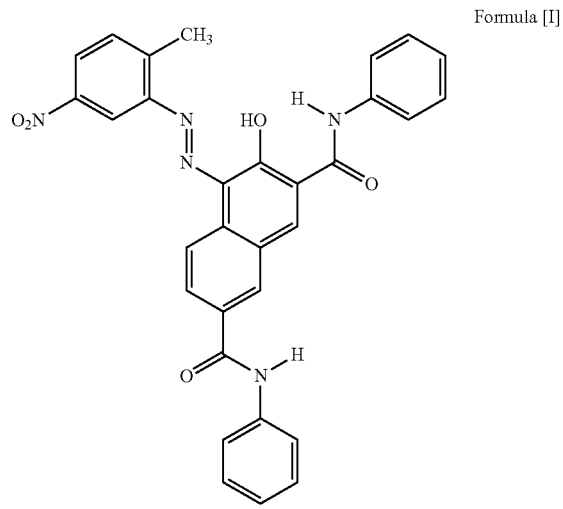

Formula [I]

[Table 7]

TABLE 5

| | Pigment | Wavelength at which transmittance is the lowest | Transmittance at 650 nm | Transmittance at 540 nm |
|---|---|---|---|---|
| Example 201 | D-1 | 570 nm | 90% | 2% |
| Example 202 | D-33 | 553 nm | 90% | 2% |
| Example 203 | D-20 | 568 nm | 89% | 2% |
| Example 204 | D-22 | 565 nm | 88% | 2% |
| Example 205 | D-213 | 570 nm | 85% | 2% |
| Example 206 | D-221 | 577 nm | 83% | 2% |
| Example 207 | D-222 | 573 nm | 85% | 2% |
| Example 208 | D-246 | 576 nm | 84% | 3% |
| Example 209 | D-35 | 563 nm | 90% | 3% |
| Example 210 | D-143 | 555 nm | 95% | 3% |
| Example 211 | D-207 | 553 nm | 89% | 3% |
| Comparative Example 201 | C.I.P.R.254 | 564 nm | 80% | 8% |
| Comparative Example 202 | Compound of formula [1] | 562 nm | 65% | 5% |

Color filters prepared by using the coloring composition of the invention for color filter containing compounds D-1, 33, 20, 22, 213, 221, 222, 246, 35, 143, and compound D-207, respectively, as coloring materials, show a sharp rise in transmittance curve and show a high transmittance in the region of from 650 to 750 nm, thus showing excellent transmittance curves. Further, the color filter of Comparative Example 1 shows a high transmittance at 540 nm, whereas color filters of Examples 201 to 211 show a low transmittance at 540 nm, thus being excellent.

Also, in comparison with the color filters obtained in Comparative Examples 201 and 202, the color filters prepared by using the coloring compositions of the invention for color filter show an extremely low transmittance for a blue light of 350 to 400 nm, which enables to display red color with high color purity.

That is, the coloring composition of the invention for color filter is useful in that, by selecting the structure of the azo pigment represented by the general formula (1), the wavelength at which transmittance sharply changes can be properly adjusted between about 540 nm and about 590 nm, whereby a red color with an optimal hue can be obtained in accordance with the wavelength of a light source of back light in a display.

[Evaluation of Heat Fastness]

Heat fastness test is conducted using color filters obtained in Examples 201 to 211, and Comparative Examples 201 and 202.

<Method of Testing Heat Fastness>

A color filter is exposed to the atmosphere at 250° C. for 90 minutes, and color difference before and after the exposure ($\Delta E^*_{ab}$) is measured by means of a spectrophotometer (Macbeth Color eye-3000; manufactured by Sakata Inx Eng., Co., Ltd.). Evaluation is conducted according to the following criteria, and the results are shown in Table 6.

<Evaluation Criteria>
A: $\Delta E^*_{ab} < 1.0$
B: $1.0 \leq \Delta E^*_{ab} < 1.1$
C: $1.1 \leq \Delta E^*_{ab}$
[Table 8]

TABLE 6

| | Pigment | Results of Heat Fastness Test Color Difference ($\Delta E^*ab$) |
|---|---|---|
| Example 201 | D-1 | A |
| Example 202 | D-33 | A |
| Example 203 | D-20 | A |
| Example 204 | D-22 | A |
| Example 205 | D-213 | A |
| Example 206 | D-221 | A |
| Example 207 | D-222 | A |
| Example 208 | D-246 | B |
| Example 209 | D-35 | B |
| Example 210 | D-143 | B |
| Example 211 | D-207 | A |
| Comparative Example 201 | P.R.254 | C |
| Comparative Example 202 | Compound of formula [1] | B |

In comparison with the sample using the pigment of Comparative Example 201, the color filters of Examples 201 to 211 prepared by using the coloring compositions of the invention for color filter respectively containing the azo compounds represented by the general formula (1) as coloring materials show the same or more heat fastness.

<Evaluation of Light Fastness>

The coated samples of 1.0 in image density used in the evaluation of tinctorial strength are used, and are irradiated with a xenon light (170000 lux; in the presence of a cut filter which cuts light having a wavelength of 325 nm or less; Suga Test Instruments Co., Ltd.) for 20 days using a fade meter. The color difference before and after irradiation ($\Delta E^*_{ab}$) is measured by means of a spectrophotometer (Macbeth Color eye-3000; manufactured by Sakata Inx Eng., Co., Ltd.). Evaluation is conducted according to the following criteria, and the results are shown in Table 7.

<Evaluation Criteria>
A: $\Delta E^*_{ab} \leq 3.0$
B: $3.0 < \Delta E^*_{ab} \leq 6.0$
C: $6.0 < \Delta E^*_{ab}$
[Table 9]

TABLE 7

| | Pigment | Results of Light Fastness Test Color Difference ($\Delta E^*ab$) |
|---|---|---|
| Example 201 | D-1 | A |
| Example 202 | D-33 | B |
| Example 203 | D-20 | A |
| Example 204 | D-22 | A |
| Example 205 | D-213 | A |
| Example 206 | D-221 | A |
| Example 207 | D-222 | A |
| Example 208 | D-246 | B |
| Example 209 | D-35 | B |
| Example 210 | D-143 | B |
| Example 211 | D-207 | A |
| Comparative Example 201 | P.R.254 | C |
| Comparative Example 202 | Compound of formula [1] | B |

In comparison with the samples using the pigments of Comparative Examples 201 and 202, respectively, the color filters of Examples 201 to 211 prepared by using the coloring compositions of the invention for color filter respectively containing the azo compounds represented by the general formula (1) as coloring materials show the same or more light fastness.

(Evaluation of Contrast)

Contrast of each of the obtained color filters is measured by using a contrast tester CT-1 manufactured by Tsubosaka Electric Co., Ltd. Evaluation is conducted according to the criteria that a sample with contrast≧23000 is ranked A, a sample with 23000>contrast≧18000 is ranked B, and a sample with 18000>contrast is ranked C, and the results are shown in Table 8.
[Table 10]

TABLE 8

| | Pigment | Contrast |
|---|---|---|
| Example 201 | D-1 | A |
| Example 202 | D-33 | A |
| Example 203 | D-20 | A |
| Example 204 | D-22 | A |
| Example 205 | D-213 | A |
| Example 206 | D-221 | A |
| Example 207 | D-222 | A |
| Example 208 | D-246 | A |
| Example 209 | D-35 | A |
| Example 210 | D-143 | B |
| Example 211 | D-207 | B |
| Comparative Example 201 | P.R.254 | A |
| Comparative Example 202 | Compound of formula [1] | C |

In comparison with the sample using the pigment of Comparative Example 202, the color filters of Examples 201 to 211 prepared by using the coloring compositions of the invention for color filter respectively containing the azo compounds represented by the general formula (1) as coloring materials show excellent contrast.

(Evaluation of Dispersion Stability with Time)

Coloring compositions 201 to 211, and comparative coloring compositions 1 and 2 prepared in Examples 201 to 211 and Comparative Examples 201 and 202, respectively, are stored in a dark room at room temperature for 2 weeks, and then degree of precipitation of foreign body is visually evaluated according to the following criteria.

<Evaluation Criteria>
A: No precipitation is observed.
B: Slight precipitation is observed.
C: Precipitation is observed.
[Table 11]

TABLE 9

| Pigment Dispersion | | Pigment | Stability with Time of Dispersion |
|---|---|---|---|
| Example 201 | Coloring composition 201 | D-1 | A |
| Example 202 | Coloring composition 202 | D-33 | A |
| Example 203 | Coloring composition 203 | D-20 | A |
| Example 204 | Coloring composition 204 | D-22 | A |
| Example 205 | Coloring composition 205 | D-213 | A |
| Example 206 | Coloring composition 206 | D-221 | A |
| Example 207 | Coloring composition 207 | D-222 | A |
| Example 208 | Coloring composition 208 | D-246 | A |
| Example 209 | Coloring composition 209 | D-35 | A |
| Example 210 | Coloring composition 210 | D-143 | B |
| Example 211 | Coloring composition 211 | D-207 | A |
| Comparative Example 201 | Comparative coloring composition 1 | P.R.254 | B |
| Comparative Example 202 | Comparative coloring composition 2 | Compound of formula [1] | C |

In comparison with the samples using the pigments of Comparative Examples 201 and 202, respectively, the color filters of Examples 201 to 211 prepared by using the coloring compositions of the invention for color filter respectively containing the azo compounds represented by the general formula (1) as coloring materials do not generate foreign body with time, thus being excellent in stability of dispersion with time.

Example 219

<Preparation of a Green Pigment Dispersion>
—Preparation of a Green Pigment Dispersion P1—

A mixture composed of 12.6 parts of a 100/55 (mass ratio) pigment mixture of C.I. Pigment Green 36 and C.I. Pigment Yellow 139, 5.2 parts of a dispersant of BYK2001 (Disperbyk; manufactured by Byk-Chemie GmbH; solid content: 45.1% by mass), 2.7 parts of a dispersing resin of benzyl methacrylate/methacrylic acid copolymer (acid value: 134 mgKOH/g; Mw=30,000), and 78.3 parts of a solvent of propylene glycol monomethyl ether acetate is mixed and dispersed in a beads mill for 15 hours to obtain a green pigment dispersion P1.

<Preparation of a Red Pigment Dispersion>
—Preparation of a Red Pigment Dispersion P2—

A mixture composed of 12.1 parts of a 100/45 (mass ratio) pigment mixture of D-1 and C.I. Pigment Yellow 139, 10.4 parts of a dispersant of BYK2001 (Disperbyk; manufactured by Byk-Chemie GmbH; solid content: 45.1% by mass), 3.8 parts of a dispersing resin of benzyl methacrylate/methacrylic acid copolymer (acid value: 134 mgKOH/g; Mw=30,000), and 73.7 parts of a solvent of propylene glycol monomethyl ether acetate is mixed and dispersed in a beads mill for 15 hours to obtain a red pigment dispersion P2.

<Preparation of a Blue Pigment Dispersion>
—Preparation of a Blue Pigment Dispersion P3—

A mixture composed of 14 parts of a 100/25 (mass ratio) pigment mixture of C.I. Pigment Blue 15:6 and C.I. Pigment Violet 23, 4.7 parts of a dispersant of BYK2001 (Disperbyk; manufactured by Byk-Chemie GmbH; solid content: 45.1% by mass), 3.5 parts of a dispersing resin of benzyl methacrylate/methacrylic acid copolymer (acid value: 134 mgKOH/g; Mw=30,000), and 77.8 parts of a solvent of propylene glycol monomethyl ether acetate is mixed and dispersed in a beads mill for 15 hours to obtain a blue pigment dispersion P3.

<Preparation of Green-colored Photo-sensitive Composition (Coating Solution) A-1>

The above-described green pigment dispersion P1 is used, and components of the following formulation are mixed and stirred to prepare a colored photo-sensitive composition A-1.
[Table 12]

| <Formulation> | |
|---|---|
| Aforesaid Green pigment dispersion P1 | 83.3 parts |
| Alkali-soluble resin: P-1 | 2.05 parts |
| OXE-01 (photopolymerization initiator; manufactured by CIBA Specialty Chemicals) | 1.2 parts |
| Monomer 1: KARAYAD DPHA (manufactured by Nippon Kayaku Co., Ltd.) | 1.4 parts |
| Monomer 2: M-305 (manufactured by Toagosei Co., Ltd.) | 1.4 parts |
| p-methoxyphenol | 0.001 part |
| Polyethylene glycol methyl ether acetate [PGMEA (hereinafter, the same abbreviation will be used); solvent] | 7.4 parts |
| Surfactant (trade name: F-781; 0.2% solution of PGMEA; manufactured by DIC Corporation) | 4.2 parts |

<Preparation of Red-colored Photo-Sensitive Composition (Coating Solution) B-1>

The above-described red pigment dispersion P2 is used, and components of the following formulation are mixed and stirred to prepare a colored photo-sensitive composition B-1.
[Table 13]

| <Formulation> | |
|---|---|
| Aforesaid Red pigment dispersion P2 | 59.6 parts |
| Alkali-soluble resin: P-1 | 1.2 parts |
| OXE-02 (photopolymerization initiator; manufactured by CIBA Specialty Chemicals) | 0.7 part |
| Monomer 1: KARAYAD DPHA (manufactured by Nippon Kayaku Co., Ltd.) | 1.6 parts |
| Monomer 2: SR-494 (manufactured by Sartomer Company, Inc..) | 1.6 parts |
| p-methoxyphenol | 0.002 part |
| Polyethylene glycol methyl ether acetate [PGMEA (hereinafter, the same abbreviation will be used); solvent] | 31 parts |
| Surfactant (trade name: F-781; 0.2% solution of PGMEA; manufactured by DIC Corporation) | 4.2 parts |

<Preparation of Blue-colored Photo-sensitive Composition (Coating Solution) C-1>

The above-described blue pigment dispersion P3 is used, and components of the following formulation are mixed and stirred to prepare a colored photo-sensitive composition C-1.

[Table 14]

| <Formulation> | |
|---|---|
| Aforesaid Blue pigment dispersion P3 | 50.6 parts |
| Alkali-soluble resin: P-1 | 2.1 parts |
| OXE-01 (photopolymerization initiator; manufactured by CIBA Specialty Chemicals) | 1.2 parts |
| Monomer 1: KARAYAD DPHA (manufactured by Nippon Kayaku Co., Ltd.) | 1.2 parts |
| Monomer 2: SR-494 (manufactured by Sartomer Company, Inc..) | 3.5 parts |
| p-methoxyphenol | 0.002 part |
| Polyethylene glycol methyl ether acetate [PGMEA (hereinafter, the same abbreviation will be used); solvent] | 36 parts |
| Surfactant (trade name: F-781; 0.2% solution of PGMEA; manufactured by DIC Corporation) | 4.2 parts |

The green-colored photo-sensitive composition A-1 having been prepared hereinbefore is coated on a silicon wafer on which 8-inch device has been formed and previously sprayed with hexamethyldisilazane, thus a photo-curable coated film being formed. Then, the coated film is subjected to heating treatment (prebake) for 180 seconds using a 100° C. hot plate so that the dry thickness of the coated film becomes 1.0 μm. Subsequently, the film is irradiated through a 1.0-μm square Bayer pattern mask at a wavelength of 365 nm using an i-line stepper exposure apparatus FPA-3000i5+ (manufactured by Canon Inc.) in an irradiation amount of from 50 to 1,000 mJ/cm$^2$ (exposure amount being changed stepwise by 50 mJ/cm$^2$). Thereafter, the silicon wafer on which the irradiated coated film is formed is placed on a horizontal rotary table of a spin shower developing machine (model DW-30; manufactured by Chemitronics Co., Ltd.), and paddle development is conducted at 23° C. for 180 seconds using a 40% diluting solution of CD-2000 (manufactured by Fujifilm Electronics Materials) to form a colored pattern on the silicon wafer.

The silicon wafer on which the colored pattern is formed is fixed on the aforesaid horizontal rotary table by vacuum-chucking system and, while rotating the silicon wafer at a rotation number of 50 rpm by means of a rotating apparatus, pure water is supplied from above the rotation center through a jet nozzle in a shower state to conduct rinsing treatment, followed by spray drying.

Next, the silicon wafer is heated for 5 minutes on a 200° C. hot plate to obtain a color film on which a pattern is formed.

Further, the same procedures as with Green except for using the above-described Red-colored photo-sensitive composition B-1 and Blue-colored photo-sensitive composition C-1 and exposing through a 1.0 μm square island pattern mask are conducted to thereby form a color filter formed by RGB patterns.

Good spectral characteristics can be confirmed by preparing a camera module using a device wherein this color filter is formed.

[Chem. 74]

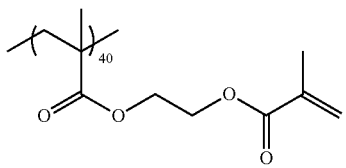

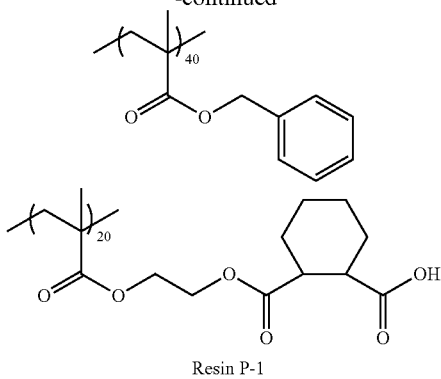

Resin P-1

Good spectral characteristics can be confirmed as in Example 5 by preparing a color filter using D-26, D-136, D-209, or D-236 in place of D-1 in Example 212 and preparing a camera module using a device wherein this color filter is formed.

Industrial Applicability

The azo pigments of the invention have high tinctorial strength, excellent coloring characteristics such as hue, and excellent durability such as light fastness, ozone fastness, and heat fastness.

Further, the pigment dispersion of the invention is a dispersion wherein the azo pigment of the invention is dispersed in various media, and is excellent in coloring characteristics, durability, ink liquid stability, and dispersion stability.

Also, according to the present invention, there are provided a coloring composition for color filter which has good dispersibility, good dispersion stability with time, heat fastness, and light fastness and which can provide a color filter capable of attaining high contrast required for color liquid crystal displays for various uses and excellent transparency required for camera modules; a color filter; and a process for its preparation.

Although the invention has been described in detail and by reference to specific embodiments, it is apparent to those skilled in the art that it is possible to add various alterations and modifications insofar as the alterations and modifications do not deviate from the spirit and the scope of the invention.

This application is based on a Japanese patent application filed on Jul. 17, 2008 (Japanese Patent Application No. 2008-186507) and a Japanese patent application filed on Sep. 2, 2008 (Japanese Patent Application No. 2008-225036), and the contents thereof are incorporated herein by reference.

The invention claimed is:

1. An azo pigment represented by the general formula (2-1), its tautomer, a salt or hydrate thereof:

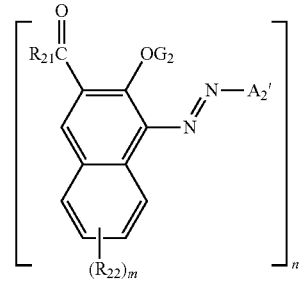

wherein $G_2$ represents a hydrogen atom, an aliphatic group, an aryl group or a heterocyclic group, $R_{21}$ represents an amino group, an aliphatic oxy group, an aliphatic group, an aryl group, or a heterocyclic group, $R_{22}$ represents a substituent, $A_2'$ represents the following general formulae (A-1) to (A-18), (A-20) to (A-28), and (A-30) to (A-32), m represents an integer of from 0 to 5, n represents an integer of from 1 to 4 and, when n=2, the formula represents a dimer formed through $R_{21}$, $R_{22}$, $G_2$, or $A_2'$ and, when n=3, the formula represents a trimer formed through $R_{21}$, $R_{22}$, $G_2$, or $A_2'$ and, when n=4, the formula represents a tetramer formed through $R_{21}$, $R_{22}$, $G_2$, or $A_2'$ and the general formula (2-1) does not contain an ionic hydrophilic group;

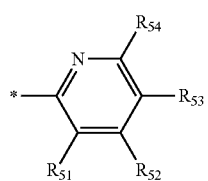
(A-1)

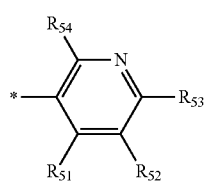
(A-2)

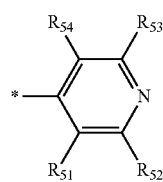
(A-3)

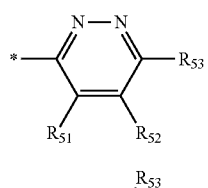
(A-4)

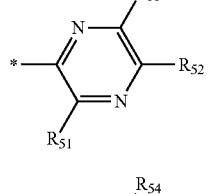
(A-5)

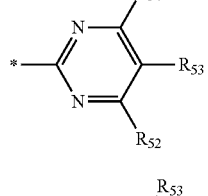
(A-6)

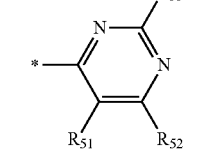
(A-7)

-continued

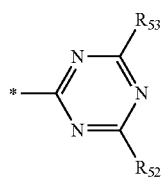
(A-8)

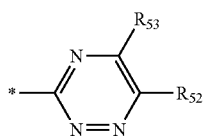
(A-9)

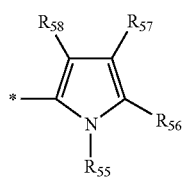
(A-10)

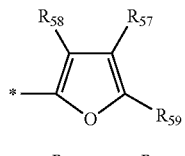
(A-11)

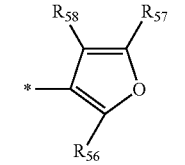
(A-12)

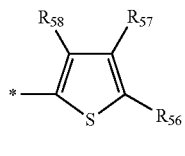
(A-13)

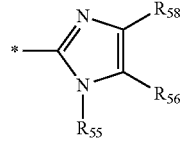
(A-14)

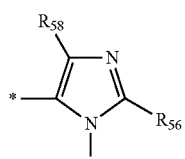
(A-15)

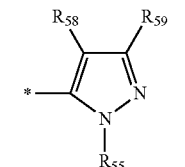
(A-16)

(A-17)

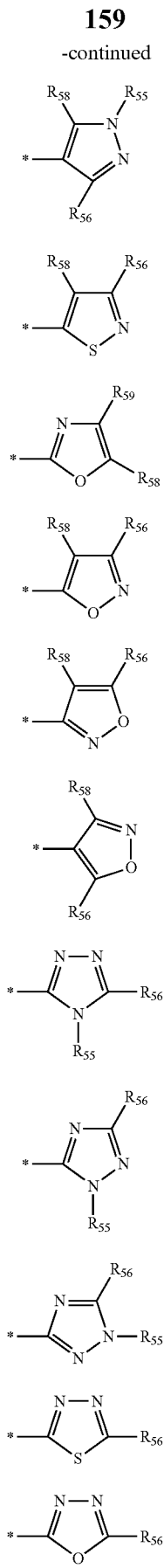
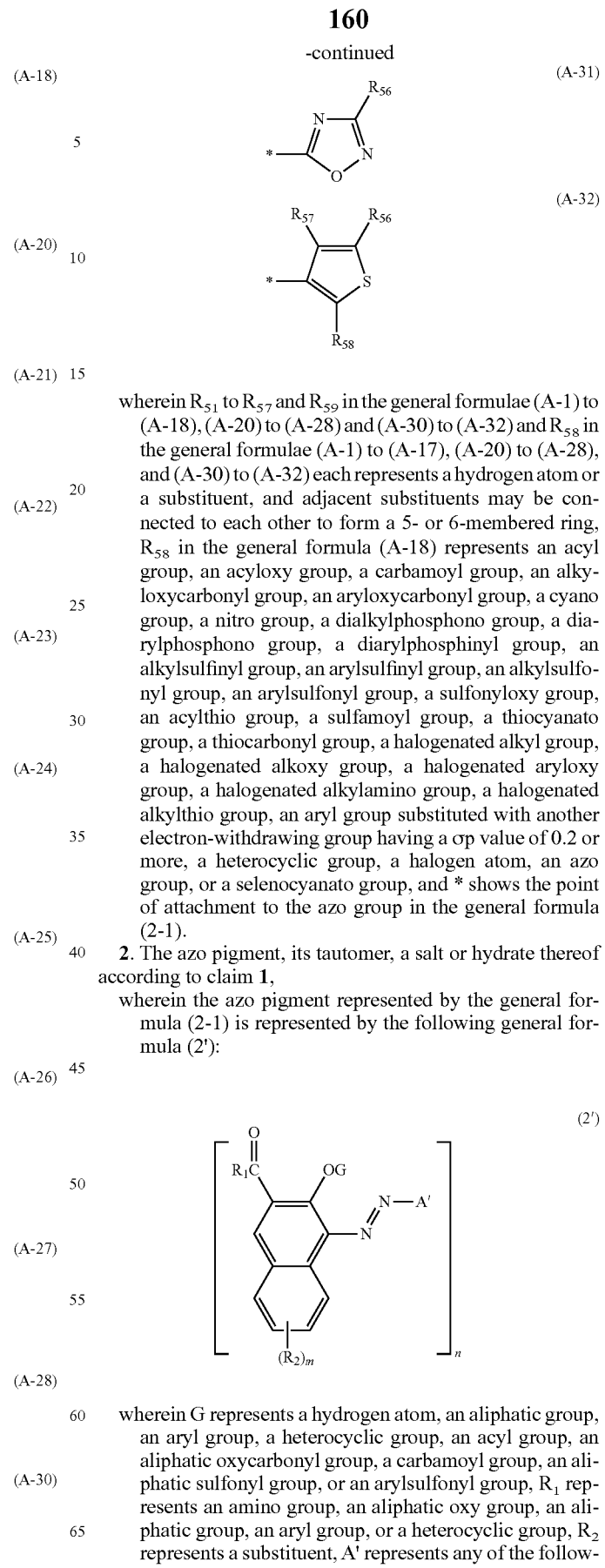

wherein $R_{51}$ to $R_{57}$ and $R_{59}$ in the general formulae (A-1) to (A-18), (A-20) to (A-28) and (A-30) to (A-32) and $R_{58}$ in the general formulae (A-1) to (A-17), (A-20) to (A-28), and (A-30) to (A-32) each represents a hydrogen atom or a substituent, and adjacent substituents may be connected to each other to form a 5- or 6-membered ring, $R_{58}$ in the general formula (A-18) represents an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanato group, a thiocarbonyl group, a halogenated alkyl group, a halogenated alkoxy group, a halogenated aryloxy group, a halogenated alkylamino group, a halogenated alkylthio group, an aryl group substituted with another electron-withdrawing group having a σp value of 0.2 or more, a heterocyclic group, a halogen atom, an azo group, or a selenocyanato group, and * shows the point of attachment to the azo group in the general formula (2-1).

2. The azo pigment, its tautomer, a salt or hydrate thereof according to claim 1,
wherein the azo pigment represented by the general formula (2-1) is represented by the following general formula (2'):

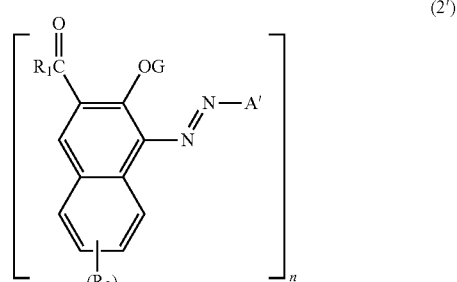

wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A' represents any of the following general formulae (A-10), (A-14) to (A-16), (A-25), and (A-26), m represents an integer of from 0 to 5, n represents an integer of from 1 to 4 and, when n=2, the formula represents a dimer formed through $R_1$, $R_2$, A', or G and, when n=3, the formula represents a trimer formed through $R_1$, $R_2$, A', or G and, when n=4, the formula represents a tetramer formed through $R_1$, $R_2$, A', or G, and the general formula (2') does not contain an ionic hydrophilic group;

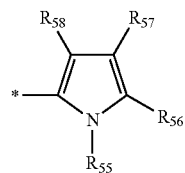
(A-10)

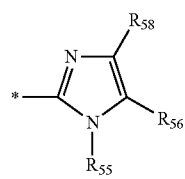
(A-14)

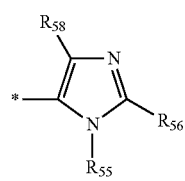
(A-15)

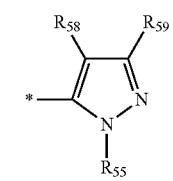
(A-16)

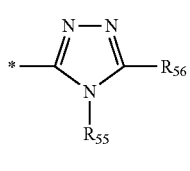
(A-25)

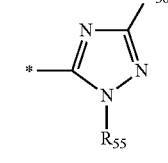
(A-26)

wherein $R_{55}$ in the general formulae (A-10), (A-14) to (A-16), and (A-25) represents a substituent, $R_{56}$ to $R_{59}$ in the general formulae (A-10), (A-14) to (A-16), (A-25), and (A-26) each independently represents a hydrogen atom or a substituent, and adjacent $R_{55}$ and $R_{56}$, $R_{57}$ and $R_{58}$, and $R_{56}$ and $R_{58}$ may be connected to each other to form a 5- or 6-membered ring, $R_{55}$ in the general formula (A-26) represents an aliphatic group, an aryl group or a heterocyclic group, and * shows the point of attachment to the azo group in the general formula (2').

3. An azo pigment represented by the general formula (3), its tautomer, a salt or hydrate thereof:

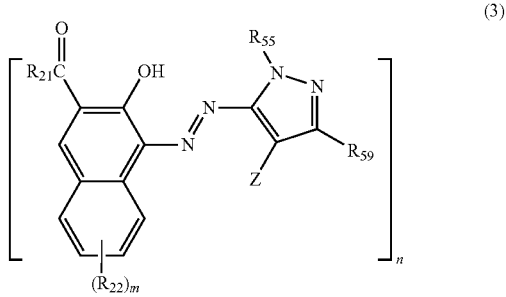
(3)

wherein $R_{21}$ represents an amino group, an aliphatic oxy group, an aliphatic group, an aryl group, or a heterocyclic group, $R_{22}$ represents a substituent, $R_{55}$ represents a substituent, $R_{59}$ represents a hydrogen atom or a substituent, m represents an integer of from 0 to 5, n represents an integer of from 1 to 4, Z represents an electron-withdrawing group having a Hammett σp value of 0.2 or more and, when n=2, the formula represents a dimer formed through $R_{21}$, $R_{22}$, $R_{55}$, $R_{59}$, or Z and, when n=3, the formula represents a trimer formed through $R_{21}$, $R_{22}$, $R_{55}$, $R_{59}$, or Z and, when n=4, the formula represents a tetramer formed through $R_{21}$, $R_{22}$, $R_{55}$, $R_{59}$, or Z, and the general formula (3) does not contain an ionic hydrophilic group.

4. The azo pigment, its tautomer, a salt or hydrate thereof according to claim 1, wherein the azo pigment represented by the general formula (2-1) is represented by the following general formula (2-2):

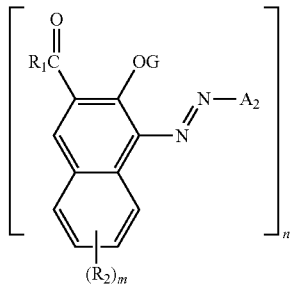
General formula (2-2)

wherein G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, $A_2$ represents any of the following formulae (A-17), (A-18), (A-20), (A-22) to (A-24), (A-27), (A-28), (A-31), and (A-32), m represents an integer of from 0 to 5, n represents an integer of from 1 to 4 and, when n=2, the formula represents a dimer formed through $R_1$, $R_2$, or $A_2$ and, when n=3, the formula represents a trimer formed through $R_1$, $R_2$, or $A_2$ and, when n=4, the formula represents a tetramer formed through $R_1$, $R_2$, or $A_2$, and the general formula (2-2) does not contain an ionic hydrophilic group;

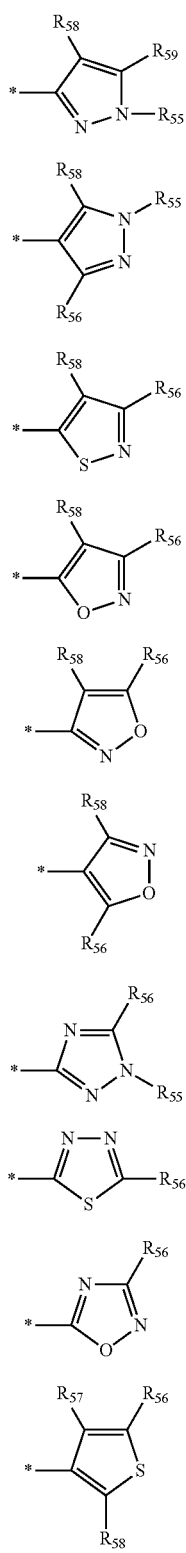

wherein in the general formulae (A-17), (A-18), (A-20), (A-22) to (A-24), (A-27), (A-28), (A-31), and (A-32), $R_{55}$ to $R_{59}$ represent a hydrogen atom or a substituent, adjacent $R_{55}$ and $R_{56}$, $R_{56}$ and $R_{57}$, $R_{55}$ and $R_{58}$, $R_{56}$ and $R_{58}$, and $R_{55}$ and $R_{59}$ may be connected to each other to form a 5- or 6-membered ring, and * shows the point of attachment to the azo group in the general formula (2-2).

5. The azo pigment, its tautomer, a salt or hydrate thereof according to claim 4, wherein the azo pigment represented by the general formula (2-2) is represented by the following general formula (2-3):

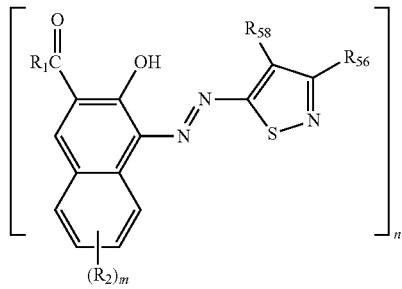

General Formula (2-3)

wherein $R_1$ represents an amino group, an aliphatic oxy group, an aliphatic group, an aryl group, or a heterocyclic group, $R_2$ represents a substituent, $R_{56}$ and $R_{58}$ represent a hydrogen atom or a substituent, m represents an integer of from 0 to 5, n represents an integer of from 1 to 4, and, when n=2, the formula represents a dimer formed through $R_1$, $R_2$, $R_{56}$, or $R_{58}$ and, when n=3, the formula represents a trimer formed through $R_1$, $R_2$, $R_{56}$, or $R_{58}$ and, when n=4, the formula represents a tetramer formed through $R_1$, $R_2$, $R_{56}$, or $R_{58}$, and the general formula (2-3) does not contain an ionic hydrophilic group.

6. A pigment dispersion containing at least one member of the azo pigment, its tautomer, a salt or hydrate thereof according to claim 1.

7. A coloring composition containing at least one member of the azo pigment, its tautomer, a salt or hydrate thereof according to claim 1.

8. An ink for inkjet recording, which uses the pigment dispersion according to claim 6.

9. A coloring composition for color filter, which contains a resin, a photo-polymerization initiator, and an azo pigment represented by the following general formula (1):

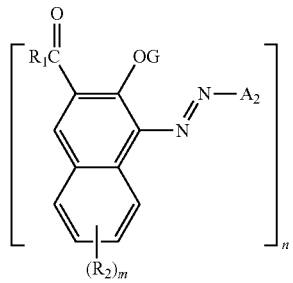

(1)

wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A represents an aromatic 5- or 6-membered heterocyclic group, m represents an integer of from 0 to 5, n represents an integer of from 1 to 4 and, when n=2, the formula represents a dimer formed through $R_1$, $R_2$, A, or G and, when n=3, the formula represents a trimer formed through $R_1$, $R_2$, A, or G and, when n=4, the formula represents a tetramer formed through $R_1$), $R_2$, A, or G, and the general formula (1) does not contain an ionic hydrophilic group.

10. The coloring composition for the color filter according to claim 9, wherein the azo compound represented by the general formula (1) is represented by the following general formula (2):

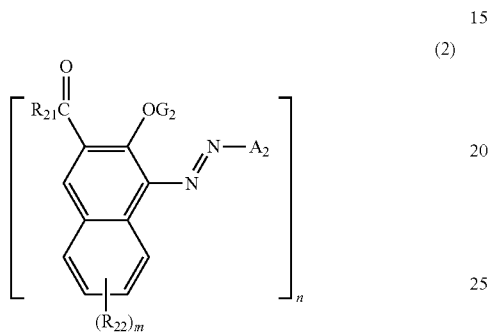

(2)

wherein $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, $R_{22}$ represents a substituent, $A_2$ represents the following general formulae (A-1) to (A-32), m and n are the same as are defined with respect to the general formula (1) and, when n=2, the formula represents a dimer formed through $R_{21}$, $R_{22}$, $G_2$, or $A_2$ and, when n=3, the formula represents a trimer formed through $R_{21}$, $R_{22}$, $G_2$, or $A_2$ and, when n=4, the formula represents a tetramer formed through $R_{21}$, $R_{22}$, $G_2$, or $A_2$, and the general formula (2) does not contain an ionic hydrophilic group;

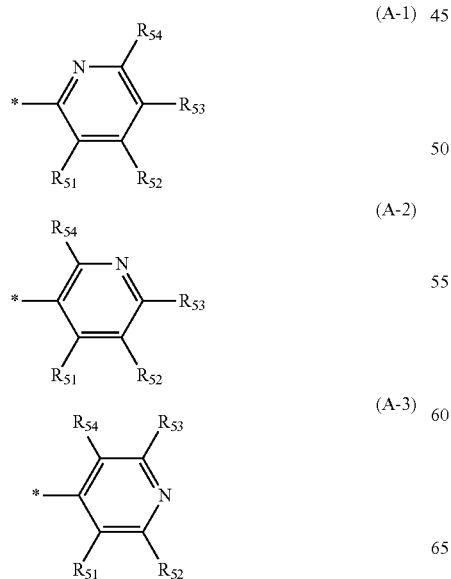

(A-1)

(A-2)

(A-3)

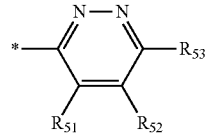 (A-4)

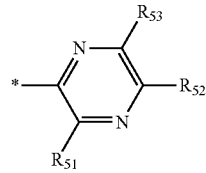 (A-5)

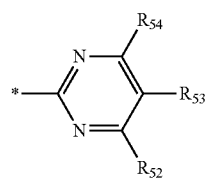 (A-6)

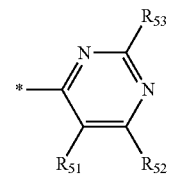 (A-7)

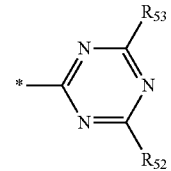 (A-8)

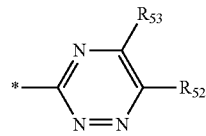 (A-9)

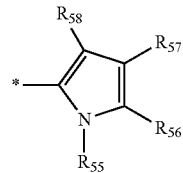 (A-10)

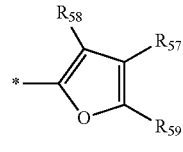 (A-11)

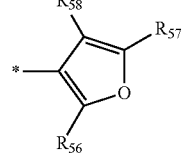 (A-12)

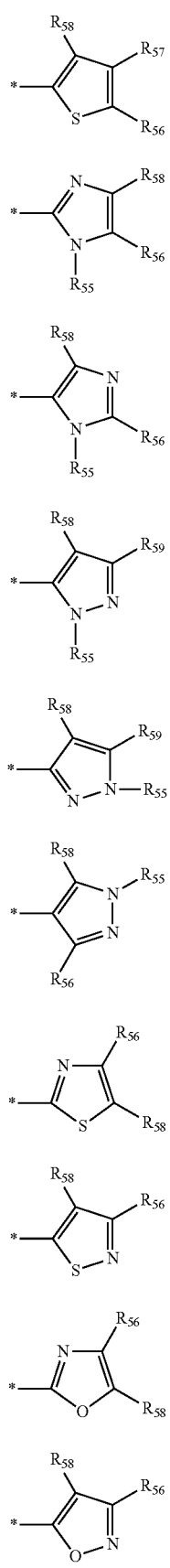
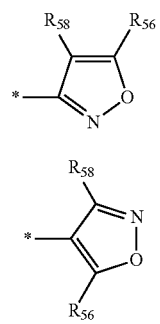
wherein in the general formulae (A-1) to (A-32), $R_{51}$ to $R_{59}$ each represents a hydrogen atom or a substituent, adjacent substituents may be connected to each other to form a 5- or 6-membered ring, and * shows the point of attachment to the azo group in the general formula (2).

11. The coloring composition for color filter according to claim 9, which further contains a polymerizable compound and a solvent.

12. The coloring composition for color filter according to claim 11, which contains the azo pigment represented by the general formula (1) in a content of from 0.01 to 2 parts by mass per 1 part by mass of the polymerizable compound.

13. The coloring composition for color filter according to claim 11, wherein the polymerizable compound is a photosensitive compound.

14. The coloring composition for color filter according to claim 9, which further contains one or more members selected from among a surfactant, a silicone series additive, a pigment series additive, a silane series coupling agent, and a titanium series coupling agent.

15. A color filter formed by using the coloring composition for color filter according to claim 9.

16. The color filter according to claim 15, which is formed according to photolithography method or inkjet method.

17. A process for preparing the coloring composition for color filter according to claim 14, which includes a step of obtaining a pigment dispersion by dispersing one or more dispersants selected from among a surfactant, a silicone series additive, a pigment series additive, a silane series coupling agent, and a titanium series coupling agent, and an azo compound represented by the general formula (1) in part of a solvent, and a step of mixing the pigment dispersion with a polymerizable compound and the rest of the solvent.

18. An azo compound represented by the general formula (2-1), its tautomer, a salt or hydrate thereof:

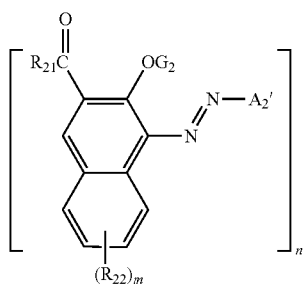

(2-1)

wherein $G_2$ represents a hydrogen atom, an aliphatic group, an aryl group, or a heterocyclic group, $R_{21}$ represents an amino group, an aliphatic oxy group, an aliphatic group, an aryl group, or a heterocyclic group, $R_{22}$ represents a substituent, $A_2'$ represents the following general formulae (A-1) to (A-18), (A-20) to (A-28), and (A-30) to (A-32), m represents an integer of from 0 to 5, n represents an integer of from 1 to 4 and, when n=2, the formula represents a dimer formed through $R_{21}$, $R_{22}$, $G_2$, or $A_2'$ and, when n=3, the formula represents a trimer formed through $R_{21}$, $R_{22}$, $G_2$, or $A_2'$ and, when n=4, the formula represents a tetramer formed through $R_{21}$, $R_{22}$, $G_2$, or $A_2'$, and the general formula (2-1) does not contain an ionic hydrophilic group:

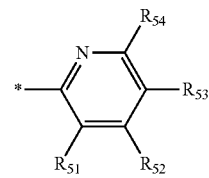
(A-1)

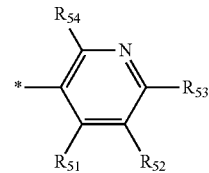
(A-2)

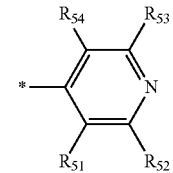
(A-3)

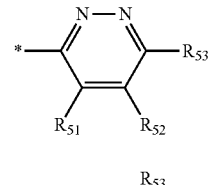
(A-4)

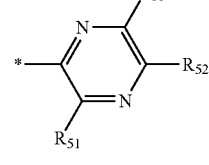
(A-5)

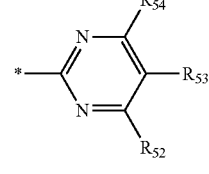
(A-6)

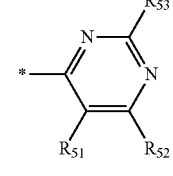
(A-7)

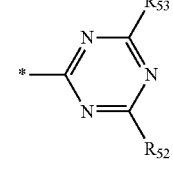
(A-8)

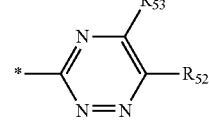
(A-9)

-continued
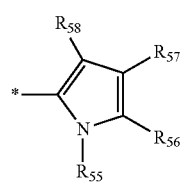 (A-10)
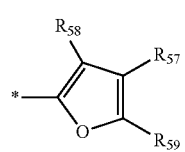 (A-11)
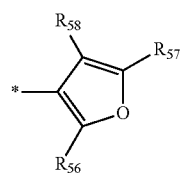 (A-12)
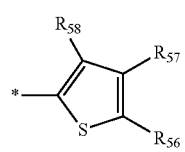 (A-13)
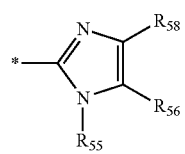 (A-14)
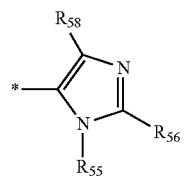 (A-15)
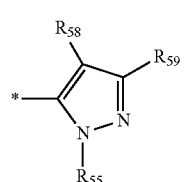 (A-16)
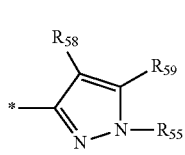 (A-17)
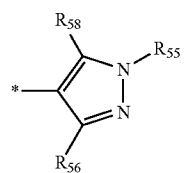 (A-18)
-continued
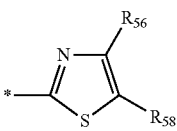 (A-19)
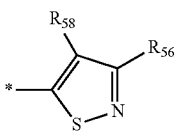 (A-20)
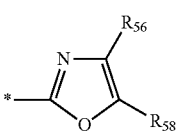 (A-21)
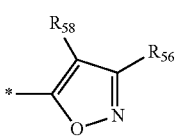 (A-22)
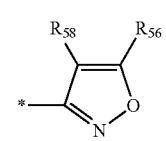 (A-23)
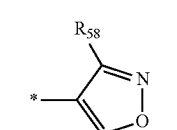 (A-24)
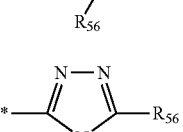 (A-25)
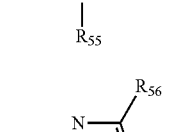 (A-26)
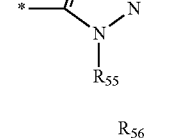 (A-27)
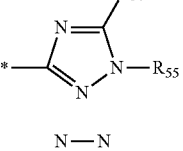 (A-28)
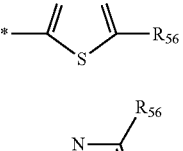 (A-29)

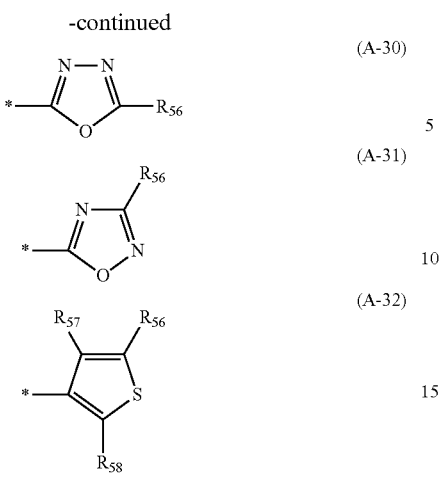

(A-30)

(A-31)

(A-32)

wherein $R_{51}$ to $R_{57}$ and $R_{59}$ in the general formulae (A-1) to (A-18), (A-20) to (A-28), and (A-30) to (A-32) and $R_{58}$ in the general formulae (A-1) to (A-17), (A-20) to (A-28), and (A-30) to (A-32) each represents a hydrogen atom or a substituent, and adjacent substituents may be connected to each other to form a 5- or 6-membered ring, $R_{58}$ in the general formula (A-18) represents an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanato group, a thiocarbonyl group, a halogenated alkyl group, a halogenated alkoxy group, a halogenated aryloxy group, a halogenated alkylamino group, a halogenated alkylthio group, an aryl group substituted with another electron-withdrawing group having a σp value of 0.2 or more, a heterocyclic group, a halogen atom, an azo group, or a selenocyanato group, and * shows the point of attachment to the azo group in the general formula (2-1).

19. The azo compound, its tautomer, a salt or hydrate thereof according to claim 18, wherein the azo compound represented by the general formula (2-1) is represented by the following general formula (2'):

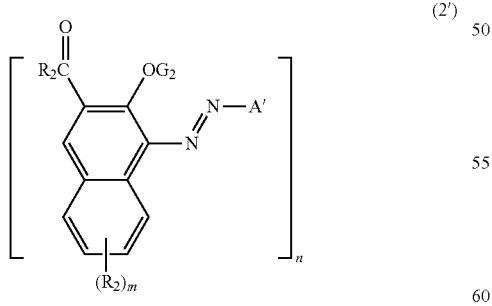

(2')

wherein G represents a hydrogen atom, an aliphatic group, an aryl group, a heterocyclic group, an acyl group, an aliphatic oxycarbonyl group, a carbamoyl group, an aliphatic sulfonyl group, or an arylsulfonyl group, $R_1$ represents an amino group, an aliphatic oxy group, an aliphatic group, an aryl group, or a heterocyclic group, $R_2$ represents a substituent, A' represents any of the following general formulae (A-10), (A-14) to (A-16), (A-25), and (A-26), m represents an integer of from 0 to 5, n represents an integer of from 1 to 4 and, when n=2, the formula represents a dimer formed through $R_1$, $R_2$, A', or G and, when n=3, the formula represents a trimer formed through $R_1$, $R_2$, A', or G and, when n=4, the formula represents a tetramer formed through $R_1$, $R_2$, $A_2'$, or G, and the general formula (2') does not contain an ionic hydrophilic group;

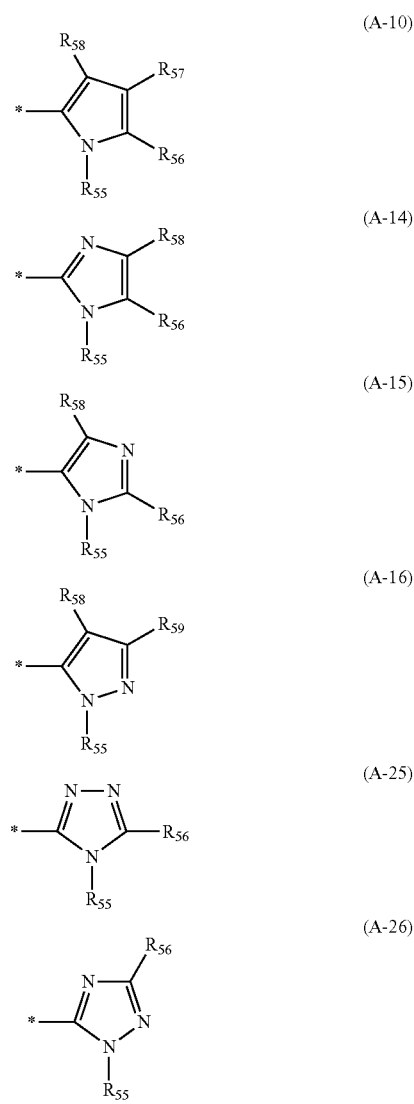

wherein $R_{55}$ in the general formulae (A-10), (A-14) to (A-16), and (A-25) represents a substituent, $R_{56}$ to $R_{59}$ in the general formulae (A-10), (A-14) to (A-16), (A-25), and (A-26) each independently represents a hydrogen atom or a substituent, and adjacent $R_{55}$ and $R_{56}$, $R_{57}$ and $R_{58}$, and $R_{56}$ and $R_{58}$ may be connected to each other to form a 5- or 6-membered ring, $R_{55}$ in the general formula (A-26) represents an aliphatic group, an aryl group, or a heterocyclic group, and * shows the point of attachment to the azo group in the general formula (2').

20. The azo compound, its tautomer, a salt or hydrate thereof according to claim 18, wherein the azo compound represented by the general formula (2-1) is represented by the following general formula (3):

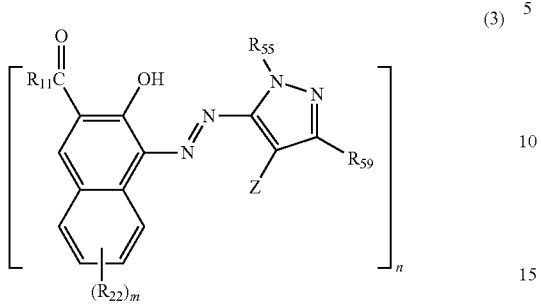

(3)

wherein $R_{21}$, $R_{22}$, $R_{55}$, $R_{59}$, m, and n are the same as those defined with respect to the general formula (2-1), Z represents an electron-withdrawing group having a Hammett σp value of 0.2 or more and, when n=2, the formula represents a dimer formed through $R_{21}$, $R_{22}$, $R_{55}$, $R_{59}$, or Z and, when n=3, the formula represents a trimer formed through $R_{21}$, $R_{22}$, $R_{55}$, $R_{59}$, or Z and, when n=4, the formula represents a tetramer formed through $R_{21}$, $R_{22}$, $R_{55}$, $R_{59}$, or Z, and the general formula (3) does not contain an ionic hydrophilic group.

21. The azo compound, its tautomer, a salt or hydrate thereof according to claim 18, wherein the azo compound represented by the general formula (2-1) is represented by the following general formula (2-2):

General Formula (2-2)

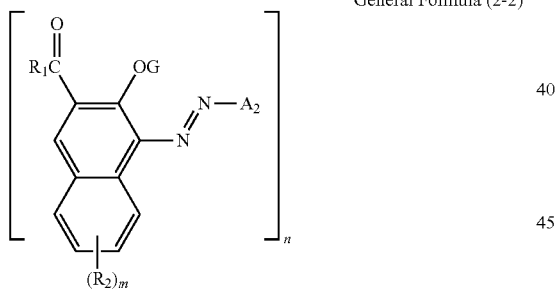

wherein G represents a hydrogen atom, an aliphatic group, an aryl group, a heterocyclic group, an acyl group, an aliphatic oxycarbonyl group, a carbamoyl group, an aliphatic sulfonyl or aryl sulfonyl group, $R_1$ represents an amino group, an aliphatic oxy group, an aliphatic group, an aryl group, or a heterocyclic group, $R_2$ represents a substituent, $A_2$ represents any of the following formulae (A-17), (A-18), (A-20), (A-22) to (A-24), (A-27), (A-28), (A-31), and (A-32), m represents an integer of from 0 to 5, n represents an integer of from 1 to 4 and, when n=2, the formula represents a dimer formed through $R_1$, $R_2$, or $A_2$ and, when n=3, the formula represents a trimer formed through $R_1$, $R_2$, or $A_2$ and, when n=4, the formula represents a tetramer formed through $R_1$, $R_2$, or $A_2$, and the general formula (2-2) does not contain an ionic hydrophilic group;

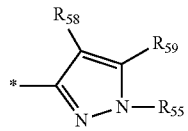

(A-17)

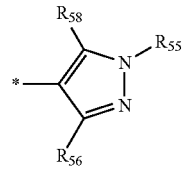

(A-18)

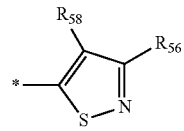

(A-20)

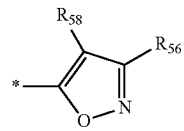

(A-22)

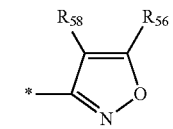

(A-23)

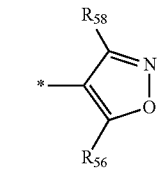

(A-24)

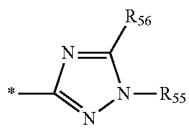

(A-27)

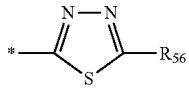

(A-28)

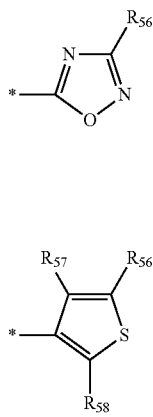

(A-31)

(A-32)

wherein in the general formulae (A-17), (A-18), (A-20), (A-22) to (A-24), (A-27), (A-28), (A-31), and (A-32), $R_{55}$ to $R_{59}$ each represents a hydrogen atom or a substituent, adjacent $R_{55}$ and $R_{56}$, $R_{56}$ and $R_{57}$, $R_{55}$ and $R_{58}$, $R_{56}$ and $R_{58}$, and $R_{55}$ and $R_{59}$ may be connected to each other to form a 5- or 6-membered ring, and * shows the point of attachment to the azo group in the general formula (2-2).

22. The azo compound, its tautomer, a salt or hydrate thereof according to claim 21, wherein the azo compound represented by the general formula (2-2) is represented by the following general formula (2-3):

General formula (2-3)

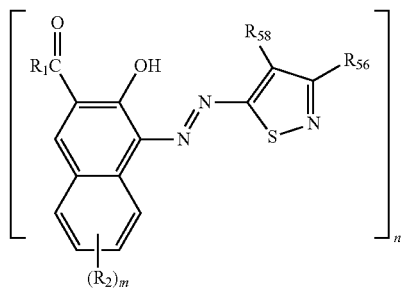

wherein $R_1$ represents an amino group, an aliphatic oxy group, an aliphatic group, an aryl group, or a heterocyclic group, $R_2$ represents a substituent, $R_{56}$ and $R_{58}$ each represents a hydrogen atom or a substituent, m represents an integer of from 0 to 5, n represents an integer of from 1 to 4, $R_{56}$ and $R_{58}$ may be connected to each other to form a 5- or 6-membered ring and, when n=2, the formula represents a dimer formed through $R_1$, $R_2$, $R_{56}$, or $R_{58}$ and, when n=3, the formula represents a trimer formed through $R_1$, $R_2$, $R_{56}$, or $R_{58}$ and, when n=4, the formula represents a tetramer formed through $R_1$, $R_2$, $R_{56}$, or $R_{58}$, and the general formula (2-3) does not contain an ionic hydrophilic group.

* * * * *